US011938219B2

(12) United States Patent
Zhang et al.

(10) Patent No.: US 11,938,219 B2

(45) Date of Patent: Mar. 26, 2024

(54) SYNTHETIC EXTRACELLULAR VESICLES FOR NOVEL THERAPIES

(71) Applicant: University of Southern California, Los Angeles, CA (US)

(72) Inventors: Yong Zhang, Los Angeles, CA (US); Xiaojing Shi, Los Angeles, CA (US); Qinqin Cheng, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 496 days.

(21) Appl. No.: 16/634,857

(22) PCT Filed: Jul. 27, 2018

(86) PCT No.: PCT/US2018/044251

§ 371 (c)(1), (2) Date: Jan. 28, 2020

(87) PCT Pub. No.: WO2019/027847

PCT Pub. Date: Feb. 7, 2019

(65) Prior Publication Data

US 2020/0405640 A1 Dec. 31, 2020

Related U.S. Application Data

(60) Provisional application No. 62/538,669, filed on Jul. 29, 2017.

(51) Int. Cl.

| | |
|---|---|
| ***A61K 9/12*** | (2006.01) |
| ***A61K 9/127*** | (2006.01) |
| ***A61K 31/4745*** | (2006.01) |
| ***C07K 14/71*** | (2006.01) |
| ***C07K 16/28*** | (2006.01) |
| ***C07K 16/32*** | (2006.01) |

(52) U.S. Cl.

CPC .......... *A61K 9/1271* (2013.01); *A61K 9/1277* (2013.01); *A61K 31/4745* (2013.01); *C07K 14/71* (2013.01); *C07K 16/2809* (2013.01); *C07K 16/283* (2013.01); *C07K 16/32* (2013.01); *C07K 2317/31* (2013.01); *C07K 2317/622* (2013.01); *C07K 2319/03* (2013.01); *C07K 2319/41* (2013.01); *C07K 2319/42* (2013.01)

(58) Field of Classification Search

CPC ................ A61K 9/1271; A61K 9/1277; A61K 31/4745; A61K 9/0019; A61K 2039/505; C07K 14/71; C07K 16/2809; C07K 16/283; C07K 16/32; C07K 2317/31; C07K 2317/622; C07K 2319/03; C07K 2319/41; C07K 2319/42; A61P 35/00

See application file for complete search history.

(56) References Cited

U.S. PATENT DOCUMENTS

| | | | | |
|---|---|---|---|---|
| 2002/0142000 A1 | 10/2002 | Digan et al. | | |
| 2012/0189630 A1 | 7/2012 | Bigner et al. | | |
| 2014/0356382 A1* | 12/2014 | Wood | A61K 47/42 | 424/178.1 |
| 2015/0203579 A1* | 7/2015 | Papadopoulos | A61P 21/04 | 600/1 |
| 2017/0058043 A1 | 3/2017 | Soliman | | |

FOREIGN PATENT DOCUMENTS

| | | |
|---|---|---|
| WO | WO-03/016522 A2 | 2/2003 |
| WO | WO-2015/002956 A1 | 1/2015 |

OTHER PUBLICATIONS

Bianchini et al. (Lancet Oncol., 15: 58-68, 2014).*

Xitong et al. (Gene, 575: 377-384, 2016).*

Gujrati, et al., "Bioengineered Bacterial Outer Membrane Vesicles as Cell-Specific Drug-Delivery Vehicles for Cancer Therapy", ACS Nano, Feb. 25, 2014, vol. 8, No. 2, pp. 1525-1537.

International Search Report and Written Opinion dated Dec. 12, 2018, from application No. PCT/US2018/044251.

Cheng et al., "Reprogramming Exosomes as Nanoscale Controllers of Cellular Immunity", Journal Of The American Chemical Society, vol. 140, No. 48, Nov. 19, 2018, pp. 16413-16417.

Extended Search Report on European Patent Application No. 18840978.3 dated Mar. 26, 2021 (12 pages).

Ferrini et al., "Bispecific Monoclonal Antibodies Directed To Cd16 And To A Tumor-Associated Antigen Induce Target-Cell Lysis By Resting Nk Cells And By A Subset Of Nk Clones", Int. J. Cancer, Wiley-Liss, Inc. vol. 48, No. 2, Jan. 1, 1991, pp. 227-233.

Frankel et al., "Targeting T Cells to Tumor Cells Using Bispecific Antibodies", Engineered Protein Scaffolds As Next-Generation Antibody Therapeutics, vol. 17, No. 3, Jun. 1, 2013, pp. 385-392.

Gilliland et al., "Universal Bispecitic Antibody for Targeting Tumor Cells for Destruction by Cytotoxic T Cells", Proc. Natl. Acad. Sci. USA, vol. 85, Oct. 1, 1988, pp. 7719-7723.

Kooijmans et al., "Display Of Gpl-Anchored Anti-EGFR Nanobodies on Extracellular Vesicles Promotes Tumour Cell Targeting", Journal of Extracellular Vesicles, vol. 5, No. 1, Jan. 16, 2016 (12 pages).

* cited by examiner

*Primary Examiner* — Nelson B Moseley, II

(74) *Attorney, Agent, or Firm* — Foley & Lardner LLP

(57) ABSTRACT

Given developing resistance of tumor cells to current chemotherapeutic and targeted therapeutic agents, novel cancer therapies with enhanced potency and specificity are substantially required. Applicant has provided herein extracellular nanoparticle vesicles that redirect immune effector cells towards cancer cells for killing. Relative to conventional immunotherapeutic antibodies with defined orientation and geometry for their distinct antigen-binding arms, antibodies displayed on spherical exosomes can promote formation of immunological synapses as well as enhanced efficacy to activate immune cells.

15 Claims, 25 Drawing Sheets

Specification includes a Sequence Listing.

1 2 3

Anti-FLAG 190 kDa 135 kDa

SEQUENCE LISTING

```
<160> NUMBER OF SEQ ID NOS: 89

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5


<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(25)
<223> OTHER INFORMATION: This sequence may encompass 0-5 "Gly Gly Gly
      Gly Ser" repeating units

<400> SEQUENCE: 2

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 3
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(24)
<223> OTHER INFORMATION: This sequence may encompass 0-6 "Gly Gly Gly
      Ser" repeating units

<400> SEQUENCE: 3

Gly Gly Gly Ser Gly Gly Gly Ser Gly Gly Gly Ser Gly Gly Gly Ser
1               5                   10                  15

Gly Gly Gly Ser Gly Gly Gly Ser
            20


<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(21)
<223> OTHER INFORMATION: This sequence may encompass 0-7 "Gly Gly Ser"
      repeating units

<400> SEQUENCE: 4

Gly Gly Ser Gly Gly Ser Gly Gly Ser Gly Gly Ser Gly Gly Ser Gly
1               5                   10                  15
```

```
Gly Ser Gly Gly Ser
            20


<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 0-4 “Glu Ala Ala
      Ala Lys” repeating units

<400> SEQUENCE: 5

Glu Ala Ala Ala Lys Glu Ala Ala Ala Lys Glu Ala Ala Ala Lys Glu
1               5                   10                  15

Ala Ala Ala Lys
            20


<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Ser Gly Gln Ala Gly Ala Ala Ala Ser Glu Ser Leu Phe Val Ser
1               5                   10                  15

Asn His Ala Tyr
            20


<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ser Thr Ser Gly Ser Gly Lys Pro Gly Ser Gly Glu Gly Ser
1               5                   10                  15


<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Gly Gly Ser Gly Gly Gly Gly Ser Gly Gly Gly Gly Ser
1               5                   10                  15


<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 9

Gly Gly Gly Gly Ser
1 5

<210> SEQ ID NO 10
<211> LENGTH: 987
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10
tatccatatg atgttccaga ttatgctggg gcccagccgg ccagatctga tatccagatg 60
acacagacaa cctcaagtct tagtgcatca ctgggagatc gtgtgactat aagctgccgc 120
gcatcacagg acattcgcaa ttatctgaat tggtatcaac agaagcctga tggcaccgtg 180
aaacttctga tctattacac cagtcgtctg catagcggtg ttccgagcaa atttcaggc 240 tcagggtcag gaaccgatta ttcactgacg attagtaatt tagaacaaga agatattgca 300
acctatttct gtcaacaggg taataccctg ccgtggacct ttgcaggtgg taccaaactg 360
gaaattaaag gaggtggcag tggaggggga agcggcggcg gttcaggagg cggttctgag 420
gtccagttac agcagagcgg tccggaactg gttaaaccgg gtgcaagcat gaaaattagc 480
tgtaaagcaa gcggttatag ctttaccggt tataccatga attgggttaa acagagccat 540
ggtaaaaatc tggaatggat gggtctgatt aatccgtata aaggtgttag cacctataat 600
cagaaattta aagataaagc aaccctgacc gttgataaaa gcagcagcac cgcatatatg 660
gaactgctga gcctgaccag cgaagatagc gccgtttact attgcgcacg cagcggttat 720
tatggtgata gcgattggta ttttgatgtt tggggtgcag gtaccaccgt taccgttagc 780
agcgggggtg gcggaagcgt cgacgaacaa aaactcatct cagaagagga tctgaatgct 840
gtgggccagg acacgcagga ggtcatcgtg gtgccacact ccttgccctt taaggtggtg 900
gtgatctcag ccatcctggc cctggtggtg ctcaccatca tctcccttat catcctcatc 960
atgctttggc agaagaagcc acgttag 987

<210> SEQ ID NO 11
<211> LENGTH: 328
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Tyr Pro Tyr Asp Val Pro Asp Tyr Ala Gly Ala Gln Pro Ala Arg Ser
1 5 10 15

Asp Ile Gln Met Thr Gln Thr Thr Ser Ser Leu Ser Ala Ser Leu Gly
20 25 30

Asp Arg Val Thr Ile Ser Cys Arg Ala Ser Gln Asp Ile Arg Asn Tyr
35 40 45

Leu Asn Trp Tyr Gln Gln Lys Pro Asp Gly Thr Val Lys Leu Leu Ile
50 55 60

Tyr Tyr Thr Ser Arg Leu His Ser Gly Val Pro Ser Lys Phe Ser Gly
65 70 75 80

Ser Gly Ser Gly Thr Asp Tyr Ser Leu Thr Ile Ser Asn Leu Glu Gln
85 90 95

```
Glu Asp Ile Ala Thr Tyr Phe Cys Gln Gln Gly Asn Thr Leu Pro Trp
            100                 105                 110

Thr Phe Ala Gly Gly Thr Lys Leu Glu Ile Lys Gly Gly Gly Ser Gly
        115                 120                 125

Gly Gly Ser Gly Gly Gly Ser Gly Gly Gly Ser Glu Val Gln Leu Gln
    130                 135                 140

Gln Ser Gly Pro Glu Leu Val Lys Pro Gly Ala Ser Met Lys Ile Ser
145                 150                 155                 160

Cys Lys Ala Ser Gly Tyr Ser Phe Thr Gly Tyr Thr Met Asn Trp Val
                165                 170                 175

Lys Gln Ser His Gly Lys Asn Leu Glu Trp Met Gly Leu Ile Asn Pro
            180                 185                 190

Tyr Lys Gly Val Ser Thr Tyr Asn Gln Lys Phe Lys Asp Lys Ala Thr
        195                 200                 205

Leu Thr Val Asp Lys Ser Ser Ser Thr Ala Tyr Met Glu Leu Leu Ser
    210                 215                 220

Leu Thr Ser Glu Asp Ser Ala Val Tyr Tyr Cys Ala Arg Ser Gly Tyr
225                 230                 235                 240

Tyr Gly Asp Ser Asp Trp Tyr Phe Asp Val Trp Gly Ala Gly Thr Thr
                245                 250                 255

Val Thr Val Ser Ser Gly Gly Gly Gly Ser Val Asp Glu Gln Lys Leu
            260                 265                 270

Ile Ser Glu Glu Asp Leu Asn Ala Val Gly Gln Asp Thr Gln Glu Val
        275                 280                 285

Ile Val Val Pro His Ser Leu Pro Phe Lys Val Val Val Ile Ser Ala
    290                 295                 300

Ile Leu Ala Leu Val Val Leu Thr Ile Ile Ser Leu Ile Ile Leu Ile
305                 310                 315                 320

Met Leu Trp Gln Lys Lys Pro Arg
                325
```

<210> SEQ ID NO 12
<211> LENGTH: 984
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
tatccatatg atgttccaga ttatgctggg gcccagccgg ccagatctga catccagatg     60

acccagtctc catcctccct gtctgcatct gtaggagaca gagtcaccat cacttgccgg    120

gcaagtcagg atgtgaatac cgcggtcgca tggtatcagc agaaaccagg gaaagcccct    180

aagctcctga tctattctgc atccttcttg tatagtgggg tcccatcaag gttcagtggc    240

agtaggtctg ggacagattt cactctcacc atcagcagtc tgcaacctga agattttgca    300

acttactact gtcaacagca ttacactacc cctccgacgt tcggccaagg taccaaggtg    360

gagatcaaac gaactggctc taccagcgga agcggaaagc ctggcagcgg cgagggctcc    420

gaagtgcagc tggtggagtc tggcggagga ctggtgcagc caggggggcag cctgagactg    480

tcttgcgccg cctccggctt caacatcaag gacacctaca tccactgggt ccgccaggca    540

ccaggcaagg gactggaatg ggtggcccgg atctacccta ccaacggcta caccagatac    600

gccgactccg tgaagggccg gttcaccatc tccgccgaca cctccaagaa caccgcctac    660

ctgcaaatga actccctgag ggccgaggac accgccgtgt actactgctc cagatgggga    720
```

```
ggcgacggct tctacgcaat ggactactgg ggccagggca ccctggtcac agtgtcctct    780

gggggtggcg gaagcgtcga cgaacaaaaa ctcatctcag aagaggatct gaatgctgtg    840

ggccaggaca cgcaggaggt catcgtggtg ccacactcct tgccctttaa ggtggtggtg    900

atctcagcca tcctggccct ggtggtgctc accatcatct cccttatcat cctcatcatg    960

ctttggcaga agaagccacg ttag                                            984


<210> SEQ ID NO 13
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Tyr Pro Tyr Asp Val Pro Asp Tyr Ala Gly Ala Gln Pro Ala Arg Ser
1               5                   10                  15

Asp Ile Gln Met Thr Gln Ser Pro Ser Ser Leu Ser Ala Ser Val Gly
            20                  25                  30

Asp Arg Val Thr Ile Thr Cys Arg Ala Ser Gln Asp Val Asn Thr Ala
        35                  40                  45

Val Ala Trp Tyr Gln Gln Lys Pro Gly Lys Ala Pro Lys Leu Leu Ile
    50                  55                  60

Tyr Ser Ala Ser Phe Leu Tyr Ser Gly Val Pro Ser Arg Phe Ser Gly
65                  70                  75                  80

Ser Arg Ser Gly Thr Asp Phe Thr Leu Thr Ile Ser Ser Leu Gln Pro
                85                  90                  95

Glu Asp Phe Ala Thr Tyr Tyr Cys Gln Gln His Tyr Thr Thr Pro Pro
            100                 105                 110

Thr Phe Gly Gln Gly Thr Lys Val Glu Ile Lys Arg Thr Gly Ser Thr
        115                 120                 125

Ser Gly Ser Gly Lys Pro Gly Ser Gly Glu Gly Ser Glu Val Gln Leu
    130                 135                 140

Val Glu Ser Gly Gly Gly Leu Val Gln Pro Gly Gly Ser Leu Arg Leu
145                 150                 155                 160

Ser Cys Ala Ala Ser Gly Phe Asn Ile Lys Asp Thr Tyr Ile His Trp
                165                 170                 175

Val Arg Gln Ala Pro Gly Lys Gly Leu Glu Trp Val Ala Arg Ile Tyr
            180                 185                 190

Pro Thr Asn Gly Tyr Thr Arg Tyr Ala Asp Ser Val Lys Gly Arg Phe
        195                 200                 205

Thr Ile Ser Ala Asp Thr Ser Lys Asn Thr Ala Tyr Leu Gln Met Asn
    210                 215                 220

Ser Leu Arg Ala Glu Asp Thr Ala Val Tyr Tyr Cys Ser Arg Trp Gly
225                 230                 235                 240

Gly Asp Gly Phe Tyr Ala Met Asp Tyr Trp Gly Gln Gly Thr Leu Val
                245                 250                 255

Thr Val Ser Ser Gly Gly Gly Gly Ser Val Asp Glu Gln Lys Leu Ile
            260                 265                 270

Ser Glu Glu Asp Leu Asn Ala Val Gly Gln Asp Thr Gln Glu Val Ile
        275                 280                 285

Val Val Pro His Ser Leu Pro Phe Lys Val Val Val Ile Ser Ala Ile
    290                 295                 300
```

```
Leu Ala Leu Val Val Leu Thr Ile Ile Ser Leu Ile Ile Leu Ile Met
305                 310                 315                 320

Leu Trp Gln Lys Lys Pro Arg
                325
```

<210> SEQ ID NO 14
<211> LENGTH: 1764
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
tatccatatg atgttccaga ttatgctggg gcccagccgg ccagatctga catccagatg     60

acccagtctc catcctccct gtctgcatct gtaggagaca gagtcaccat cacttgccgg    120

gcaagtcagg atgtgaatac cgcggtcgca tggtatcagc agaaaccagg gaaagcccct    180

aagctcctga tctattctgc atccttcttg tatagtgggg tcccatcaag gttcagtggc    240

agtaggtctg ggacagattt cactctcacc atcagcagtc tgcaacctga agattttgca    300

acttactact gtcaacagca ttacactacc cctccgacgt tcggccaagg taccaaggtg    360

gagatcaaac gaactggctc taccagcgga agcggaaagc ctggcagcgg cgagggctcc    420

gaagtgcagc tggtggagtc tggcggagga ctggtgcagc caggggggcag cctgagactg    480

tcttgcgccg cctccggctt caacatcaag gacacctaca tccactgggt ccgccaggca    540

ccaggcaagg gactggaatg ggtggcccgg atctacccta ccaacggcta caccagatac    600

gccgactccg tgaagggccg gttcaccatc tccgccgaca cctccaagaa caccgcctac    660

ctgcaaatga actccctgag ggccgaggac accgccgtgt actactgctc cagatgggga    720

ggcgacggct tctacgcaat ggactactgg ggccagggca ccctggtcac agtgtcctct    780

ggcggtggcg gatcaggcgg gggaggctca ggcggaggtg gcagcgatat ccagatgaca    840

cagacaacct caagtcttag tgcatcactg ggagatcgtg tgactataag ctgccgcgca    900

tcacaggaca ttcgcaatta tctgaattgg tatcaacaga agcctgatgg caccgtgaaa    960

cttctgatct attacaccag tcgtctgcat agcggtgttc cgagcaaatt ttcaggctca   1020

gggtcaggaa ccgattattc actgacgatt agtaatttag aacaagaaga tattgcaacc   1080

tatttctgtc aacagggtaa taccctgccg tggacctttg caggtggtac caaactggaa   1140

attaaaggag gtggcagtgg agggggaagc ggcggcggtt caggaggcgg ttctgaggtc   1200

cagttacagc agagcggtcc ggaactggtt aaaccgggtg caagcatgaa aattagctgt   1260

aaagcaagcg gttatagctt taccggttat accatgaatt gggttaaaca gagccatggt   1320

aaaaatctgg aatggatggg tctgattaat ccgtataaag gtgttagcac ctataatcag   1380

aaatttaaag ataaagcaac cctgaccgtt gataaaagca gcagcaccgc atatatggaa   1440

ctgctgagcc tgaccagcga agatagcgcc gtttactatt gcgcacgcag cggttattat   1500

ggtgatagcg attggtattt tgatgtttgg ggtgcaggta ccaccgttac cgttagcagc   1560

gggggtggcg gaagcgtcga cgaacaaaaa ctcatctcag aagaggatct gaatgctgtg   1620

ggccaggaca cgcaggaggt catcgtggtg ccacactcct tgccctttaa ggtggtggtg   1680

atctcagcca tcctggccct ggtggtgctc accatcatct cccttatcat cctcatcatg   1740

ctttggcaga agaagccacg ttag                                           1764
```

<210> SEQ ID NO 15

```
<211> LENGTH: 587
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Tyr Pro Tyr Asp Val Pro Asp Tyr Ala Gly Ala Gln Pro Ala Arg Ser
1               5                   10                  15

Asp Ile Gln Met Thr Gln Ser Pro Ser Ser Leu Ser Ala Ser Val Gly
            20                  25                  30

Asp Arg Val Thr Ile Thr Cys Arg Ala Ser Gln Asp Val Asn Thr Ala
        35                  40                  45

Val Ala Trp Tyr Gln Gln Lys Pro Gly Lys Ala Pro Lys Leu Leu Ile
    50                  55                  60

Tyr Ser Ala Ser Phe Leu Tyr Ser Gly Val Pro Ser Arg Phe Ser Gly
65                  70                  75                  80

Ser Arg Ser Gly Thr Asp Phe Thr Leu Thr Ile Ser Ser Leu Gln Pro
                85                  90                  95

Glu Asp Phe Ala Thr Tyr Tyr Cys Gln Gln His Tyr Thr Thr Pro Pro
            100                 105                 110

Thr Phe Gly Gln Gly Thr Lys Val Glu Ile Lys Arg Thr Gly Ser Thr
        115                 120                 125

Ser Gly Ser Gly Lys Pro Gly Ser Gly Glu Gly Ser Glu Val Gln Leu
    130                 135                 140

Val Glu Ser Gly Gly Gly Leu Val Gln Pro Gly Gly Ser Leu Arg Leu
145                 150                 155                 160

Ser Cys Ala Ala Ser Gly Phe Asn Ile Lys Asp Thr Tyr Ile His Trp
                165                 170                 175

Val Arg Gln Ala Pro Gly Lys Gly Leu Glu Trp Val Ala Arg Ile Tyr
            180                 185                 190

Pro Thr Asn Gly Tyr Thr Arg Tyr Ala Asp Ser Val Lys Gly Arg Phe
        195                 200                 205

Thr Ile Ser Ala Asp Thr Ser Lys Asn Thr Ala Tyr Leu Gln Met Asn
    210                 215                 220

Ser Leu Arg Ala Glu Asp Thr Ala Val Tyr Tyr Cys Ser Arg Trp Gly
225                 230                 235                 240

Gly Asp Gly Phe Tyr Ala Met Asp Tyr Trp Gly Gln Gly Thr Leu Val
                245                 250                 255

Thr Val Ser Ser Gly Gly Gly Gly Ser Gly Gly Gly Gly Ser Gly Gly
            260                 265                 270

Gly Gly Ser Asp Ile Gln Met Thr Gln Thr Thr Ser Ser Leu Ser Ala
        275                 280                 285

Ser Leu Gly Asp Arg Val Thr Ile Ser Cys Arg Ala Ser Gln Asp Ile
    290                 295                 300

Arg Asn Tyr Leu Asn Trp Tyr Gln Gln Lys Pro Asp Gly Thr Val Lys
305                 310                 315                 320

Leu Leu Ile Tyr Tyr Thr Ser Arg Leu His Ser Gly Val Pro Ser Lys
                325                 330                 335

Phe Ser Gly Ser Gly Ser Gly Thr Asp Tyr Ser Leu Thr Ile Ser Asn
            340                 345                 350

Leu Glu Gln Glu Asp Ile Ala Thr Tyr Phe Cys Gln Gln Gly Asn Thr
        355                 360                 365

Leu Pro Trp Thr Phe Ala Gly Gly Thr Lys Leu Glu Ile Lys Gly Gly
```

```
    370                 375                 380

Gly Ser Gly Gly Gly Ser Gly Gly Gly Ser Gly Gly Gly Ser Glu Val
385                 390                 395                 400

Gln Leu Gln Gln Ser Gly Pro Glu Leu Val Lys Pro Gly Ala Ser Met
                405                 410                 415

Lys Ile Ser Cys Lys Ala Ser Gly Tyr Ser Phe Thr Gly Tyr Thr Met
            420                 425                 430

Asn Trp Val Lys Gln Ser His Gly Lys Asn Leu Glu Trp Met Gly Leu
        435                 440                 445

Ile Asn Pro Tyr Lys Gly Val Ser Thr Tyr Asn Gln Lys Phe Lys Asp
    450                 455                 460

Lys Ala Thr Leu Thr Val Asp Lys Ser Ser Ser Thr Ala Tyr Met Glu
465                 470                 475                 480

Leu Leu Ser Leu Thr Ser Glu Asp Ser Ala Val Tyr Tyr Cys Ala Arg
                485                 490                 495

Ser Gly Tyr Tyr Gly Asp Ser Asp Trp Tyr Phe Asp Val Trp Gly Ala
            500                 505                 510

Gly Thr Thr Val Thr Val Ser Ser Gly Gly Gly Gly Ser Val Asp Glu
        515                 520                 525

Gln Lys Leu Ile Ser Glu Glu Asp Leu Asn Ala Val Gly Gln Asp Thr
    530                 535                 540

Gln Glu Val Ile Val Val Pro His Ser Leu Pro Phe Lys Val Val Val
545                 550                 555                 560

Ile Ser Ala Ile Leu Ala Leu Val Val Leu Thr Ile Ile Ser Leu Ile
                565                 570                 575

Ile Leu Ile Met Leu Trp Gln Lys Lys Pro Arg
            580                 585
```

<210> SEQ ID NO 16
<211> LENGTH: 1764
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
tatccatatg atgttccaga ttatgctggg gcccagccgg ccagatctga tatccagatg     60

acacagacaa cctcaagtct tagtgcatca ctgggagatc gtgtgactat aagctgccgc    120

gcatcacagg acattcgcaa ttatctgaat tggtatcaac agaagcctga tggcaccgtg    180

aaacttctga tctattacac cagtcgtctg catagcggtg ttccgagcaa attttcaggc    240

tcagggtcag gaaccgatta ttcactgacg attagtaatt tagaacaaga agatattgca    300

acctatttct gtcaacaggg taataccctg ccgtggacct ttgcaggtgg taccaaactg    360

gaaattaaag gaggtggcag tggagggga agcggcggcg gttcaggagg cggttctgag    420

gtccagttac agcagagcgg tccggaactg gttaaaccgg gtgcaagcat gaaaattagc    480

tgtaaagcaa gcggttatag ctttaccggt tataccatga attgggttaa acagagccat    540

ggtaaaaatc tggaatggat gggtctgatt aatccgtata aaggtgttag cacctataat    600

cagaaattta aagataaagc aaccctgacc gttgataaaa gcagcagcac cgcatatatg    660

gaactgctga gcctgaccag cgaagatagc gccgtttact attgcgcacg cagcggttat    720

tatggtgata gcgattggta ttttgatgtt tggggtgcag gtaccaccgt taccgttagc    780

agcggcggtg gcggatcagg cgggggaggc tcaggcggag gtggcagcga catccagatg    840
```

```
acccagtctc catcctccct gtctgcatct gtaggagaca gagtcaccat cacttgccgg    900

gcaagtcagg atgtgaatac cgcggtcgca tggtatcagc agaaaccagg gaaagcccct    960

aagctcctga tctattctgc atccttcttg tatagtgggg tcccatcaag gttcagtggc   1020

agtaggtctg ggacagattt cactctcacc atcagcagtc tgcaacctga agattttgca   1080

acttactact gtcaacagca ttacactacc cctccgacgt tcggccaagg taccaaggtg   1140

gagatcaaac gaactggctc taccagcgga agcggaaagc ctggcagcgg cgagggctcc   1200

gaagtgcagc tggtggagtc tggcggagga ctggtgcagc caggggggcag cctgagactg   1260

tcttgcgccg cctccggctt caacatcaag gacacctaca tccactgggt ccgccaggca   1320

ccaggcaagg gactggaatg ggtggcccgg atctacccta ccaacggcta caccagatac   1380

gccgactccg tgaagggccg gttcaccatc tccgccgaca cctccaagaa caccgcctac   1440

ctgcaaatga actccctgag ggccgaggac accgccgtgt actactgctc cagatgggga   1500

ggcgacggct tctacgcaat ggactactgg ggccagggca ccctggtcac agtgtcctct   1560

gggggtggcg gaagcgtcga cgaacaaaaa ctcatctcag aagaggatct gaatgctgtg   1620

ggccaggaca cgcaggaggt catcgtggtg ccacactcct tgccctttaa ggtggtggtg   1680

atctcagcca tcctggccct ggtggtgctc accatcatct cccttatcat cctcatcatg   1740

ctttggcaga agaagccacg ttag                                          1764
```

```
<210> SEQ ID NO 17
<211> LENGTH: 587
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Tyr Pro Tyr Asp Val Pro Asp Tyr Ala Gly Ala Gln Pro Ala Arg Ser
1               5                   10                  15

Asp Ile Gln Met Thr Gln Thr Thr Ser Ser Leu Ser Ala Ser Leu Gly
            20                  25                  30

Asp Arg Val Thr Ile Ser Cys Arg Ala Ser Gln Asp Ile Arg Asn Tyr
        35                  40                  45

Leu Asn Trp Tyr Gln Gln Lys Pro Asp Gly Thr Val Lys Leu Leu Ile
    50                  55                  60

Tyr Tyr Thr Ser Arg Leu His Ser Gly Val Pro Ser Lys Phe Ser Gly
65                  70                  75                  80

Ser Gly Ser Gly Thr Asp Tyr Ser Leu Thr Ile Ser Asn Leu Glu Gln
                85                  90                  95

Glu Asp Ile Ala Thr Tyr Phe Cys Gln Gln Gly Asn Thr Leu Pro Trp
            100                 105                 110

Thr Phe Ala Gly Gly Thr Lys Leu Glu Ile Lys Gly Gly Gly Ser Gly
        115                 120                 125

Gly Gly Ser Gly Gly Gly Ser Gly Gly Gly Ser Glu Val Gln Leu Gln
    130                 135                 140

Gln Ser Gly Pro Glu Leu Val Lys Pro Gly Ala Ser Met Lys Ile Ser
145                 150                 155                 160

Cys Lys Ala Ser Gly Tyr Ser Phe Thr Gly Tyr Thr Met Asn Trp Val
                165                 170                 175

Lys Gln Ser His Gly Lys Asn Leu Glu Trp Met Gly Leu Ile Asn Pro
            180                 185                 190
```

```
Tyr Lys Gly Val Ser Thr Tyr Asn Gln Lys Phe Lys Asp Lys Ala Thr
        195                 200                 205

Leu Thr Val Asp Lys Ser Ser Ser Thr Ala Tyr Met Glu Leu Leu Ser
    210                 215                 220

Leu Thr Ser Glu Asp Ser Ala Val Tyr Tyr Cys Ala Arg Ser Gly Tyr
225                 230                 235                 240

Tyr Gly Asp Ser Asp Trp Tyr Phe Asp Val Trp Gly Ala Gly Thr Thr
                245                 250                 255

Val Thr Val Ser Ser Gly Gly Gly Gly Ser Gly Gly Gly Gly Ser Gly
            260                 265                 270

Gly Gly Gly Ser Asp Ile Gln Met Thr Gln Ser Pro Ser Ser Leu Ser
        275                 280                 285

Ala Ser Val Gly Asp Arg Val Thr Ile Thr Cys Arg Ala Ser Gln Asp
    290                 295                 300

Val Asn Thr Ala Val Ala Trp Tyr Gln Gln Lys Pro Gly Lys Ala Pro
305                 310                 315                 320

Lys Leu Leu Ile Tyr Ser Ala Ser Phe Leu Tyr Ser Gly Val Pro Ser
                325                 330                 335

Arg Phe Ser Gly Ser Arg Ser Gly Thr Asp Phe Thr Leu Thr Ile Ser
            340                 345                 350

Ser Leu Gln Pro Glu Asp Phe Ala Thr Tyr Tyr Cys Gln Gln His Tyr
        355                 360                 365

Thr Thr Pro Pro Thr Phe Gly Gln Gly Thr Lys Val Glu Ile Lys Arg
    370                 375                 380

Thr Gly Ser Thr Ser Gly Ser Gly Lys Pro Gly Ser Gly Glu Gly Ser
385                 390                 395                 400

Glu Val Gln Leu Val Glu Ser Gly Gly Gly Leu Val Gln Pro Gly Gly
                405                 410                 415

Ser Leu Arg Leu Ser Cys Ala Ala Ser Gly Phe Asn Ile Lys Asp Thr
            420                 425                 430

Tyr Ile His Trp Val Arg Gln Ala Pro Gly Lys Gly Leu Glu Trp Val
        435                 440                 445

Ala Arg Ile Tyr Pro Thr Asn Gly Tyr Thr Arg Tyr Ala Asp Ser Val
    450                 455                 460

Lys Gly Arg Phe Thr Ile Ser Ala Asp Thr Ser Lys Asn Thr Ala Tyr
465                 470                 475                 480

Leu Gln Met Asn Ser Leu Arg Ala Glu Asp Thr Ala Val Tyr Tyr Cys
                485                 490                 495

Ser Arg Trp Gly Gly Asp Gly Phe Tyr Ala Met Asp Tyr Trp Gly Gln
            500                 505                 510

Gly Thr Leu Val Thr Val Ser Ser Gly Gly Gly Gly Ser Val Asp Glu
        515                 520                 525

Gln Lys Leu Ile Ser Glu Glu Asp Leu Asn Ala Val Gly Gln Asp Thr
    530                 535                 540

Gln Glu Val Ile Val Val Pro His Ser Leu Pro Phe Lys Val Val Val
545                 550                 555                 560

Ile Ser Ala Ile Leu Ala Leu Val Val Leu Thr Ile Ile Ser Leu Ile
                565                 570                 575

Ile Leu Ile Met Leu Trp Gln Lys Lys Pro Arg
            580                 585
```

<210> SEQ ID NO 18
<211> LENGTH: 1950

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 18

```
gactacaaag acgatgacga caagggtacc ggaggaagcc aggtgcagct gaagcagtct     60
ggccctggac tggtgcagcc tagccagagc ctgagcatca cctgtaccgt gtccggcttc    120
agcctgacca actacggcgt gcactgggtg cgacagagcc ctggcaaagg cctggaatgg    180
ctgggagtga tttggagcgg cggcaacacc gactacaaca ccccccttcac cagcagactg    240
tccatcaaca aggacaacag caagagccag gtgttcttca agatgaacag cctgcagagc    300
aacgacaccg ccatctacta ctgcgctaga gccctgacct actatgacta cgagttcgcc    360
tactggggcc agggcacact cgtgacagtg tctgccggcg gaggtggatc tggaggcggt    420
ggcagcggtg gaggcggatc tgacatcctg ctgacccaga gccccgtgat cctgtccgtg    480
tctcctggcg agagagtgtc cttcagctgc agagccagcc agagcatcgg caccaacatc    540
cactggtatc agcagaggac caacggcagc cccagactgc tgattaagta cgccagcgag    600
tccatcagcg gcatccccag cagattcagc ggcagcggct ctggcaccga cttcaccctg    660
agcatcaaca gcgtggaaag cgaggatatc gccgactact actgccagca gaacaacaac    720
tggcccacca ccttcggcgc tggcaccaag ctggaactga agggcgggag cttgatagtt    780
aatttgacag attcaaaggg tacttgcctt tatgcagaat gggagatgaa cttcacaata    840
acctacgaaa ctacaaacca aaccaataaa actataacca tagcagtacc ggacaaggcg    900
acacacgatg gaagcagttg tggggacgac cggaatagtg ccaaaataat gatacaattt    960
ggattcgctg tctcttgggc tgtgaacttt accaaagaag catctcatta ttcaattcat   1020
gacatcgtgc tttcctacaa cacttctgat agcacagtat ttcctggtgc tgtagctaaa   1080
ggagttcata ctgttaaaaa tcctgagaac ttcaaagttc cattggacgt gatctttaag   1140
tgcaatagtg ttttaactta caacctgact cctgtcgttc agaagtattg ggtattcac   1200
ctccaggctt ttgtccaaaa tggtacagtg agtaaaaatg aacaagtgtg tgaagaggat   1260
caaactccga ccactgtagc acccatcatt cacaccactg ccccatcgac tacaactaca   1320
ctcactccaa cttcaacacc cactccaacg ccaactccaa caccaaccgt tggaaactac   1380
agcattagaa atggcaatac tacctgtctg ctggctacta tggggttaca actgaacatc   1440
actgaggaga aagtgccttt catttttaac atcaaccctg ccacaaccaa cttcaccgga   1500
agctgtcaac ctcaaagtgc tcaacttagg ctgaacaaca gccaaattaa gtatcttgac   1560
tttatctttg ctgtgaaaaa tgaaaaacgg ttctatctga aggaagtgaa tgtctatatg   1620
tatttggcta atggatcagc tttcaacatt tccaacaaga accttagctt ctgggacgcc   1680
cctctgggaa gttcttatat gtgcaacaaa gagcaggtgc tttctgtgtc gagggcgttt   1740
cagatcaaca cctttaacct aaaggtgcaa ccttttaatg tgacaaaagg acagtattct   1800
acagcagagg aatgcgccgc tgactccgac ctgaacttcc tgatccccgt cgccgtgggc   1860
gtcgccctcg gcttcctcat catcgctgtg ttcatcagct acatgatcgg caggagaaag   1920
agcagaaccg gctaccaaag cgtgtaataa                                    1950
```

<210> SEQ ID NO 19
<211> LENGTH: 648
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Asp Tyr Lys Asp Asp Asp Asp Lys Gly Thr Gly Gly Ser Gln Val Gln
1               5                   10                  15

Leu Lys Gln Ser Gly Pro Gly Leu Val Gln Pro Ser Gln Ser Leu Ser
            20                  25                  30

Ile Thr Cys Thr Val Ser Gly Phe Ser Leu Thr Asn Tyr Gly Val His
        35                  40                  45

Trp Val Arg Gln Ser Pro Gly Lys Gly Leu Glu Trp Leu Gly Val Ile
    50                  55                  60

Trp Ser Gly Gly Asn Thr Asp Tyr Asn Thr Pro Phe Thr Ser Arg Leu
65                  70                  75                  80

Ser Ile Asn Lys Asp Asn Ser Lys Ser Gln Val Phe Phe Lys Met Asn
                85                  90                  95

Ser Leu Gln Ser Asn Asp Thr Ala Ile Tyr Tyr Cys Ala Arg Ala Leu
            100                 105                 110

Thr Tyr Tyr Asp Tyr Glu Phe Ala Tyr Trp Gly Gln Gly Thr Leu Val
        115                 120                 125

Thr Val Ser Ala Gly Gly Gly Gly Ser Gly Gly Gly Gly Ser Gly Gly
    130                 135                 140

Gly Gly Ser Asp Ile Leu Leu Thr Gln Ser Pro Val Ile Leu Ser Val
145                 150                 155                 160

Ser Pro Gly Glu Arg Val Ser Phe Ser Cys Arg Ala Ser Gln Ser Ile
                165                 170                 175

Gly Thr Asn Ile His Trp Tyr Gln Gln Arg Thr Asn Gly Ser Pro Arg
            180                 185                 190

Leu Leu Ile Lys Tyr Ala Ser Glu Ser Ile Ser Gly Ile Pro Ser Arg
        195                 200                 205

Phe Ser Gly Ser Gly Ser Gly Thr Asp Phe Thr Leu Ser Ile Asn Ser
    210                 215                 220

Val Glu Ser Glu Asp Ile Ala Asp Tyr Tyr Cys Gln Gln Asn Asn Asn
225                 230                 235                 240

Trp Pro Thr Thr Phe Gly Ala Gly Thr Lys Leu Glu Leu Lys Gly Gly
                245                 250                 255

Ser Leu Ile Val Asn Leu Thr Asp Ser Lys Gly Thr Cys Leu Tyr Ala
            260                 265                 270

Glu Trp Glu Met Asn Phe Thr Ile Thr Tyr Glu Thr Thr Asn Gln Thr
        275                 280                 285

Asn Lys Thr Ile Thr Ile Ala Val Pro Asp Lys Ala Thr His Asp Gly
    290                 295                 300

Ser Ser Cys Gly Asp Asp Arg Asn Ser Ala Lys Ile Met Ile Gln Phe
305                 310                 315                 320

Gly Phe Ala Val Ser Trp Ala Val Asn Phe Thr Lys Glu Ala Ser His
                325                 330                 335

Tyr Ser Ile His Asp Ile Val Leu Ser Tyr Asn Thr Ser Asp Ser Thr
            340                 345                 350

Val Phe Pro Gly Ala Val Ala Lys Gly Val His Thr Val Lys Asn Pro
        355                 360                 365

Glu Asn Phe Lys Val Pro Leu Asp Val Ile Phe Lys Cys Asn Ser Val
    370                 375                 380

Leu Thr Tyr Asn Leu Thr Pro Val Val Gln Lys Tyr Trp Gly Ile His
```

```
385                 390                 395                 400

Leu Gln Ala Phe Val Gln Asn Gly Thr Val Ser Lys Asn Glu Gln Val
                405                 410                 415

Cys Glu Glu Asp Gln Thr Pro Thr Thr Val Ala Pro Ile Ile His Thr
            420                 425                 430

Thr Ala Pro Ser Thr Thr Thr Thr Leu Thr Pro Thr Ser Thr Pro Thr
        435                 440                 445

Pro Thr Pro Thr Pro Thr Pro Thr Val Gly Asn Tyr Ser Ile Arg Asn
    450                 455                 460

Gly Asn Thr Thr Cys Leu Leu Ala Thr Met Gly Leu Gln Leu Asn Ile
465                 470                 475                 480

Thr Glu Glu Lys Val Pro Phe Ile Phe Asn Ile Asn Pro Ala Thr Thr
                485                 490                 495

Asn Phe Thr Gly Ser Cys Gln Pro Gln Ser Ala Gln Leu Arg Leu Asn
            500                 505                 510

Asn Ser Gln Ile Lys Tyr Leu Asp Phe Ile Phe Ala Val Lys Asn Glu
        515                 520                 525

Lys Arg Phe Tyr Leu Lys Glu Val Asn Val Tyr Met Tyr Leu Ala Asn
    530                 535                 540

Gly Ser Ala Phe Asn Ile Ser Asn Lys Asn Leu Ser Phe Trp Asp Ala
545                 550                 555                 560

Pro Leu Gly Ser Ser Tyr Met Cys Asn Lys Glu Gln Val Leu Ser Val
                565                 570                 575

Ser Arg Ala Phe Gln Ile Asn Thr Phe Asn Leu Lys Val Gln Pro Phe
            580                 585                 590

Asn Val Thr Lys Gly Gln Tyr Ser Thr Ala Glu Glu Cys Ala Ala Asp
        595                 600                 605

Ser Asp Leu Asn Phe Leu Ile Pro Val Ala Val Gly Val Ala Leu Gly
    610                 615                 620

Phe Leu Ile Ile Ala Val Phe Ile Ser Tyr Met Ile Gly Arg Arg Lys
625                 630                 635                 640

Ser Arg Thr Gly Tyr Gln Ser Val
                645
```

<210> SEQ ID NO 20
<211> LENGTH: 1962
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
gactacaaag acgatgacga caagggtacc ggtggcagcg atatccagat gacacagaca      60

acctcaagtc ttagtgcatc actgggagat cgtgtgacta taagctgccg cgcatcacag     120

gacattcgca attatctgaa ttggtatcaa cagaagcctg atggcaccgt gaaacttctg     180

atctattaca ccagtcgtct gcatagcggt gttccgagca aattttcagg ctcagggtca     240

ggaaccgatt attcactgac gattagtaat ttagaacaag aagatattgc aacctatttc     300

tgtcaacagg gtaataccct gccgtggacc tttgcaggtg gtaccaaact ggaaattaaa     360

ggaggtggca gtggaggggg aagcggcggc ggttcaggag gcggttctga ggtccagtta     420

cagcagagcg gtccggaact ggttaaaccg ggtgcaagca tgaaaattag ctgtaaagca     480

agcggttata gctttaccgg ttataccatg aattgggtta aacagagcca tggtaaaaat     540
```

```
ctggaatgga tgggtctgat taatccgtat aaaggtgtta gcacctataa tcagaaattt    600

aaagataaag caaccctgac cgttgataaa agcagcagca ccgcatatat ggaactgctg    660

agcctgacca gcgaagatag cgccgtttac tattgcgcac gcagcggtta ttatggtgat    720

agcgattggt attttgatgt ttggggtgca ggtaccaccg ttaccgttag cagcggcggg    780

agcttgatag ttaatttgac agattcaaag ggtacttgcc tttatgcaga atgggagatg    840

aacttcacaa taacctacga aactacaaac caaaccaata aaactataac catagcagta    900

ccggacaagg cgacacacga tggaagcagt tgtggggacg accggaatag tgccaaaata    960

atgatacaat ttggattcgc tgtctcttgg gctgtgaact ttaccaaaga agcatctcat   1020

tattcaattc atgacatcgt gctttcctac aacacttctg atagcacagt atttcctggt   1080

gctgtagcta aaggagttca tactgttaaa aatcctgaga acttcaaagt tccattggac   1140

gtgatcttta agtgcaatag tgttttaact tacaacctga ctcctgtcgt tcagaagtat   1200

tggggtattc acctccaggc ttttgtccaa aatggtacag tgagtaaaaa tgaacaagtg   1260

tgtgaagagg atcaaactcc gaccactgta gcacccatca ttcacaccac tgccccatcg   1320

actacaacta cactcactcc aacttcaaca cccactccaa cgccaactcc aacaccaacc   1380

gttggaaact acagcattag aaatggcaat actacctgtc tgctggctac tatggggtta   1440

caactgaaca tcactgagga gaaagtgcct ttcattttta acatcaaccc tgccacaacc   1500

aacttcaccg gaagctgtca acctcaaagt gctcaactta ggctgaacaa cagccaaatt   1560

aagtatcttg actttatctt tgctgtgaaa aatgaaaaac ggttctatct gaaggaagtg   1620

aatgtctata tgtatttggc taatggatca gctttcaaca tttccaacaa gaaccttagc   1680

ttctgggacg cccctctggg aagttcttat atgtgcaaca aagagcaggt gctttctgtg   1740

tcgagggcgt ttcagatcaa cacctttaac ctaaaggtgc aaccttttaa tgtgacaaaa   1800

ggacagtatt ctacagcaga ggaatgcgcc gctgactccg acctgaactt cctgatcccc   1860

gtcgccgtgg gcgtcgccct cggcttcctc atcatcgctg tgttcatcag ctacatgatc   1920

ggcaggagaa agagcagaac cggctaccaa agcgtgtaat aa                      1962
```

<210> SEQ ID NO 21
<211> LENGTH: 652
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Asp Tyr Lys Asp Asp Asp Asp Lys Gly Thr Gly Gly Ser Asp Ile Gln
1               5                   10                  15

Met Thr Gln Thr Thr Ser Ser Leu Ser Ala Ser Leu Gly Asp Arg Val
            20                  25                  30

Thr Ile Ser Cys Arg Ala Ser Gln Asp Ile Arg Asn Tyr Leu Asn Trp
        35                  40                  45

Tyr Gln Gln Lys Pro Asp Gly Thr Val Lys Leu Leu Ile Tyr Tyr Thr
    50                  55                  60

Ser Arg Leu His Ser Gly Val Pro Ser Lys Phe Ser Gly Ser Gly Ser
65                  70                  75                  80

Gly Thr Asp Tyr Ser Leu Thr Ile Ser Asn Leu Glu Gln Glu Asp Ile
                85                  90                  95

Ala Thr Tyr Phe Cys Gln Gln Gly Asn Thr Leu Pro Trp Thr Phe Ala
            100                 105                 110
```

```
Gly Gly Thr Lys Leu Glu Ile Lys Gly Gly Gly Ser Gly Gly Gly Ser
        115                 120                 125

Gly Gly Gly Ser Gly Gly Gly Ser Glu Val Gln Leu Gln Gln Ser Gly
    130                 135                 140

Pro Glu Leu Val Lys Pro Gly Ala Ser Met Lys Ile Ser Cys Lys Ala
145                 150                 155                 160

Ser Gly Tyr Ser Phe Thr Gly Tyr Thr Met Asn Trp Val Lys Gln Ser
                165                 170                 175

His Gly Lys Asn Leu Glu Trp Met Gly Leu Ile Asn Pro Tyr Lys Gly
            180                 185                 190

Val Ser Thr Tyr Asn Gln Lys Phe Lys Asp Lys Ala Thr Leu Thr Val
        195                 200                 205

Asp Lys Ser Ser Ser Thr Ala Tyr Met Glu Leu Leu Ser Leu Thr Ser
    210                 215                 220

Glu Asp Ser Ala Val Tyr Tyr Cys Ala Arg Ser Gly Tyr Tyr Gly Asp
225                 230                 235                 240

Ser Asp Trp Tyr Phe Asp Val Trp Gly Ala Gly Thr Thr Val Thr Val
                245                 250                 255

Ser Ser Gly Gly Ser Leu Ile Val Asn Leu Thr Asp Ser Lys Gly Thr
            260                 265                 270

Cys Leu Tyr Ala Glu Trp Glu Met Asn Phe Thr Ile Thr Tyr Glu Thr
        275                 280                 285

Thr Asn Gln Thr Asn Lys Thr Ile Thr Ile Ala Val Pro Asp Lys Ala
    290                 295                 300

Thr His Asp Gly Ser Ser Cys Gly Asp Asp Arg Asn Ser Ala Lys Ile
305                 310                 315                 320

Met Ile Gln Phe Gly Phe Ala Val Ser Trp Ala Val Asn Phe Thr Lys
                325                 330                 335

Glu Ala Ser His Tyr Ser Ile His Asp Ile Val Leu Ser Tyr Asn Thr
            340                 345                 350

Ser Asp Ser Thr Val Phe Pro Gly Ala Val Ala Lys Gly Val His Thr
        355                 360                 365

Val Lys Asn Pro Glu Asn Phe Lys Val Pro Leu Asp Val Ile Phe Lys
    370                 375                 380

Cys Asn Ser Val Leu Thr Tyr Asn Leu Thr Pro Val Val Gln Lys Tyr
385                 390                 395                 400

Trp Gly Ile His Leu Gln Ala Phe Val Gln Asn Gly Thr Val Ser Lys
                405                 410                 415

Asn Glu Gln Val Cys Glu Glu Asp Gln Thr Pro Thr Thr Val Ala Pro
            420                 425                 430

Ile Ile His Thr Thr Ala Pro Ser Thr Thr Thr Thr Leu Thr Pro Thr
        435                 440                 445

Ser Thr Pro Thr Pro Thr Pro Thr Pro Thr Pro Thr Val Gly Asn Tyr
    450                 455                 460

Ser Ile Arg Asn Gly Asn Thr Thr Cys Leu Leu Ala Thr Met Gly Leu
465                 470                 475                 480

Gln Leu Asn Ile Thr Glu Glu Lys Val Pro Phe Ile Phe Asn Ile Asn
                485                 490                 495

Pro Ala Thr Thr Asn Phe Thr Gly Ser Cys Gln Pro Gln Ser Ala Gln
            500                 505                 510

Leu Arg Leu Asn Asn Ser Gln Ile Lys Tyr Leu Asp Phe Ile Phe Ala
        515                 520                 525
```

```
Val Lys Asn Glu Lys Arg Phe Tyr Leu Lys Glu Val Asn Val Tyr Met
    530                 535                 540

Tyr Leu Ala Asn Gly Ser Ala Phe Asn Ile Ser Asn Lys Asn Leu Ser
545                 550                 555                 560

Phe Trp Asp Ala Pro Leu Gly Ser Ser Tyr Met Cys Asn Lys Glu Gln
                565                 570                 575

Val Leu Ser Val Ser Arg Ala Phe Gln Ile Asn Thr Phe Asn Leu Lys
            580                 585                 590

Val Gln Pro Phe Asn Val Thr Lys Gly Gln Tyr Ser Thr Ala Glu Glu
        595                 600                 605

Cys Ala Ala Asp Ser Asp Leu Asn Phe Leu Ile Pro Val Ala Val Gly
    610                 615                 620

Val Ala Leu Gly Phe Leu Ile Ile Ala Val Phe Ile Ser Tyr Met Ile
625                 630                 635                 640

Gly Arg Arg Lys Ser Arg Thr Gly Tyr Gln Ser Val
                645                 650
```

```
<210> SEQ ID NO 22
<211> LENGTH: 2730
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

gactacaaag acgatgacga caagggtacc ggaggaagcc aggtgcagct gaagcagtct     60

ggccctggac tggtgcagcc tagccagagc ctgagcatca cctgtaccgt gtccggcttc    120

agcctgacca actacggcgt gcactgggtg cgacagagcc ctggcaaagg cctggaatgg    180

ctgggagtga tttggagcgg cggcaacacc gactacaaca ccccttcac cagcagactg    240

tccatcaaca aggacaacag caagagccag gtgttcttca agatgaacag cctgcagagc    300

aacgacaccg ccatctacta ctgcgctaga gccctgacct actatgacta cgagttcgcc    360

tactggggcc agggcacact cgtgacagtg tctgccggcg gaggtggatc tggaggcggt    420

ggcagcggtg gaggcggatc tgacatcctg ctgacccaga gccccgtgat cctgtccgtg    480

tctcctggcg agagagtgtc cttcagctgc agagccagcc agagcatcgg caccaacatc    540

cactggtatc agcagaggac caacggcagc cccagactgc tgattaagta cgccagcgag    600

tccatcagcg gcatccccag cagattcagc ggcagcggct ctggcaccga cttcaccctg    660

agcatcaaca gcgtggaaag cgaggatatc gccgactact actgccagca gaacaacaac    720

tggcccacca ccttcggcgc tggcaccaag ctggaactga agggcggtgg cggatcaggc    780

gggggaggct caggcggagg tggcagcgat atccagatga cacagacaac ctcaagtctt    840

agtgcatcac tgggagatcg tgtgactata agctgccgcg catcacagga cattcgcaat    900

tatctgaatt ggtatcaaca gaagcctgat ggcaccgtga aacttctgat ctattacacc    960

agtcgtctgc atagcggtgt tccgagcaaa ttttcaggct cagggtcagg aaccgattat   1020

tcactgacga ttagtaattt agaacaagaa gatattgcaa cctatttctg tcaacagggt   1080

aataccctgc cgtggacctt tgcaggtggt accaaactgg aaattaaagg aggtggcagt   1140

ggagggggaa gcggcggcgg ttcaggaggc ggttctgagg tccagttaca gcagagcggt   1200

ccggaactgg ttaaaccggg tgcaagcatg aaaattagct gtaaagcaag cggttatagc   1260

tttaccggtt ataccatgaa ttgggttaaa cagagccatg gtaaaaatct ggaatggatg   1320
```

ggtctgatta atccgtataa aggtgttagc acctataatc agaaatttaa agataaagca 1380
accctgaccg ttgataaaag cagcagcacc gcatatatgg aactgctgag cctgaccagc 1440
gaagatagcg ccgtttacta ttgcgcacgc agcggttatt atggtgatag cgattggtat 1500
tttgatgttt ggggtgcagg taccaccgtt accgttagca gcggcgggag cttgatagtt 1560
aatttgacag attcaaaggg tacttgcctt tatgcagaat gggagatgaa cttcacaata 1620
acctacgaaa ctacaaacca aaccaataaa actataacca tagcagtacc ggacaaggcg 1680
acacacgatg gaagcagttg tggggacgac cggaatagtg ccaaaataat gatacaattt 1740
ggattcgctg tctcttgggc tgtgaacttt accaaagaag catctcatta ttcaattcat 1800
gacatcgtgc tttcctacaa cacttctgat agcacagtat ttcctggtgc tgtagctaaa 1860
ggagttcata ctgttaaaaa tcctgagaac ttcaaagttc cattggacgt gatctttaag 1920
tgcaatagtg ttttaactta caacctgact cctgtcgttc agaagtattg ggtattcac 1980 ctccaggctt ttgtccaaaa tggtacagtg agtaaaaatg aacaagtgtg tgaagaggat 2040
caaactccga ccactgtagc acccatcatt cacaccactg ccccatcgac tacaactaca 2100
ctcactccaa cttcaacacc cactccaacg ccaactccaa caccaaccgt tggaaactac 2160
agcattagaa atggcaatac tacctgtctg ctggctacta tggggttaca actgaacatc 2220
actgaggaga aagtgccttt catttttaac atcaaccctg ccacaaccaa cttcaccgga 2280
agctgtcaac ctcaaagtgc tcaacttagg ctgaacaaca gccaaattaa gtatcttgac 2340
tttatctttg ctgtgaaaaa tgaaaaacgg ttctatctga aggaagtgaa tgtctatatg 2400
tatttggcta atggatcagc tttcaacatt tccaacaaga accttagctt ctgggacgcc 2460
cctctgggaa gttcttatat gtgcaacaaa gagcaggtgc tttctgtgtc gagggcgttt 2520
cagatcaaca cctttaacct aaaggtgcaa ccttttaatg tgacaaaagg acagtattct 2580
acagcagagg aatgcgccgc tgactccgac ctgaacttcc tgatccccgt cgccgtgggc 2640
gtcgccctcg gcttcctcat catcgctgtg ttcatcagct acatgatcgg caggagaaag 2700
agcagaaccg gctaccaaag cgtgtaataa 2730

<210> SEQ ID NO 23
<211> LENGTH: 908
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Asp Tyr Lys Asp Asp Asp Asp Lys Gly Thr Gly Gly Ser Gln Val Gln
1               5                   10                  15

Leu Lys Gln Ser Gly Pro Gly Leu Val Gln Pro Ser Gln Ser Leu Ser
            20                  25                  30

Ile Thr Cys Thr Val Ser Gly Phe Ser Leu Thr Asn Tyr Gly Val His
        35                  40                  45

Trp Val Arg Gln Ser Pro Gly Lys Gly Leu Glu Trp Leu Gly Val Ile
    50                  55                  60

Trp Ser Gly Gly Asn Thr Asp Tyr Asn Thr Pro Phe Thr Ser Arg Leu
65                  70                  75                  80

Ser Ile Asn Lys Asp Asn Ser Lys Ser Gln Val Phe Phe Lys Met Asn
                85                  90                  95

Ser Leu Gln Ser Asn Asp Thr Ala Ile Tyr Tyr Cys Ala Arg Ala Leu
            100                 105                 110
```

```
Thr Tyr Tyr Asp Tyr Glu Phe Ala Tyr Trp Gly Gln Gly Thr Leu Val
        115                 120                 125

Thr Val Ser Ala Gly Gly Gly Gly Ser Gly Gly Gly Gly Ser Gly Gly
    130                 135                 140

Gly Gly Ser Asp Ile Leu Leu Thr Gln Ser Pro Val Ile Leu Ser Val
145                 150                 155                 160

Ser Pro Gly Glu Arg Val Ser Phe Ser Cys Arg Ala Ser Gln Ser Ile
                165                 170                 175

Gly Thr Asn Ile His Trp Tyr Gln Gln Arg Thr Asn Gly Ser Pro Arg
            180                 185                 190

Leu Leu Ile Lys Tyr Ala Ser Glu Ser Ile Ser Gly Ile Pro Ser Arg
        195                 200                 205

Phe Ser Gly Ser Gly Ser Gly Thr Asp Phe Thr Leu Ser Ile Asn Ser
    210                 215                 220

Val Glu Ser Glu Asp Ile Ala Asp Tyr Tyr Cys Gln Gln Asn Asn Asn
225                 230                 235                 240

Trp Pro Thr Thr Phe Gly Ala Gly Thr Lys Leu Glu Leu Lys Gly Gly
                245                 250                 255

Gly Gly Ser Gly Gly Gly Gly Ser Gly Gly Gly Gly Ser Asp Ile Gln
            260                 265                 270

Met Thr Gln Thr Thr Ser Ser Leu Ser Ala Ser Leu Gly Asp Arg Val
        275                 280                 285

Thr Ile Ser Cys Arg Ala Ser Gln Asp Ile Arg Asn Tyr Leu Asn Trp
    290                 295                 300

Tyr Gln Gln Lys Pro Asp Gly Thr Val Lys Leu Leu Ile Tyr Tyr Thr
305                 310                 315                 320

Ser Arg Leu His Ser Gly Val Pro Ser Lys Phe Ser Gly Ser Gly Ser
                325                 330                 335

Gly Thr Asp Tyr Ser Leu Thr Ile Ser Asn Leu Glu Gln Glu Asp Ile
            340                 345                 350

Ala Thr Tyr Phe Cys Gln Gln Gly Asn Thr Leu Pro Trp Thr Phe Ala
        355                 360                 365

Gly Gly Thr Lys Leu Glu Ile Lys Gly Gly Gly Ser Gly Gly Gly Ser
    370                 375                 380

Gly Gly Gly Ser Gly Gly Gly Ser Glu Val Gln Leu Gln Gln Ser Gly
385                 390                 395                 400

Pro Glu Leu Val Lys Pro Gly Ala Ser Met Lys Ile Ser Cys Lys Ala
                405                 410                 415

Ser Gly Tyr Ser Phe Thr Gly Tyr Thr Met Asn Trp Val Lys Gln Ser
            420                 425                 430

His Gly Lys Asn Leu Glu Trp Met Gly Leu Ile Asn Pro Tyr Lys Gly
        435                 440                 445

Val Ser Thr Tyr Asn Gln Lys Phe Lys Asp Lys Ala Thr Leu Thr Val
    450                 455                 460

Asp Lys Ser Ser Ser Thr Ala Tyr Met Glu Leu Leu Ser Leu Thr Ser
465                 470                 475                 480

Glu Asp Ser Ala Val Tyr Tyr Cys Ala Arg Ser Gly Tyr Tyr Gly Asp
                485                 490                 495

Ser Asp Trp Tyr Phe Asp Val Trp Gly Ala Gly Thr Thr Val Thr Val
            500                 505                 510

Ser Ser Gly Gly Ser Leu Ile Val Asn Leu Thr Asp Ser Lys Gly Thr
        515                 520                 525
```

```
Cys Leu Tyr Ala Glu Trp Glu Met Asn Phe Thr Ile Thr Tyr Glu Thr
    530                 535                 540

Thr Asn Gln Thr Asn Lys Thr Ile Thr Ile Ala Val Pro Asp Lys Ala
545                 550                 555                 560

Thr His Asp Gly Ser Ser Cys Gly Asp Asp Arg Asn Ser Ala Lys Ile
                565                 570                 575

Met Ile Gln Phe Gly Phe Ala Val Ser Trp Ala Val Asn Phe Thr Lys
            580                 585                 590

Glu Ala Ser His Tyr Ser Ile His Asp Ile Val Leu Ser Tyr Asn Thr
        595                 600                 605

Ser Asp Ser Thr Val Phe Pro Gly Ala Val Ala Lys Gly Val His Thr
    610                 615                 620

Val Lys Asn Pro Glu Asn Phe Lys Val Pro Leu Asp Val Ile Phe Lys
625                 630                 635                 640

Cys Asn Ser Val Leu Thr Tyr Asn Leu Thr Pro Val Val Gln Lys Tyr
                645                 650                 655

Trp Gly Ile His Leu Gln Ala Phe Val Gln Asn Gly Thr Val Ser Lys
            660                 665                 670

Asn Glu Gln Val Cys Glu Glu Asp Gln Thr Pro Thr Thr Val Ala Pro
        675                 680                 685

Ile Ile His Thr Thr Ala Pro Ser Thr Thr Thr Thr Leu Thr Pro Thr
    690                 695                 700

Ser Thr Pro Thr Pro Thr Pro Thr Pro Thr Pro Thr Val Gly Asn Tyr
705                 710                 715                 720

Ser Ile Arg Asn Gly Asn Thr Thr Cys Leu Leu Ala Thr Met Gly Leu
                725                 730                 735

Gln Leu Asn Ile Thr Glu Glu Lys Val Pro Phe Ile Phe Asn Ile Asn
            740                 745                 750

Pro Ala Thr Thr Asn Phe Thr Gly Ser Cys Gln Pro Gln Ser Ala Gln
        755                 760                 765

Leu Arg Leu Asn Asn Ser Gln Ile Lys Tyr Leu Asp Phe Ile Phe Ala
    770                 775                 780

Val Lys Asn Glu Lys Arg Phe Tyr Leu Lys Glu Val Asn Val Tyr Met
785                 790                 795                 800

Tyr Leu Ala Asn Gly Ser Ala Phe Asn Ile Ser Asn Lys Asn Leu Ser
                805                 810                 815

Phe Trp Asp Ala Pro Leu Gly Ser Ser Tyr Met Cys Asn Lys Glu Gln
            820                 825                 830

Val Leu Ser Val Ser Arg Ala Phe Gln Ile Asn Thr Phe Asn Leu Lys
        835                 840                 845

Val Gln Pro Phe Asn Val Thr Lys Gly Gln Tyr Ser Thr Ala Glu Glu
    850                 855                 860

Cys Ala Ala Asp Ser Asp Leu Asn Phe Leu Ile Pro Val Ala Val Gly
865                 870                 875                 880

Val Ala Leu Gly Phe Leu Ile Ile Ala Val Phe Ile Ser Tyr Met Ile
                885                 890                 895

Gly Arg Arg Lys Ser Arg Thr Gly Tyr Gln Ser Val
            900                 905
```

<210> SEQ ID NO 24
<211> LENGTH: 2730
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
gactacaaag acgatgacga caagggtacc ggtggcagcg atatccagat gacacagaca     60
acctcaagtc ttagtgcatc actgggagat cgtgtgacta taagctgccg cgcatcacag    120
gacattcgca attatctgaa ttggtatcaa cagaagcctg atggcaccgt gaaacttctg    180
atctattaca ccagtcgtct gcatagcggt gttccgagca aattttcagg ctcagggtca    240
ggaaccgatt attcactgac gattagtaat ttagaacaag aagatattgc aacctatttc    300
tgtcaacagg gtaataccct gccgtggacc tttgcaggtg gtaccaaact ggaaattaaa    360
ggaggtggca gtggaggggg aagcggcggc ggttcaggag gcggttctga ggtccagtta    420
cagcagagcg gtccggaact ggttaaaccg ggtgcaagca tgaaaattag ctgtaaagca    480
agcggttata gctttaccgg ttataccatg aattgggtta aacagagcca tggtaaaaat    540
ctggaatgga tgggtctgat taatccgtat aaaggtgtta gcacctataa tcagaaattt    600
aaagataaag caaccctgac cgttgataaa agcagcagca ccgcatatat ggaactgctg    660
agcctgacca gcgaagatag cgccgtttac tattgcgcac gcagcggtta ttatggtgat    720
agcgattggt attttgatgt ttggggtgca ggtaccaccg ttaccgttag cagcggaggt    780
ggcggaagtg gaggaggtgg ctctggcggt ggaggaagcc aggtgcagct gaagcagtct    840
ggccctggac tggtgcagcc tagccagagc ctgagcatca cctgtaccgt gtccggcttc    900
agcctgacca actacggcgt gcactgggtg cgacagagcc ctggcaaagg cctggaatgg    960
ctgggagtga tttggagcgg cggcaacacc gactacaaca ccccccttcac cagcagactg   1020
tccatcaaca aggacaacag caagagccag gtgttcttca agatgaacag cctgcagagc   1080
aacgacaccg ccatctacta ctgcgctaga gccctgacct actatgacta cgagttcgcc   1140
tactggggcc agggcacact cgtgacagtg tctgccggcg gaggtggatc tggaggcggt   1200
ggcagcggtg gaggcggatc tgacatcctg ctgacccaga gccccgtgat cctgtccgtg   1260
tctcctggcg agagagtgtc cttcagctgc agagccagcc agagcatcgg caccaacatc   1320
cactggtatc agcagaggac caacggcagc cccagactgc tgattaagta cgccagcgag   1380
tccatcagcg gcatccccag cagattcagc ggcagcggct ctggcaccga cttcaccctg   1440
agcatcaaca gcgtggaaag cgaggatatc gccgactact actgccagca gaacaacaac   1500
tggcccacca ccttcggcgc tggcaccaag ctggaactga agggcgggag cttgatagtt   1560
aatttgacag attcaaaggg tacttgcctt tatgcagaat gggagatgaa cttcacaata   1620
acctacgaaa ctacaaacca aaccaataaa actataacca tagcagtacc ggacaaggcg   1680
acacacgatg gaagcagttg tggggacgac cggaatagtg ccaaaataat gatacaattt   1740
ggattcgctg tctcttgggc tgtgaacttt accaaagaag catctcatta ttcaattcat   1800
gacatcgtgc tttcctacaa cacttctgat agcacagtat ttcctggtgc tgtagctaaa   1860
ggagttcata ctgttaaaaa tcctgagaac ttcaaagttc cattggacgt gatctttaag   1920
tgcaatagtg ttttaactta caacctgact cctgtcgttc agaagtattg ggtattcac    1980
ctccaggctt ttgtccaaaa tggtacagtg agtaaaaatg aacaagtgtg tgaagaggat   2040
caaactccga ccactgtagc acccatcatt cacaccactg ccccatcgac tacaactaca   2100
ctcactccaa cttcaacacc cactccaacg ccaactccaa caccaaccgt tggaaactac   2160
agcattagaa atggcaatac tacctgtctg ctggctacta tggggttaca actgaacatc   2220
actgaggaga aagtgccttt catttttaac atcaaccctg ccacaaccaa cttcaccgga   2280
```

```
agctgtcaac ctcaaagtgc tcaacttagg ctgaacaaca gccaaattaa gtatcttgac   2340

tttatctttg ctgtgaaaaa tgaaaaacgg ttctatctga aggaagtgaa tgtctatatg   2400

tatttggcta atggatcagc tttcaacatt tccaacaaga accttagctt ctgggacgcc   2460

cctctgggaa gttcttatat gtgcaacaaa gagcaggtgc tttctgtgtc gagggcgttt   2520

cagatcaaca cctttaacct aaaggtgcaa ccttttaatg tgacaaaagg acagtattct   2580

acagcagagg aatgcgccgc tgactccgac ctgaacttcc tgatccccgt cgccgtgggc   2640

gtcgccctcg gcttcctcat catcgctgtg ttcatcagct acatgatcgg caggagaaag   2700

agcagaaccg gctaccaaag cgtgtaataa                                     2730
```

```
<210> SEQ ID NO 25
<211> LENGTH: 908
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Tyr Lys Asp Asp Asp Asp Lys Gly Thr Gly Gly Ser Asp Ile Gln
1               5                   10                  15

Met Thr Gln Thr Thr Ser Ser Leu Ser Ala Ser Leu Gly Asp Arg Val
            20                  25                  30

Thr Ile Ser Cys Arg Ala Ser Gln Asp Ile Arg Asn Tyr Leu Asn Trp
        35                  40                  45

Tyr Gln Gln Lys Pro Asp Gly Thr Val Lys Leu Leu Ile Tyr Tyr Thr
    50                  55                  60

Ser Arg Leu His Ser Gly Val Pro Ser Lys Phe Ser Gly Ser Gly Ser
65                  70                  75                  80

Gly Thr Asp Tyr Ser Leu Thr Ile Ser Asn Leu Glu Gln Glu Asp Ile
                85                  90                  95

Ala Thr Tyr Phe Cys Gln Gln Gly Asn Thr Leu Pro Trp Thr Phe Ala
            100                 105                 110

Gly Gly Thr Lys Leu Glu Ile Lys Gly Gly Gly Ser Gly Gly Gly Ser
        115                 120                 125

Gly Gly Gly Ser Gly Gly Gly Ser Glu Val Gln Leu Gln Gln Ser Gly
    130                 135                 140

Pro Glu Leu Val Lys Pro Gly Ala Ser Met Lys Ile Ser Cys Lys Ala
145                 150                 155                 160

Ser Gly Tyr Ser Phe Thr Gly Tyr Thr Met Asn Trp Val Lys Gln Ser
                165                 170                 175

His Gly Lys Asn Leu Glu Trp Met Gly Leu Ile Asn Pro Tyr Lys Gly
            180                 185                 190

Val Ser Thr Tyr Asn Gln Lys Phe Lys Asp Lys Ala Thr Leu Thr Val
        195                 200                 205

Asp Lys Ser Ser Ser Thr Ala Tyr Met Glu Leu Leu Ser Leu Thr Ser
    210                 215                 220

Glu Asp Ser Ala Val Tyr Tyr Cys Ala Arg Ser Gly Tyr Tyr Gly Asp
225                 230                 235                 240

Ser Asp Trp Tyr Phe Asp Val Trp Gly Ala Gly Thr Thr Val Thr Val
                245                 250                 255

Ser Ser Gly Gly Gly Gly Ser Gly Gly Gly Gly Ser Gly Gly Gly Gly
            260                 265                 270
```

```
Ser Gln Val Gln Leu Lys Gln Ser Gly Pro Gly Leu Val Gln Pro Ser
        275                 280                 285

Gln Ser Leu Ser Ile Thr Cys Thr Val Ser Gly Phe Ser Leu Thr Asn
    290                 295                 300

Tyr Gly Val His Trp Val Arg Gln Ser Pro Gly Lys Gly Leu Glu Trp
305                 310                 315                 320

Leu Gly Val Ile Trp Ser Gly Gly Asn Thr Asp Tyr Asn Thr Pro Phe
                325                 330                 335

Thr Ser Arg Leu Ser Ile Asn Lys Asp Asn Ser Lys Ser Gln Val Phe
            340                 345                 350

Phe Lys Met Asn Ser Leu Gln Ser Asn Asp Thr Ala Ile Tyr Tyr Cys
        355                 360                 365

Ala Arg Ala Leu Thr Tyr Tyr Asp Tyr Glu Phe Ala Tyr Trp Gly Gln
    370                 375                 380

Gly Thr Leu Val Thr Val Ser Ala Gly Gly Gly Gly Ser Gly Gly Gly
385                 390                 395                 400

Gly Ser Gly Gly Gly Gly Ser Asp Ile Leu Leu Thr Gln Ser Pro Val
                405                 410                 415

Ile Leu Ser Val Ser Pro Gly Glu Arg Val Ser Phe Ser Cys Arg Ala
            420                 425                 430

Ser Gln Ser Ile Gly Thr Asn Ile His Trp Tyr Gln Gln Arg Thr Asn
        435                 440                 445

Gly Ser Pro Arg Leu Leu Ile Lys Tyr Ala Ser Glu Ser Ile Ser Gly
    450                 455                 460

Ile Pro Ser Arg Phe Ser Gly Ser Gly Ser Gly Thr Asp Phe Thr Leu
465                 470                 475                 480

Ser Ile Asn Ser Val Glu Ser Glu Asp Ile Ala Asp Tyr Tyr Cys Gln
                485                 490                 495

Gln Asn Asn Asn Trp Pro Thr Thr Phe Gly Ala Gly Thr Lys Leu Glu
            500                 505                 510

Leu Lys Gly Gly Ser Leu Ile Val Asn Leu Thr Asp Ser Lys Gly Thr
        515                 520                 525

Cys Leu Tyr Ala Glu Trp Glu Met Asn Phe Thr Ile Thr Tyr Glu Thr
    530                 535                 540

Thr Asn Gln Thr Asn Lys Thr Ile Thr Ile Ala Val Pro Asp Lys Ala
545                 550                 555                 560

Thr His Asp Gly Ser Ser Cys Gly Asp Asp Arg Asn Ser Ala Lys Ile
                565                 570                 575

Met Ile Gln Phe Gly Phe Ala Val Ser Trp Ala Val Asn Phe Thr Lys
            580                 585                 590

Glu Ala Ser His Tyr Ser Ile His Asp Ile Val Leu Ser Tyr Asn Thr
        595                 600                 605

Ser Asp Ser Thr Val Phe Pro Gly Ala Val Ala Lys Gly Val His Thr
    610                 615                 620

Val Lys Asn Pro Glu Asn Phe Lys Val Pro Leu Asp Val Ile Phe Lys
625                 630                 635                 640

Cys Asn Ser Val Leu Thr Tyr Asn Leu Thr Pro Val Val Gln Lys Tyr
                645                 650                 655

Trp Gly Ile His Leu Gln Ala Phe Val Gln Asn Gly Thr Val Ser Lys
            660                 665                 670

Asn Glu Gln Val Cys Glu Glu Asp Gln Thr Pro Thr Thr Val Ala Pro
        675                 680                 685

Ile Ile His Thr Thr Ala Pro Ser Thr Thr Thr Thr Leu Thr Pro Thr
```

```
    690                 695                 700

Ser Thr Pro Thr Pro Thr Pro Thr Pro Thr Pro Thr Val Gly Asn Tyr
705                 710                 715                 720

Ser Ile Arg Asn Gly Asn Thr Thr Cys Leu Leu Ala Thr Met Gly Leu
                725                 730                 735

Gln Leu Asn Ile Thr Glu Glu Lys Val Pro Phe Ile Phe Asn Ile Asn
            740                 745                 750

Pro Ala Thr Thr Asn Phe Thr Gly Ser Cys Gln Pro Gln Ser Ala Gln
        755                 760                 765

Leu Arg Leu Asn Asn Ser Gln Ile Lys Tyr Leu Asp Phe Ile Phe Ala
    770                 775                 780

Val Lys Asn Glu Lys Arg Phe Tyr Leu Lys Glu Val Asn Val Tyr Met
785                 790                 795                 800

Tyr Leu Ala Asn Gly Ser Ala Phe Asn Ile Ser Asn Lys Asn Leu Ser
                805                 810                 815

Phe Trp Asp Ala Pro Leu Gly Ser Ser Tyr Met Cys Asn Lys Glu Gln
            820                 825                 830

Val Leu Ser Val Ser Arg Ala Phe Gln Ile Asn Thr Phe Asn Leu Lys
        835                 840                 845

Val Gln Pro Phe Asn Val Thr Lys Gly Gln Tyr Ser Thr Ala Glu Glu
    850                 855                 860

Cys Ala Ala Asp Ser Asp Leu Asn Phe Leu Ile Pro Val Ala Val Gly
865                 870                 875                 880

Val Ala Leu Gly Phe Leu Ile Ile Ala Val Phe Ile Ser Tyr Met Ile
                885                 890                 895

Gly Arg Arg Lys Ser Arg Thr Gly Tyr Gln Ser Val
            900                 905
```

```
<210> SEQ ID NO 26
<211> LENGTH: 975
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

tatccatatg atgttccaga ttatgctggg gcccagccgg ccagatctca ggtgcagctg      60

aagcagtctg gccctggact ggtgcagcct agccagagcc tgagcatcac ctgtaccgtg     120

tccggcttca gcctgaccaa ctacggcgtg cactgggtgc gacagagccc tggcaaaggc     180

ctggaatggc tgggagtgat ttggagcggc ggcaacaccg actacaacac cccctcacc      240

agcagactgt ccatcaacaa ggacaacagc aagagccagg tgttcttcaa gatgaacagc     300

ctgcagagca acgacaccgc catctactac tgcgctagag ccctgaccta ctatgactac     360

gagttcgcct actggggcca gggcacactc gtgacagtgt ctgccggcgg aggtggatct     420

ggaggcggtg gcagcggtgg aggcggatct gacatcctgc tgacccagag ccccgtgatc     480

ctgtccgtgt ctcctggcga gagagtgtcc ttcagctgca gagccagcca gagcatcggc     540

accaacatcc actggtatca gcagaggacc aacggcagcc ccagactgct gattaagtac     600

gccagcgagt ccatcagcgg catccccagc agattcagcg gcagcggctc tggcaccgac     660

ttcaccctga gcatcaacag cgtggaaagc gaggatatcg ccgactacta ctgccagcag     720

aacaacaact ggcccaccac cttcggcgct ggcaccaagc tggaactgaa gggcgggggc     780

ggaagcgtcg acgaacaaaa actcatctca gaagaggatc tgaatgctgt gggccaggac     840
```

acgcaggagg tcatcgtggt gccacactcc ttgcccttta aggtggtggt gatctcagcc 900
atcctggccc tggtggtgct caccatcatc tcccttatca tcctcatcat gctttggcag 960
aagaagccac gttag 975

<210> SEQ ID NO 27
<211> LENGTH: 324
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

Tyr Pro Tyr Asp Val Pro Asp Tyr Ala Gly Ala Gln Pro Ala Arg Ser
1 5 10 15

Gln Val Gln Leu Lys Gln Ser Gly Pro Gly Leu Val Gln Pro Ser Gln
20 25 30

Ser Leu Ser Ile Thr Cys Thr Val Ser Gly Phe Ser Leu Thr Asn Tyr
35 40 45

Gly Val His Trp Val Arg Gln Ser Pro Gly Lys Gly Leu Glu Trp Leu
50 55 60

Gly Val Ile Trp Ser Gly Gly Asn Thr Asp Tyr Asn Thr Pro Phe Thr
65 70 75 80

Ser Arg Leu Ser Ile Asn Lys Asp Asn Ser Lys Ser Gln Val Phe Phe
85 90 95

Lys Met Asn Ser Leu Gln Ser Asn Asp Thr Ala Ile Tyr Tyr Cys Ala
100 105 110

Arg Ala Leu Thr Tyr Tyr Asp Tyr Glu Phe Ala Tyr Trp Gly Gln Gly
115 120 125

Thr Leu Val Thr Val Ser Ala Gly Gly Gly Gly Ser Gly Gly Gly Gly
130 135 140

Ser Gly Gly Gly Gly Ser Asp Ile Leu Leu Thr Gln Ser Pro Val Ile
145 150 155 160

Leu Ser Val Ser Pro Gly Glu Arg Val Ser Phe Ser Cys Arg Ala Ser
165 170 175

Gln Ser Ile Gly Thr Asn Ile His Trp Tyr Gln Gln Arg Thr Asn Gly
180 185 190

Ser Pro Arg Leu Leu Ile Lys Tyr Ala Ser Glu Ser Ile Ser Gly Ile
195 200 205

Pro Ser Arg Phe Ser Gly Ser Gly Ser Gly Thr Asp Phe Thr Leu Ser
210 215 220

Ile Asn Ser Val Glu Ser Glu Asp Ile Ala Asp Tyr Tyr Cys Gln Gln
225 230 235 240

Asn Asn Asn Trp Pro Thr Thr Phe Gly Ala Gly Thr Lys Leu Glu Leu
245 250 255

Lys Gly Gly Gly Gly Ser Val Asp Glu Gln Lys Leu Ile Ser Glu Glu
260 265 270

Asp Leu Asn Ala Val Gly Gln Asp Thr Gln Glu Val Ile Val Val Pro
275 280 285

His Ser Leu Pro Phe Lys Val Val Val Ile Ser Ala Ile Leu Ala Leu
290 295 300

Val Val Leu Thr Ile Ile Ser Leu Ile Ile Leu Ile Met Leu Trp Gln
305 310 315 320

Lys Lys Pro Arg

<210> SEQ ID NO 28
<211> LENGTH: 987
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28
tatccatatg atgttccaga ttatgctggg gcccagccgg ccagatctga tatccagatg 60
acacagacaa cctcaagtct tagtgcatca ctgggagatc gtgtgactat aagctgccgc 120
gcatcacagg acattcgcaa ttatctgaat tggtatcaac agaagcctga tggcaccgtg 180
aaacttctga tctattacac cagtcgtctg catagcggtg ttccgagcaa attttcaggc 240
tcagggtcag gaaccgatta ttcactgacg attagtaatt tagaacaaga agatattgca 300
acctatttct gtcaacaggg taataccctg ccgtggacct ttgcaggtgg taccaaactg 360
gaaattaaag gaggtggcag tggaggggga agcggcggcg gttcaggagg cggttctgag 420
gtccagttac agcagagcgg tccggaactg gttaaaccgg gtgcaagcat gaaaattagc 480
tgtaaagcaa gcggttatag ctttaccggt tataccatga attgggttaa acagagccat 540
ggtaaaaatc tggaatggat gggtctgatt aatccgtata aaggtgttag cacctataat 600
cagaaattta aagataaagc aaccctgacc gttgataaaa gcagcagcac cgcatatatg 660
gaactgctga gcctgaccag cgaagatagc gccgtttact attgcgcacg cagcggttat 720
tatggtgata gcgattggta ttttgatgtt tggggtgcag gtaccaccgt taccgttagc 780
agcggcgggg gcggaagcgt cgacgaacaa aaactcatct cagaagagga tctgaatgct 840
gtgggccagg acacgcagga ggtcatcgtg gtgccacact ccttgccctt taaggtggtg 900
gtgatctcag ccatcctggc cctggtggtg ctcaccatca tctcccttat catcctcatc 960
atgctttggc agaagaagcc acgttag 987

<210> SEQ ID NO 29
<211> LENGTH: 1755
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29
tatccatatg atgttccaga ttatgctggg gcccagccgg ccagatctca ggtgcagctg 60
aagcagtctg gccctggact ggtgcagcct agccagagcc tgagcatcac ctgtaccgtg 120
tccggcttca gcctgaccaa ctacggcgtg cactgggtgc gacagagccc tggcaaaggc 180
ctggaatggc tgggagtgat ttggagcggc ggcaacaccg actacaacac ccccttcacc 240
agcagactgt ccatcaacaa ggacaacagc aagagccagg tgttcttcaa gatgaacagc 300
ctgcagagca acgacaccgc catctactac tgcgctagag ccctgaccta ctatgactac 360
gagttcgcct actggggcca gggcacactc gtgacagtgt ctgccggcgg aggtggatct 420
ggaggcggtg gcagcggtgg aggcggatct gacatcctgc tgacccagag ccccgtgatc 480
ctgtccgtgt ctcctggcga gagagtgtcc ttcagctgca gagccagcca gagcatcggc 540
accaacatcc actggtatca gcagaggacc aacggcagcc ccagactgct gattaagtac 600
gccagcgagt ccatcagcgg catccccagc agattcagcg gcagcggctc tggcaccgac 660
ttcaccctga gcatcaacag cgtggaaagc gaggatatcg ccgactacta ctgccagcag 720
aacaacaact ggcccaccac cttcggcgct ggcaccaagc tggaactgaa gggcggtggc 780
ggatcaggcg gggaggctc aggcggaggt ggcagcgata tccagatgac acagacaacc 840
tcaagtctta gtgcatcact gggagatcgt gtgactataa gctgccgcgc atcacaggac 900
attcgcaatt atctgaattg gtatcaacag aagcctgatg gcaccgtgaa acttctgatc 960
tattacacca gtcgtctgca tagcggtgtt ccgagcaaat tttcaggctc agggtcagga 1020
accgattatt cactgacgat tagtaattta gaacaagaag atattgcaac ctatttctgt 1080
caacagggta ataccctgcc gtggaccttt gcaggtggta ccaaactgga aattaaagga 1140
ggtggcagtg gaggggggaag cggcggcggt tcaggaggcg gttctgaggt ccagttacag 1200
cagagcggtc cggaactggt taaaccgggt gcaagcatga aaattagctg taaagcaagc 1260
ggttatagct ttaccggtta taccatgaat tgggttaaac agagccatgg taaaaatctg 1320
gaatggatgg gtctgattaa tccgtataaa ggtgttagca cctataatca gaaatttaaa 1380
gataaagcaa ccctgaccgt tgataaaagc agcagcaccg catatatgga actgctgagc 1440
ctgaccagcg aagatagcgc cgtttactat tgcgcacgca gcggttatta tggtgatagc 1500
gattggtatt ttgatgtttg gggtgcaggt accaccgtta ccgttagcag cggcgggggc 1560
ggaagcgtcg acgaacaaaa actcatctca gaagaggatc tgaatgctgt gggccaggac 1620
acgcaggagg tcatcgtggt gccacactcc ttgcccttta aggtggtggt gatctcagcc 1680
atcctggccc tggtggtgct caccatcatc tcccttatca tcctcatcat gctttggcag 1740
aagaagccac gttag 1755

<210> SEQ ID NO 30
<211> LENGTH: 584
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Tyr Pro Tyr Asp Val Pro Asp Tyr Ala Gly Ala Gln Pro Ala Arg Ser
1 5 10 15

Gln Val Gln Leu Lys Gln Ser Gly Pro Gly Leu Val Gln Pro Ser Gln
20 25 30

Ser Leu Ser Ile Thr Cys Thr Val Ser Gly Phe Ser Leu Thr Asn Tyr
35 40 45

Gly Val His Trp Val Arg Gln Ser Pro Gly Lys Gly Leu Glu Trp Leu
50 55 60

Gly Val Ile Trp Ser Gly Gly Asn Thr Asp Tyr Asn Thr Pro Phe Thr
65 70 75 80

Ser Arg Leu Ser Ile Asn Lys Asp Asn Ser Lys Ser Gln Val Phe Phe
85 90 95

Lys Met Asn Ser Leu Gln Ser Asn Asp Thr Ala Ile Tyr Tyr Cys Ala
100 105 110

Arg Ala Leu Thr Tyr Tyr Asp Tyr Glu Phe Ala Tyr Trp Gly Gln Gly
115 120 125

Thr Leu Val Thr Val Ser Ala Gly Gly Gly Gly Ser Gly Gly Gly Gly
130 135 140

Ser Gly Gly Gly Gly Ser Asp Ile Leu Leu Thr Gln Ser Pro Val Ile
145 150 155 160

```
Leu Ser Val Ser Pro Gly Glu Arg Val Ser Phe Ser Cys Arg Ala Ser
                165                 170                 175

Gln Ser Ile Gly Thr Asn Ile His Trp Tyr Gln Gln Arg Thr Asn Gly
            180                 185                 190

Ser Pro Arg Leu Leu Ile Lys Tyr Ala Ser Glu Ser Ile Ser Gly Ile
        195                 200                 205

Pro Ser Arg Phe Ser Gly Ser Gly Ser Gly Thr Asp Phe Thr Leu Ser
    210                 215                 220

Ile Asn Ser Val Glu Ser Glu Asp Ile Ala Asp Tyr Tyr Cys Gln Gln
225                 230                 235                 240

Asn Asn Asn Trp Pro Thr Thr Phe Gly Ala Gly Thr Lys Leu Glu Leu
                245                 250                 255

Lys Gly Gly Gly Gly Ser Gly Gly Gly Gly Ser Gly Gly Gly Gly Ser
            260                 265                 270

Asp Ile Gln Met Thr Gln Thr Thr Ser Ser Leu Ser Ala Ser Leu Gly
        275                 280                 285

Asp Arg Val Thr Ile Ser Cys Arg Ala Ser Gln Asp Ile Arg Asn Tyr
    290                 295                 300

Leu Asn Trp Tyr Gln Gln Lys Pro Asp Gly Thr Val Lys Leu Leu Ile
305                 310                 315                 320

Tyr Tyr Thr Ser Arg Leu His Ser Gly Val Pro Ser Lys Phe Ser Gly
                325                 330                 335

Ser Gly Ser Gly Thr Asp Tyr Ser Leu Thr Ile Ser Asn Leu Glu Gln
            340                 345                 350

Glu Asp Ile Ala Thr Tyr Phe Cys Gln Gln Gly Asn Thr Leu Pro Trp
        355                 360                 365

Thr Phe Ala Gly Gly Thr Lys Leu Glu Ile Lys Gly Gly Gly Ser Gly
    370                 375                 380

Gly Gly Ser Gly Gly Gly Ser Gly Gly Gly Ser Glu Val Gln Leu Gln
385                 390                 395                 400

Gln Ser Gly Pro Glu Leu Val Lys Pro Gly Ala Ser Met Lys Ile Ser
                405                 410                 415

Cys Lys Ala Ser Gly Tyr Ser Phe Thr Gly Tyr Thr Met Asn Trp Val
            420                 425                 430

Lys Gln Ser His Gly Lys Asn Leu Glu Trp Met Gly Leu Ile Asn Pro
        435                 440                 445

Tyr Lys Gly Val Ser Thr Tyr Asn Gln Lys Phe Lys Asp Lys Ala Thr
    450                 455                 460

Leu Thr Val Asp Lys Ser Ser Ser Thr Ala Tyr Met Glu Leu Leu Ser
465                 470                 475                 480

Leu Thr Ser Glu Asp Ser Ala Val Tyr Tyr Cys Ala Arg Ser Gly Tyr
                485                 490                 495

Tyr Gly Asp Ser Asp Trp Tyr Phe Asp Val Trp Gly Ala Gly Thr Thr
            500                 505                 510

Val Thr Val Ser Ser Gly Gly Gly Gly Ser Val Asp Glu Gln Lys Leu
        515                 520                 525

Ile Ser Glu Glu Asp Leu Asn Ala Val Gly Gln Asp Thr Gln Glu Val
    530                 535                 540

Ile Val Val Pro His Ser Leu Pro Phe Lys Val Val Val Ile Ser Ala
545                 550                 555                 560

Ile Leu Ala Leu Val Val Leu Thr Ile Ile Ser Leu Ile Ile Leu Ile
                565                 570                 575

Met Leu Trp Gln Lys Lys Pro Arg
```

580

<210> SEQ ID NO 31
<211> LENGTH: 1755
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 31

```
tatccatatg atgttccaga ttatgctggg gcccagccgg ccagatctga tatccagatg     60
acacagacaa cctcaagtct tagtgcatca ctgggagatc gtgtgactat aagctgccgc    120
gcatcacagg acattcgcaa ttatctgaat tggtatcaac agaagcctga tggcaccgtg    180
aaacttctga tctattacac cagtcgtctg catagcggtg ttccgagcaa attttcaggc    240
tcagggtcag gaaccgatta ttcactgacg attagtaatt tagaacaaga agatattgca    300
acctatttct gtcaacaggg taataccctg ccgtggacct ttgcaggtgg taccaaactg    360
gaaattaaag gaggtggcag tggaggggga agcggcggcg gttcaggagg cggttctgag    420
gtccagttac agcagagcgg tccggaactg gttaaaccgg gtgcaagcat gaaaattagc    480
tgtaaagcaa gcggttatag ctttaccggt tataccatga attgggttaa acagagccat    540
ggtaaaaatc tggaatggat gggtctgatt aatccgtata aaggtgttag cacctataat    600
cagaaattta aagataaagc aaccctgacc gttgataaaa gcagcagcac cgcatatatg    660
gaactgctga gcctgaccag cgaagatagc gccgtttact attgcgcacg cagcggttat    720
tatggtgata gcgattggta ttttgatgtt tggggtgcag gtaccaccgt taccgttagc    780
agcggaggtg gcggaagtgg aggaggtggc tctggcggtg gaggaagcca ggtgcagctg    840
aagcagtctg gccctggact ggtgcagcct agccagagcc tgagcatcac ctgtaccgtg    900
tccggcttca gcctgaccaa ctacggcgtg cactgggtgc gacagagccc tggcaaaggc    960
ctggaatggc tgggagtgat ttggagcggc ggcaacaccg actacaacac cccttcacc   1020
agcagactgt ccatcaacaa ggacaacagc aagagccagg tgttcttcaa gatgaacagc   1080
ctgcagagca acgacaccgc catctactac tgcgctagag ccctgaccta ctatgactac   1140
gagttcgcct actggggcca gggcacactc gtgacagtgt ctgccggcgg aggtggatct   1200
ggaggcggtg gcagcggtgg aggcggatct gacatcctgc tgacccagag ccccgtgatc   1260
ctgtccgtgt ctcctggcga gagagtgtcc ttcagctgca gagccagcca gagcatcggc   1320
accaacatcc actggtatca gcagaggacc aacggcagcc ccagactgct gattaagtac   1380
gccagcgagt ccatcagcgg catccccagc agattcagcg gcagcggctc tggcaccgac   1440
ttcaccctga gcatcaacag cgtggaaagc gaggatatcg ccgactacta ctgccagcag   1500
aacaacaact ggcccaccac cttcggcgct ggcaccaagc tggaactgaa gggcgggggc   1560
ggaagcgtcg acgaacaaaa actcatctca gaagaggatc tgaatgctgt gggccaggac   1620
acgcaggagg tcatcgtggt gccacactcc ttgcccttta aggtggtggt gatctcagcc   1680
atcctggccc tggtggtgct caccatcatc tcccttatca tcctcatcat gctttggcag   1740
aagaagccac gttag                                                    1755
```

<210> SEQ ID NO 32
<211> LENGTH: 584
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 32

```
Tyr Pro Tyr Asp Val Pro Asp Tyr Ala Gly Ala Gln Pro Ala Arg Ser
1               5                   10                  15

Asp Ile Gln Met Thr Gln Thr Thr Ser Ser Leu Ser Ala Ser Leu Gly
            20                  25                  30

Asp Arg Val Thr Ile Ser Cys Arg Ala Ser Gln Asp Ile Arg Asn Tyr
        35                  40                  45

Leu Asn Trp Tyr Gln Gln Lys Pro Asp Gly Thr Val Lys Leu Leu Ile
    50                  55                  60

Tyr Tyr Thr Ser Arg Leu His Ser Gly Val Pro Ser Lys Phe Ser Gly
65                  70                  75                  80

Ser Gly Ser Gly Thr Asp Tyr Ser Leu Thr Ile Ser Asn Leu Glu Gln
                85                  90                  95

Glu Asp Ile Ala Thr Tyr Phe Cys Gln Gln Gly Asn Thr Leu Pro Trp
            100                 105                 110

Thr Phe Ala Gly Gly Thr Lys Leu Glu Ile Lys Gly Gly Gly Ser Gly
        115                 120                 125

Gly Gly Ser Gly Gly Gly Ser Gly Gly Gly Ser Glu Val Gln Leu Gln
    130                 135                 140

Gln Ser Gly Pro Glu Leu Val Lys Pro Gly Ala Ser Met Lys Ile Ser
145                 150                 155                 160

Cys Lys Ala Ser Gly Tyr Ser Phe Thr Gly Tyr Thr Met Asn Trp Val
                165                 170                 175

Lys Gln Ser His Gly Lys Asn Leu Glu Trp Met Gly Leu Ile Asn Pro
            180                 185                 190

Tyr Lys Gly Val Ser Thr Tyr Asn Gln Lys Phe Lys Asp Lys Ala Thr
        195                 200                 205

Leu Thr Val Asp Lys Ser Ser Ser Thr Ala Tyr Met Glu Leu Leu Ser
    210                 215                 220

Leu Thr Ser Glu Asp Ser Ala Val Tyr Tyr Cys Ala Arg Ser Gly Tyr
225                 230                 235                 240

Tyr Gly Asp Ser Asp Trp Tyr Phe Asp Val Trp Gly Ala Gly Thr Thr
                245                 250                 255

Val Thr Val Ser Ser Gly Gly Gly Gly Ser Gly Gly Gly Gly Ser Gly
            260                 265                 270

Gly Gly Gly Ser Gln Val Gln Leu Lys Gln Ser Gly Pro Gly Leu Val
        275                 280                 285

Gln Pro Ser Gln Ser Leu Ser Ile Thr Cys Thr Val Ser Gly Phe Ser
    290                 295                 300

Leu Thr Asn Tyr Gly Val His Trp Val Arg Gln Ser Pro Gly Lys Gly
305                 310                 315                 320

Leu Glu Trp Leu Gly Val Ile Trp Ser Gly Gly Asn Thr Asp Tyr Asn
                325                 330                 335

Thr Pro Phe Thr Ser Arg Leu Ser Ile Asn Lys Asp Asn Ser Lys Ser
            340                 345                 350

Gln Val Phe Phe Lys Met Asn Ser Leu Gln Ser Asn Asp Thr Ala Ile
        355                 360                 365

Tyr Tyr Cys Ala Arg Ala Leu Thr Tyr Tyr Asp Tyr Glu Phe Ala Tyr
    370                 375                 380

Trp Gly Gln Gly Thr Leu Val Thr Val Ser Ala Gly Gly Gly Gly Ser
385                 390                 395                 400
```

```
Gly Gly Gly Gly Ser Gly Gly Gly Gly Ser Asp Ile Leu Leu Thr Gln
                405                 410                 415

Ser Pro Val Ile Leu Ser Val Ser Pro Gly Glu Arg Val Ser Phe Ser
            420                 425                 430

Cys Arg Ala Ser Gln Ser Ile Gly Thr Asn Ile His Trp Tyr Gln Gln
        435                 440                 445

Arg Thr Asn Gly Ser Pro Arg Leu Leu Ile Lys Tyr Ala Ser Glu Ser
    450                 455                 460

Ile Ser Gly Ile Pro Ser Arg Phe Ser Gly Ser Gly Ser Gly Thr Asp
465                 470                 475                 480

Phe Thr Leu Ser Ile Asn Ser Val Glu Ser Glu Asp Ile Ala Asp Tyr
                485                 490                 495

Tyr Cys Gln Gln Asn Asn Asn Trp Pro Thr Thr Phe Gly Ala Gly Thr
            500                 505                 510

Lys Leu Glu Leu Lys Gly Gly Gly Gly Ser Val Asp Glu Gln Lys Leu
        515                 520                 525

Ile Ser Glu Glu Asp Leu Asn Ala Val Gly Gln Asp Thr Gln Glu Val
    530                 535                 540

Ile Val Val Pro His Ser Leu Pro Phe Lys Val Val Val Ile Ser Ala
545                 550                 555                 560

Ile Leu Ala Leu Val Val Leu Thr Ile Ile Ser Leu Ile Ile Leu Ile
                565                 570                 575

Met Leu Trp Gln Lys Lys Pro Arg
            580


<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33

tatccatatg atgttccaga ttatgct                                          27


<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

tacccatacg atgttccaga ttacgct                                          27


<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Pro Tyr Asp Val Pro Asp Tyr Ala
1               5


<210> SEQ ID NO 36
```

<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
gactacaaag acgatgacga caag 24

<210> SEQ ID NO 37
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Asp Tyr Lys Asp His Asp Gly Asp Tyr Lys Asp His Asp Ile Asp Tyr
1 5 10 15

Lys Asp Asp Asp Asp Lys
20

<210> SEQ ID NO 38
<211> LENGTH: 5718
<212> TYPE: DNA
<213> ORGANISM: Homo sapiens

<400> SEQUENCE: 38
ctcctgaggc tgccagcagc cagcagtgac tgcccgccct atctgggacc caggatcgct 60
ctgtgagcaa cttggagcca gagaggagat caacaaggag gaggagagag ccggcccctc 120
agccctgctg cccagcagca gcctgtgctc gccctgccca acgcagacag ccagacccag 180
ggcggcccct ctggcggctc tgctcctccc gaaggatgct tggggagtga ggcgaagctg 240
ggccgctcct ctcccctaca gcagcccccct tcctccatcc ctctgttctc ctgagccttc 300
aggagcctgc accagtcctg cctgtccttc tactcagctg ttacccactc tgggaccagc 360
agtctttctg ataactggga gagggcagta aggaggactt cctggagggg gtgactgtcc 420
agagcctgga actgtgccca caccagaagc catcagcagc aaggacacca tgcggcttcc 480
gggtgcgatg ccagctctgg ccctcaaagg cgagctgctg ttgctgtctc tcctgttact 540
tctggaacca cagatctctc agggcctggt cgtcacaccc ccggggccag agcttgtcct 600
caatgtctcc agcaccttcg ttctgacctg ctcgggttca gctccggtgg tgtgggaacg 660
gatgtcccag gagcccccac aggaaatggc caaggcccag gatggcacct tctccagcgt 720
gctcacactg accaacctca ctgggctaga cacgggagaa tacttttgca cccacaatga 780
ctcccgtgga ctggagaccg atgagcggaa acggctctac atctttgtgc cagatcccac 840
cgtgggcttc ctccctaatg atgccgagga actattcatc tttctcacgg aaataactga 900
gatcaccatt ccatgccgag taacagaccc acagctggtg gtgacactgc acgagaagaa 960
aggggacgtt gcactgcctg tcccctatga tcaccaacgt ggcttttctg gtatctttga 1020
ggacagaagc tacatctgca aaaccaccat tggggacagg gaggtggatt ctgatgccta 1080
ctatgtctac agactccagg tgtcatccat caacgtctct gtgaacgcag tgcagactgt 1140
ggtccgccag ggtgagaaca tcaccctcat gtgcattgtg atcgggaatg aggtggtcaa 1200
cttcgagtgg acataccccc gcaaagaaag tgggcggctg gtggagccgg tgactgactt 1260
cctcttggat atgccttacc acatccgctc catcctgcac atccccagtg ccgagttaga 1320

```
agactcgggg acctacacct gcaatgtgac ggagagtgtg aatgaccatc aggatgaaaa   1380
ggccatcaac atcaccgtgg ttgagagcgg ctacgtgcgg ctcctgggag aggtgggcac   1440
actacaattt gctgagctgc atcggagccg gacactgcag gtagtgttcg aggcctaccc   1500
accgcccact gtcctgtggt tcaaagacaa ccgcaccctg ggcgactcca gcgctggcga   1560
aatcgccctg tccacgcgca acgtgtcgga gacccggtat gtgtcagagc tgacactggt   1620
tcgcgtgaag gtggcagagg ctggccacta caccatgcgg gccttccatg aggatgctga   1680
ggtccagctc tccttccagc tacagatcaa tgtccctgtc cgagtgctgg agctaagtga   1740
gagccaccct gacagtgggg aacagacagt ccgctgtcgt ggccggggca tgccccagcc   1800
gaacatcatc tggtctgcct gcagagacct caaaaggtgt ccacgtgagc tgccgcccac   1860
gctgctgggg aacagttccg aagaggagag ccagctggag actaacgtga cgtactggga   1920
ggaggagcag gagtttgagg tggtgagcac actgcgtctg cagcacgtgg atcggccact   1980
gtcggtgcgc tgcacgctgc gcaacgctgt gggccaggac acgcaggagg tcatcgtggt   2040
gccacactcc ttgcccttta aggtggtggt gatctcagcc atcctggccc tggtggtgct   2100
caccatcatc tcccttatca tcctcatcat gctttggcag aagaagccac gttacgagat   2160
ccgatggaag gtgattgagt ctgtgagctc tgacggccat gagtacatct acgtggaccc   2220
catgcagctg ccctatgact ccacgtggga gctgccgcgg gaccagcttg tgctgggacg   2280
caccctcggc tctggggcct ttgggcaggt ggtggaggcc acggctcatg gcctgagcca   2340
ttctcaggcc acgatgaaag tggccgtcaa gatgcttaaa tccacagccc gcagcagtga   2400
gaagcaagcc cttatgtcgg agctgaagat catgagtcac cttgggcccc acctgaacgt   2460
ggtcaacctg ttgggggcct gcaccaaagg aggacccatc tatatcatca ctgagtactg   2520
ccgctacgga gacctggtgg actacctgca ccgcaacaaa cacaccttcc tgcagcacca   2580
ctccgacaag cgccgcccgc ccagcgcgga gctctacagc aatgctctgc ccgttgggct   2640
cccccctgccc agccatgtgt ccttgaccgg ggagagcgac ggtggctaca tggacatgag   2700
caaggacgag tcggtggact atgtgcccat gctggacatg aaaggagacg tcaaatatgc   2760
agacatcgag tcctccaact acatggcccc ttacgataac tacgttccct ctgcccctga   2820
gaggacctgc cgagcaactt tgatcaacga gtctccagtg ctaagctaca tggacctcgt   2880
gggcttcagc taccaggtgg ccaatggcat ggagtttctg gcctccaaga actgcgtcca   2940
cagagacctg gcggctagga acgtgctcat ctgtgaaggc aagctggtca agatctgtga   3000
ctttggcctg gctcgagaca tcatgcggga ctcgaattac atctccaaag gcagcacctt   3060
tttgccttta aagtggatgg ctccggagag catcttcaac agcctctaca ccaccctgag   3120
cgacgtgtgg tccttcggga tcctgctctg ggagatcttc accttgggtg gcacccctta   3180
cccagagctg cccatgaacg agcagttcta caatgccatc aaacggggtt accgcatggc   3240
ccagcctgcc catgcctccg acgagatcta tgagatcatg cagaagtgct gggaagagaa   3300
gtttgagatt cggcccccct tctcccagct ggtgctgctt ctcgagagac tgttgggcga   3360
aggttacaaa aagaagtacc agcaggtgga tgaggagttt ctgaggagtg accacccagc   3420
catccttcgg tcccaggccc gcttgcctgg gttccatggc ctccgatctc ccctggacac   3480
cagctccgtc ctctatactg ccgtgcagcc caatgagggt gacaacgact atatcatccc   3540
cctgcctgac cccaaacccg aggttgctga cgagggccca ctggagggtt cccccagcct   3600
agccagctcc accctgaatg aagtcaacac ctcctcaacc atctcctgtg acagccccct   3660
```

```
ggagccccag gacgaaccag agccagagcc ccagcttgag ctccaggtgg agccggagcc   3720

agagctggaa cagttgccgg attcggggtg ccctgcgcct cgggcggaag cagaggatag   3780

cttcctgtag gggctggcc cctaccctgc cctgcctgaa gctcccccc tgccagcacc   3840

cagcatctcc tggcctggcc tgaccgggct tcctgtcagc caggctgccc ttatcagctg   3900

tccccttctg gaagctttct gctcctgacg tgttgtgccc caaaccctgg ggctggctta   3960

ggaggcaaga aaactgcagg ggccgtgacc agccctctgc ctccagggag gccaactgac   4020

tctgagccag ggttccccca gggaactcag ttttcccata tgtaagatgg gaaagttagg   4080

cttgatgacc cagaatctag gattctctcc ctggctgaca ggtggggaga ccgaatccct   4140

ccctgggaag attcttggag ttactgaggt ggtaaattaa ctttttctg ttcagccagc   4200

taccccctcaa ggaatcatag ctctctcctc gcacttttat ccacccagga gctagggaag   4260

agaccctagc ctccctggct gctggctgag ctagggccta gccttgagca gtgttgcctc   4320

atccagaaga aagccagtct cctccctatg atgccagtcc ctgcgttccc tggcccgagc   4380

tggtctgggg ccattaggca gcctaattaa tgctggaggc tgagccaagt acaggacacc   4440

cccagcctgc agcccttgcc cagggcactt ggagcacacg cagccatagc aagtgcctgt   4500

gtccctgtcc ttcaggccca tcagtcctgg ggcttttttct ttatcaccct cagtcttaat   4560

ccatccacca gagtctagaa ggccagacgg gccccgcatc tgtgatgaga atgtaaatgt   4620

gccagtgtgg agtggccacg tgtgtgtgcc agtatatggc cctggctctg cattggacct   4680

gctatgaggc tttggaggaa tccctcaccc tctctgggcc tcagtttccc cttcaaaaaa   4740

tgaataagtc ggacttatta actctgagtg ccttgccagc actaacattc tagagtattc   4800

caggtggttg cacatttgtc cagatgaagc aaggccatat accctaaact tccatcctgg   4860

gggtcagctg ggctcctggg agattccaga tcacacatca cactctgggg actcaggaac   4920

catgcccctt ccccaggccc ccagcaagtc tcaagaacac agctgcacag gccttgactt   4980

agagtgacag ccggtgtcct ggaaagcccc cagcagctgc cccagggaca tgggaagacc   5040

acgggacctc tttcactacc cacgatgacc tccgggggta tcctgggcaa aagggacaaa   5100

gagggcaaat gagatcacct cctgcagccc accactccag cacctgtgcc gaggtctgcg   5160

tcgaagacag aatggacagt gaggacagtt atgtcttgta aaagacaaga agcttcagat   5220

gggtacccca agaaggatgt gagaggtggg cgctttggag gtttgcccct cacccaccag   5280

ctgccccatc cctgaggcag cgctccatgg gggtatggtt ttgtcactgc ccagacctag   5340

cagtgacatc tcattgtccc cagcccagtg ggcattggag gtgccagggg agtcagggtt   5400

gtagccaaga cgcccccgca cggggagggt tgggaagggg gtgcaggaag ctcaacccct   5460

ctgggcacca accctgcatt gcaggttggc accttacttc cctgggatcc ccagagttgg   5520

tccaaggagg gagagtgggt tctcaatacg gtaccaaaga tataatcacc taggtttaca   5580

aatattttta ggactcacgt taactcacat ttatacagca gaaatgctat tttgtatgct   5640

gttaagtttt tctatctgtg tacttttttt taagggaaag attttaatat taaacctggt   5700

gcttctcact cacaaaaa                                                  5718
```

<210> SEQ ID NO 39
<211> LENGTH: 1106
<212> TYPE: PRT
<213> ORGANISM: Homo sapiens

<400> SEQUENCE: 39

Met Arg Leu Pro Gly Ala Met Pro Ala Leu Ala Leu Lys Gly Glu Leu

```
1               5                   10                  15

Leu Leu Leu Ser Leu Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
    370                 375                 380

Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430
```

```
Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
    450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
        515                 520                 525

Pro Phe Lys Val Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
        675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
        755                 760                 765

Ser Asn Tyr Met Ala Pro Tyr Asp Asn Tyr Val Pro Ser Ala Pro Glu
    770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
        835                 840                 845
```

```
Arg Asp Ile Met Arg Asp Ser Asn Tyr Ile Ser Lys Gly Ser Thr Phe
    850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
        915                 920                 925

Ala Ser Asp Glu Ile Tyr Glu Ile Met Gln Lys Cys Trp Glu Glu Lys
    930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990

Pro Gly Phe His Gly Leu Arg Ser  Pro Leu Asp Thr Ser  Ser Val Leu
        995                 1000                1005

Tyr Thr  Ala Val Gln Pro Asn  Glu Gly Asp Asn Asp  Tyr Ile Ile
    1010                1015                1020

Pro Leu  Pro Asp Pro Lys Pro  Glu Val Ala Asp Glu  Gly Pro Leu
    1025                1030                1035

Glu Gly  Ser Pro Ser Leu Ala  Ser Ser Thr Leu Asn  Glu Val Asn
    1040                1045                1050

Thr Ser  Ser Thr Ile Ser Cys  Asp Ser Pro Leu Glu  Pro Gln Asp
    1055                1060                1065

Glu Pro  Glu Pro Glu Pro Gln  Leu Glu Leu Gln Val  Glu Pro Glu
    1070                1075                1080

Pro Glu  Leu Glu Gln Leu Pro  Asp Ser Gly Cys Pro  Ala Pro Arg
    1085                1090                1095

Ala Glu  Ala Glu Asp Ser Phe  Leu
    1100                1105
```

<210> SEQ ID NO 40
<211> LENGTH: 4076
<212> TYPE: DNA
<213> ORGANISM: Homo sapiens

<400> SEQUENCE: 40

```
aagaaagagc cccgccccta gtcttatgac tcgcactgaa gcgccgattc ctggcttttg      60

caaggctgtg gtcggtggtc atcagtgctc ttgacccagg tccagcgagc cttttccctg     120

gtgttgcagc tgttgttgta ccgccgccgt cgccgccgtc gccgcctgct ctgcggggtc     180

atggtgtgct tccgcctctt cccggttccg ggctcagggc tcgttctggt ctgcctagtc     240

ctgggagctg tgcggtctta tgcattggaa cttaatttga cagattcaga aaatgccact     300

tgcctttatg caaaatggca gatgaatttc acagtacgct atgaaactac aaataaaact     360

tataaaactg taaccatttc agaccatggc actgtgacat ataatggaag catttgtggg     420

gatgatcaga atggtcccaa aatagcagtg cagttcggac ctggcttttc ctggattgcg     480

aattttacca aggcagcatc tacttattca attgacagcg tctcattttc ctacaacact     540

ggtgataaca caacatttcc tgatgctgaa gataaaggaa ttcttactgt tgatgaactt     600
```

```
ttggccatca gaattccatt gaatgacctt tttagatgca atagtttatc aactttggaa    660
aagaatgatg ttgtccaaca ctactgggat gttcttgtac aagcttttgt ccaaaatggc    720
acagtgagca caaatgagtt cctgtgtgat aaagacaaaa cttcaacagt ggcacccacc    780
atacacacca ctgtgccatc tcctactaca acacctactc caaaggaaaa accagaagct    840
ggaacctatt cagttaataa tggcaatgat acttgtctgc tggctaccat ggggctgcag    900
ctgaacatca ctcaggataa ggttgcttca gttattaaca tcaaccccaa tacaactcac    960
tccacaggca gctgccgttc tcacactgct ctacttagac tcaatagcag caccattaag   1020
tatctagact ttgtctttgc tgtgaaaaat gaaaaccgat tttatctgaa ggaagtgaac   1080
atcagcatgt atttggttaa tggctccgtt ttcagcattg caaataacaa tctcagctac   1140
tgggatgccc ccctgggaag ttcttatatg tgcaacaaag agcagactgt ttcagtgtct   1200
ggagcatttc agataaatac ctttgatcta agggttcagc ctttcaatgt gacacaagga   1260
aagtattcta cagcccaaga gtgttcgctg gatgatgaca ccattctaat cccaattata   1320
gttggtgctg gtctttcagg cttgattatc gttatagtga ttgcttacgt aattggcaga   1380
agaaaaagtt atgctggata tcagactctg taacactaat caatacgtga tctctgttac   1440
aaaagaaaaa agcaagtaca agttccaaca tgcaatactg gtcaacttaa ggtatattta   1500
gttgcagtcc agctctttag aatgggtggt atggggggatt tcaaacttaa acaaaaaaact   1560
atcaactaca aattagttgc ctgactttgg tttttccaac caaggaattt aaaactgtta   1620
tttttacagc aaaagatgtg caaaatcact ggattataag ttctatttta ctgtcttgaa   1680
ttagtatttc agtgttttca ttttagacat tcagactaaa aatacaccgt ttagaaaaaa   1740
caatttttga aaaagagatt ttttttccct gcaggtagtt gagttggaac aacatgttct   1800
accgtggatt tgtacttgct ccttttgctc tttttgtgtg tgtgtgtgtg tgtgtgtgtg   1860
tgtgtgtgtg tgtgattttt gtttgcaggt taacttagct actttggcat tgctgcatat   1920
ttgacctttg agagatataa tagtagattt gaacaggggc tggtattatt atgttcttag   1980
caataaatgc ttttctaatg ccttttgaat acatttgtat ttatgtggct gtaatgacaa   2040
aagatacaaa agctttttaa aatttagagt aggtattaat cttattgttt aatctttttt   2100
ttaaaaaaac tggatatttc aatcttttaa attgcaatat ataagactat tccaactggg   2160
catttcaatc catttttttag gtgctttaga gataattgct tgccagtgcc aattgagggc   2220
attagtactt tgtgctcata aattggcctc tgtatgcagt actaaaatta atgcagattt   2280
ctctttagcc ttccaacatt tcttgttgat agtgatgtat tttattattt tctttttctt   2340
aagaaatgcc agtgtgtcct agaacctaga taacgaagtg cacttacact tataaaataa   2400
cttgcatcta ggctgggcgt ggcggctcac gcctgtaatc ccagcacttt gggaggccga   2460
agtgggtgga tcacttgagg ccaggagttt gagaccagcc tggccaacat ggtgaaaccc   2520
catctctatc agaaatacaa aaaattagct gggcgtggtg gtgggcgcct gtaatcccag   2580
ttactcggga ggctgaggca ggagaatcac ttgaacccgg gaggcagagg ttgcggtgag   2640
ccaagagcgc accattgcac tccagcctgg gcgacaaaaa cgaaactcca tctcaaaaca   2700
aaacaaaaca aaacaaacaa acaaacaaaa cttgcatcta accaaaaagt cttggtttta   2760
tcttaatcca ttaaaaagtt gttctttgtt tccagcttgc attgattgct acaacatcac   2820
taatttggct ttcacattta aatggttctg tgctaatcaa aactttcgtt gttattattc   2880
attatggtag aatcattttt aattcacgtg ctttgtgttc agttttgtgg tctgagagat   2940
gtaccaattg tcaaattacc gtgtaccacc taatgtttat aggagaaagc aaaatacatc   3000
```

```
agcttggtag ttaacacatc aaatatttct tgctgcttct aggagaactt ttttggtgtg   3060

tgttggaatg gctgagcaaa tattaaaatt gttaatatgc agccatatat ggaaggttcc   3120

tgtggggttg ttttttcgtg ttttttttt ttttgtggtg ggattatgtg cctcccattc   3180

actagaaaat gagaaaattg tctgggttcc aaaatattga cattgaatgg atcaatacac   3240

acacacagac atatatatat atatgcacac atatataggc agttgcatgc tagcatgggt   3300

atttttataa caatataact gagttatatt ggaattataa atattttccg tcacttaaat   3360

ttgttctttg tttagcctga aaacctttat ggctcaagat cagattcctg actaacccct   3420

ctcttagagc tacagcgagc tgcattacca gcttaaaaca cttcttaggg attaaatata   3480

gatgtaattt ttcaaaatcg tttttaattt aaactgtgtt ttagtgtaaa attgttaacc   3540

ttgtaagatg gataatgtgt ataagaatgt aggccttaac tatttcacat gagtcaaaac   3600

aaagcagctt taaaaaaata attggaagca caagtgcatg gcactgactg aatgctgtta   3660

atatttctaa aagtttctac attcagatta tatgcctgat tcatagtaaa atacctctaa   3720

taaacactgt tttatagaaa acctgacttc agtgaatatt tttgtatttt acatgggcca   3780

gtttatatac tgctatttac actattattt cctatagcta catgttcttt gtaccttttg   3840

tagttttatt tgtattacta gattcatacc ttgatggtaa cgctctatct ggttttgggt   3900

gtttttcatg ttttagcatt tgtataaaga aactggtcca tgtaaatact ttccatgttt   3960

tttcttcaaa tgtttaaacc actagttgat gtatggtatc tttagatatt tgcctgtctg   4020

tttgctcaaa attgcttcta aaacaataaa gattctttta tttcttaagg caaaaa       4076
```

<210> SEQ ID NO 41
<211> LENGTH: 410
<212> TYPE: PRT
<213> ORGANISM: Homo sapiens

<400> SEQUENCE: 41

```
Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
    50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
```

```
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
            340                 345                 350

Gln Pro Phe Asn Val Thr Gln Gly Lys Tyr Ser Thr Ala Gln Glu Cys
        355                 360                 365

Ser Leu Asp Asp Asp Thr Ile Leu Ile Pro Ile Ile Val Gly Ala Gly
    370                 375                 380

Leu Ser Gly Leu Ile Ile Val Ile Val Ile Ala Tyr Val Ile Gly Arg
385                 390                 395                 400

Arg Lys Ser Tyr Ala Gly Tyr Gln Thr Leu
                405                 410


<210> SEQ ID NO 42
<211> LENGTH: 1886
<212> TYPE: DNA
<213> ORGANISM: Homo sapiens

<400> SEQUENCE: 42

agtccgcctc tggccagctt gggcggagcg cacggccagt gggaggtgct gagccgcctg      60

atttattccg gtcccagagg agaaggcgcc agaaccccgc ggggtctgag cagcccagcg     120

tgcccattcc agcgcccgcg tccccgcagc atgccgcgcc cccgcctgct ggccgcgctg     180

tgcggcgcgc tgctctgcgc ccccagcctc ctcgtcgccc tggatatctg ttccaaaaac     240

ccctgccaca acggtggttt atgcgaggag atttcccaag aagtgcgagg agatgtcttc     300

ccctcgtaca cctgcacgtg ccttaagggc tacgcgggca accactgtga gacgaaatgt     360

gtcgagccac tgggcctgga gaatgggaac attgccaact cacagatcgc cgcctcgtct     420

gtgcgtgtga ccttcttggg tttgcagcat tgggtcccgg agctggcccg cctgaaccgc     480

gcaggcatgg tcaatgcctg gacacccagc agcaatgacg ataacccctg gatccaggtg     540

aacctgctgc ggaggatgtg ggtaacaggt gtggtgacgc agggtgccag ccgcttggcc     600

agtcatgagt acctgaaggc cttcaaggtg gcctacagcc ttaatggaca cgaattcgat     660

ttcatccatg atgttaataa aaaacacaag gagtttgtgg gtaactggaa caaaaacgcg     720

gtgcatgtca acctgtttga gacccctgtg gaggctcagt acgtgagatt gtaccccacg     780

agctgccaca cggcctgcac tctgcgcttt gagctactgg gctgtgagct gaacggatgc     840
```

```
gccaatcccc tgggcctgaa gaataacagc atccctgaca agcagatcac ggcctccagc    900

agctacaaga cctggggctt gcatctcttc agctggaacc cctcctatgc acggctggac    960

aagcagggca acttcaacgc ctgggttgcg gggagctacg gtaacgatca gtggctgcag   1020

atcttccctg gcaactggga caaccactcc cacaagaaga acttgtttga gacgcccatc   1080

ctggctcgct atgtgcgcat cctgcctgta gcctggcaca accgcatcgc cctgcgcctg   1140

gagctgctgg gctgttagtg gccacctgcc acccccaggt cttcctgctt tccatgggcc   1200

cgctgcctct tggcttctca gcccctttaa atcaccatag ggctggggac tggggaaggg   1260

gagggtgttc agaggcagca ccaccacaca gtcacccctc cctccctctt tcccaccctc   1320

cacctctcac gggccctgcc ccagccccta agccccgtcc cctaaccccc agtcctcact   1380

gtcctgtttt cttaggcact gagggatctg agtaggtctg ggatggacag gaaagggcaa   1440

agtagggcgt gtggtttccc tgcccctgtc cggaccgccg atcccaggtg cgtgtgtctc   1500

tgtctctcct agcccctctc tcacacatca cattcccatg gtggcctcaa gaaaggcccg   1560

gaagcgccag gctggagata acagcctctt gcccgtcggc cctgcgtcgg ccctggggta   1620

ccatgtggcc acaactgctg tggcccccctg tccccaagac acttcccctt gtctccctgg  1680

ttgcctctct tgccccttgt cctgaagccc agcgacacag aagggggtgg ggcgggtcta   1740

tggggagaaa gggagcgagg tcagaggagg gcatgggttg gcagggtggg cgtttggggc   1800

cctctatgct ggcttttcac cccagaggac acaggcagct tccaaaatat atttatcttc   1860

ttcacgggaa aaaaaaaaaa aaaaaa                                        1886


<210> SEQ ID NO 43
<211> LENGTH: 335
<212> TYPE: PRT
<213> ORGANISM: Homo sapiens

<400> SEQUENCE: 43

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Leu Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
```

```
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
        275                 280                 285

Leu Gln Ile Phe Pro Gly Asn Trp Asp Asn His Ser His Lys Lys Asn
    290                 295                 300

Leu Phe Glu Thr Pro Ile Leu Ala Arg Tyr Val Arg Ile Leu Pro Val
305                 310                 315                 320

Ala Trp His Asn Arg Ile Ala Leu Arg Leu Glu Leu Leu Gly Cys
                325                 330                 335
```

```
<210> SEQ ID NO 44
<211> LENGTH: 3740
<212> TYPE: DNA
<213> ORGANISM: Homo sapiens

<400> SEQUENCE: 44

gggacggcgg cggcgcagct cggaacccgc cagggtccag ggtccaggtt ccagcgcccg      60

gcggcccagg caccccccga gcccagctcc acacaccgtt cctggatctc ctctccccag     120

gcggagcgtg cccctgccca gtccagtgac cttcgcctgt tggagccctg gttaattttt     180

gcccagtctg cctgttgtgg ggctcctccc ctttggggat ataagcccgg cctggggctg     240

ctccgttctc tgcctggcct gaggctccct gagccgcctc cccaccatca ccatggccaa     300

gggcttctat atttccaagt ccctgggcat cctggggatc ctcctgggcg tggcagccgt     360

gtgcacaatc atcgcactgt cagtggtgta ctcccaggag aagaacaaga acgccaacag     420

ctcccccgtg gcctccacca ccccgtccgc ctcagccacc accaaccccg cctcggccac     480

caccttggac caaagtaaag cgtggaatcg ttaccgcctc cccaacacgc tgaaacccga     540

ttcctaccgg gtgacgctga gaccgtacct cacccccaat gacaggggcc tgtacgtttt     600

taagggctcc agcaccgtcc gtttcacctg caaggaggcc actgacgtca tcatcatcca     660

cagcaagaag ctcaactaca ccctcagcca ggggcacagg gtggtcctgc gtggtgtggg     720

aggctcccag ccccccgaca ttgacaagac tgagctggtg gagcccaccg agtacctggt     780

ggtgcacctc aagggctccc tggtgaagga cagccagtat gagatggaca gcgagttcga     840

gggggagttg gcagatgacc tggcgggctt ctaccgcagc gagtacatgg agggcaatgt     900

cagaaaggtg gtggccacta cacagatgca ggctgcagat gcccggaagt ccttcccatg     960

cttcgatgag ccggccatga aggccgagtt caacatcacg cttatccacc ccaaggacct    1020

gacagccctg tccaacatgc ttcccaaagg tcccagcacc ccacttccag aagaccccaa    1080

ctggaatgtc actgagttcc acaccacgcc caagatgtcc acgtacttgc tggccttcat    1140

tgtcagtgag ttcgactacg tggagaagca ggcatccaat ggtgtcttga tccggatctg    1200

ggcccggccc agtgccattg cggcgggcca cggcgattat gccctgaacg tgacgggccc    1260
```

```
catccttaac ttctttgctg gtcattatga cacaccctac ccactcccaa aatcagacca   1320
gattggcctg ccagacttca acgccggcgc catggagaac tggggactgg tgacctaccg   1380
ggagaactcc ctgctgttcg accccctgtc ctcctccagc agcaacaagg agcgggtggt   1440
cactgtgatt gctcatgagc tggcccacca gtggttcggg aacctggtga ccatagagtg   1500
gtggaatgac ctgtggctga acgagggctt cgcctcctac gtggagtacc tgggtgctga   1560
ctatgcggag cccacctgga acttgaaaga cctcatggtg ctgaatgatg tgtaccgcgt   1620
gatggcagtg gatgcactgg cctcctccca cccgctgtcc acacccgcct cggagatcaa   1680
cacgccggcc cagatcagtg agctgtttga cgccatctcc tacagcaagg gcgcctcagt   1740
cctcaggatg ctctccagct tcctgtccga ggacgtattc aagcagggcc tggcgtccta   1800
cctccacacc tttgcctacc agaacaccat ctacctgaac ctgtgggacc acctgcagga   1860
ggctgtgaac aaccggtcca tccaactccc caccaccgtg cgggacatca tgaaccgctg   1920
gaccctgcag atgggcttcc cggtcatcac ggtggatacc agcacgggga ccctttccca   1980
ggagcacttc ctccttgacc ccgattccaa tgttacccgc ccctcagaat tcaactacgt   2040
gtggattgtg cccatcacat ccatcagaga tggcagacag cagcaggact actggctgat   2100
agatgtaaga gcccagaacg atctcttcag cacatcaggc aatgagtggg tcctgctgaa   2160
cctcaatgtg acgggctatt accgggtgaa ctacgacgaa gagaactgga ggaagattca   2220
gactcagctg cagagagacc actcggccat ccctgtcatc aatcgggcac agatcattaa   2280
tgacgccttc aacctggcca gtgcccataa ggtccctgtc actctggcgc tgaacaacac   2340
cctcttcctg attgaagaga gacagtacat gccctgggag gccgccctga gcagcctgag   2400
ctacttcaag ctcatgtttg accgctccga ggtctatggc cccatgaaga actacctgaa   2460
gaagcaggtc acacccctct tcattcactt cagaaataat accaacaact ggagggagat   2520
cccagaaaac ctgatggacc agtacagcga ggttaatgcc atcagcaccg cctgctccaa   2580
cggagttcca gagtgtgagg agatggtctc tggccttttc aagcagtgga tggagaaccc   2640
caataataac ccgatccacc ccaacctgcg gtccaccgtc tactgcaacg ctatcgccca   2700
gggcggggag gaggagtggg acttcgcctg ggagcagttc cgaaatgcca cactggtcaa   2760
tgaggctgac aagctccggg cagccctggc ctgcagcaaa gagttgtgga tcctgaacag   2820
gtacctgagc tacaccctga acccggactt aatccggaag caggacgcca cctctaccat   2880
catcagcatt accaacaacg tcattgggca aggtctggtc tgggactttg tccagagcaa   2940
ctggaagaag ctttttaacg attatggtgg tggctcgttc tccttctcca acctcatcca   3000
ggcagtgaca cgacgattct ccaccgagta tgagctgcag cagctggagc agttcaagaa   3060
ggacaacgag gaaacaggct tcggctcagg cacccgggcc ctggagcaag ccctggagaa   3120
gacgaaagcc aacatcaagt gggtgaagga gaacaaggag gtggtgctcc agtggttcac   3180
agaaaacagc aaatagtccc cagcccttga agtcacccgg cccccatgca aggtgcccac   3240
atgtgtccat cccagcggct ggtgcagggc ctccattcct ggagcccgag gcaccagtgt   3300
cctcccctca aggacaaagt ctccagccca cgttctctct gcctgtgagc cagtctagtt   3360
cctgatgacc caggctgcct gagcacctcc cagcccctgc ccctcatgcc aaccccgccc   3420
taggcctggc atggcacctg tcgcccagtg ccctggggct gatctcaggg aagcccagct   3480
ccagggccag atgagcagaa gctctcgatg gacaatgaac ggccttgctg gggccgccc    3540
tgtaccctct ttcacctttc cctaaagacc ctaaatctga ggaatcaaca gggcagcaga   3600
tctgtatatt tttttctaag agaaaatgta aataaaggat ttctagatga aaaaaaaaaa   3660
```

```
aaaaaaaaaa aaaaaaaaaa aaaaaaaaaa aaaaaaaaaa aaaaaaaaaa aaaaaaaaaa   3720

aaaaaaaaaa aaaaaaaaaa                                               3740


<210> SEQ ID NO 45
<211> LENGTH: 967
<212> TYPE: PRT
<213> ORGANISM: Homo sapiens

<400> SEQUENCE: 45

Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
            20                  25                  30

Tyr Ser Gln Glu Lys Asn Lys Asn Ala Asn Ser Ser Pro Val Ala Ser
        35                  40                  45

Thr Thr Pro Ser Ala Ser Ala Thr Thr Asn Pro Ala Ser Ala Thr Thr
    50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
    290                 295                 300

Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                325                 330                 335

Pro Leu Pro Lys Ser Asp Gln Ile Gly Leu Pro Asp Phe Asn Ala Gly
            340                 345                 350
```

```
Ala Met Glu Asn Trp Gly Leu Val Thr Tyr Arg Glu Asn Ser Leu Leu
        355                 360                 365

Phe Asp Pro Leu Ser Ser Ser Ser Ser Asn Lys Glu Arg Val Val Thr
    370                 375                 380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
                405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
        435                 440                 445

Leu Ala Ser Ser His Pro Leu Ser Thr Pro Ala Ser Glu Ile Asn Thr
    450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
                485                 490                 495

Lys Gln Gly Leu Ala Ser Tyr Leu His Thr Phe Ala Tyr Gln Asn Thr
            500                 505                 510

Ile Tyr Leu Asn Leu Trp Asp His Leu Gln Glu Ala Val Asn Asn Arg
        515                 520                 525

Ser Ile Gln Leu Pro Thr Thr Val Arg Asp Ile Met Asn Arg Trp Thr
    530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
                565                 570                 575

Pro Ser Glu Phe Asn Tyr Val Trp Ile Val Pro Ile Thr Ser Ile Arg
            580                 585                 590

Asp Gly Arg Gln Gln Gln Asp Tyr Trp Leu Ile Asp Val Arg Ala Gln
        595                 600                 605

Asn Asp Leu Phe Ser Thr Ser Gly Asn Glu Trp Val Leu Leu Asn Leu
    610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
                645                 650                 655

Asn Arg Ala Gln Ile Ile Asn Asp Ala Phe Asn Leu Ala Ser Ala His
            660                 665                 670

Lys Val Pro Val Thr Leu Ala Leu Asn Asn Thr Leu Phe Leu Ile Glu
        675                 680                 685

Glu Arg Gln Tyr Met Pro Trp Glu Ala Ala Leu Ser Ser Leu Ser Tyr
    690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
                725                 730                 735

Thr Asn Asn Trp Arg Glu Ile Pro Glu Asn Leu Met Asp Gln Tyr Ser
            740                 745                 750

Glu Val Asn Ala Ile Ser Thr Ala Cys Ser Asn Gly Val Pro Glu Cys
        755                 760                 765

Glu Glu Met Val Ser Gly Leu Phe Lys Gln Trp Met Glu Asn Pro Asn
```

```
    770                 775                 780

Asn Asn Pro Ile His Pro Asn Leu Arg Ser Thr Val Tyr Cys Asn Ala
785                 790                 795                 800

Ile Ala Gln Gly Gly Glu Glu Glu Trp Asp Phe Ala Trp Glu Gln Phe
                805                 810                 815

Arg Asn Ala Thr Leu Val Asn Glu Ala Asp Lys Leu Arg Ala Ala Leu
            820                 825                 830

Ala Cys Ser Lys Glu Leu Trp Ile Leu Asn Arg Tyr Leu Ser Tyr Thr
        835                 840                 845

Leu Asn Pro Asp Leu Ile Arg Lys Gln Asp Ala Thr Ser Thr Ile Ile
    850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
                885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
        915                 920                 925

Gly Phe Gly Ser Gly Thr Arg Ala Leu Glu Gln Ala Leu Glu Lys Thr
    930                 935                 940

Lys Ala Asn Ile Lys Trp Val Lys Glu Asn Lys Glu Val Val Leu Gln
945                 950                 955                 960

Trp Phe Thr Glu Asn Ser Lys
                965


<210> SEQ ID NO 46
<211> LENGTH: 1321
<212> TYPE: DNA
<213> ORGANISM: Homo sapiens

<400> SEQUENCE: 46

cttttcccgg cacatgcgca ccgcagcggg tcgcgcgccc taaggagtgg cactttttaa      60

aagtgcagcc ggagaccagc ctacagccgc ctgcatctgt atccagcgcc aggtcccgcc     120

agtcccagct gcgcgcgccc cccagtcccg cacccgttcg gcccaggcta agttagccct     180

caccatgccg gtcaaaggag gcaccaagtg catcaaatac ctgctgttcg gatttaactt     240

catcttctgg cttgccggga ttgctgtcct tgccattgga ctatggctcc gattcgactc     300

tcagaccaag agcatcttcg agcaagaaac taataataat aattccagct tctacacagg     360

agtctatatt ctgatcggag ccggcgccct catgatgctg gtgggcttcc tgggctgctg     420

cggggctgtg caggagtccc agtgcatgct gggactgttc ttcggcttcc tcttggtgat     480

attcgccatt gaaatagctg cggccatctg gggatattcc cacaaggatg aggtgattaa     540

ggaagtccag gagttttaca aggacaccta caacaagctg aaaaccaagg atgagcccca     600

gcgggaaacg ctgaaagcca tccactatgc gttgaactgc tgtggtttgg ctgggggcgt     660

ggaacagttt atctcagaca tctgccccaa gaaggacgta ctcgaaacct tcaccgtgaa     720

gtcctgtcct gatgccatca aagaggtctt cgacaataaa ttccacatca tcggcgcagt     780

gggcatcggc attgccgtgg tcatgatatt tggcatgatc ttcagtatga tcttgtgctg     840

tgctatccgc aggaaccgcg agatggtcta gagtcagctt acatccctga gcaggaaagt     900

ttacccatga agattggtgg gatttttttgt ttgtttgttt tgttttgttt gttgtttgtt     960

gtttgttttt ttgccactaa ttttagtatt cattctgcat tgctagataa aagctgaagt    1020
```

tactttatgt ttgtctttta atgcttcatt caatattgac atttgtagtt gagcgggggg 1080
tttggtttgc tttggtttat attttttcag ttgtttgttt ttgcttgtta tattaagcag 1140
aaatcctgca atgaaaggta ctatatttgc tagactctag acaagatatt gtacataaaa 1200
gaattttttt gtctttaaat agatacaaat gtctatcaac tttaatcaag ttgtaactta 1260
tattgaagac aatttgatac ataataaaaa attatgacaa tgtcctggac tggtaaaaaa 1320
a 1321

<210> SEQ ID NO 47
<211> LENGTH: 228
<212> TYPE: PRT
<213> ORGANISM: Homo sapiens

<400> SEQUENCE: 47

Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
            20                  25                  30

Leu Trp Leu Arg Phe Asp Ser Gln Thr Lys Ser Ile Phe Glu Gln Glu
        35                  40                  45

Thr Asn Asn Asn Asn Ser Ser Phe Tyr Thr Gly Val Tyr Ile Leu Ile
    50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ala Ile Trp Gly Tyr Ser
            100                 105                 110

His Lys Asp Glu Val Ile Lys Glu Val Gln Glu Phe Tyr Lys Asp Thr
        115                 120                 125

Tyr Asn Lys Leu Lys Thr Lys Asp Glu Pro Gln Arg Glu Thr Leu Lys
    130                 135                 140

Ala Ile His Tyr Ala Leu Asn Cys Cys Gly Leu Ala Gly Gly Val Glu
145                 150                 155                 160

Gln Phe Ile Ser Asp Ile Cys Pro Lys Lys Asp Val Leu Glu Thr Phe
                165                 170                 175

Thr Val Lys Ser Cys Pro Asp Ala Ile Lys Glu Val Phe Asp Asn Lys
            180                 185                 190

Phe His Ile Ile Gly Ala Val Gly Ile Gly Ile Ala Val Val Met Ile
        195                 200                 205

Phe Gly Met Ile Phe Ser Met Ile Leu Cys Cys Ala Ile Arg Arg Asn
    210                 215                 220

Arg Glu Met Val
225

<210> SEQ ID NO 48
<211> LENGTH: 735
<212> TYPE: DNA
<213> ORGANISM: Homo sapiens

<400> SEQUENCE: 48
gatatccaga tgacacagac aacctcaagt cttagtgcat cactgggaga tcgtgtgact 60
ataagctgcc gcgcatcaca ggacattcgc aattatctga attggtatca acagaagcct 120
gatggcaccg tgaaacttct gatctattac accagtcgtc tgcatagcgg tgttccgagc 180

```
aaattttcag gctcagggtc aggaaccgat tattcactga cgattagtaa tttagaacaa    240

gaagatattg caacctattt ctgtcaacag ggtaataccc tgccgtggac ctttgcaggt    300

ggtaccaaac tggaaattaa aggaggtggc agtggagggg gaagcggcgg cggttcagga    360

ggcggttctg aggtccagtt acagcagagc ggtccggaac tggttaaacc gggtgcaagc    420

atgaaaatta gctgtaaagc aagcggttat agctttaccg gttataccat gaattgggtt    480

aaacagagcc atggtaaaaa tctggaatgg atgggtctga ttaatccgta taaaggtgtt    540

agcacctata atcagaaatt taaagataaa gcaaccctga ccgttgataa aagcagcagc    600

accgcatata tggaactgct gagcctgacc agcgaagata gcgccgttta ctattgcgca    660

cgcagcggtt attatggtga tagcgattgg tattttgatg tttggggtgc aggtaccacc    720

gttaccgtta gcagc                                                     735

<210> SEQ ID NO 49
<211> LENGTH: 732
<212> TYPE: DNA
<213> ORGANISM: Homo sapiens

<400> SEQUENCE: 49

gacatccaga tgacccagtc tccatcctcc ctgtctgcat ctgtaggaga cagagtcacc     60

atcacttgcc gggcaagtca ggatgtgaat accgcggtcg catggtatca gcagaaacca    120

gggaaagccc ctaagctcct gatctattct gcatccttct tgtatagtgg ggtcccatca    180

aggttcagtg gcagtaggtc tgggacagat ttcactctca ccatcagcag tctgcaacct    240

gaagattttg caacttacta ctgtcaacag cattacacta cccctccgac gttcggccaa    300

ggtaccaagg tggagatcaa acgaactggc tctaccagcg gaagcggaaa gcctggcagc    360

ggcgagggct ccgaagtgca gctggtggag tctggcggag gactggtgca gccagggggc    420

agcctgagac tgtcttgcgc cgcctccggc ttcaacatca aggacaccta catccactgg    480

gtccgccagg caccaggcaa gggactggaa tgggtggccc ggatctaccc taccaacggc    540

tacaccagat acgccgactc cgtgaagggc cggttcacca tctccgccga cacctccaag    600

aacaccgcct acctgcaaat gaactccctg agggccgagg acaccgccgt gtactactgc    660

tccagatggg gaggcgacgg cttctacgca atggactact ggggccaggg caccctggtc    720

acagtgtcct ct                                                        732

<210> SEQ ID NO 50
<211> LENGTH: 723
<212> TYPE: DNA
<213> ORGANISM: Homo sapiens

<400> SEQUENCE: 50

caggtgcagc tgaagcagtc tggccctgga ctggtgcagc ctagccagag cctgagcatc     60

acctgtaccg tgtccggctt cagcctgacc aactacggcg tgcactgggt gcgacagagc    120

cctggcaaag gcctggaatg gctgggagtg atttggagcg gcggcaacac cgactacaac    180

acccccttca ccagcagact gtccatcaac aaggacaaca gcaagagcca ggtgttcttc    240

aagatgaaca gcctgcagag caacgacacc gccatctact actgcgctag agccctgacc    300

tactatgact acgagttcgc ctactggggc cagggcacac tcgtgacagt gtctgccggc    360

ggaggtggat ctggaggcgg tggcagcggt ggaggcggat ctgacatcct gctgacccag    420

agccccgtga tcctgtccgt gtctcctggc gagagagtgt ccttcagctg cagagccagc    480
```

```
cagagcatcg gcaccaacat ccactggtat cagcagagga ccaacggcag ccccagactg    540

ctgattaagt acgccagcga gtccatcagc ggcatcccca gcagattcag cggcagcggc    600

tctggcaccg acttcaccct gagcatcaac agcgtggaaa gcgaggatat cgccgactac    660

tactgccagc agaacaacaa ctggcccacc accttcggcg ctggcaccaa gctggaactg    720

aag                                                                   723


<210> SEQ ID NO 51
<211> LENGTH: 1225
<212> TYPE: PRT
<213> ORGANISM: Homo sapiens

<400> SEQUENCE: 51

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
```

```
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
    450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525

His Cys Leu Pro Cys His Pro Glu Cys Gln Pro Gln Asn Gly Ser Val
    530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser Cys Val Asp Leu Asp
        595                 600                 605

Asp Lys Gly Cys Pro Ala Glu Gln Arg Ala Ser Pro Leu Thr Ser Ile
    610                 615                 620

Ile Ser Ala Val Val Gly Ile Leu Leu Val Val Val Leu Gly Val Val
625                 630                 635                 640

Phe Gly Ile Leu Ile Lys Arg Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
        675                 680                 685

Glu Leu Arg Lys Val Lys Val Leu Gly Ser Gly Ala Phe Gly Thr Val
    690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750
```

```
Ser Arg Leu Leu Gly Ile Cys Leu Thr Ser Thr Val Gln Leu Val Thr
      755                760                765

Gln Leu Met Pro Tyr Gly Cys Leu Leu Asp His Val Arg Glu Asn Arg
    770                775                780

Gly Arg Leu Gly Ser Gln Asp Leu Leu Asn Trp Cys Met Gln Ile Ala
785                790                795                800

Lys Gly Met Ser Tyr Leu Glu Asp Val Arg Leu Val His Arg Asp Leu
                805                810                815

Ala Ala Arg Asn Val Leu Val Lys Ser Pro Asn His Val Lys Ile Thr
            820                825                830

Asp Phe Gly Leu Ala Arg Leu Leu Asp Ile Asp Glu Thr Glu Tyr His
        835                840                845

Ala Asp Gly Gly Lys Val Pro Ile Lys Trp Met Ala Leu Glu Ser Ile
    850                855                860

Leu Arg Arg Arg Phe Thr His Gln Ser Asp Val Trp Ser Tyr Gly Val
865                870                875                880

Thr Val Trp Glu Leu Met Thr Phe Gly Ala Lys Pro Tyr Asp Gly Ile
                885                890                895

Pro Ala Arg Glu Ile Pro Asp Leu Leu Glu Lys Gly Glu Arg Leu Pro
            900                905                910

Gln Pro Pro Ile Cys Thr Ile Asp Val Tyr Met Ile Met Val Lys Cys
        915                920                925

Trp Met Ile Asp Ser Glu Cys Arg Pro Arg Phe Arg Glu Leu Val Ser
    930                935                940

Glu Phe Ser Arg Met Ala Arg Asp Pro Gln Arg Phe Val Val Ile Gln
945                950                955                960

Asn Glu Asp Leu Gly Pro Ala Ser Pro Leu Asp Ser Thr Phe Tyr Arg
                965                970                975

Ser Leu Leu Glu Asp Asp Asp Met Gly Asp Leu Val Asp Ala Glu Glu
            980                985                990

Tyr Leu Val Pro Gln Gln Gly Phe  Phe Cys Pro Asp Pro  Ala Pro Gly
        995                1000                1005

Ala Gly  Gly Met Val His His  Arg His Arg Ser Ser  Ser Thr Arg
    1010                1015                1020

Ser Gly  Gly Gly Asp Leu Thr  Leu Gly Leu Glu Pro  Ser Glu Glu
    1025                1030                1035

Glu Ala  Pro Arg Ser Pro Leu  Ala Pro Ser Glu Gly  Ala Gly Ser
    1040                1045                1050

Asp Val  Phe Asp Gly Asp Leu  Gly Met Gly Ala Ala  Lys Gly Leu
    1055                1060                1065

Gln Ser  Leu Pro Thr His Asp  Pro Ser Pro Leu Gln  Arg Tyr Ser
    1070                1075                1080

Glu Asp  Pro Thr Val Pro Leu  Pro Ser Glu Thr Asp  Gly Tyr Val
    1085                1090                1095

Ala Pro  Leu Thr Cys Ser Pro  Gln Pro Glu Tyr Val  Asn Gln Pro
    1100                1105                1110

Asp Val  Arg Pro Gln Pro Pro  Ser Pro Arg Glu Gly  Pro Leu Pro
    1115                1120                1125

Ala Ala  Arg Pro Ala Gly Ala  Thr Leu Glu Arg Pro  Lys Thr Leu
    1130                1135                1140

Ser Pro  Gly Lys Asn Gly Val  Val Lys Asp Val Phe  Ala Phe Gly
    1145                1150                1155
```

```
Gly Ala  Val Glu Asn Pro Glu  Tyr Leu Thr Pro Gln  Gly Gly Ala
    1160                 1165                 1170

Ala Pro  Gln Pro His Pro Pro  Pro Ala Phe Ser Pro  Ala Phe Asp
    1175                 1180                 1185

Asn Leu  Tyr Tyr Trp Asp Gln  Asp Pro Pro Glu Arg  Gly Ala Pro
    1190                 1195                 1200

Pro Ser  Thr Phe Lys Gly Thr  Pro Thr Ala Glu Asn  Pro Glu Tyr
    1205                 1210                 1215

Leu Gly  Leu Asp Val Pro Val
    1220                 1225


<210> SEQ ID NO 52
<211> LENGTH: 183
<212> TYPE: PRT
<213> ORGANISM: Homo sapiens

<400> SEQUENCE: 52

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Gly Gln Phe Pro
    130                 135                 140

Met Val Pro Ser Gly Leu Thr Pro Gln Pro Ala Gln Asp Trp Tyr Leu
145                 150                 155                 160

Leu Asp Asp Asp Pro Arg Leu Leu Thr Leu Ser Ala Ser Ser Lys Val
                165                 170                 175

Pro Val Thr Leu Ala Ala Val
            180


<210> SEQ ID NO 53
<211> LENGTH: 1091
<212> TYPE: PRT
<213> ORGANISM: Homo sapiens

<400> SEQUENCE: 53

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60
```

```
Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Gly Gln Lys
    130                 135                 140

Cys Asp Pro Ser Cys Pro Asn Gly Ser Cys Trp Gly Ala Gly Glu Glu
145                 150                 155                 160

Asn Cys Gln Lys Leu Thr Lys Ile Ile Cys Ala Gln Gln Cys Ser Gly
                165                 170                 175

Arg Cys Arg Gly Lys Ser Pro Ser Asp Cys Cys His Asn Gln Cys Ala
            180                 185                 190

Ala Gly Cys Thr Gly Pro Arg Glu Ser Asp Cys Leu Val Cys Arg Lys
        195                 200                 205

Phe Arg Asp Glu Ala Thr Cys Lys Asp Thr Cys Pro Pro Leu Met Leu
    210                 215                 220

Tyr Asn Pro Thr Thr Tyr Gln Met Asp Val Asn Pro Glu Gly Lys Tyr
225                 230                 235                 240

Ser Phe Gly Ala Thr Cys Val Lys Lys Cys Pro Arg Asn Tyr Val Val
                245                 250                 255

Thr Asp His Gly Ser Cys Val Arg Ala Cys Gly Ala Asp Ser Tyr Glu
            260                 265                 270

Met Glu Glu Asp Gly Val Arg Lys Cys Lys Lys Cys Glu Gly Pro Cys
        275                 280                 285

Arg Lys Val Cys Asn Gly Ile Gly Ile Gly Glu Phe Lys Asp Ser Leu
    290                 295                 300

Ser Ile Asn Ala Thr Asn Ile Lys His Phe Lys Asn Cys Thr Ser Ile
305                 310                 315                 320

Ser Gly Asp Leu His Ile Leu Pro Val Ala Phe Arg Gly Asp Ser Phe
                325                 330                 335

Thr His Thr Pro Pro Leu Asp Pro Gln Glu Leu Asp Ile Leu Lys Thr
            340                 345                 350

Val Lys Glu Ile Thr Gly Phe Leu Leu Ile Gln Ala Trp Pro Glu Asn
        355                 360                 365

Arg Thr Asp Leu His Ala Phe Glu Asn Leu Glu Ile Ile Arg Gly Arg
    370                 375                 380

Thr Lys Gln His Gly Gln Phe Ser Leu Ala Val Val Ser Leu Asn Ile
385                 390                 395                 400

Thr Ser Leu Gly Leu Arg Ser Leu Lys Glu Ile Ser Asp Gly Asp Val
                405                 410                 415

Ile Ile Ser Gly Asn Lys Asn Leu Cys Tyr Ala Asn Thr Ile Asn Trp
            420                 425                 430

Lys Lys Leu Phe Gly Thr Ser Gly Gln Lys Thr Lys Ile Ile Ser Asn
        435                 440                 445

Arg Gly Glu Asn Ser Cys Lys Ala Thr Gly Gln Val Cys His Ala Leu
    450                 455                 460

Cys Ser Pro Glu Gly Cys Trp Gly Pro Glu Pro Arg Asp Cys Val Ser
465                 470                 475                 480

Cys Arg Asn Val Ser Arg Gly Arg Glu Cys Val Asp Lys Cys Asn Leu
```

```
                485                 490                 495

Leu Glu Gly Glu Pro Arg Glu Phe Val Glu Asn Ser Glu Cys Ile Gln
            500                 505                 510

Cys His Pro Glu Cys Leu Pro Gln Ala Met Asn Ile Thr Cys Thr Gly
        515                 520                 525

Arg Gly Pro Asp Asn Cys Ile Gln Cys Ala His Tyr Ile Asp Gly Pro
    530                 535                 540

His Cys Val Lys Thr Cys Pro Ala Gly Val Met Gly Glu Asn Asn Thr
545                 550                 555                 560

Leu Val Trp Lys Tyr Ala Asp Ala Gly His Val Cys His Leu Cys His
                565                 570                 575

Pro Asn Cys Thr Tyr Gly Cys Thr Gly Pro Gly Leu Glu Gly Cys Pro
            580                 585                 590

Thr Asn Gly Pro Lys Ile Pro Ser Ile Ala Thr Gly Met Val Gly Ala
        595                 600                 605

Leu Leu Leu Leu Leu Val Val Ala Leu Gly Ile Gly Leu Phe Met Arg
    610                 615                 620

Arg Arg His Ile Val Arg Lys Arg Thr Leu Arg Arg Leu Leu Gln Glu
625                 630                 635                 640

Arg Glu Leu Val Glu Pro Leu Thr Pro Ser Gly Glu Ala Pro Asn Gln
                645                 650                 655

Ala Leu Leu Arg Ile Leu Lys Glu Thr Glu Phe Lys Lys Ile Lys Val
            660                 665                 670

Leu Gly Ser Gly Ala Phe Gly Thr Val Tyr Lys Gly Leu Trp Ile Pro
        675                 680                 685

Glu Gly Glu Lys Val Lys Ile Pro Val Ala Ile Lys Glu Leu Arg Glu
    690                 695                 700

Ala Thr Ser Pro Lys Ala Asn Lys Glu Ile Leu Asp Glu Ala Tyr Val
705                 710                 715                 720

Met Ala Ser Val Asp Asn Pro His Val Cys Arg Leu Leu Gly Ile Cys
                725                 730                 735

Leu Thr Ser Thr Val Gln Leu Ile Thr Gln Leu Met Pro Phe Gly Cys
            740                 745                 750

Leu Leu Asp Tyr Val Arg Glu His Lys Asp Asn Ile Gly Ser Gln Tyr
        755                 760                 765

Leu Leu Asn Trp Cys Val Gln Ile Ala Lys Gly Met Asn Tyr Leu Glu
    770                 775                 780

Asp Arg Arg Leu Val His Arg Asp Leu Ala Ala Arg Asn Val Leu Val
785                 790                 795                 800

Lys Thr Pro Gln His Val Lys Ile Thr Asp Phe Gly Leu Ala Lys Leu
                805                 810                 815

Leu Gly Ala Glu Glu Lys Glu Tyr His Ala Glu Gly Gly Lys Val Pro
            820                 825                 830

Ile Lys Trp Met Ala Leu Glu Ser Ile Leu His Arg Ile Tyr Thr His
        835                 840                 845

Gln Ser Asp Val Trp Ser Tyr Gly Val Thr Val Trp Glu Leu Met Thr
    850                 855                 860

Phe Gly Ser Lys Pro Tyr Asp Gly Ile Pro Ala Ser Glu Ile Ser Ser
865                 870                 875                 880

Ile Leu Glu Lys Gly Glu Arg Leu Pro Gln Pro Pro Ile Cys Thr Ile
                885                 890                 895

Asp Val Tyr Met Ile Met Val Lys Cys Trp Met Ile Asp Ala Asp Ser
            900                 905                 910
```

```
Arg Pro Lys Phe Arg Glu Leu Ile Ile Glu Phe Ser Lys Met Ala Arg
        915                 920                 925

Asp Pro Gln Arg Tyr Leu Val Ile Gln Gly Asp Glu Arg Met His Leu
    930                 935                 940

Pro Ser Pro Thr Asp Ser Asn Phe Tyr Arg Ala Leu Met Asp Glu Glu
945                 950                 955                 960

Asp Met Asp Asp Val Val Asp Ala Asp Glu Tyr Leu Ile Pro Gln Gln
                965                 970                 975

Gly Phe Phe Ser Ser Pro Ser Thr Ser Arg Thr Pro Leu Leu Ser Ser
            980                 985                 990

Leu Ser Ala Thr Ser Asn Asn Ser  Thr Val Ala Cys Ile  Asp Arg Asn
        995                 1000                 1005

Gly Leu  Gln Ser Cys Pro Ile  Lys Glu Asp Ser Phe  Leu Gln Arg
    1010                 1015                 1020

Tyr Ser  Ser Asp Pro Thr Gly  Ala Leu Thr Glu Asp  Ser Ile Asp
    1025                 1030                 1035

Asp Thr  Phe Leu Pro Val Pro  Gly Glu Trp Leu Val  Trp Lys Gln
    1040                 1045                 1050

Ser Cys  Ser Ser Thr Ser Ser  Thr His Ser Ala Ala  Ala Ser Leu
    1055                 1060                 1065

Gln Cys  Pro Ser Gln Val Leu  Pro Pro Ala Ser Pro  Glu Gly Glu
    1070                 1075                 1080

Thr Val  Ala Asp Leu Gln Thr  Gln
    1085                 1090
```

<210> SEQ ID NO 54
<211> LENGTH: 171
<212> TYPE: PRT
<213> ORGANISM: Homo sapiens

<400> SEQUENCE: 54

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

```
<210> SEQ ID NO 55
<211> LENGTH: 207
<212> TYPE: PRT
<213> ORGANISM: Homo sapiens

<400> SEQUENCE: 55

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205


<210> SEQ ID NO 56
<211> LENGTH: 182
<212> TYPE: PRT
<213> ORGANISM: Homo sapiens

<400> SEQUENCE: 56

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
```

130 135 140

Ser Arg Ala Ser Asp Lys Gln Thr Leu Leu Pro Asn Asp Gln Leu Tyr
145 150 155 160

Gln Pro Leu Lys Asp Arg Glu Asp Asp Gln Tyr Ser His Leu Gln Gly
165 170 175

Asn Gln Leu Arg Arg Asn
180

<210> SEQ ID NO 57
<211> LENGTH: 359
<212> TYPE: PRT
<213> ORGANISM: Homo sapiens

<400> SEQUENCE: 57

Met Ala Glu Gly Thr Leu Trp Gln Ile Leu Cys Val Ser Ser Asp Ala
1 5 10 15

Gln Pro Gln Thr Phe Glu Gly Val Lys Gly Ala Asp Pro Pro Thr Leu
20 25 30

Pro Pro Gly Ser Phe Leu Pro Gly Pro Val Leu Trp Trp Gly Ser Leu
35 40 45

Ala Arg Leu Gln Thr Glu Lys Ser Asp Glu Val Ser Arg Lys Gly Asn
50 55 60

Trp Trp Val Thr Glu Met Gly Gly Gly Ala Gly Glu Arg Leu Phe Thr
65 70 75 80

Ser Ser Cys Leu Val Gly Leu Val Pro Leu Gly Leu Arg Ile Ser Leu
85 90 95

Val Thr Cys Pro Leu Gln Cys Gly Ile Met Trp Gln Leu Leu Leu Pro
100 105 110

Thr Ala Leu Leu Leu Leu Val Ser Ala Gly Met Arg Thr Glu Asp Leu
115 120 125

Pro Lys Ala Val Val Phe Leu Glu Pro Gln Trp Tyr Arg Val Leu Glu
130 135 140

Lys Asp Ser Val Thr Leu Lys Cys Gln Gly Ala Tyr Ser Pro Glu Asp
145 150 155 160

Asn Ser Thr Gln Trp Phe His Asn Glu Ser Leu Ile Ser Ser Gln Ala
165 170 175

Ser Ser Tyr Phe Ile Asp Ala Ala Thr Val Asp Asp Ser Gly Glu Tyr
180 185 190

Arg Cys Gln Thr Asn Leu Ser Thr Leu Ser Asp Pro Val Gln Leu Glu
195 200 205

Val His Ile Gly Trp Leu Leu Leu Gln Ala Pro Arg Trp Val Phe Lys
210 215 220

Glu Glu Asp Pro Ile His Leu Arg Cys His Ser Trp Lys Asn Thr Ala
225 230 235 240

Leu His Lys Val Thr Tyr Leu Gln Asn Gly Lys Gly Arg Lys Tyr Phe
245 250 255

His His Asn Ser Asp Phe Tyr Ile Pro Lys Ala Thr Leu Lys Asp Ser
260 265 270

Gly Ser Tyr Phe Cys Arg Gly Leu Phe Gly Ser Lys Asn Val Ser Ser
275 280 285

Glu Thr Val Asn Ile Thr Ile Thr Gln Gly Leu Ala Val Ser Thr Ile
290 295 300

Ser Ser Phe Phe Pro Pro Gly Tyr Gln Val Ser Phe Cys Leu Val Met
305 310 315 320

```
Val Leu Leu Phe Ala Val Asp Thr Gly Leu Tyr Phe Ser Val Lys Thr
                325                 330                 335

Asn Ile Arg Ser Ser Thr Arg Asp Trp Lys Asp His Lys Phe Lys Trp
            340                 345                 350

Arg Lys Asp Pro Gln Asp Lys
        355


<210> SEQ ID NO 58
<211> LENGTH: 233
<212> TYPE: PRT
<213> ORGANISM: Homo sapiens

<400> SEQUENCE: 58

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Asn Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230


<210> SEQ ID NO 59
<211> LENGTH: 458
<212> TYPE: PRT
<213> ORGANISM: Homo sapiens

<400> SEQUENCE: 59

Met Asn Arg Gly Val Pro Phe Arg His Leu Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45
```

```
Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
                245                 250                 255

Lys Asn Lys Glu Val Ser Val Lys Arg Val Thr Gln Asp Pro Lys Leu
            260                 265                 270

Gln Met Gly Lys Lys Leu Pro Leu His Leu Thr Leu Pro Gln Ala Leu
        275                 280                 285

Pro Gln Tyr Ala Gly Ser Gly Asn Leu Thr Leu Ala Leu Glu Ala Lys
    290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Ala Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val Gln Pro Met Ala Leu Ile
385                 390                 395                 400

Val Leu Gly Gly Val Ala Gly Leu Leu Leu Phe Ile Gly Leu Gly Ile
                405                 410                 415

Phe Phe Cys Val Arg Cys Arg His Arg Arg Arg Gln Ala Glu Arg Met
            420                 425                 430

Ser Gln Ile Lys Arg Leu Leu Ser Glu Lys Lys Thr Cys Gln Cys Pro
        435                 440                 445

His Arg Phe Gln Lys Thr Cys Ser Pro Ile
    450                 455
```

```
<210> SEQ ID NO 60
<211> LENGTH: 235
<212> TYPE: PRT
<213> ORGANISM: Homo sapiens

<400> SEQUENCE: 60

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235


<210> SEQ ID NO 61
<211> LENGTH: 198
<212> TYPE: PRT
<213> ORGANISM: Homo sapiens

<400> SEQUENCE: 61

Met Arg Pro Arg Leu Trp Leu Leu Leu Ala Ala Gln Leu Thr Val Leu
1               5                   10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

Ser His His Glu Phe Leu Ala Leu Trp Asp Ser Ala Lys Gly Thr Ile
65                  70                  75                  80

His Gly Glu Glu Val Glu Gln Glu Lys Ile Ala Val Phe Arg Asp Ala
                85                  90                  95

Ser Arg Phe Ile Leu Asn Leu Thr Ser Val Lys Pro Glu Asp Ser Gly
```

```
            100                 105                 110

Ile Tyr Phe Cys Met Ile Val Gly Ser Pro Glu Leu Thr Phe Gly Lys
        115                 120                 125

Gly Thr Gln Leu Ser Val Val Asp Phe Leu Pro Thr Thr Ala Gln Pro
    130                 135                 140

Thr Lys Lys Ser Thr Leu Lys Lys Arg Val Cys Arg Leu Pro Arg Pro
145                 150                 155                 160

Glu Thr Gln Lys Gly Leu Lys Gly Lys Val Tyr Gln Glu Pro Leu Ser
                165                 170                 175

Pro Asn Ala Cys Met Asp Thr Thr Ala Ile Leu Gln Pro His Arg Ser
            180                 185                 190

Cys Leu Thr His Gly Ser
        195


<210> SEQ ID NO 62
<211> LENGTH: 1086
<212> TYPE: PRT
<213> ORGANISM: Homo sapiens

<400> SEQUENCE: 62

Met Lys Asp Ser Cys Ile Thr Val Met Ala Met Ala Leu Leu Ser Gly
1               5                   10                  15

Phe Phe Phe Phe Ala Pro Ala Ser Ser Tyr Asn Leu Asp Val Arg Gly
            20                  25                  30

Ala Arg Ser Phe Ser Pro Pro Arg Ala Gly Arg His Phe Gly Tyr Arg
        35                  40                  45

Val Leu Gln Val Gly Asn Gly Val Ile Val Gly Ala Pro Gly Glu Gly
    50                  55                  60

Asn Ser Thr Gly Ser Leu Tyr Gln Cys Gln Ser Gly Thr Gly His Cys
65                  70                  75                  80

Leu Pro Val Thr Leu Arg Gly Ser Asn Tyr Thr Ser Lys Tyr Leu Gly
                85                  90                  95

Met Thr Leu Ala Thr Asp Pro Thr Asp Gly Ser Ile Leu Phe Ala Ala
            100                 105                 110

Val Gln Phe Ser Thr Ser Tyr Lys Thr Glu Phe Asp Phe Ser Asp Tyr
        115                 120                 125

Val Lys Arg Lys Asp Pro Asp Ala Leu Leu Lys His Val Lys His Met
    130                 135                 140

Leu Leu Leu Thr Asn Thr Phe Gly Ala Ile Asn Tyr Val Ala Thr Glu
145                 150                 155                 160

Val Phe Arg Glu Glu Leu Gly Ala Arg Pro Asp Ala Thr Lys Val Leu
                165                 170                 175

Ile Ile Ile Thr Asp Gly Glu Ala Thr Asp Ser Gly Asn Ile Asp Ala
            180                 185                 190

Ala Lys Asp Ile Ile Arg Tyr Ile Ile Gly Ile Gly Lys His Phe Gln
        195                 200                 205

Thr Lys Glu Ser Gln Glu Thr Leu His Lys Phe Ala Ser Lys Pro Ala
    210                 215                 220

Ser Glu Phe Val Lys Ile Leu Asp Thr Phe Glu Lys Leu Lys Asp Leu
225                 230                 235                 240

Phe Thr Glu Leu Gln Lys Lys Ile Tyr Val Ile Glu Gly Thr Ser Lys
                245                 250                 255

Gln Asp Leu Thr Ser Phe Asn Met Glu Leu Ser Ser Ser Gly Ile Ser
            260                 265                 270
```

```
Ala Asp Leu Ser Arg Gly His Ala Val Val Gly Ala Val Gly Ala Lys
        275                 280                 285

Asp Trp Ala Gly Gly Phe Leu Asp Leu Lys Ala Asp Leu Gln Asp Asp
    290                 295                 300

Thr Phe Ile Gly Asn Glu Pro Leu Thr Pro Glu Val Arg Ala Gly Tyr
305                 310                 315                 320

Leu Gly Tyr Thr Val Thr Trp Leu Pro Ser Arg Gln Lys Thr Ser Leu
                325                 330                 335

Leu Ala Ser Gly Ala Pro Arg Tyr Gln His Met Gly Arg Val Leu Leu
            340                 345                 350

Phe Gln Glu Pro Gln Gly Gly Gly His Trp Ser Gln Val Gln Thr Ile
        355                 360                 365

His Gly Thr Gln Ile Gly Ser Tyr Phe Gly Gly Glu Leu Cys Gly Val
    370                 375                 380

Asp Val Asp Gln Asp Gly Glu Thr Glu Leu Leu Leu Ile Gly Ala Pro
385                 390                 395                 400

Leu Phe Tyr Gly Glu Gln Arg Gly Gly Arg Val Phe Ile Tyr Gln Arg
                405                 410                 415

Arg Gln Leu Gly Phe Glu Glu Val Ser Glu Leu Gln Gly Asp Pro Gly
            420                 425                 430

Tyr Pro Leu Gly Arg Phe Gly Glu Ala Ile Thr Ala Leu Thr Asp Ile
        435                 440                 445

Asn Gly Asp Gly Leu Val Asp Val Ala Val Gly Ala Pro Leu Glu Glu
    450                 455                 460

Gln Gly Ala Val Tyr Ile Phe Asn Gly Arg His Gly Gly Leu Ser Pro
465                 470                 475                 480

Gln Pro Ser Gln Arg Ile Glu Gly Thr Gln Val Leu Ser Gly Ile Gln
                485                 490                 495

Trp Phe Gly Arg Ser Ile His Gly Val Lys Asp Leu Glu Gly Asp Gly
            500                 505                 510

Leu Ala Asp Val Ala Val Gly Ala Glu Ser Gln Met Ile Val Leu Ser
        515                 520                 525

Ser Arg Pro Val Val Asp Met Val Thr Leu Met Ser Phe Ser Pro Ala
    530                 535                 540

Glu Ile Pro Val His Glu Val Glu Cys Ser Tyr Ser Thr Ser Asn Lys
545                 550                 555                 560

Met Lys Glu Gly Val Asn Ile Thr Ile Cys Phe Gln Ile Lys Ser Leu
                565                 570                 575

Ile Pro Gln Phe Gln Gly Arg Leu Val Ala Asn Leu Thr Tyr Thr Leu
            580                 585                 590

Gln Leu Asp Gly His Arg Thr Arg Arg Arg Gly Leu Phe Pro Gly Gly
        595                 600                 605

Arg His Glu Leu Arg Arg Asn Ile Ala Val Thr Thr Ser Met Ser Cys
    610                 615                 620

Thr Asp Phe Ser Phe His Phe Pro Val Cys Val Gln Asp Leu Ile Ser
625                 630                 635                 640

Pro Ile Asn Val Ser Leu Asn Phe Ser Leu Trp Glu Glu Glu Gly Thr
                645                 650                 655

Pro Arg Asp Gln Arg Ala Gly Lys Asp Ile Pro Pro Ile Leu Arg Pro
            660                 665                 670

Ser Leu His Ser Glu Thr Trp Glu Ile Pro Phe Glu Lys Asn Cys Gly
        675                 680                 685

Glu Asp Lys Lys Cys Glu Ala Asn Leu Arg Val Ser Phe Ser Pro Ala
```

```
    690                 695                 700

Arg Ser Arg Ala Leu Arg Leu Thr Ala Phe Ala Ser Leu Ser Val Glu
705                 710                 715                 720

Leu Ser Leu Ser Asn Leu Glu Glu Asp Ala Tyr Trp Val Gln Leu Asp
                725                 730                 735

Leu His Phe Pro Pro Gly Leu Ser Phe Arg Lys Val Glu Met Leu Lys
            740                 745                 750

Pro His Ser Gln Ile Pro Val Ser Cys Glu Glu Leu Pro Glu Glu Ser
        755                 760                 765

Arg Leu Leu Ser Arg Ala Leu Ser Cys Asn Val Ser Ser Pro Ile Phe
    770                 775                 780

Lys Ala Gly His Ser Val Ala Leu Gln Met Met Phe Asn Thr Leu Val
785                 790                 795                 800

Asn Ser Ser Trp Gly Asp Ser Val Glu Leu His Ala Asn Val Thr Cys
                805                 810                 815

Asn Asn Glu Asp Ser Asp Leu Leu Glu Asp Asn Ser Ala Thr Thr Ile
            820                 825                 830

Ile Pro Ile Leu Tyr Pro Ile Asn Ile Leu Ile Gln Asp Gln Glu Asp
        835                 840                 845

Ser Thr Leu Tyr Val Ser Phe Thr Pro Lys Gly Pro Lys Ile His Gln
    850                 855                 860

Val Lys His Met Tyr Gln Val Arg Ile Gln Pro Ser Ile His Asp His
865                 870                 875                 880

Asn Ile Pro Thr Leu Glu Ala Val Val Gly Val Pro Gln Pro Pro Ser
                885                 890                 895

Glu Gly Pro Ile Thr His Gln Trp Ser Val Gln Met Glu Pro Pro Val
            900                 905                 910

Pro Cys His Tyr Glu Asp Leu Glu Arg Leu Pro Asp Ala Ala Glu Pro
        915                 920                 925

Cys Leu Pro Gly Ala Leu Phe Arg Cys Pro Val Val Phe Arg Gln Glu
    930                 935                 940

Ile Leu Val Gln Val Ile Gly Thr Leu Glu Leu Val Gly Glu Ile Glu
945                 950                 955                 960

Ala Ser Ser Met Phe Ser Leu Cys Ser Ser Leu Ser Ile Ser Phe Asn
                965                 970                 975

Ser Ser Lys His Phe His Leu Tyr Gly Ser Asn Ala Ser Leu Ala Gln
            980                 985                 990

Val Val Met Lys Val Asp Val Val  Tyr Glu Lys Gln Met  Leu Tyr Leu
        995                 1000                 1005

Tyr Val  Leu Ser Gly Ile Gly  Gly Leu Leu Leu Leu  Leu Leu Ile
    1010                 1015                 1020

Phe Ile  Val Leu Tyr Lys Val  Gly Phe Phe Lys Arg  Asn Leu Lys
    1025                 1030                 1035

Glu Lys  Met Glu Ala Gly Arg  Gly Val Pro Asn Gly  Ile Pro Ala
    1040                 1045                 1050

Glu Asp  Ser Glu Gln Leu Ala  Ser Gly Gln Glu Ala  Gly Asp Pro
    1055                 1060                 1065

Gly Cys  Leu Lys Pro Leu His  Glu Lys Asp Ser Glu  Ser Gly Gly
    1070                 1075                 1080

Gly Lys  Asp
    1085
```

<210> SEQ ID NO 63

```
<211> LENGTH: 557
<212> TYPE: PRT
<213> ORGANISM: Homo sapiens

<400> SEQUENCE: 63

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
            340                 345                 350

Ser Leu Pro Thr Pro Thr Ser Gly Leu Gly Arg Ala Gln Arg Trp Ala
        355                 360                 365

Ala Gly Leu Gly Gly Thr Ala Pro Ser Tyr Gly Asn Pro Ser Ser Asp
    370                 375                 380

Val Gln Ala Asp Gly Ala Leu Gly Ser Arg Ser Pro Pro Gly Val Gly
```

```
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
            420                 425                 430

Ser Gln Asp Gly Ser Gly Tyr Glu Asn Pro Glu Asp Glu Pro Leu Gly
        435                 440                 445

Pro Glu Asp Glu Asp Ser Phe Ser Asn Ala Glu Ser Tyr Glu Asn Glu
    450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Ala
                485                 490                 495

Gly Ser Gln Ser Tyr Glu Asp Met Arg Gly Ile Leu Tyr Ala Ala Pro
            500                 505                 510

Gln Leu Arg Ser Ile Arg Gly Gln Pro Gly Pro Asn His Glu Glu Asp
        515                 520                 525

Ala Asp Ser Tyr Glu Asn Met Asp Asn Pro Asp Gly Pro Asp Pro Ala
    530                 535                 540

Trp Gly Gly Gly Gly Arg Met Gly Thr Trp Ser Thr Arg
545                 550                 555


<210> SEQ ID NO 64
<211> LENGTH: 297
<212> TYPE: PRT
<213> ORGANISM: Homo sapiens

<400> SEQUENCE: 64

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205
```

```
Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295


<210> SEQ ID NO 65
<211> LENGTH: 272
<212> TYPE: PRT
<213> ORGANISM: Homo sapiens

<400> SEQUENCE: 65

Met Asp Ser Tyr Leu Leu Met Trp Gly Leu Leu Thr Phe Ile Met Val
1               5                   10                  15

Pro Gly Cys Gln Ala Glu Leu Cys Asp Asp Asp Pro Pro Glu Ile Pro
            20                  25                  30

His Ala Thr Phe Lys Ala Met Ala Tyr Lys Glu Gly Thr Met Leu Asn
        35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205

Ser Glu Thr Ser Cys Leu Val Thr Thr Thr Asp Phe Gln Ile Gln Thr
    210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270


<210> SEQ ID NO 66
```

<211> LENGTH: 237
<212> TYPE: PRT
<213> ORGANISM: Homo sapiens

<400> SEQUENCE: 66

```
Met Pro Leu Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gln Asn Pro Thr
            100                 105                 110

Thr Gly Ile Phe Pro Gly Asp Gly Ser Gly Lys Gln Glu Thr Arg Ala
        115                 120                 125

Gly Val Val His Gly Ala Ile Gly Gly Ala Gly Val Thr Ala Leu Leu
    130                 135                 140

Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

Gly Ser Ala Ser Pro Lys His Gln Lys Lys Ser Lys Leu His Gly Pro
            180                 185                 190

Thr Glu Thr Ser Ser Cys Ser Gly Ala Ala Pro Thr Val Glu Met Asp
        195                 200                 205

Glu Glu Leu His Tyr Ala Ser Leu Asn Phe His Gly Met Asn Pro Ser
    210                 215                 220

Lys Asp Thr Ser Thr Glu Tyr Ser Glu Val Arg Thr Gln
225                 230                 235
```

<210> SEQ ID NO 67
<211> LENGTH: 277
<212> TYPE: PRT
<213> ORGANISM: Homo sapiens

<400> SEQUENCE: 67

```
Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110
```

```
Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
        275


<210> SEQ ID NO 68
<211> LENGTH: 261
<212> TYPE: PRT
<213> ORGANISM: Homo sapiens

<400> SEQUENCE: 68

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
```

```
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260


<210> SEQ ID NO 69
<211> LENGTH: 193
<212> TYPE: PRT
<213> ORGANISM: Homo sapiens

<400> SEQUENCE: 69

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro


<210> SEQ ID NO 70
<211> LENGTH: 300
<212> TYPE: PRT
<213> ORGANISM: Homo sapiens

<400> SEQUENCE: 70

Met Val Leu Leu Trp Leu Thr Leu Leu Leu Ile Ala Leu Pro Cys Leu
1               5                   10                  15

Leu Gln Thr Lys Glu Gly Gly Lys Pro Trp Ala Gly Ala Glu Asn Leu
            20                  25                  30

Thr Cys Trp Ile His Asp Val Asp Phe Leu Ser Cys Ser Trp Ala Val
        35                  40                  45

Gly Pro Gly Ala Pro Ala Asp Val Gln Tyr Asp Leu Tyr Leu Asn Val
    50                  55                  60
```

```
Ala Asn Arg Arg Gln Gln Tyr Glu Cys Leu His Tyr Lys Thr Asp Ala
65                  70                  75                  80

Gln Gly Thr Arg Ile Gly Cys Arg Phe Asp Asp Ile Ser Arg Leu Ser
                85                  90                  95

Ser Gly Ser Gln Ser Ser His Ile Leu Val Arg Gly Arg Ser Ala Ala
            100                 105                 110

Phe Gly Ile Pro Cys Thr Asp Lys Phe Val Val Phe Ser Gln Ile Glu
        115                 120                 125

Ile Leu Thr Pro Pro Asn Met Thr Ala Lys Cys Asn Lys Thr His Ser
    130                 135                 140

Phe Met His Trp Lys Met Arg Ser His Phe Asn Arg Lys Phe Arg Tyr
145                 150                 155                 160

Glu Leu Gln Ile Gln Lys Arg Met Gln Pro Val Ile Thr Glu Gln Val
                165                 170                 175

Arg Asp Arg Thr Ser Phe Gln Leu Leu Asn Pro Gly Thr Tyr Thr Val
            180                 185                 190

Gln Ile Arg Ala Arg Glu Arg Val Tyr Glu Phe Leu Ser Ala Trp Ser
        195                 200                 205

Thr Pro Gln Arg Phe Glu Cys Asp Gln Glu Glu Gly Ala Asn Thr Arg
    210                 215                 220

Ala Trp Arg Thr Ser Leu Leu Ile Ala Leu Gly Thr Leu Leu Ala Leu
225                 230                 235                 240

Val Cys Val Phe Val Ile Cys Arg Arg Tyr Leu Val Met Gln Arg Leu
                245                 250                 255

Phe Pro Arg Ile Pro His Met Lys Asp Pro Ile Gly Asp Ser Phe Gln
            260                 265                 270

Asn Asp Lys Leu Val Val Trp Glu Ala Gly Lys Ala Gly Leu Glu Glu
        275                 280                 285

Cys Leu Val Thr Glu Val Gln Val Val Gln Lys Thr
    290                 295                 300


<210> SEQ ID NO 71
<211> LENGTH: 314
<212> TYPE: PRT
<213> ORGANISM: Homo sapiens

<400> SEQUENCE: 71

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
```

```
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
    210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
        275                 280                 285

Ser Arg Lys Lys Arg Met Ala Lys Tyr Glu Lys Ala Glu Ile Lys Glu
    290                 295                 300

Met Gly Glu Met His Arg Glu Leu Asn Ala
305                 310


<210> SEQ ID NO 72
<211> LENGTH: 275
<212> TYPE: PRT
<213> ORGANISM: Homo sapiens

<400> SEQUENCE: 72

Met Trp Ile Asp Phe Phe Thr Tyr Ser Ser Met Ser Glu Glu Val Thr
1               5                   10                  15

Tyr Ala Asp Leu Gln Phe Gln Asn Ser Ser Glu Met Glu Lys Ile Pro
            20                  25                  30

Glu Ile Gly Lys Phe Gly Glu Lys Ala Pro Pro Ala Pro Ser His Val
        35                  40                  45

Trp Arg Pro Ala Ala Leu Phe Leu Thr Leu Leu Cys Leu Leu Leu Leu
    50                  55                  60

Ile Gly Leu Gly Val Leu Ala Ser Met Phe His Val Thr Leu Lys Ile
65                  70                  75                  80

Glu Met Lys Lys Met Asn Lys Leu Gln Asn Ile Ser Glu Glu Leu Gln
                85                  90                  95

Arg Asn Ile Ser Leu Gln Leu Met Ser Asn Met Asn Ile Ser Asn Lys
            100                 105                 110

Ile Arg Asn Leu Ser Thr Thr Leu Gln Thr Ile Ala Thr Lys Leu Cys
        115                 120                 125

Arg Glu Leu Tyr Ser Lys Glu Gln Glu His Lys Cys Lys Pro Cys Pro
    130                 135                 140

Arg Arg Trp Ile Trp His Lys Asp Ser Cys Tyr Phe Leu Ser Asp Asp
145                 150                 155                 160

Val Gln Thr Trp Gln Glu Ser Lys Met Ala Cys Ala Ala Gln Asn Ala
                165                 170                 175

Ser Leu Leu Lys Ile Asn Asn Lys Asn Ala Leu Glu Phe Ile Lys Ser
            180                 185                 190
```

```
Gln Ser Arg Ser Tyr Asp Tyr Trp Leu Gly Leu Ser Pro Glu Glu Asp
        195                 200                 205

Ser Thr Arg Gly Met Arg Val Asp Asn Ile Ile Asn Ser Ser Ala Trp
    210                 215                 220

Val Ile Arg Asn Ala Pro Asp Leu Asn Asn Met Tyr Cys Gly Tyr Ile
225                 230                 235                 240

Asn Arg Leu Tyr Val Gln Tyr Tyr His Cys Thr Tyr Lys Lys Arg Met
                245                 250                 255

Ile Cys Glu Lys Met Ala Asn Pro Val Gln Leu Gly Ser Thr Tyr Phe
            260                 265                 270

Arg Glu Ala
        275


<210> SEQ ID NO 73
<211> LENGTH: 174
<212> TYPE: PRT
<213> ORGANISM: Homo sapiens

<400> SEQUENCE: 73

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Ala Lys Glu Lys Lys Pro Ser Tyr
145                 150                 155                 160

Asn Arg Gly Leu Cys Glu Asn Ala Pro Asn Arg Ala Arg Met
                165                 170


<210> SEQ ID NO 74
<211> LENGTH: 288
<212> TYPE: PRT
<213> ORGANISM: Homo sapiens

<400> SEQUENCE: 74

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60
```

```
Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 75
<211> LENGTH: 176
<212> TYPE: PRT
<213> ORGANISM: Homo sapiens

<400> SEQUENCE: 75

```
Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
            20                  25                  30

Val Thr Ser Glu His Glu Leu Thr Cys Gln Ala Glu Gly Tyr Pro Lys
        35                  40                  45

Ala Glu Val Ile Trp Thr Ser Ser Asp His Gln Val Leu Ser Gly Lys
    50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Thr Asn Glu Ile Phe Tyr Cys Thr
                85                  90                  95

Phe Arg Arg Leu Asp Pro Glu Glu Asn His Thr Ala Glu Leu Val Ile
            100                 105                 110

Pro Glu Leu Pro Leu Ala His Pro Pro Asn Glu Arg Thr His Leu Val
        115                 120                 125

Ile Leu Gly Ala Ile Leu Leu Cys Leu Gly Val Ala Leu Thr Phe Ile
    130                 135                 140

Phe Arg Leu Arg Lys Gly Arg Met Met Asp Val Lys Lys Cys Gly Ile
145                 150                 155                 160
```

```
Gln Asp Thr Asn Ser Lys Lys Gln Ser Asp Thr His Leu Glu Glu Thr
                165                 170                 175


<210> SEQ ID NO 76
<211> LENGTH: 277
<212> TYPE: PRT
<213> ORGANISM: Homo sapiens

<400> SEQUENCE: 76

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275


<210> SEQ ID NO 77
<211> LENGTH: 241
<212> TYPE: PRT
<213> ORGANISM: Homo sapiens

<400> SEQUENCE: 77

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30
```

```
Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
                85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175

Val Leu Leu Leu Thr Ser Ala Gln Leu Gly Leu His Ile Trp Gln Leu
            180                 185                 190

Arg Ser Gln Cys Met Trp Pro Arg Glu Thr Gln Leu Leu Leu Glu Val
        195                 200                 205

Pro Pro Ser Thr Glu Asp Ala Arg Ser Cys Gln Phe Pro Glu Glu Glu
    210                 215                 220

Arg Gly Glu Arg Ser Ala Glu Glu Lys Gly Arg Leu Gly Asp Leu Trp
225                 230                 235                 240

Val
```

<210> SEQ ID NO 78
<211> LENGTH: 199
<212> TYPE: PRT
<213> ORGANISM: Homo sapiens

<400> SEQUENCE: 78

```
Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160
```

```
Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195


<210> SEQ ID NO 79
<211> LENGTH: 534
<212> TYPE: PRT
<213> ORGANISM: Homo sapiens

<400> SEQUENCE: 79

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
```

```
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
            500                 505                 510

Ser Lys Thr Ala Leu Gln Pro Leu Lys His Ser Asp Ser Lys Glu Asp
        515                 520                 525

Asp Gly Gln Glu Ile Ala
    530
```

<210> SEQ ID NO 80
<211> LENGTH: 187
<212> TYPE: PRT
<213> ORGANISM: Homo sapiens

<400> SEQUENCE: 80

```
Met Phe Arg Gly Arg Thr Ala Val Phe Ala Asp Gln Val Ile Val Gly
1               5                   10                  15

Asn Ala Ser Leu Arg Leu Lys Asn Val Gln Leu Thr Asp Ala Gly Thr
            20                  25                  30

Tyr Lys Cys Tyr Ile Ile Thr Ser Lys Gly Lys Gly Asn Ala Asn Leu
        35                  40                  45

Glu Tyr Lys Thr Gly Ala Phe Ser Met Pro Glu Val Asn Val Asp Tyr
    50                  55                  60

Asn Ala Ser Ser Glu Thr Leu Arg Cys Glu Ala Pro Arg Trp Phe Pro
65                  70                  75                  80

Gln Pro Thr Val Val Trp Ala Ser Gln Val Asp Gln Gly Ala Asn Phe
                85                  90                  95

Ser Glu Val Ser Asn Thr Ser Phe Glu Leu Asn Ser Glu Asn Val Thr
            100                 105                 110

Met Lys Val Val Ser Val Leu Tyr Asn Val Thr Ile Asn Asn Thr Tyr
        115                 120                 125

Ser Cys Met Ile Glu Asn Asp Ile Ala Lys Ala Thr Gly Asp Ile Lys
    130                 135                 140

Val Thr Glu Ser Glu Ile Lys Arg Arg Ser His Leu Gln Leu Leu Asn
145                 150                 155                 160
```

```
Ser Lys Ala Ser Leu Cys Val Ser Ser Phe Phe Ala Ile Ser Trp Ala
            165                 170                 175

Leu Leu Pro Leu Ser Pro Tyr Leu Met Leu Lys
            180                 185


<210> SEQ ID NO 81
<211> LENGTH: 525
<212> TYPE: PRT
<213> ORGANISM: Homo sapiens

<400> SEQUENCE: 81

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350
```

```
Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525


<210> SEQ ID NO 82
<211> LENGTH: 301
<212> TYPE: PRT
<213> ORGANISM: Homo sapiens

<400> SEQUENCE: 82

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
```

```
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300


<210> SEQ ID NO 83
<211> LENGTH: 719
<212> TYPE: PRT
<213> ORGANISM: Homo sapiens

<400> SEQUENCE: 83

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270
```

```
Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Lys His Val Ile Tyr Ala Pro Ser Ser His Asn Lys Tyr Ala Gly Glu
            660                 665                 670

Ser Phe Pro Gly Ile Tyr Asp Ala Leu Phe Asp Ile Glu Ser Lys Val
        675                 680                 685

Asp Pro Ser Lys Ala Trp Gly Glu Val Lys Arg Gln Ile Tyr Val Ala
```

```
    690                 695                 700

Ala Phe Thr Val Gln Ala Ala Ala Glu Thr Leu Ser Glu Val Ala
705                 710                 715


<210> SEQ ID NO 84
<211> LENGTH: 461
<212> TYPE: PRT
<213> ORGANISM: Homo sapiens

<400> SEQUENCE: 84

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350
```

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 85
<211> LENGTH: 488
<212> TYPE: PRT
<213> ORGANISM: Homo sapiens

<400> SEQUENCE: 85

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

```
Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485
```

<210> SEQ ID NO 86
<211> LENGTH: 257
<212> TYPE: PRT
<213> ORGANISM: Homo sapiens

<400> SEQUENCE: 86

```
Met Ala Gln Arg Met Thr Thr Gln Leu Leu Leu Leu Leu Val Trp Val
1               5                   10                  15

Ala Val Val Gly Glu Ala Gln Thr Arg Ile Ala Trp Ala Arg Thr Glu
            20                  25                  30

Leu Leu Asn Val Cys Met Asn Ala Lys His His Lys Glu Lys Pro Gly
        35                  40                  45

Pro Glu Asp Lys Leu His Glu Gln Cys Arg Pro Trp Arg Lys Asn Ala
    50                  55                  60

Cys Cys Ser Thr Asn Thr Ser Gln Glu Ala His Lys Asp Val Ser Tyr
65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
    130                 135                 140

Asp Cys Arg Thr Ser Tyr Thr Cys Lys Ser Asn Trp His Lys Gly Trp
```

```
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Ala Met Ser Gly Ala Gly Pro Trp Ala
225                 230                 235                 240

Ala Trp Pro Phe Leu Leu Ser Leu Ala Leu Met Leu Leu Trp Leu Leu
                245                 250                 255

Ser


<210> SEQ ID NO 87
<211> LENGTH: 255
<212> TYPE: PRT
<213> ORGANISM: Homo sapiens

<400> SEQUENCE: 87

Met Val Trp Lys Trp Met Pro Leu Leu Leu Leu Leu Val Cys Val Ala
1               5                   10                  15

Thr Met Cys Ser Ala Gln Asp Arg Thr Asp Leu Leu Asn Val Cys Met
            20                  25                  30

Asp Ala Lys His His Lys Thr Lys Pro Gly Pro Glu Asp Lys Leu His
        35                  40                  45

Asp Gln Cys Ser Pro Trp Lys Lys Asn Ala Cys Cys Thr Ala Ser Thr
    50                  55                  60

Ser Gln Glu Leu His Lys Asp Thr Ser Arg Leu Tyr Asn Phe Asn Trp
65                  70                  75                  80

Asp His Cys Gly Lys Met Glu Pro Ala Cys Lys Arg His Phe Ile Gln
                85                  90                  95

Asp Thr Cys Leu Tyr Glu Cys Ser Pro Asn Leu Gly Pro Trp Ile Gln
            100                 105                 110

Gln Val Asn Gln Ser Trp Arg Lys Glu Arg Phe Leu Asp Val Pro Leu
        115                 120                 125

Cys Lys Glu Asp Cys Gln Arg Trp Trp Glu Asp Cys His Thr Ser His
    130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255
```

```
<210> SEQ ID NO 88
<211> LENGTH: 245
<212> TYPE: PRT
<213> ORGANISM: Homo sapiens

<400> SEQUENCE: 88

Met Asp Met Ala Trp Gln Met Met Gln Leu Leu Leu Leu Ala Leu Val
1               5                   10                  15

Thr Ala Ala Gly Ser Ala Gln Pro Arg Ser Ala Arg Ala Arg Thr Asp
            20                  25                  30

Leu Leu Asn Val Cys Met Asn Ala Lys His His Lys Thr Gln Pro Ser
        35                  40                  45

Pro Glu Asp Glu Leu Tyr Gly Gln Cys Ser Pro Trp Lys Lys Asn Ala
    50                  55                  60

Cys Cys Thr Ala Ser Thr Ser Gln Glu Leu His Lys Asp Thr Ser Arg
65                  70                  75                  80

Leu Tyr Asn Phe Asn Trp Asp His Cys Gly Lys Met Glu Pro Thr Cys
                85                  90                  95

Lys Arg His Phe Ile Gln Asp Ser Cys Leu Tyr Glu Cys Ser Pro Asn
            100                 105                 110

Leu Gly Pro Trp Ile Arg Gln Val Asn Gln Ser Trp Arg Lys Glu Arg
        115                 120                 125

Ile Leu Asn Val Pro Leu Cys Lys Glu Asp Cys Glu Arg Trp Trp Glu
    130                 135                 140

Asp Cys Arg Thr Ser Tyr Thr Cys Lys Ser Asn Trp His Lys Gly Trp
145                 150                 155                 160

Asn Trp Thr Ser Gly Ile Asn Glu Cys Pro Ala Gly Ala Leu Cys Ser
                165                 170                 175

Thr Phe Glu Ser Tyr Phe Pro Thr Pro Ala Ala Leu Cys Glu Gly Leu
            180                 185                 190

Trp Ser His Ser Phe Lys Val Ser Asn Tyr Ser Arg Gly Ser Gly Arg
        195                 200                 205

Cys Ile Gln Met Trp Phe Asp Ser Ala Gln Gly Asn Pro Asn Glu Glu
    210                 215                 220

Val Ala Lys Phe Tyr Ala Ala Ala Met Asn Ala Gly Ala Pro Ser Arg
225                 230                 235                 240

Gly Ile Ile Asp Ser
                245


<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Tyr Lys Asp Asp Asp Asp Lys
1               5
```

SYNTHETIC EXTRACELLULAR VESICLES FOR NOVEL THERAPIES

CROSS-REFERENCE TO RELATED APPLICATION

The present application is a U.S. national stage application under 35 U.S.C. § 371 of International Application No. PCT/US2018/044251, filed Jul. 27, 2018, which in turn claims priority of U.S. Provisional Application No. 62/538,669, filed Jul. 29, 2017, the contents of each of which are incorporated by reference in their entireties.

SEQUENCE LISTING

The instant application contains a Sequence Listing which has been submitted electronically in ASCII format and is hereby incorporated by reference in its entirety. Said ASCII copy, created on Jan. 28, 2020, is named 064189-9133 SL.txt and is 263,305 bytes in size.

BACKGROUND

Exosomes are natural membranous vesicles with a diameter of 30-200 nm. They are generated through inward invagination of endosomal membranes which form multi-vesicular bodies (MVBs), followed by release into the extracellular milieu upon fusion of the MVBs with the plasma membrane. As endogenous nanocarriers secreted by various types of cells, exosomes play important roles in cell-cell communication through transfer of mRNA, miRNA, receptors, enzymes, cytokines, etc. Importantly, the membrane of exosome is characterized by a phospholipid bilayer and abundant tetraspanin CD9 on its surface, facilitating direct membrane fusion with target cells. This fusion mode circumvents the endosomal-lysosomal pathway required for the synthetic vehicles and promotes cellular delivery of therapeutic agents. Thus, exosome and other extracellular vesicles are under investigation as therapeutic treatments.

SUMMARY OF THE DISCLOSURE

Provided herein are novel extracellular vesicles that can simultaneously target both a pathological cell such as a cancer or an immune cell for combinatorial immunotherapy. Relative to conventional, immunotherapeutic bispecific antibodies with geometrically and orientationally defined antigen-binding arms, the multivalent dual-targeted vesicles of this disclosure are displayed on a spherical surface and have higher potential to promote formation of immunological synapses as well as enhanced efficacy to activate immune cells. Combined with immune checkpoint inhibitors, such bispecific extracellular vesicles are engineered to augment efficacy of immunotherapy. Therefore, the engineered multifunctional extracellular vesicles represent novel nanomedicines with enhanced efficacy and safety, leading to the development of first-in-class immunotherapeutics for cancer and other diseases and disorders.

In one aspect, this disclosure provides an isolated, engineered extracellular vesicle comprising, or alternatively consisting essentially of, or yet further consisting of one or more antigen binding domain(s) fused to an extracellular vesicle addressing domain. Non-limiting examples of the extracellular vesicle domains are from the group of vesicles that include one or more from the group of: an exosome, a liposome, a microvesicle, and an apoptotic body. The antigen binding domains are fused to the extracellular vesicle addressing domain by chemical or recombinant techniques. The isolated, engineered vesicles can be modified and isolated from a variety of cell types, e.g., prokaryotic or eukaryotic, e.g., eukaryotic such as mammalian such as human, canine, equine, feline, bovine, rat, murine, ovine, and simian. Additional examples include yeast cells, bacterial cells and plant cells. Non-limiting examples include Expi293F cells, HeLa cells, HEK293T, MDA-MB-231, immature dendritic cells, and stem cells.

In one aspect, the one or more antigen binding domains are selected from the group of: an antibody, a multi-specific antibody, a monoclonal antibody, an scFv antibody fragment, a single domain antibody, a heavy chain variable domain (VH), a light chain variable domain (VL), a bispecific antibody, or a bispecific antibody fragment, a multi-specific antibody fragment, Fab, F(ab)'2, Fab', and Fv. antibody fragment, or an equivalent of each thereof. Non-limiting examples of antibodies and fragments and derivatives thereof are of the group of antibodies: anti-HER2; anti-HER3; anti-EGFR; anti-CD3; anti-CD16; anti-CD4; anti-CD8; anti-CD11a; anti-CD19; anti-CD20; anti-CD25; anti-CD33; anti-CD40; anti-CD40L; anti-CD70; anti-CD123; anti-EpCAM; anti-CLL-1; anti-CTLA-4; anti-PD-1; anti-PD-L1; anti-OX40; anti-GITR; anti-ICOS; anti-B7-H3; anti-B7-H4; anti-LAG3; anti-TIM3; anti-PSMA; anti-factor IXa; anti-factor X; and anti-folate receptor, fragments or derivatives thereof.

In another aspect, the antigen binding domain specifically recognizes and binds an immune cell. In a further aspect, the engineered vesicle comprises, or alternatively consists essentially of, or yet further consists of different antigen binding domains, e.g., one or more specific to a cancer or tumor cell and one or more specific to an immune cell.

Examples of antigen binding domains include those that bind an antigen of the group of: a tumor antigen, a cancer antigen, an antigen expressed on an immune cell, activated coagulation factor IX, factor X, an antigen involved in immune regulation such as a cell surface receptor that mediates the reaction of an immune cell (e.g., a T cell, a macrophage or a natural killer cell) or a checkpoint inhibitor, e.g., PDL1, CTLA-4, B7-H3, B7-H4, LAG3, PD1, TIM-3, or a checkpoint activator, e.g. CD40, OX40, GITR, and ICOS.

When the antigen binding domain is specific for a cancer antigen, examples of such include a cancer antigen is selected from the groups of breast cancer, lung cancer, colorectal cancer, kidney cancer, prostate cancer, brain cancer, pancreatic cancer, ovarian cancer, liver cancer, bladder cancer, lymphoma, melanoma, a solid malignant cancer or a blood cancer. Specific examples include HER2 or EGFR expressed on breast cancer or colorectal cancer.

When the antigen binding domain is specific for an immune cell, non-limiting examples of immune cells are selected from the group of: a CD3+ T cell, a CD16+ cell, a CD16+NK cell, a CD4 cell, a CD8 cell, a CD19 cell, a CD20 cell, or a B cell.

In a further aspect, the engineered vesicles contain an effective amount of a therapeutic agent. Non-limiting examples of such include small molecular immune checkpoint modulators, a small molecular chemotherapeutic drug, an RNA-based therapeutics (siRNA, or miRNA), a therapeutic protein, a therapeutic peptide, an immune regulatory factor, an immune checkpoint inhibitor, an immune agonist, anti-PD1, anti-PDL1, anti-CTLA4 siRNA, an inhibitor of indoleamine-pyrrole 2,3-dioxygenase (IDO) such as GDC-0919 and indoximod, an agonist of Toll-like receptors (TLR)

TLRs such as Motolimod, and Resiquimod. More than one therapeutic agent can be encapsulated in the vesicle. For example, in one aspect, the more than one therapeutic agent is selected to target both tumor cell and tumor stroma cells in a solid tumor for synergistic anti-tumor effect. In another aspect, the more than one therapeutic agents are selected to block two immune checkpoint inhibitors simultaneously, e.g., anti-PD1, anti-PDL1 and anti-CTLA4 siRNA. In one aspect the plurality targets the immune checkpoint inhibitors are anti-PDL1 and anti-CTLA4.

Also provided herein are methods for the preparing and isolating the engineered vesicles and compositions containing them. In one aspect, the vesicles are processed by freeze-drying.

The compositions comprising, or alternatively consisting essentially of, or yet further consisting of the engineered vesicles can further comprise, or alternatively consist essentially of, or yet further consist of an effective amount of a therapeutic agent to work in combination with the engineered vesicle. These can be combined with carriers, such as a pharmaceutically acceptable carrier.

The compositions are useful for treating a disease or eliciting an immune response by administering an effective amount of a disease-relevant engineered vesicle, that is, wherein the engineered vesicle expresses an antigen binding domain specific to a disease to be treated. For example the vesicle would comprise, or alternatively consist essentially of, or yet further consist of an antigen binding domain specific for a specific tumor or cancer antigen when the disease to be treated is cancer. The methods and compositions are useful to treat or inhibit the progression of cancer, hyperplasia, neurodegenerative disease, Alzheimer's disease, cardiovascular disease, metabolic disease, vasculitis, viral infection, fungal infection, bacterial infection, diabetic retinopathy, macular degeneration, autoimmune disease, edema, pulmonary hypertension, sepsis, myocardial angiogenesis, plaque neovascularization, restenosis, neointima formation after vascular trauma, telangiectasia, hemophiliac joints, angiofibroma, fibrosis associated with chronic inflammation, lung fibrosis, deep venous thrombosis or wound granulation.

In a particular embodiment, the compositions and methods are useful in cancer immunotherapy and the engineered vesicle displays an antigen binding domain for the cancer cell and an antigen binding domain specific for the immune cell. In a further aspect, the engineered vesicle comprises, or alternatively consists essentially of, or yet further consists of a therapeutic agent to treat the cancer. More than one therapeutic agent can be encapsulated in the vesicle. For example, in one aspect, engineered vesicles are administered wherein more than one therapeutic agent is selected to target both tumor cell and tumor stroma cells in a solid tumor for synergistic anti-tumor effect. In another aspect, an effective amount of an engineered vesicle is administered having more than one therapeutic agents to block two immune checkpoint inhibitors simultaneously, e.g., anti-PD1, anti-PD-L1 and anti-CTLA4 siRNA. In one aspect, the plurality targets the immune checkpoint inhibitors are anti-PDL1 siRNA and anti-CTLA4 siRNA.

Also provided are fusion polypeptides that are useful to recombinantly prepare the engineered vesicles and polynucleotides encoding the polypeptides. In one aspect the polynucleotide encodes a fusion polypeptide comprising, or alternatively consisting essentially of, or yet further consisting of: an immune effector cell binding domain or an antigen binding domain, a linker polypeptide, and an exosome addressing domain. In one aspect, the polynucleotide encodes a fusion polypeptide that comprises, or alternatively consists essentially of, or yet further consists of an antigen binding domain that specifically recognize and bind an antigen of the group of: a tumor antigen, a cancer antigen, an activated coagulation factor IX, and factor X. Non-limiting examples of cancer antigens are selected from the groups of breast cancer, lung cancer, colorectal cancer, kidney cancer, prostate cancer, brain cancer, pancreatic cancer, a solid malignant cancer or a blood cancer. In a further aspect, the cancer is a breast cancer or a colorectal cancer, and the antigen is HER2 or EGFR expressed on the cancer cell. The polynucleotides can be operatively linked to regulatory elements to drive expression of the polynucleotide and can be further contained within a vector, e.g. a plasmid or a viral vector. Host cells containing the polynucleotides and/or polypeptides and methods of expressing the polynucleotides are further provided herein, as well as the polypeptides encoded by the polynucleotides. The host cells are prokaryotic or eukaryotic cells. The polynucleotides and polypeptides can further comprise, or alternatively consist essentially of, or yet further consist of a detectable and/or a purification label.

In a particular aspect, the antigen binding domain specifically recognizes and binds a receptor present on a CD3+ T cell or a CD16+NK cell.

Linker polypeptides can be present in the fusion polypeptide.

In a yet further aspect, the antigen binding domain comprises, or alternatively consists essentially of, or yet further consists of an anti-HER2 scFv antibody fragment or an anti-EGFR scFv antibody fragment.

In another aspect, the fusion polypeptide comprises: an immune effector binding domain, first linker polypeptide, an antigen binding domain, a second linker, and an exosome membrane protein or polypeptide. In a further aspect, the fusion polypeptide comprises, or alternatively consists essentially of, or yet further consists of a myc polypeptide protein tag derived from the c-myc gene product and/or a human influenza hemagglutinin epitope.

Further provided are polynucleotides encoding the fusion polypeptides, vectors and host cells containing them as well as recombinant methods for expressing the fusion polypeptides.

Also provided is a method to prepare the engineered exosome by transducing a population of cells comprising, or alternatively consisting essentially of, or yet further consisting of vesicles, such as exosomes, with a vector comprising, or alternatively consisting essentially of, or yet further consisting of the polynucleotides encoding the fusion polypeptides as described above and then isolating the transduced vesicles. In a further aspect, the method comprises, or alternatively consists essentially of, or yet further consists of chemical conjugation of the antigen binding domains to an exosome membrane protein or polypeptide located on exterior of the vesicle.

In a further aspect, the method comprises, or alternatively consists essentially of, or yet further consists of encapsulating a therapeutic agent into the engineered vesicle.

BRIEF DESCRIPTION OF THE DRAWINGS

FIG. 1A: A bispecific antibody was fused with exosomal membrane protein for surface display. FIG. 1B: Two distinct scFv antibodies were separately fused with the same or different exosomal proteins for surface display.

(GGGGS)n, n=0-5 (SEQ ID NO: 2)

(GGGS)n, n=0-6 (SEQ ID NO: 3)

(GGS)n, n=0-7 (SEQ ID NO: 4)

(EAAAK)n, n=0-4 (SEQ ID NO: 5)

PSGQAGAAASESLFVSNHAY (SEQ ID NO: 6)

GSTSGSGKPGSGEGS (SEQ ID NO: 7)

Representative types of antibody fragments (antigen binding fragments) include: single-chain variable fragment (scFv); heavy chain variable domain (VH); light chain variable domain (VL); single-domain antibody; and a multi-specific antibody fragment. Representative antigen binding domains include: anti-HER2; anti-HER3; anti-EGFR; anti-CD3; anti-CD16; anti-CD4; anti-CD8; anti-CD11a; anti-CD19; anti-CD20; anti-CD25; anti-CD33; anti-CD40; anti-CD40L; anti-CD70; anti-CD123; anti-EpCAM; anti-CLL-1; anti-CTLA-4; anti-PD-1; anti-PD-L1; anti-OX40; anti-GITR; anti-ICOS; anti-B7-H3; anti-B7-H4; anti-LAG3; anti-TIM3; anti-PSMA; anti-factor IXa; anti-factor X; and anti-folate receptor, fragments and derivatives thereof. Representative exosomal membrane proteins (also termed herein as an "extracellular vesicle addressing domain") include: platelet-derived growth factor receptor (PDGFR); lysosomal-associated membrane protein 2b (Lamp2b); lactadherin-C1C2 domain; CD13; and CD9.

Figure 3:
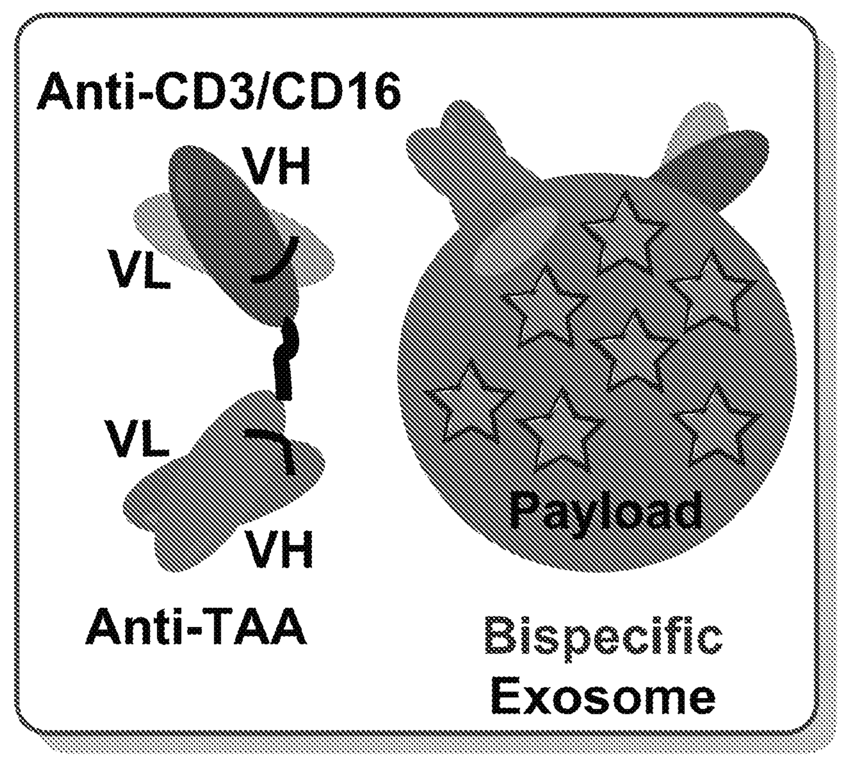

FIG. 3 is a schematic of a bispecific exosome nanoparticles for novel cancer immunotherapy. TAA is tumor-associated antigen.

Figure 4A:
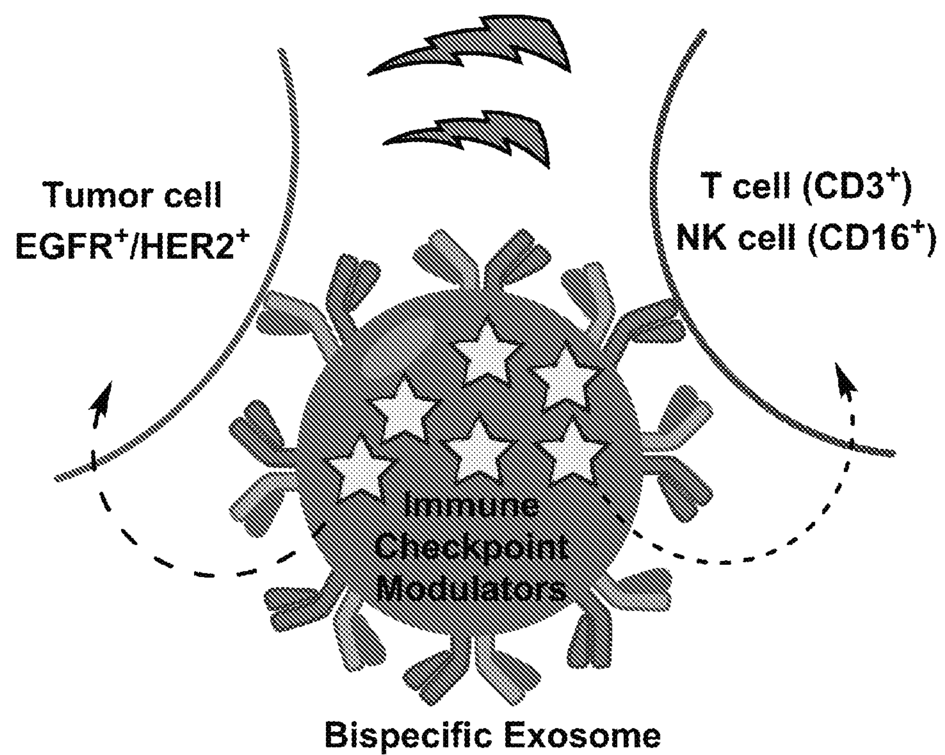

FIG. 4A is a schematic of a bispecific antibody-targeted exosomes for cancer immunotherapy.

Figure 4B:
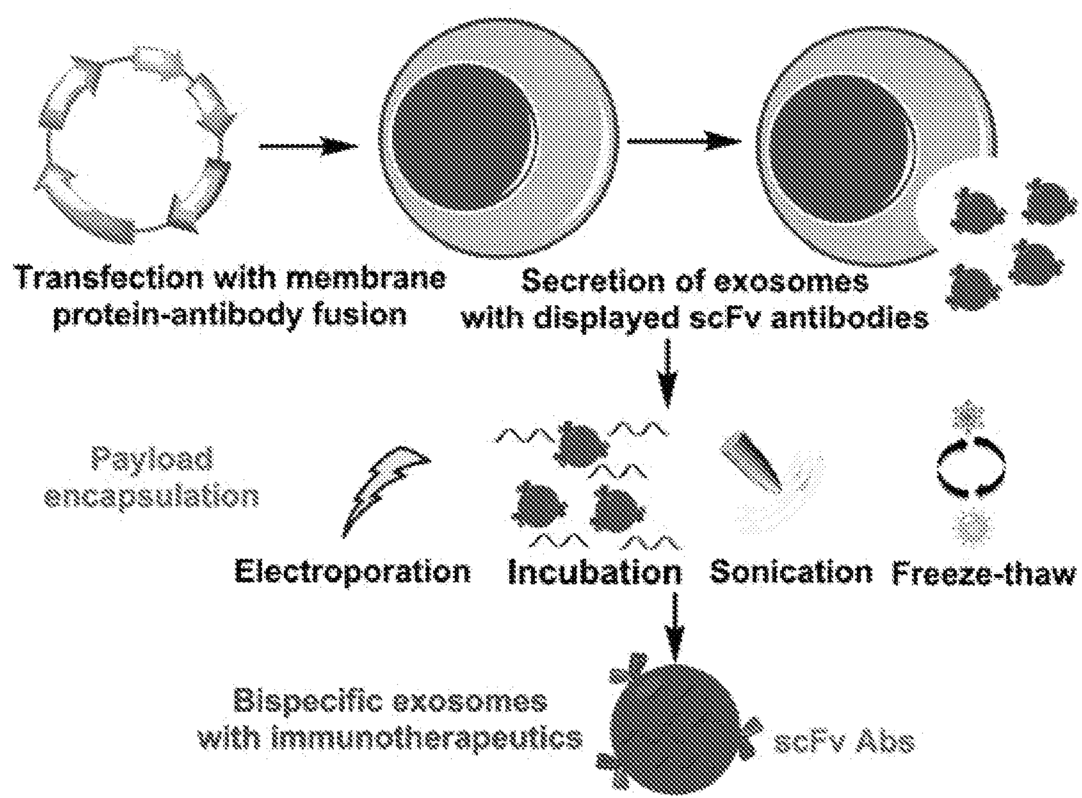

FIG. 4B depicts a method to encapsulate the therapeutic drug or payload into the exosomes.

Figure 5:
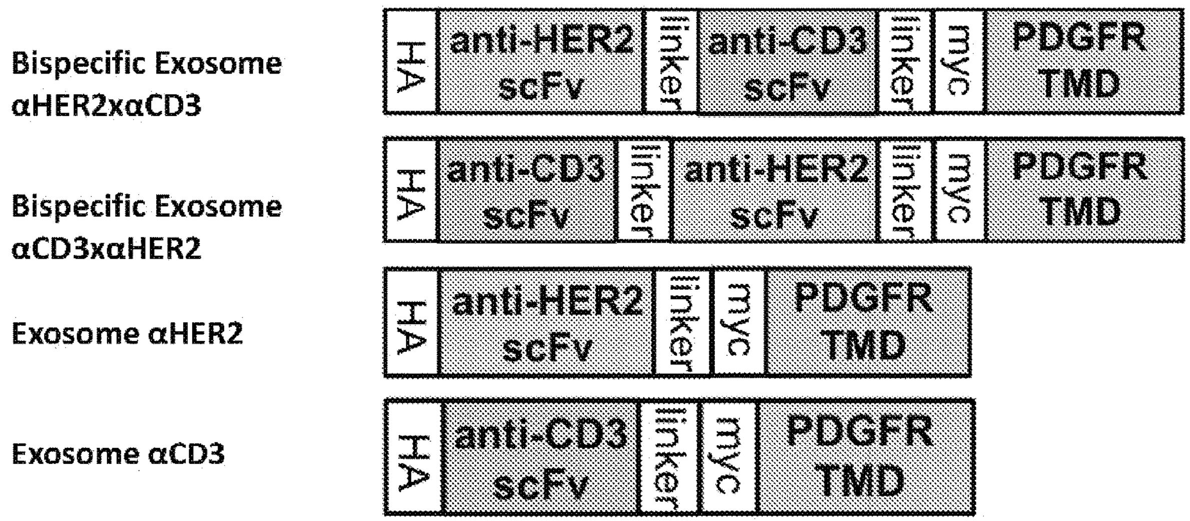

FIG. 5 depicts schemes of fusion proteins for exosome engineering. Abbreviations: Platelet-derived growth factor receptors (PDGFR) are cell surface tyrosine kinase receptors for members of the platelet-derived growth factor (PDGF) family. Exosomal membrane protein (trans-membrane domain (TMD)) of PDGFR 49 aa, widely used to express protein on cell membrane surface. HA is human influenza hemagglutinin epitope. Myc is a polypeptide protein tag derived from the c-myc gene product.

Figure 6:
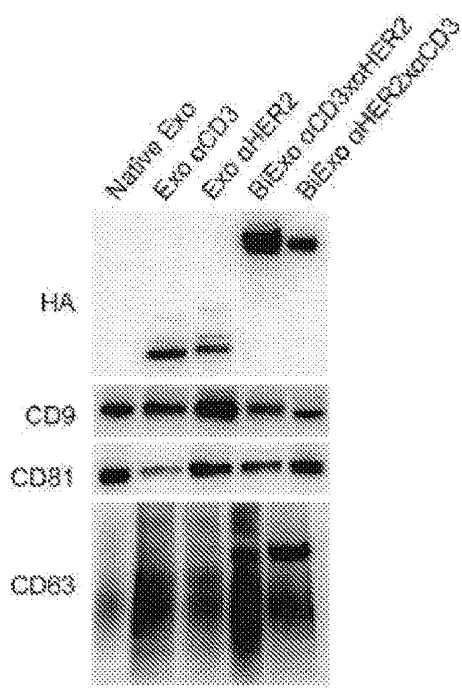

FIG. 6 is a Western blot of bispecific exosomes targeting HER2 and CD3. Lanes from left to right are as follows: 1. native exosome; 2. anti-CD3 exosomes; 3. anti-HER2 exosomes; 4. bispecific exosome anti-CD3 and anti-HER2; and 5. bispecific exosome anti-HER2 and anti-CD3.

Figure 7:
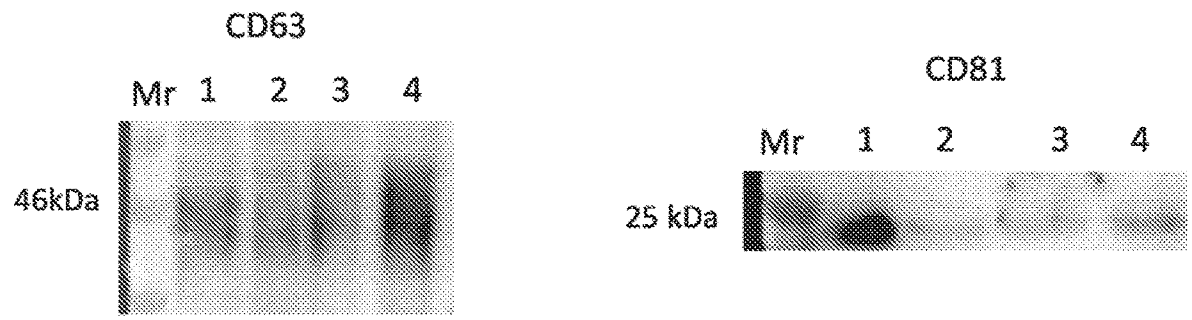

FIG. 7 is a Western blot of bispecific exosomes targeting HER2 and CD3. Lanes are as follows: 1. blank exosome; 2. bispecific exosome anti-CD3 and anti-HER2 exosomes; 3. anti-HER2 exosomes; and 4. anti-CD3 exomes.

Figure 8:
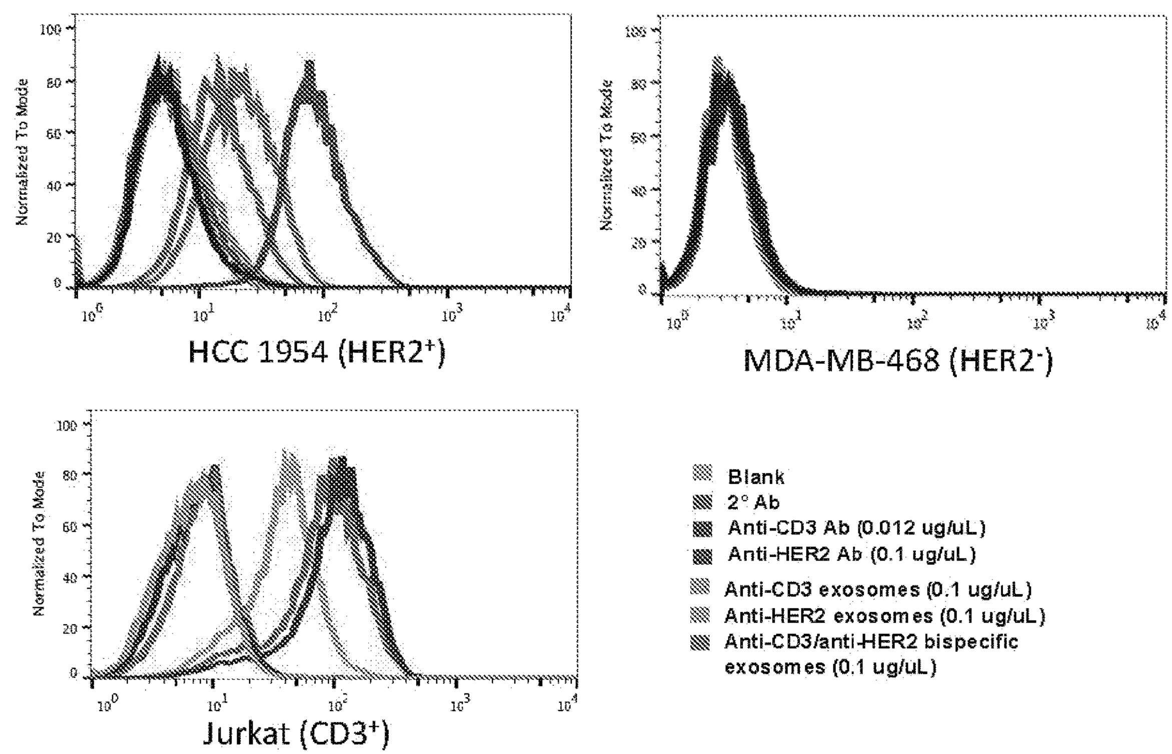

FIG. 8 is flow cytometry analysis of generated bispecific exosomes targeting HER2 and CD3.

Figure 9:
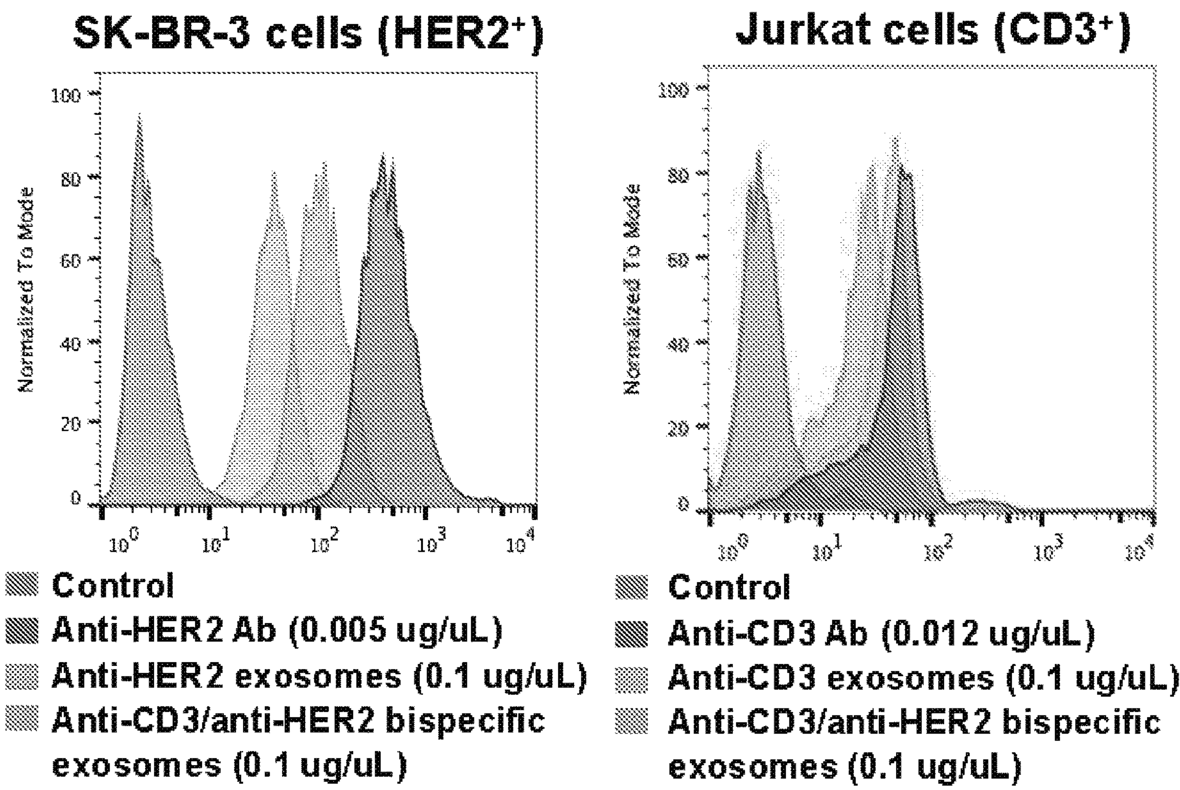

FIG. 9 is flow cytometry analysis of the generated mono-specific and bispecific exosomes targeting HER2 and CD3

Figure 10:
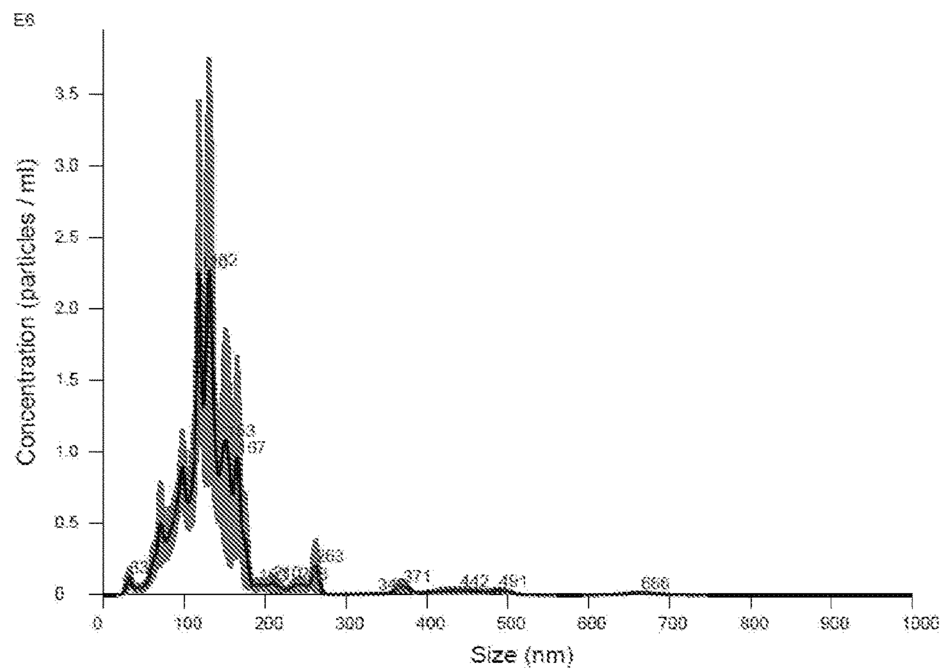

FIG. 10 shows the size distribution of the isolated mono-specific and bispecific exosomes by nanoparticle tracking analysis (NTA).

Figure 11:
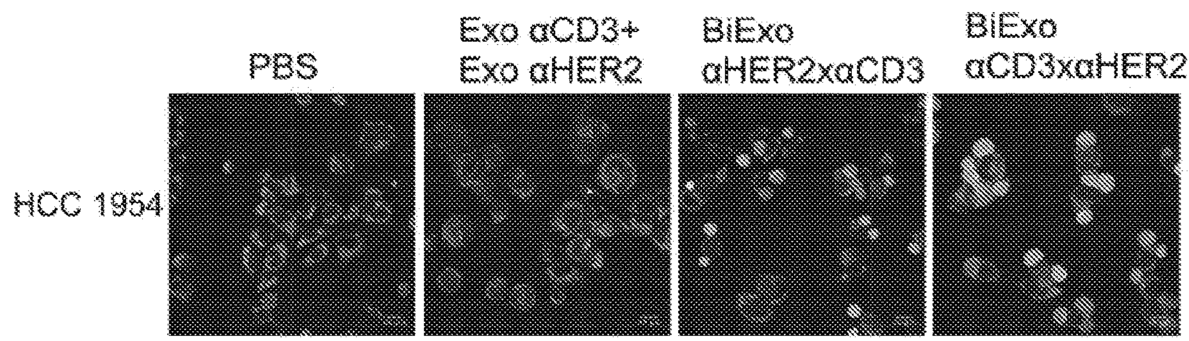

FIG. 11 shows fluorescence microscopy of the interaction between HCC1954 cells (dark) and Jurkat cells (light) in the presence of (from left to right) PBS, 1:1 mixture of anti-HER2 and anti-CD3 mono-specific exosomes, anti-HER2/anti-CD3 bispecific exosomes, and anti-CD3/anti-HER2 bispecific exosomes. 0.1 μg/μL exosome in 100 μL.

Figure 12:
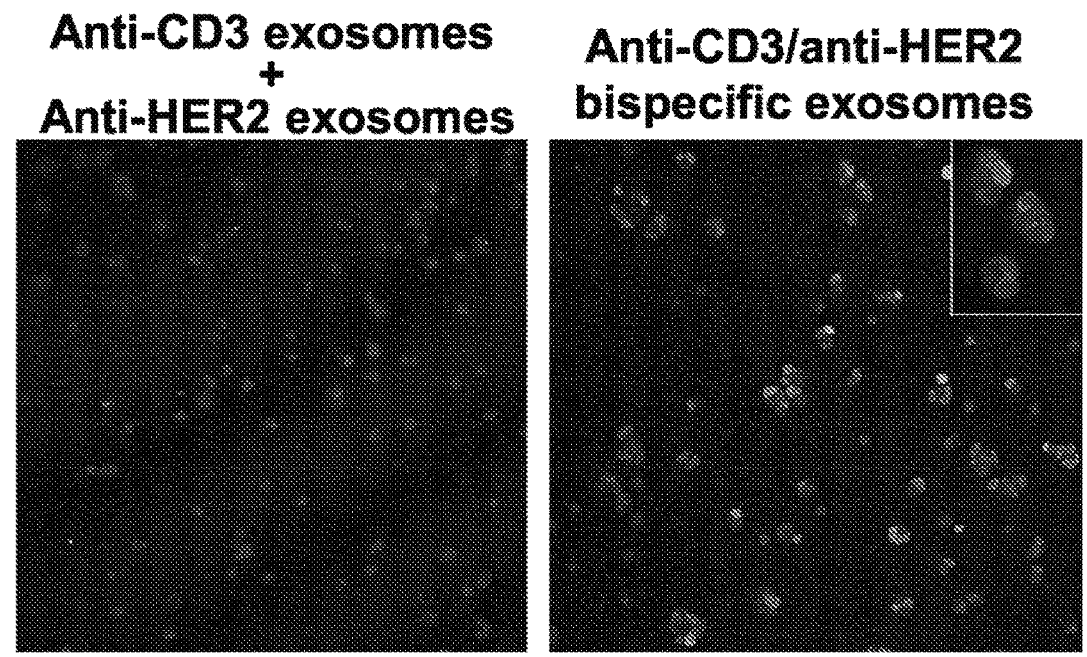

FIG. 12 shows fluorescence microscopy of the interaction between SK-BR-3 cells (dark) and Jurkat cells (light) in the presence of anti-CD3/anti-HER2 bispecific exosomes (right) or a mixture of anti-HER2 and anti-CD3 mono-specific exosomes (left).

Figure 13:
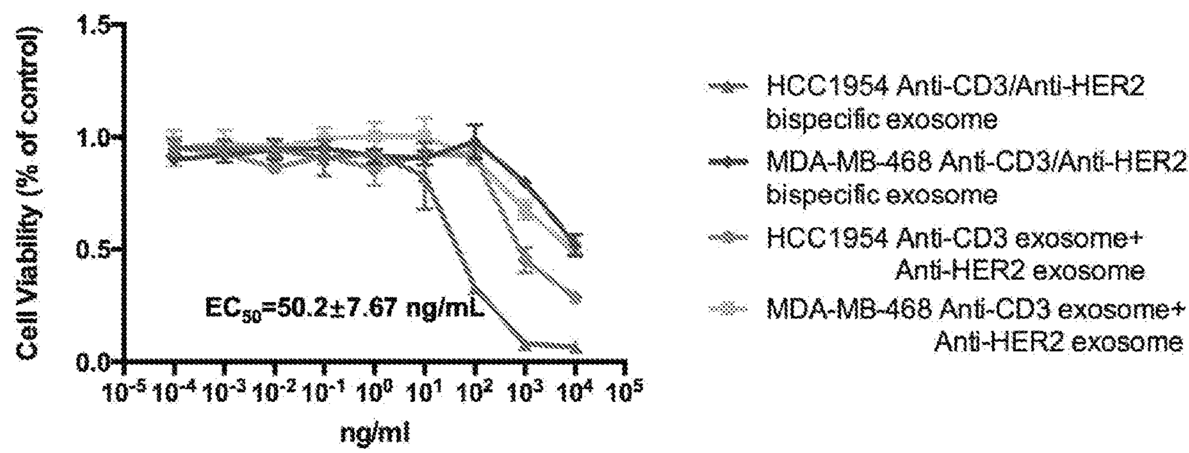
Figure 14:
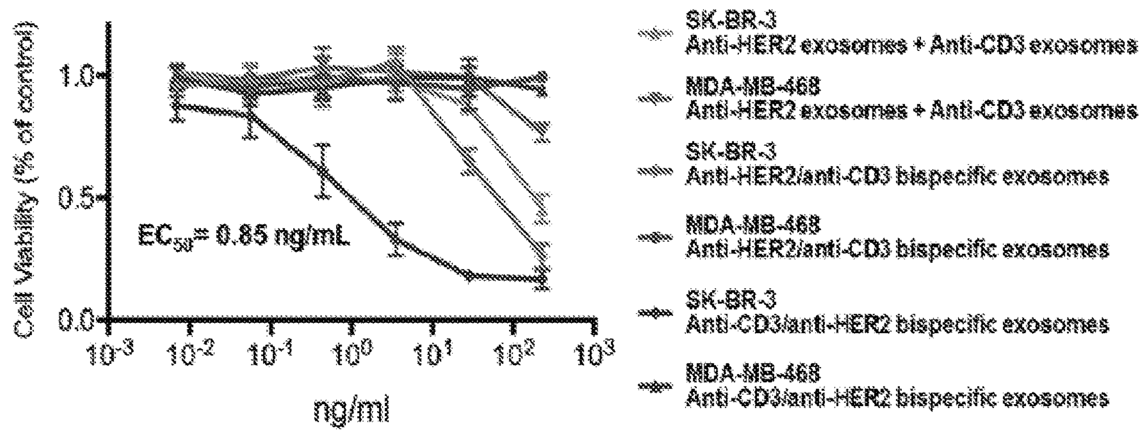

FIG. 13 depicts results pertaining to in vitro cytotoxicity of anti-CD3/anti-HER2 bispecific exosomes or a mixture of anti-HER2 and anti-CD3 mono-specific exosomes against HCC1954 and MDA-MB-468 cell lines. E:T=8:1 48 h FIG. 14 depicts results pertaining to in vitro cytotoxicity of anti-CD3/anti-HER2 and anti-HER2/anti-CD3 bispecific exosomes or a mixture of anti-HER2 and anti-CD3 mono-specific exosomes against SK-BR-3 and MDA-MB-468 cell lines.

Figure 15:
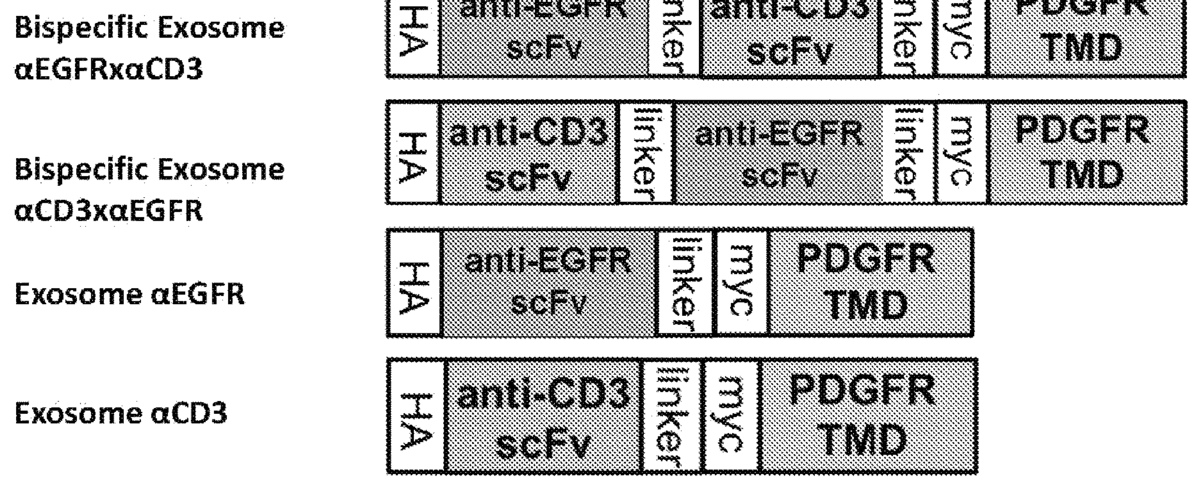

FIG. 15 shows schemes of scFv-PDGFR fusion proteins. PDGFR: Platelet-derived growth factor receptors. HA: human influenza hemagglutinin epitope. myc: a polypeptide protein tag derived from the c-myc gene product. linker: GGGGS or a repeat thereof.

Figure 16:
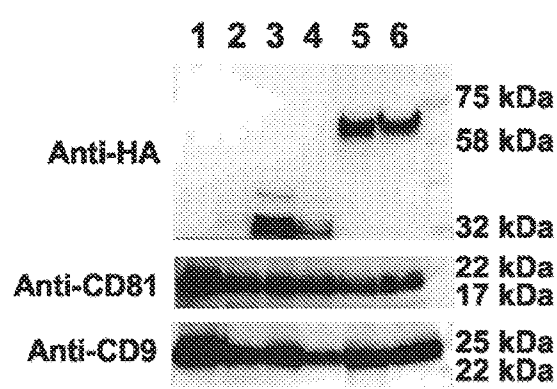

FIG. 16 shows a western blot of the generated exosomes. Lanes from left to right are: 1. Blank exosomes; 2. Anti-EGFR exosomes; 3. Anti-CD3 exosomes; 4. Anti-EGFR/Anti-CD3 co-transfected exosomes; 5. Anti-EGFR/anti-CD3 bispecific exosomes; and 6. Anti-CD3/anti-EGFR bispecific exosomes.

Figure 17A:
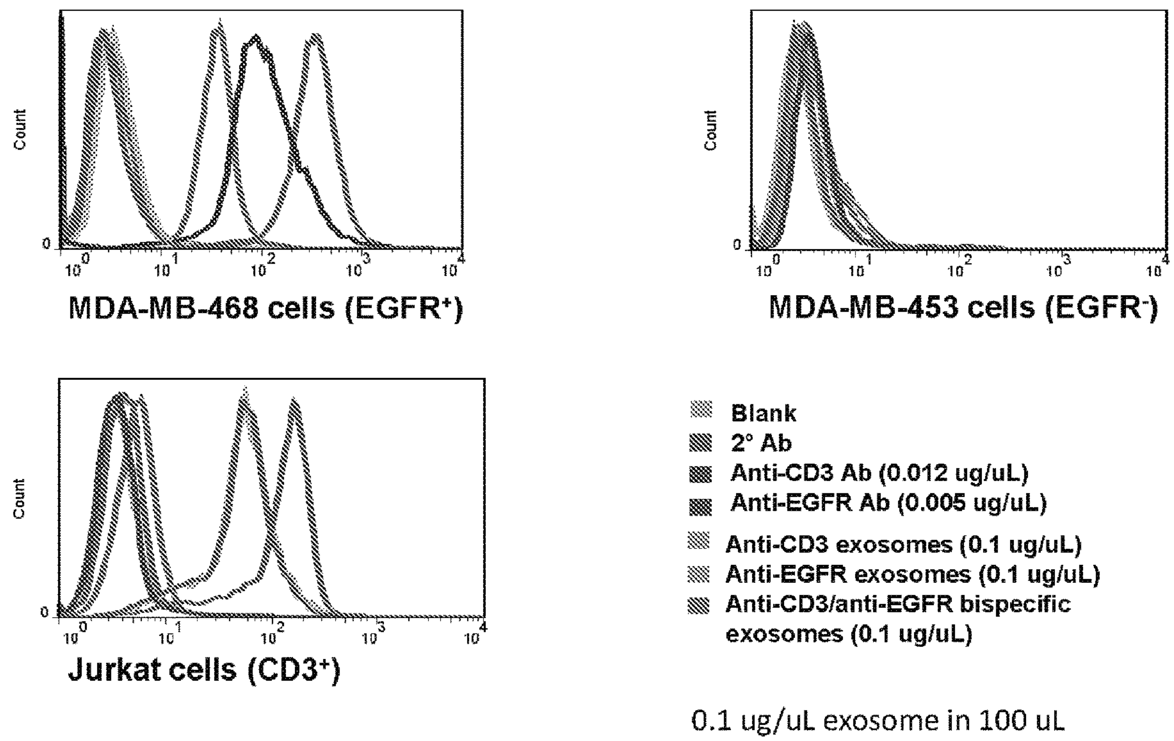
Figure 17B:
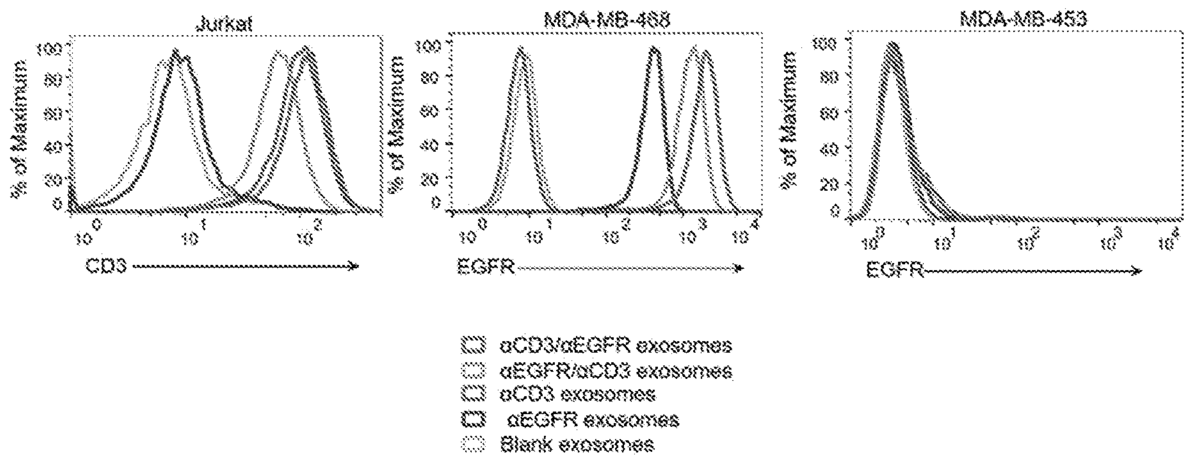
Figure 17C:
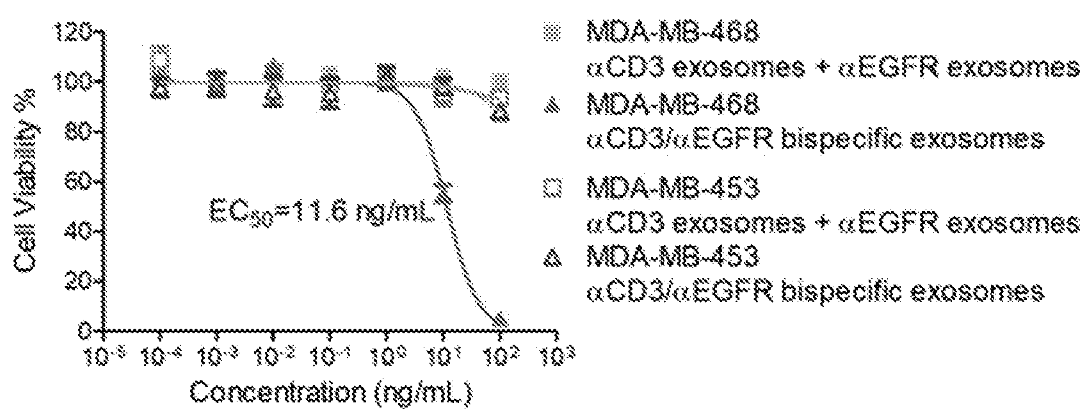

FIG. 17A-C: FIG. 17A shows flow cytometry analysis bispecific exosomes targeting EGFR and CD3 and anti-CD3 and anti-EGFR monospecific exosomes at a concentration of 0.1 μg/uL exosome in 100 μL. FIG. 17B shows additional flow cytometry analysis bispecific exosomes targeting EGFR and CD3 and anti-CD3 and anti-EGFR monospecific exosomes at a concentration of 0.1 μg/uL exosome in 100 μL. FIG. 17C shows in vitro cytotoxicity results of anti-CD3/anti-EGFR bispecific exosomes or mixture of mono-specific anti-CD3 and anti-EGFR exosomes against MDA-MB-468 and -453 cell lines. Tumor cell was peripheral blood mononuclear cell (PBMC)=1: 10, incubated 40 h, then measured by MTT.

Figure 18:
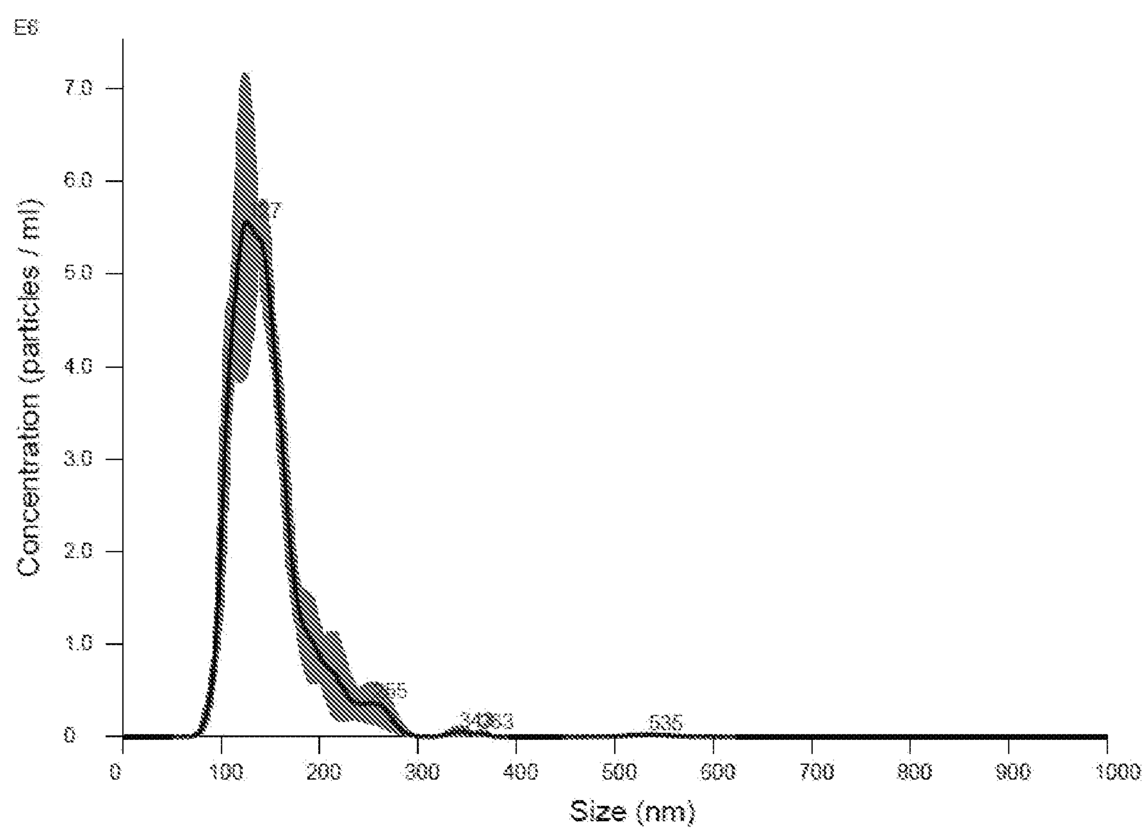

FIG. 18. Shows size distribution of the isolated native exosomes and bispecific exosomes targeting EGFR and CD3 by nanoparticle tracking analysis (NTA).

Figure 19:
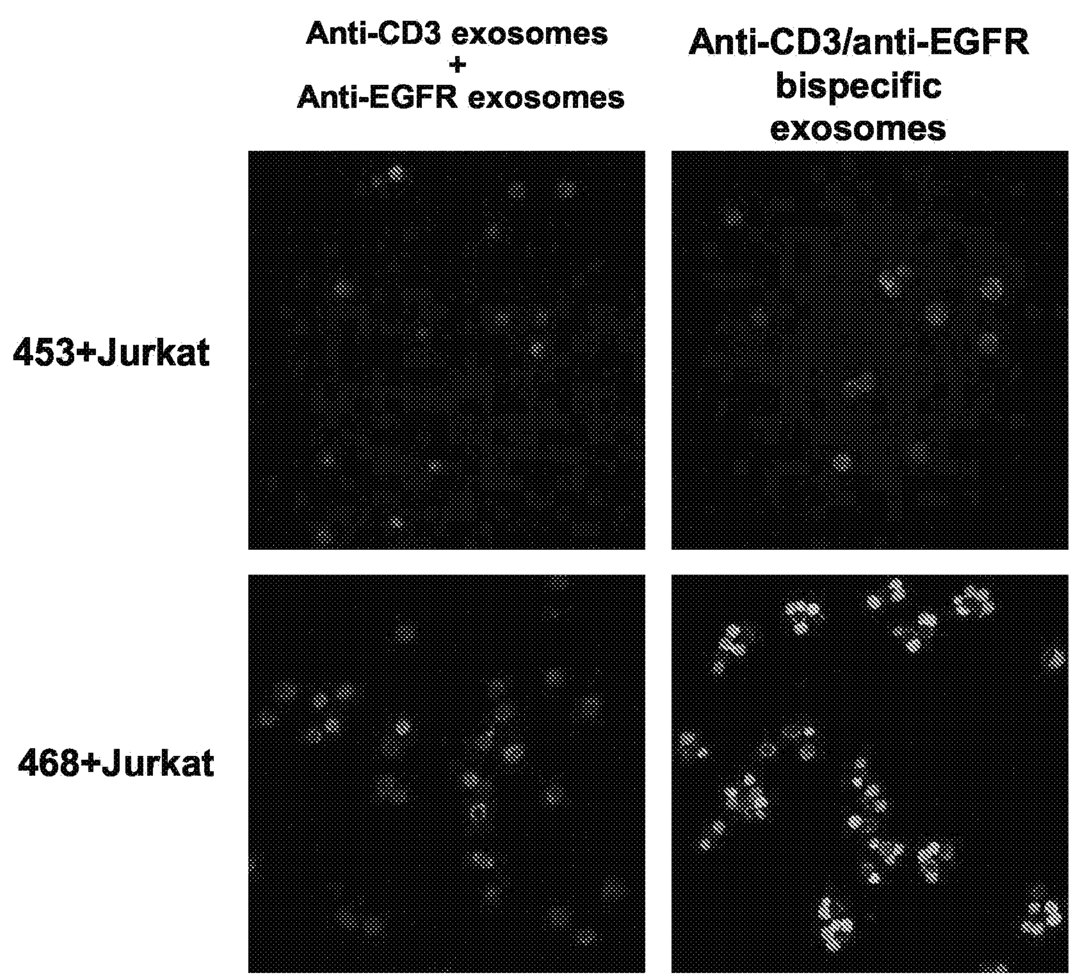

FIG. 19 shows fluorescence microscopy of the interaction between MDA-MB-468 (bottom row) or -453 (top row) cells (dark) and Jurkat cells (light) in the presence of anti-CD3/anti-EGFR bispecific exosomes (right column) or mixture of mono-specific anti-CD3 and anti-EGFR exosomes (left column). Concentrations were 0.1 μg/uL exosome in 100 μL.

Figure 20:
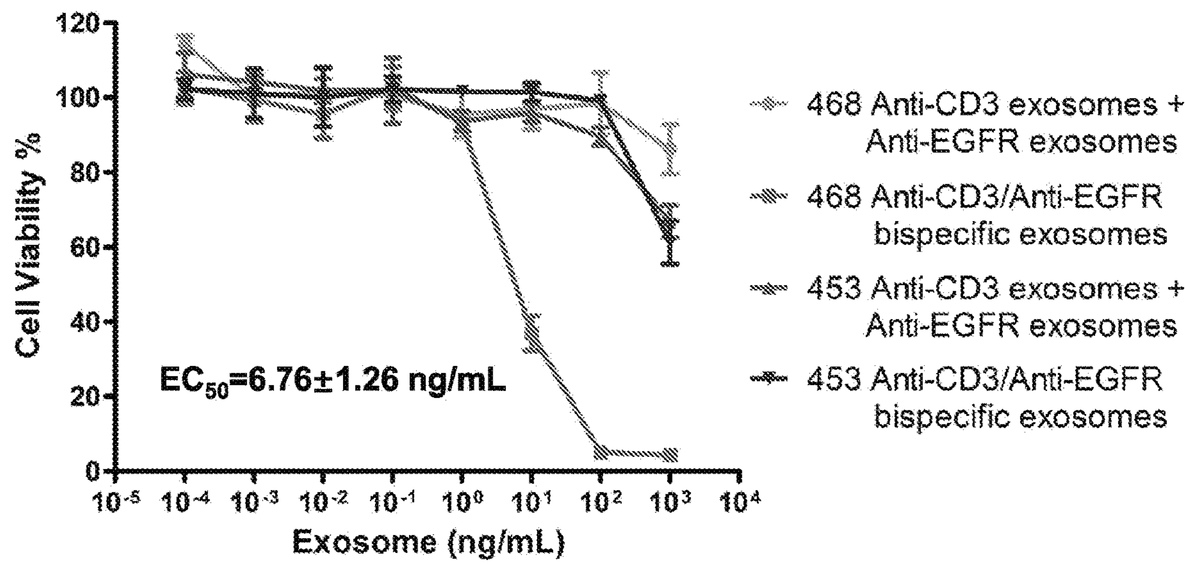

FIG. 20 Shows in vitro cytotoxicity results of anti-CD3/anti-EGFR bispecific exosomes or mixture of mono-specific anti-CD3 and anti-EGFR exosomes against MDA-MB-468 and -453 cell lines. Tumor cell was peripheral blood mononuclear cell (PBMC)=1: 8, incubated 48 h, then measured by MTT.

Figure 21:
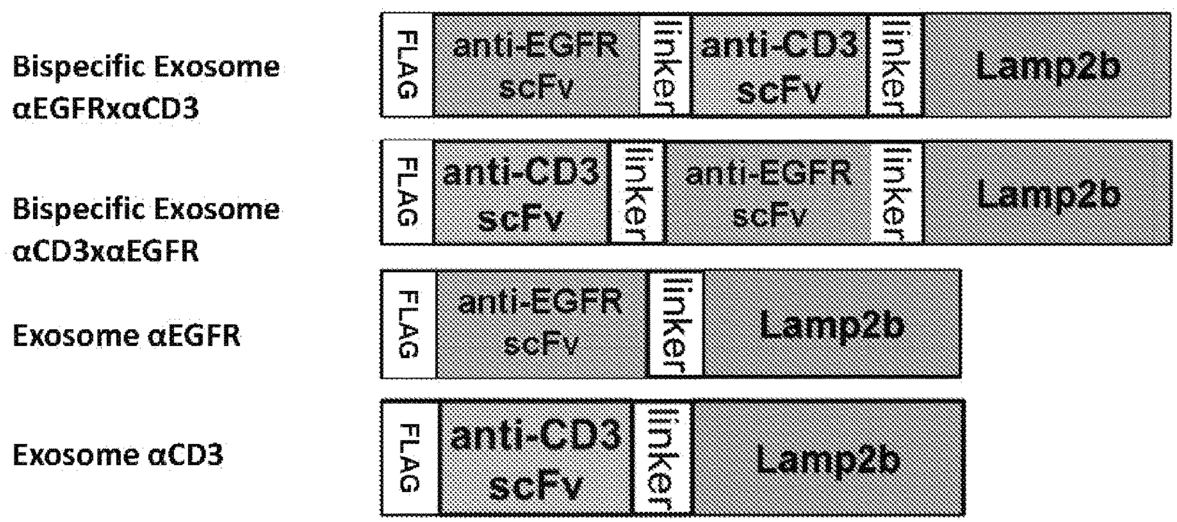

FIG. 21 shows schemes of fusion proteins for exosome engineering. Lysosomal-associated membrane protein 2b (Lamp2b) is an exosomal membrane protein. FLAG is a short, hydrophilic protein epitope tag or label.

Figures 22, 23:
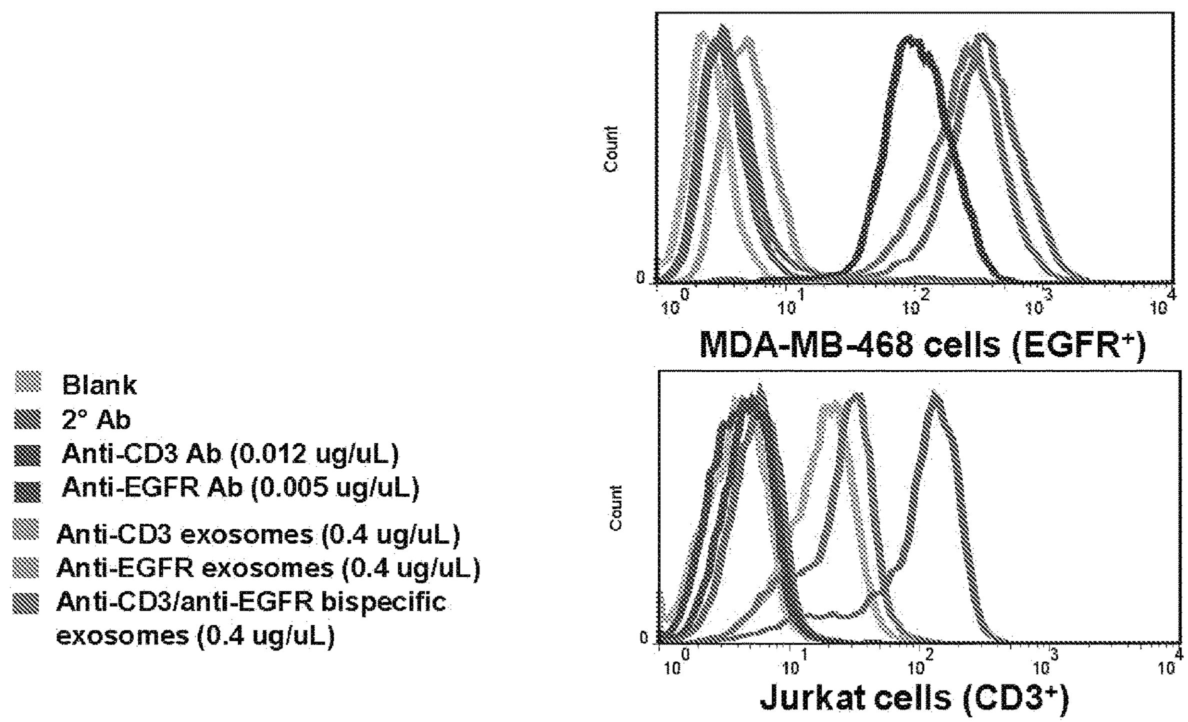

FIG. 22 shows a western blot of the generated exosomes. Lane assignments are: 1. anti-EGFR exosomes; 2. anti-CD3 exosomes; and 3. anti-CD3/anti-EGFR bispecific exosomes.

FIG. 23 shows a flow cytometry analysis of the generated bispecific and monospecific exosomes if this disclosure.

Figure 24:
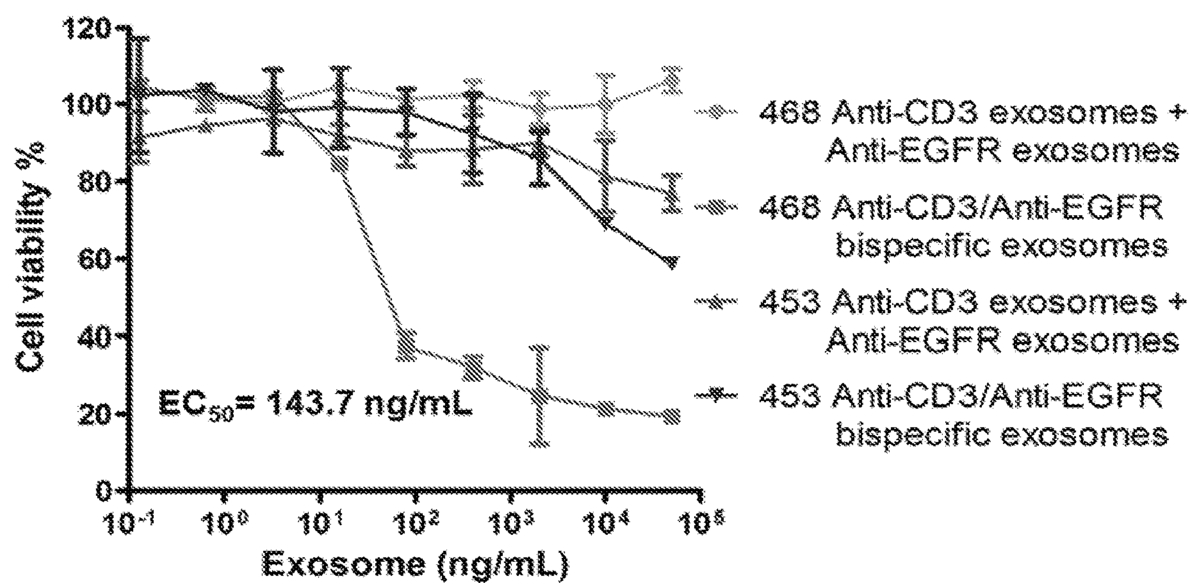

FIG. 24 Shows in vitro cytotoxicity results of anti-CD3/anti-EGFR bispecific exosomes or mixture of mono-specific anti-CD3 and anti-EGFR exosomes against MDA-MB-468 and -453 cell lines.

Figure 25:
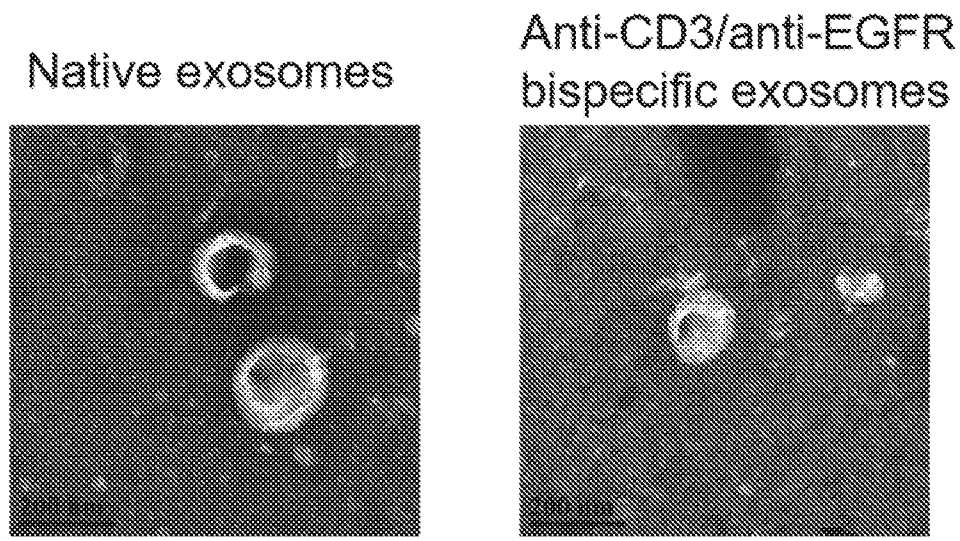

FIG. 25 depicts native exosomes and bispecific exosomes targeting EGFR and CD3. Negative staining transmission electron microscopy image of native exosomes and the generated Bispecific Exosome αCD3×αEGFR.

Figure 26:
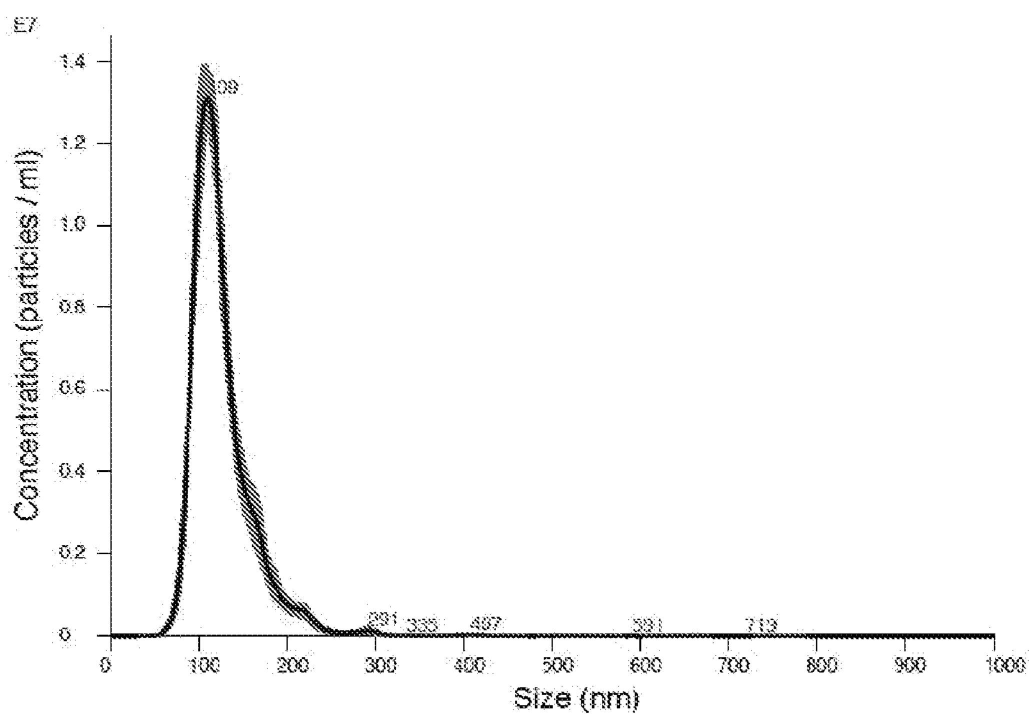

FIG. 26 shows the size distribution of the generated bispecific exosome αCD3×αHER2 as evaluated through nanoparticle tracking analysis.

Figure 27:
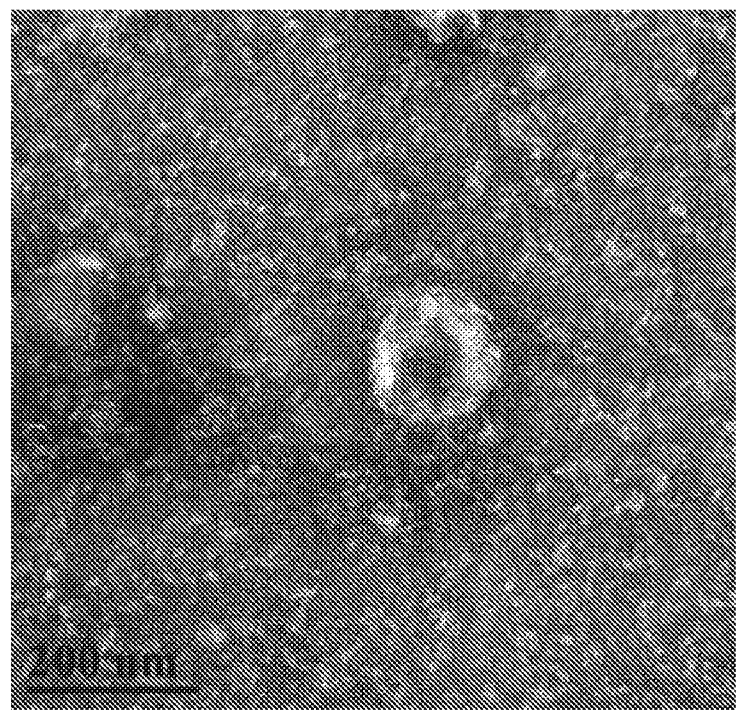

FIG. 27 shows a negative staining transmission electron microscopy image of the generated Bispecific Exosome αCD3×αHER2. Refer to transmission electron microscopy (TEM).

Figure 28:
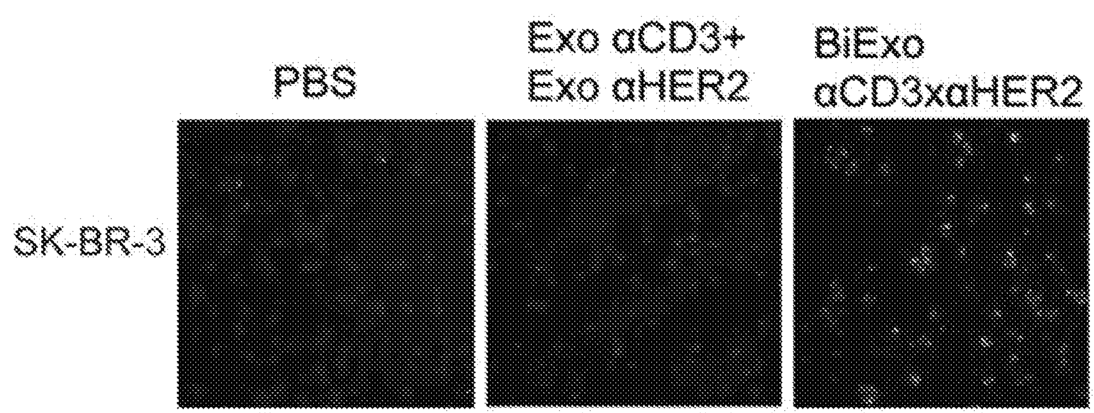

FIG. 28 shows fluorescence microscope images of the interaction between SK-BR-3 cells (dark) and Jurkat cells (light) in the presence of (from left to right) PBS, 1:1 mixture of anti-HER2 and anti-CD3 mono-specific exosomes, and anti-CD3/anti-HER2 bispecific exosomes. 0.1 μg/μL exosome in 100 μL.

Figure 29:
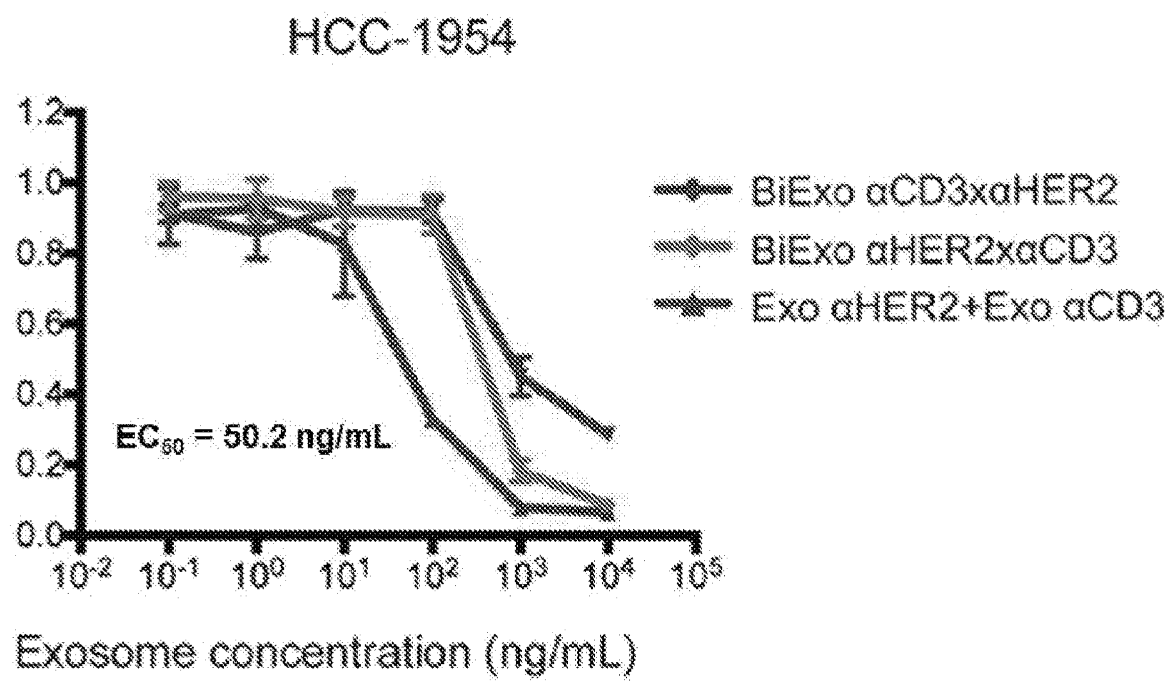

FIG. 29 shows in vitro cytotoxicity of anti-CD3/anti-HER2 bispecific exosomes. Non-activated hPBMC were incubated with HCC-1954 cells (HER2+) at an E:T ratio of 10 for 40 hours in the presence of bispecific exosomes or a mixture of monospecific exosomes. After removing hPBMC suspension, the cell viabilities of target cells were measured through MTT assays.

Figure 30:
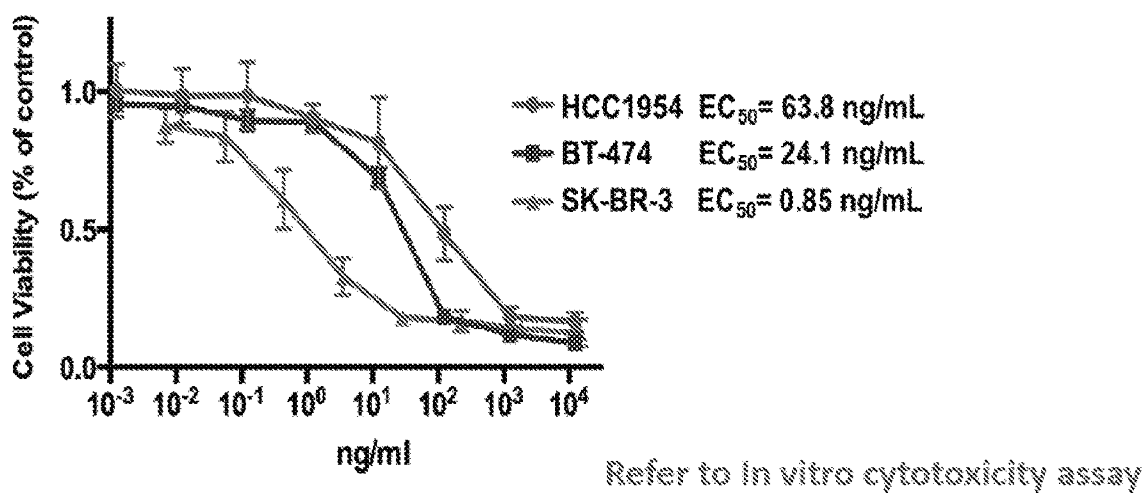

FIG. 30 shows in vitro cytotoxicity of anti-CD3/anti-HER2 bispecific exosomes. Non-activated hPBMC were incubated with SK-BR-3, BT-474, and HCC1954 cells at an E:T ratio of 10 for 40 hours in the presence of bispecific exosomes. After removing hPBMC suspension, the cell viabilities of target cells were measured through MTT assays.

Figure 31:
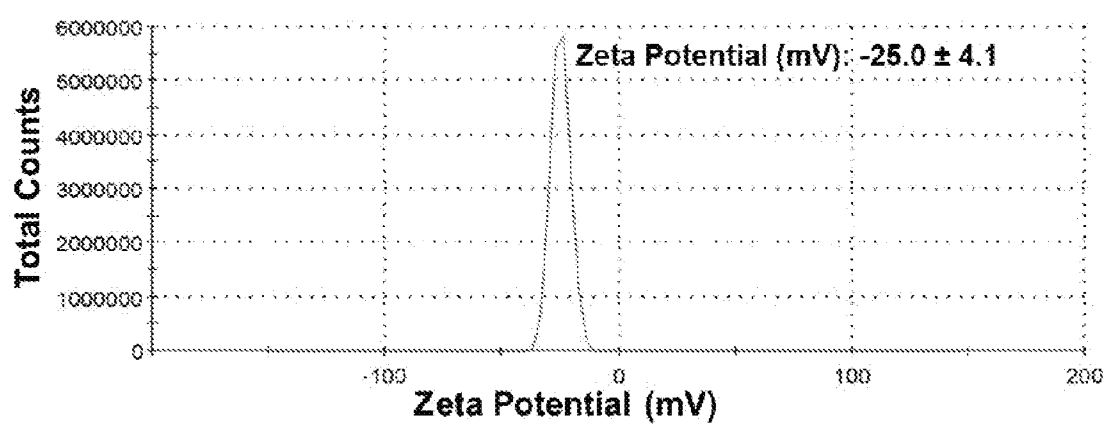

FIG. 31 depicts bispecific exosomes targeting EGFR and CD3. Zeta potential analysis of the generated bispecific exosomes αCD3×αEGFR.

Figures 32A, 32B:
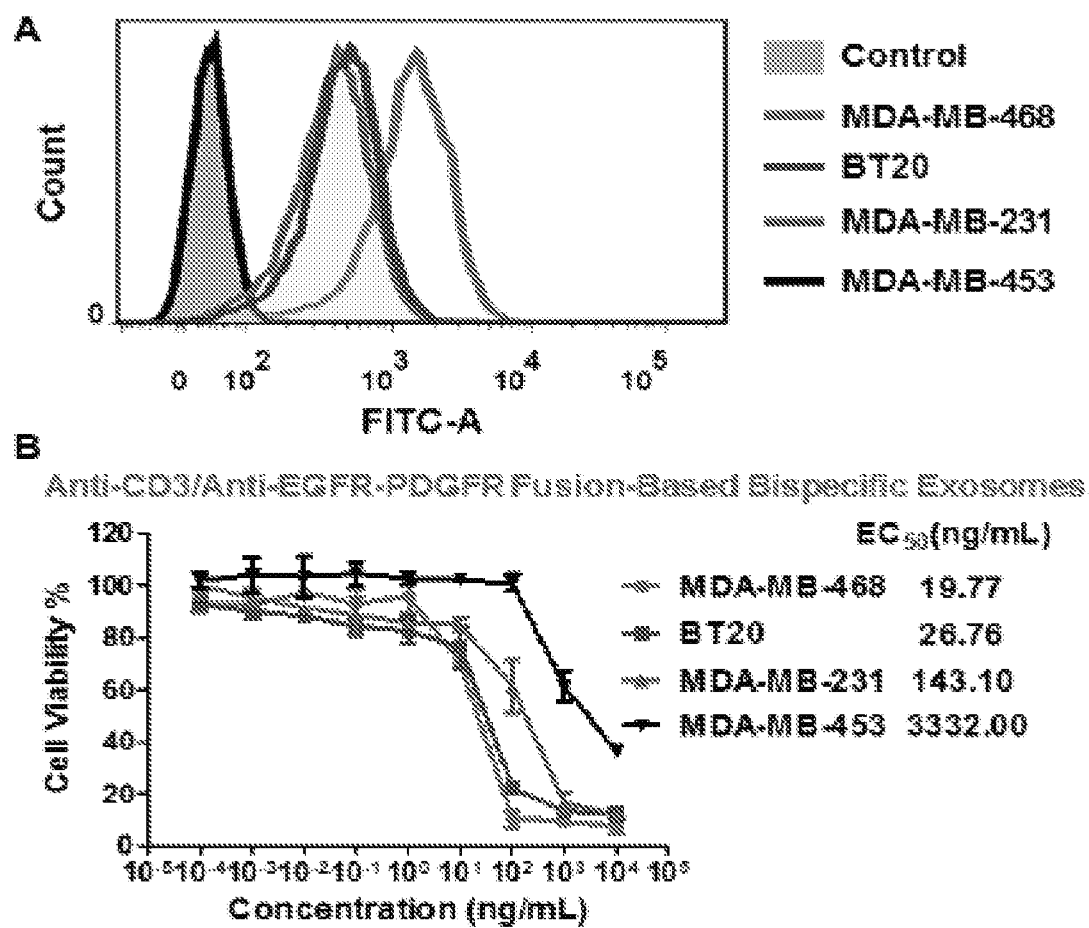

FIG. 32A-B: FIG. 32. A shows flow cytometric analysis of EGFR expression for various TNBC cell lines. FIG. 32B shows in vitro cytotoxicity of the bispecific exosomes for different TNBC cell lines. Non-activated hPBMCs were incubated with different TNBC cell lines at an E:T ratio of 10 for 40 hours in the presence of bispecific exosomes. After removing hPBMCs suspension, cell viabilities of target cells were measured through MTT assays.

Figures 33A, 33B, 33C, 33D, 33E:
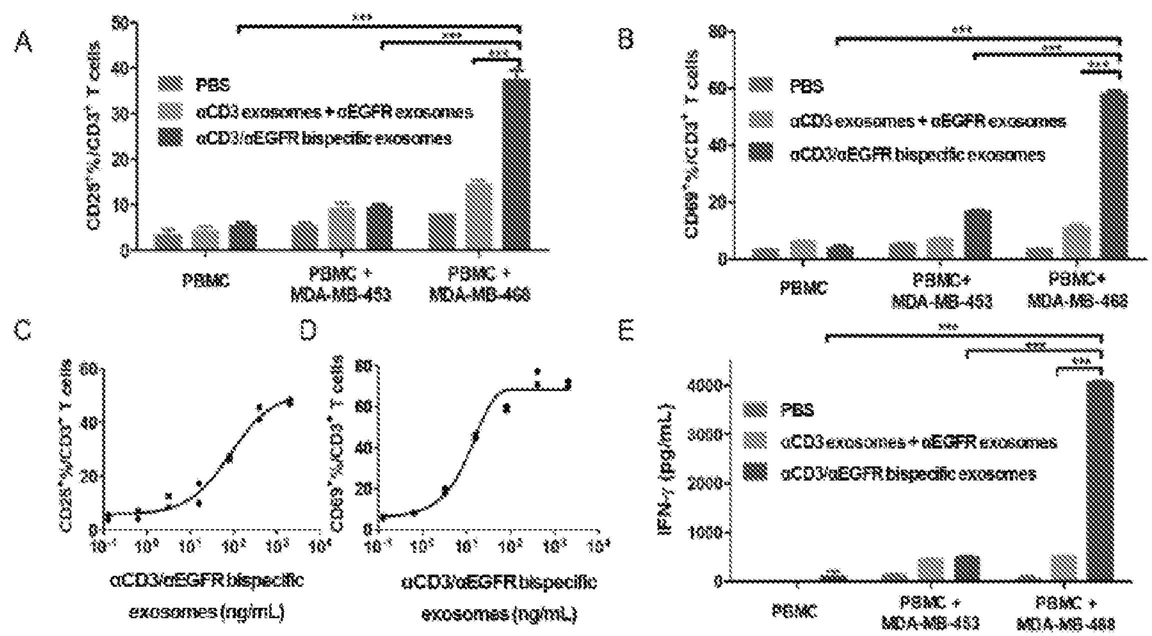

FIGS. 33A-33E relate to bispecific exosomes targeting EGFR and CD3 and in vitro characterization of T-cell activation mediated by anti-CD3/anti-EGFR bispecific exosomes. Non-activated hPBMCs were incubated with bispecific exosomes or a mixture of monospecific exosomes in the absence or presence of MDA-MB-468 cells (EGFR*) and MDA-BD-453 cells ($EGFR^-$) at an E:T ratio of 10 for 20 hours. Expression levels of CD23 and CD69 on T-cell surface were analyzed by flow cytometry. FIGS. 33A, 33B and 33E show MDA-MB-468 cell-dependent activation of T cells by the generated bispecific exosomes as evaluated by T-cell surface activation markers CD25 (FIG. 33A) and CD69 (FIG. 33B), and secreted IFN-γ (FIG. 33E). The percentages of CD25+ and CD69+ T cells were analyzed by flow cytometry. The levels of secreted IFN-γ in culture media were determined by ELISA. FIGS. 33C and 33D show dose-dependent activation of T cells by the generated bispecific exosomes as evaluated by T-cell surface activation markers CD25 (FIG. 33A) and CD69 (FIG. 33B), and secreted IFN-γ (FIG. 33E). *** P<0.001 with respect to the absence of target cells or with the negative control cells. One-way ANOVA with Tukey post hoc tests was used to compare mean SD.

Figures 34A, 34B, 34C:
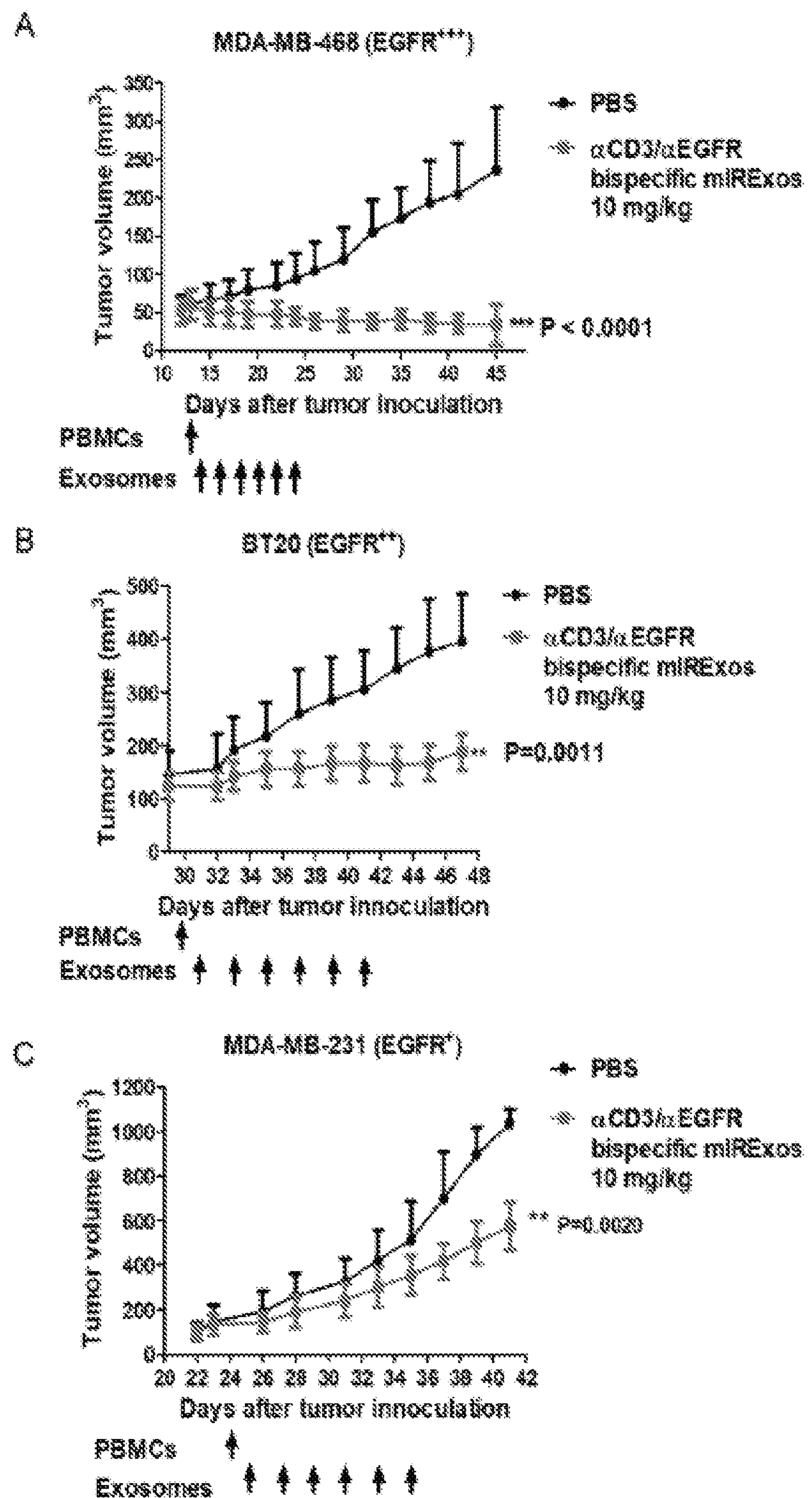

FIGS. 34A-34C show in vivo efficacy comparison of αCD3/aEGFR bispecific exosomes in three human triple negative breast cancer (TNBC) xenograft models, MDA-MB-468 (FIG. 34A), BT20 (FIG. 34B) and MDA-MB-231 (FIG. 34C). Two-four days after subcutaneous implantation of $5\times10^6$ MDA-MB-468/BT20 cancer cells or $1.5\times10^6$ MDA-MB-231 cells in 50% Matrigel respectively, female NSG mice (n=5) received one intraperitoneal (IP) injection of $20\times10^6$ non-activated human PBMCs. One days after the PBMCs injection, mice were treated intravenously with six doses of αCD3/aEGFR bispecific exosomes (10 mg/kg) or PBS every other day. Tumors were measured thrice a week with calipers. Each data point represents mean tumor volume in each group. *P<0.001, P=0.0011, or P=0.0020, with respect to the PBS control group. Student t test with repeated measures was used to compare mean SD of two groups.

Figure 35:
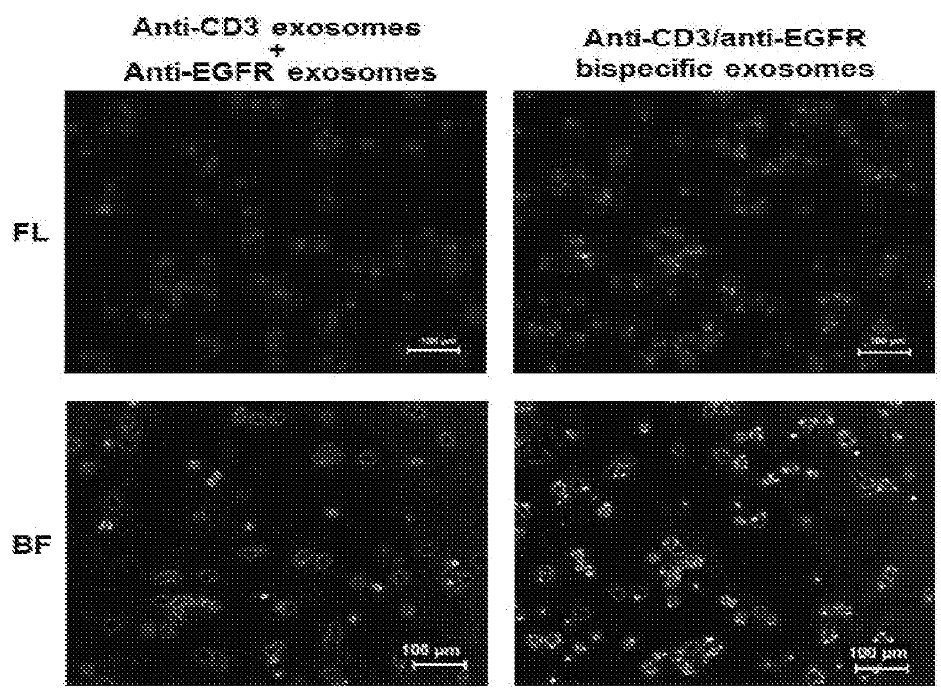

FIG. 35 depicts bispecific exosomes targeting EGFR and CD3. Bispecific binding of the anti-CD3/anti-EGFR exosomes based on antibody-Lamp2b fusion. Right panel: fluorescence (FL) and brightfield (BF) microscope images of MDA-MB-468 cells (dark) and Jurkat cells (light) in the presence of anti-CD3/anti-EGFR bispecific exosomes. Left panel: a mixture of anti-CD3 exosomes and anti-EGFR exosomes at 1:1 ratio was used as a negative control.

DETAILED DESCRIPTION Definitions

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present invention, the preferred methods and materials are now described. All publications mentioned herein are incorporated by reference to disclose and describe the methods and/or materials in connection with which the publications are cited.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated, that all numerical designations are preceded by the term "about." It also is to be understood, although not always explicitly stated, that the reagents described herein are merely exemplary and that equivalents of such are known in the art.

It must be noted that as used herein and in the appended claims, the singular forms "a," "an," and "the" include plural referents unless the context clearly dictates otherwise. Thus, for example, reference to "a cell" includes a plurality of cells.

Definitions

The following definitions assist in defining the meets and bounds of the inventions as described herein. Unless specifically noted, the embodiments describing "cell-derived vesicles" shall include "exosomes," "liposomes, and "microvesicles" alone or in combination. When the term "exosome" is used as an example, it is understood that liposomes and microvesicles can be substituted therein.

The term "about" when used before a numerical designation, e.g., temperature, time, amount, concentration, and such other, including a range, indicates approximations which may vary by (+) or (−) 10%, 5% or 1%.

The terms "administering" or "administration" in reference to delivering engineered vesicles to a subject include any route of introducing or delivering to a subject the engineered vesicles to perform the intended function. Administration can be carried out by any suitable route, including orally, intranasally, parenterally (intravenously, intramuscularly, intraperitoneally, or subcutaneously), intracranially, or topically. Additional routes of administration include intraorbital, infusion, intraarerial, intracapsular, intracardiac, intradernal intrapuhnonary, intraspinal intrasternal, intrathecal intrauterine, intravenous, subarachnoid, subcapsular, subcutaneous, transmucosal, or transtracheal. Administration includes self-administration and the administration by another.

"Comprising" or "comprises" is intended to mean that the compositions, for example media, and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this disclosure.

As used herein, the term "modified" or "engineered" relative to naturally-occurring cell-derived vesicles, refers to cell-derived vesicles (e.g., extracellular vesicles such as exosomes, liposomes and/or microvesicles) that have been altered such that they differ from a naturally occurring cell-derived vesicles.

The term "polypeptide" is used interchangeably with the term "protein" and in its broadest sense refers to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to natural and/or unnatural or synthetic amino acids, including glycine and both the D and L optical isomers, amino acid analogs and peptidomimetics. A peptide of three or more amino acids is commonly called an oligopeptide if the peptide chain is short. If the peptide chain is long, the peptide is commonly called a polypeptide or a protein. The term "peptide fragment," as used herein, also refers to a peptide chain.

The phrase "equivalent polypeptide" or "equivalent peptide fragment" or simply "equivalent" referring to a protein or peptide, refers to protein, polynucleotide, or peptide fragment which hybridizes to the exemplified polynucleotide or peptide fragment under stringent conditions and which exhibit similar biological activity in vivo, e.g., approximately 100%, or alternatively, over 90% or alternatively over 85% or alternatively over 70%, as compared to the standard or control biological activity. Additional embodiments within the scope of this invention are identified by having more than 60%, or alternatively, more than 65%, or alternatively, more than 70%, or alternatively, more than 75%, or alternatively, more than 80%, or alternatively, more than 85%, or alternatively, more than 90%, or alternatively, more than 95%, or alternatively more than 97%, or alternatively, more than 98% or 99% sequence homology. Percentage homology can be determined by sequence comparison using programs such as BLAST run under appropriate conditions. In one aspect, the program is run under default parameters.

The term "polynucleotide" refers to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, or EST), exons, introns, messenger RNA (mRNA), transfer RNA, ribosomal RNA, ribozymes, cDNA, RNAi, siRNA, recombinant polynucleotides, branched polynucleotides, plasmids, vectors, isolated DNA of any sequence, isolated RNA of any sequence, nucleic acid probes and primers. A polynucleotide can comprise, or alternatively consist essentially of, or yet further consist of modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

"Anti-cancer therapeutic" refers to any drug useful in the treatment of cancer. Various kinds of anti-cancer drugs are alkylating agents (cisplatin, chlorambucil, procarbazine, carmustine etc.), antimetabolites (methotrexate, cytarabine, gemcitabine etc.), anti-microtubule agents (vinblastine, paclitaxel etc.), topoisomerase inhibitors (etoposide, doxorubicin etc.), and cytotoxic agents (bleomycin, mitomycin etc.).

"Homology" or "identity" or "similarity" are synonymously and refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Preferably, default parameters are used for alignment. One alignment program is BLAST, using default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+SwissProtein+SPupdate+PIR. Details of these programs can be found at the following Internet address: http://www.ncbi.nlm.nih.gov/blast/Blast.cgi, last accessed on Nov. 26, 2007. Biologically equivalent polynucleotides are those having the specified percent homology and encoding a polypeptide having the same or similar biological activity.

A "gene" refers to a polynucleotide containing at least one open reading frame (ORF) that is capable of encoding a particular polypeptide or protein after being transcribed and translated. Any of the polynucleotide or polypeptide sequences described herein may be used to identify larger fragments or full-length coding sequences of the gene with which they are associated. Methods of isolating larger fragment sequences are known to those of skill in the art.

The term "express" refers to the production of a gene product such as RNA or a polypeptide or protein.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in aneukaryotic cell.

"Cancer associated antigen," "tumor antigen," or "cancer antigen" refers to an antigenic substance produced in tumor cells, i.e., it triggers an immune response in the host. Non-limiting examples include alphafetoprotein (AFP), carcinoembryonic antigen, CA-125, MUC-1, epithelial tumor antigen, tyrosinase, and melanoma-associated antigen.

A "gene product" or alternatively a "gene expression product" refers to the RNA when a gene is transcribed or amino acid (e.g., peptide or polypeptide) generated when a gene is transcribed and translated.

"Small molecular immune checkpoint modulators" are small molecules (less than 900 daltons) capable of modulating an "immune checkpoint" or regulator of immune activation. "Immune checkpoint" may refer to a receptor target. Non-limiting examples of immune checkpoints include PD-1/PD-L1, CTLA4, CD27, CD28, CD40, CD122, CD137, OX40, GITR, ICOS, A2AR, B7-H3, B7-H4, BTLA, CTLA-4, IDO, KIR, LAG3, TIM-3, and VISTA. "Immune checkpoint inhibitors" refers to small molecules or macromolecules which act as inhibitors of an immune checkpoint.

"Immune regulatory factor" refers to a protein which regulates the immune system.

"Immune agonist" refers to an agent which can stimulate the immune system.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced there from.

Applicants have provided herein the polypeptide and/or polynucleotide sequences for use in gene and protein transfer and expression techniques described below. It should be understood, although not always explicitly stated that the sequences provided herein can be used to provide the expression product as well as substantially identical sequences that produce a protein that has the same biological properties. These "biologically equivalent" or "biologically active" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions. Specific polypeptide sequences are provided as examples of particular embodiments. Modifications to the sequences to amino acids with alternate amino acids that have similar charge. Additionally, an equivalent polynucleotide is one that hybridizes under stringent conditions to the reference polynucleotide or its complement. Alternatively, an equivalent polypeptide or protein is one that is expressed from an equivalent polynucleotide.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise, or alternatively consist essentially of, or yet further consist of two strands forming a duplex structure, three or more strands forming a multi-stranded complex, a single self-hybridizing strand, or any combination of these. A hybridization reaction may constitute a step in a more extensive process, such as the initiation of a PC reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

A "vector" is defined as any molecule that can carry inserted polynucleotides into a host cell. Examples of vectors are liposomes, micelles, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide of this invention can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extra-chromosomal replicon (e.g., a plasmid) or a nuclear or mitochondrial chromosome. A number of vectors are known to be capable of mediating transfer of genes to mammalian cells, as is known in the art and described herein.

A "viral vector" is defined as a recombinantly produced virus or viral particle that comprises, or alternatively consists essentially of, or yet further consists of a polynucleotide to be delivered into a host cell, either in vivo, ex vivo or in vitro. Examples of viral vectors include retroviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827. In aspects where gene transfer is mediated by a retroviral vector, a vector construct refers to the polynucleotide comprising, or alternatively consisting essentially of, or yet further consisting of the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising, or alternatively consisting essentially of, or yet further consisting of the viral genome or part thereof, and a transgene. Adenoviruses (Ads) are a relatively well characterized, homogenous group of viruses, including over 50 serotypes. See, e.g., International PCT Application No. WO 95/27071. Ads do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, CA) and Promega Biotech (Madison, WI). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

The terms "culture" or "culturing" refer to the in vitro propagation of cells or organisms on or in media of various kinds. It is understood that the descendants of a cell grown in culture may not be completely identical (i.e., morphologically, genetically, or phenotypically) to the parent cell.

"Liposomes" are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C═C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, distearoylphosphatidylethanolamine (DSPE), dioleoylphosphatidylcholine (DOPC), dipalmitoylphosphatidylcholine (DPPC), palmitoyloteoylphosphatidylcholine (POPC), palmitoyloleoylphosphatidylethanolamine (POPE) and dioleoylphosphatidylethanolamine 4-(N-maleimido-triethyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioteoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs).

As used herein the term "apoptotic body" intends the vesicles that are produced when a cell breaks down. Apoptotic bodies consist of cytoplasm with tightly packed organelles with or without a nuclear fragment.

An extracellular vesicle addressing domain (also referred to herein as an "exosomal membrane protein" or "exosome addressing domain") is a peptide or a protein that targets other peptides or proteins of interests to the surface of extracellular vesicle, or mediate distribution of other peptides or proteins of interests on extracellular vesicles. Non-limiting examples of such include platelet-derived growth factor receptor (PDGFR), Lam2b, lactadherin C1C2 domain, CD13 and CD9. Examples of the amino acid sequences of the polypeptides and encoding nucleic acids are provided in the sequence listings of the fusion polypeptides, provided herein. Also intended are biological equivalents of these sequences, wherein a biological equivalent nucleic acid, polynucleotide or oligonucleotide or peptide is one having at least 80% sequence identity, or alternatively at least 85% sequence identity, or alternatively at least 90% sequence identity, or alternatively at least 92% sequence identity, or alternatively at least 95% sequence identity, or alternatively at least 97% sequence identity, or alternatively at least 98% sequence identity to the reference nucleic acid, polynucleotide, oligonucleotide or peptide. In alternative embodiment, the equivalent or biological equivalent hybridizes to the reference polynucleotide or oligonucleotide or its complement under conditions of high stringency. In a further aspect, the equivalent or biological equivalent is a peptide encoded by a polynucleotide that hybridizes to the polynucleotide encoding the reference peptide or its complement under conditions of high stringency.

As used herein the term "fused" intends conjugated or joined by a chemical bond, for example a covalent bond.

As used herein, the term "antigen binding domain" refers to any protein or polypeptide domain that can specifically bind to an antigen target or cell surface receptor. Non-limiting examples include an antibody, an antibody fragment, a single domain antibody, a bispecific antibody, a fragment of a bispecific antibody, an scFv antibody fragment, a heavy chain variable domain (VH), a light chain variable domain (VL). Non-limiting examples of the amino acid sequence and polynucleotides encoding such are provided herein. Also intended within the scope of this disclosure are biological equivalents of the exemplified polypeptide and polynucleotide sequences.

In one aspect, the antigen binding domain binds to an antigenic determinant or epitope on an immune cell, such as an T cell, NK cell, a CD4+ T cell, a CD8+ T cell, a CD19+ cell, a CD20+ cell, a macrophage, or a B cell. Non-limiting examples of the amino acid sequence and polynucleotides encoding such are provided herein. Also intended within the scope of this disclosure are biological equivalents of the exemplified polypeptide and polynucleotide sequences.

As used herein, the terms "antigen binding domain, ""antibody," "antibodies" and "immunoglobulin" includes whole antibodies and any antigen binding fragment or a single chain thereof. Thus the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', $F(ab)_2$, Fv, scFv, dsFv, Fd fragments, dAb, VH, VL, VhH, and V-NAR domains; minibodies, diabodies, triabodies, tetrabodies and kappa bodies; multi-specific antibody fragments formed from antibody fragments and one or more isolated. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, at least one portion of a binding protein, chimeric antibodies, humanized antibodies, single-chain antibodies, and fusion proteins comprising, or alternatively consisting essentially of, or yet further consisting of an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues.

"Fusion polypeptide" refers to polypeptides created through the joining of two or more genes that originally coded for separate polypeptides.

The antibodies can be polyclonal, monoclonal, multi-specific (e.g., bispecific antibodies), and antibody fragments, so long as they exhibit the desired biological activity. Antibodies can be isolated from any suitable biological source, e.g., murine, rat, sheep and canine.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise, or alternatively consist essentially of, or yet further consist of a linker peptide that is not found in native human antibodies. For example, an Fv can comprise, or alternatively consist essentially of, or yet further consist of a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

A "human monoclonal antibody" refers to antibodies displaying a single binding specificity which have variable and constant regions derived from human germline immunoglobulin sequences. The term also intends recombinant human antibodies. Methods to making these antibodies are known in the art.

The term "recombinant human antibody" as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. Methods to making these antibodies are known in the art.

As used herein, chimeric antibodies are antibodies whose light and heavy chain genes have been constructed, typically by genetic engineering, from antibody variable and constant region genes belonging to different species.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region of the recipient are replaced by residues from a variable region of a non-human species (donor antibody) such as mouse, rat, rabbit, or non-human primate having the desired specificity, affinity and capacity. Humanized antibodies may comprise, or alternatively consist essentially of, or yet further consist of residues that are not found in the recipient antibody or in the donor antibody. The humanized antibody can optionally also comprise, or alternatively consist essentially of, or yet further consist of at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. In general, humanized antibodies are expected to produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

"Small molecular chemotherapy drug" as used herein refers to a drug of less than about 900 daltons in mass useful in the treatment of cancer. Non-limiting examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabinc, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca americanaproteins* (PAPI, PAPII, and PAP-S), *Momordica charantia* inhibitor, curcin, crotin, *Sapaonaria officinalis* inhibitor, gelonin, mitogellin, restrietocin, phenomycin, enomycin toxins and mixed toxins.

As used herein, the term "antibody derivative," or simply "derivative" in reference to an antibody comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

A "linker" or "peptide linker" or "linker polypeptide" refers to a peptide sequence linked to either the N-terminus or the C-terminus of a polypeptide sequence. In one aspect, the linker is from about 1 to about 20 amino acid residues long or alternatively 2 to about 10, about 3 to about 5 amino acid residues long. Examples of peptide linkers include (GGGGS)n, n=0-5 (SEQ ID NO: 2); (GGGS)n, n=0-6 (SEQ ID NO: 3); (GGS)n, n=0-7 (SEQ ID NO: 4); (EAAAK)n, n=0-4 (SEQ ID NO: 5); PSGQAGAAASESLFVSNHAY (SEQ ID NO: 6); and GSTSGSGKPGSGEGS (SEQ ID NO: 7).

HER2 or human epidermal growth factor receptor 2, is a gene that is known to play a role in the development of breast cancer. The HER2 gene makes HER2 proteins. HER2 proteins are receptors on breast cells. The protein coding sequence of the gene is known in the art, e.g., see genecards.org/cgi-bin/carddisp.pl?gene=ERBB2, last accessed on Mar. 28, 2016. Antibodies and fragments to the HER2 receptor are known in the art.

The term "EGFR" or "epidermal growth factor receptor" refers to the human protein having a GenBank Gene ID No. 1956 or any mammal homologue. Antibodies and fragments thereof that bind EGFR are known in the art.

"Isolated" referring to fusion proteins or vesicles, refers to a protein or vesicle that has been isolated, not necessarily purified, from the cell and/or biological matrix in which it was previously contained.

As used herein, the term "label" intends a directly or indirectly detectable compound or composition that is conjugated directly or indirectly to the composition to be detected or isolated, e.g., N-terminal histidine tags (N-His), HA tag, FLAG tag, 6×His tag (SEQ ID NO: 1), magnetically active isotopes, e.g., $^{115}Sn$, $^{117}Sn$ and $^{119}Sn$, a non-radioactive isotopes such as $^{13}C$ and $^{15}N$, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals ($6^{th}$ ed). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

In some aspects, "label" refers to a purification label that aids in the purification of the compound to which it is attached. The label may impart the compound with physical properties supporting its purification through techniques including, but not limited to, affinity chromatography, ion-exchange chromatography, and reverse or regular phase liquid chromatography.

As used herein, the term "contacting" refers to combining or mixing, in this case a cell with a polynucleotide or a biological sample with a vesicle.

"Bispecific" refers to a property of an antibody wherein the antibody can simultaneously bind two different types of antigen. "Multi-specific" refers to the binding of more than one type of antigen.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Examples include of a eukaryotic cell include yeast, higher plant, insect and mammalian cells. Non-limiting examples of eukaryotic cells or hosts include mammalian such as simian, bovine, porcine, murine, rat, or human. Also included are avian and reptilian. Additional non-limiting examples include Expi293F cells, HeLa cells, HEK293T, MDA-MB-231, immature dendritic cells, and stem cells.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 μm in diameter and 10 μm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

Non-limiting examples of eukaryotic and prokaryotic cells include bacterial cells, yeast cells, insect cells, animal cells, mammalian cells, murine cells, rat cells, sheep cells, simian cells and human cells. Examples of bacterial cells include *Escherichia coli, Salmonella enterica* and *Streptococcus gordonii*. The cells can be purchased from a commercial vendor such as the American Type Culture Collection (ATCC, Rockville Maryland, USA) or cultured from an isolate using methods known in the art. Examples of suitable eukaryotic cells include, but are not limited to 293T HEK cells, as well as the hamster cell line BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis, Yarrowia*, or *Pichia*. See e.g., U.S. Pat. Nos. 4,812,405; 4,818,700; 4,929,555; 5,736,383; 5,955,349; 5,888,768 and 6,258,559. Examples of plant cells include grape cells, grapefruit cells, ginger cells and carrot cells. See the web address ncbi.nlm.nih.gov/pmc/articles/PMC4851829; NCT01294072; and NCT01668849. The term "immune effector cells" refers to cells capable of binding an antigen and which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates. Certain diseased tissue expresses specific antigens and CTLs specific for these antigens have been identified.

The term "immune effector molecule" as used herein, refers to molecules capable of antigen-specific binding, and includes antibodies, T cell antigen receptors, B cell antigen receptors, and MHC Class I and Class II molecules.

"Immune response" broadly refers to the antigen-specific responses of lymphocytes to foreign substances. The terms "immunogen" and "immunogenic" refer to molecules with the capacity to elicit an immune response. All immunogens are antigens, however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules. The compositions of this disclosure can be used to induce an immune response in a subject in need thereof by administering an effective amount of the appropriate engineered extracellular vesicle.

The terms "patient," "subject," or "mammalian subject" are used interchangeably herein and include any mammal in need of the treatment or prophylactic methods described herein (e.g., methods for the treatment or prophylaxis of cancer, hemophilia). Such mammals include, particularly humans (e.g., fetal humans, human infants, human teens, human adults, etc.). Other mammals in need of such treatment or prophylaxis can include non-human mammals such as dogs, cats, or other domesticated animals, horses, livestock, laboratory animals (e.g., lagomorphs, non-human primates, etc.), and the like. The subject may be male or female.

The term "purified population," relative to naturally occurring vesicles, as used herein refers to plurality of vesicles that have undergone one or more processes of selection for the enrichment or isolation of the desired vesicle population relative to some or all of some other component with which engineered extracellular vesicles are normally found in culture media or in nature. Alternatively, "purified" can refer to the removal or reduction of residual undesired components found in the conditioned media (e.g., cell debris, soluble proteins, etc.). A "highly purified population" as used herein, refers to a population of vesicles in which at least 65%, at least 70%, at least 75%, at least 80%, at least 85%, at least 90%, at least 95%, at least 98%, at least 99% or 100% of cell debris and soluble proteins (e.g., proteins derived from fetal bovine serum and the like) in the conditioned media along with the cell-derived vesicles are removed.

The terms "treatment," "treat," "treating," etc. as used herein, include but are not limited to, alleviating a symptom of a disease or condition (e.g., cancer) or a condition associated with cancer and/or reducing, suppressing, inhibiting, lessening, ameliorating or affecting the progression, severity, and/or scope of the disease or condition. "Treatments" refer to one or both of therapeutic treatment and can separately relate to prophylactic or preventative measures as desired. Prevention may not be obtainable for certain diseased or conditions and for those conditions, prevention is excluded from the term treatment. In one aspect, prevention is excluded from the terms "treatment, treat, or treating." Subjects in need of treatment include those already affected by a disease or disorder or undesired physiological condition as well as those in which the disease or disorder or undesired physiological condition is to be prevented.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at www.cancer.gov, last visited on May 1, 2008. Typically, a patient is given a subsequent chemotherapy regimen because the patient did not show a positive clinical or sub-clinical response to the first line therapy or the first line therapy has stopped.

As described in more detail below, the engineered vesicles can contain chemotherapeutic agents. The following are non-limiting examples of such. Cetuximab (MC-C225) is marketed under the name Erbitux®. Cetuximab is a chimeric (mouse/human) monoclonal antibody, an epidermal growth factor receptor (EGFR) inhibitor, given by intravenous injection for treatment of metastatic colorectal cancer and head and neck cancer. Cetuximab is manufactured and distributed in North America by ImClone and Bristol-Myers Squibb, while in the rest of the world distribution is by Merck KGaA. In one aspect, an equivalent of cetuximab is an antibody directed to EGFR, or a small molecule targeting EGFR or inhibiting EGFR. In another aspect, an equivalent of cetuximab may also include homologs of cetuximab, mutant cetuximab, recombinant cetuximab that retains substantially the same function of cetuximab. Panitumumab (INN), formerly ABX-EGF, is a fully human monoclonal antibody specific to the epidermal growth factor receptor. Panitumumab is manufactured by Amgen and marketed as Vectibix. In one aspect, an equivalent of panitumumab is an antibody directed to EGFR, or a small molecule targeting EGFR or inhibiting EGFR. In another aspect, an equivalent of panitumumab may also include homologs of panitumumab, mutant panitumumab, recombinant panitumumab that retains substantially the same function of panitumumab. Irinotecan (CPT-11) is sold under the trade name of Camptosar®. It is a semi-synthetic analogue of the alkaloid camptothecin, which is activated by hydrolysis to SN-38 and targets topoisomerase I. Chemical equivalents are those that inhibit the interaction of topoisomerase I and DNA to form a catalytically active topoisomerase I-DNA complex. Chemical equivalents inhibit cell cycle progression at G2-M phase resulting in the disruption of cell proliferation. An equivalent of irinotecan is a composition that inhibits a topoisomerase. Non-limiting examples of an equivalent of irinotecan include topotecan, camptothecin and lamellarin D, etoposide, or doxorubicin. Oxaliplatin (trans–/–diaminocyclohexane oxalatoplatinum; L-OHP; CAS No. 61825-94-3) is sold under the trade name of Elotaxin. It is a platinum derivative that causes cell cytotoxicity. Oxaliplatin forms both inter- and intra-strand cross links in DNA, which prevent DNA replication and transcription, causing cell death. Non-limiting examples of an equivalent of oxaliplatin include carboplatin and cisplatin. Topoisomerase inhibitors are agents designed to interfere with the action of topoisomerase enzymes (topoisomerase I and II), which are enzymes that control the changes in DNA structure by catalyzing the breaking and rejoining of the phosphodiester backbone of DNA strands during the normal cell cycle. In one aspect, topoisomerase inhibitors include irinotecan, topotecan, camptothecin and lamellarin D, or compounds targeting topoisomerase IA. In another aspect, topoisomerase inhibitors include etoposide, doxorubicin or compounds targeting topoisomerase II. Pyrimidine antimetabolite includes, without limitation, fluorouracil (5-FU), its equivalents and prodrugs. In one embodiment, a pyrimidine antimetabolite is a chemical that inhibits the use of a pyrimidine. The presence of antimetabolites can have toxic effects on cells, such as halting cell growth and cell division, so these compounds can be used as chemotherapy for cancer. Fluorouracil (5-FU) belongs to the family of therapy drugs called pyrimidine based anti-metabolites. It is a pyrimidine analog, which is transformed into different cytotoxic metabolites that are then incorporated into DNA and RNA thereby inducing cell cycle arrest and apoptosis. Chemical equivalents are pyrimidine analogs which result in disruption of DNA replication. Chemical equivalents inhibit cell cycle progression at S phase resulting in the disruption of cell cycle and consequently apoptosis. Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xeloda), S-1 (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487. "5-FU based adjuvant therapy" refers to 5-FU alone or alternatively the combination of 5-FU with other treatments, that include, but are not limited to radiation, methyl-CCNU, leucovorin, oxaliplatin, irinotecin, mitomycin, cytarabine, levamisole. Specific treatment adjuvant regimens are known in the art as FOLFOX, FOLFOX4, FOLFIRI, MOF (semustine (methyl-CCNU), vincrisine (Oncovin) and 5-FU). For a review of these therapies see Beaven and Goldberg (2006) Oncology 20(5):461-470. An example of such is an effective amount of 5-FU and Leucovorin. Other chemotherapeutics can be added, e.g., oxaliplatin or irinotecan. Capecitabine is a prodrug of (5-FU) that is converted to its active form by the tumor-specific enzyme PynPase following a pathway of three enzymatic steps and two intermediary metabolites, 5'-deoxy-5-fluorocytidine (5'-DFCR) and 5'-deoxy-5-fluorouridine (5'-DFUR). Capecitabine is marketed by Roche under the trade name Xeloda®. A therapy comprising, or alternatively consisting essentially of, or yet further consisting of a pyrimidine antimetabolite includes, without limitation, a pyrimidine antimetabolite alone or alternatively the combination of a pyrimidine antimetabolite with other treatments, that include, but are not limited to, radiation, methyl-CCNU, leucovorin, oxaliplatin, irinotecin, mitomycin, cytarabine, levamisole. Specific treatment adjuvant regimens are known in the art as FOLFOX, FOLFOX4, FOLFOX6, FOLFIRI, MOF (semustine (methyl-CCNU), vincrisine (Oncovin) and 5-FU). For a review of these therapies see Beaven and Goldberg (2006) *Oncology* 20(5):461-470. An example of such is an effective amount of 5-FU and Leucovorin. Other chemotherapeutics can be added, e.g., oxaliplatin or irinotecan. FOLFIRI is a chemotherapy regimen for treatment of colorectal cancer. It is made up of the following drugs: FOL—folinic acid (leucovorin), a vitamin B derivative used as a "rescue" drug for high doses of the drug methotrexate and that modulates/potentiates/reduces the side effects of fluorouracil; 5-fluorouracil (5-FU), a pyrimidine analog and antimetabolite which incorporates into the DNA molecule and stops synthesis; and IRI—irinotecan (Camptosar), a topoisomerase inhibitor, which prevents DNA from uncoiling and duplicating. FOLFOX is a chemotherapy regimen for treatment of colorectal cancer and is made up of the following drugs: FOL—folinic acid (leucovorin), 5-fluorouracil (5-FU), and OX—oxaliplatin. FOLFOXFIRI is a chemotherapy regimen for treatment of colorectal cancer and is made up of the following drugs: FOL—folinic acid (leucovorin), 5-fluorouracil (5-FU), OX-oxaliplatin and IRI—irinotecan (Camptosar).

As used herein, the term "microRNAs" or "miRNAs" refers to post-transcriptional regulators that typically bind to complementary sequences in the three prime untranslated regions (3' UTRs) of target messenger RNA transcripts (mRNAs), usually resulting in gene silencing. Typically, miRNAs are short, non-coding ribonucleic acid (RNA) molecules, for example, 21 or 22 nucleotides long. The terms "microRNA" and "miRNA" are used interchangeably.

In one aspect, the therapeutic agent is a short interfering RNA, also known as siRNA. Methods to prepare and screen interfering RNA and select for the ability to block polynucleotide expression are known in the art and non-limiting examples of which are shown below. These interfering RNA are provided by this invention alone or in combination with a suitable vector or within a host cell. Compositions containing the RNAi are further provided. RNAi is useful to knock-out or knock-down select functions in a cell or tissue as known in the art.

siRNA sequences can be designed by obtaining the target mRNA sequence and determining an appropriate siRNA complementary sequence. siRNAs of the invention are designed to interact with a target sequence, meaning they complement a target sequence sufficiently to hybridize to that sequence. An siRNA can be 100% identical to the target sequence. However, homology of the siRNA sequence to the target sequence can be less than 100% as long as the siRNA can hybridize to the target sequence. Thus, for example, the siRNA molecule can be at least 70%, 75%, 80%, 85%, 90%, 95%, 96%, 97%, 98%, 99% or 100% identical to the target sequence or the complement of the target sequence. Therefore, siRNA molecules with insertions, deletions or single point mutations relative to a target may also be used. The generation of several different siRNA sequences per target mRNA is recommended to allow screening for the optimal target sequence. A homology search, such as a BLAST search, should be performed to ensure that the siRNA sequence does not contain homology to any known mammalian gene. In one aspect, the targets of the siRNA is of the group of anti-PD1, anti-PDL2 and anti-CTLA4.

Researchers have determined that certain characteristics are common in siRNA molecules that effectively silence their target gene (Duxbury (2004) J. Surgical Res. 117:339-344; Ui-Tei et al. (2004) Nucl. Acids Res. 32:936-48). As a general guide, siRNAs that include one or more of the following conditions are particularly useful in gene silencing in mammalian cells: GC ratio of between 45-55%, no runs of more than 9 G/C residues, G/C at the 5' end of the sense strand; A/U at the 5' end of the antisense strand; and at least 5 A/U residues in the first 7 bases of the 5' terminal of the antisense strand.

siRNA are, in general, from about 10 to about 30 nucleotides in length. For example, the siRNA can be 10-30 nucleotides long, 12-28 nucleotides long, 15-25 nucleotides long, 19-23 nucleotides long, or 21-23 nucleotides long. When an siRNA contains two strands of different lengths, the longer of the strands designates the length of the siRNA. In this situation, the unpaired nucleotides of the longer strand would form an overhang.

The term siRNA includes short hairpin RNAs (shRNAs). shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides long. For example, the stem can be 10-30 nucleotides long, 12-28 nucleotides long, 15-25 nucleotides long, 19-23 nucleotides long, or 21-23 nucleotides long.

Tools to assist siRNA design are readily available to the public. For example, a computer-based siRNA design tool is available on the internet at www.dharmacon.com, last accessed on Nov. 26, 2007.

As used herein, the term "homogeneous" in reference to a population of engineered vesicles refers to population of vesicles that have the same identify or a similar amount of one or more antigen binding domain(s) and/or payload. A homogenous population is one wherein about 65%, about 70%, about 75%, about 80%, about 85%, about 90%, about 95%, about 98%, or 100% of the vesicles share the one or more antigen binding domain(s) and/or payload.

As used herein, the term "heterogeneous" in reference to a population of engineered vesicles refers to population of vesicles that have differing identity or differing amount of one or more antigen binding domain(s) and/or payload.

As used herein, the term "pharmaceutically acceptable carrier" refers to any of the standard pharmaceutical carriers such as sterile solutions, tablets, coated tablets, and capsules. Typically such carriers contain excipients such as starch, milk, sugar, certain types of clay, gelatin, stearic acids or salts thereof, magnesium or calcium stearate, talc, vegetable fats or oils, gums, glycols, or other known excipients. Such carriers may also include flavor and color additives or other ingredients. Examples of pharmaceutically acceptable carriers include, but are not limited to, the following: water, saline, buffers, inert, nontoxic solids (e.g., mannitol, talc). Compositions comprising, or alternatively consisting essentially of, or yet further consisting of such carriers are formulated by well-known conventional methods. Depending on the intended mode of administration and the intended use, the compositions may be in the form of solid, semi-solid, or liquid dosage forms, such, for example, as powders, granules, crystals, liquids, suspensions, liposomes, pastes, creams, salves, etc., and may be in unit-dosage forms suitable for administration of relatively precise dosages.

An "effective amount" intends an amount sufficient to effect beneficial or desired results. An effective amount can be administered in one or more administrations, applications or dosages. Such delivery is dependent on a number of variables including the time period for which the individual dosage unit is to be used, the bioavailability of the therapeutic agent, the route of administration, etc. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for patient administration. In general, one will desire to administer an amount of the compound that is effective to achieve a serum level commensurate with the concentrations found to be effective in vitro. Determination of these parameters is well within the skill of the art. These considerations, as well as effective formulations and administration procedures are well known in the art and are described in standard textbooks.

As used herein, the term "vector" refers to a non-chromosomal nucleic acid comprising, or alternatively consisting essentially of, or yet further consisting of an intact replicon such that the vector may be replicated when placed within a cell, for example by a process of transformation. Vectors may be viral or non-viral. Viral vectors include plasmids, retroviruses, lentiviruses, adenoviruses, herpesvirus, bacculoviruses, modified bacculoviruses, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising, or alternatively consisting essentially of, or yet further consisting of DNA condensed with cationic polymers such as heterogeneous polylysine, defined-length oligopeptides, and polyethylene imine, in some cases contained in liposomes; and the use of ternary complexes comprising, or alternatively consisting essentially of, or yet further consisting of a virus and polylysine-DNA.

A "viral vector" is defined as a recombinantly produced virus or viral particle that comprises a polynucleotide to be delivered into a cell, either in vivo, ex vivo or in vitro. Examples of viral vectors include retroviral vectors, lentiviral vectors, adenovirus vectors, adeno-associated virus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5:434-439 and Ying, et al. (1999) Nat. Med. 5(7):823-827.

Extracellular cell-derived vesicles, also referred to as extracellular vesicles, are membrane surrounded structures that are released by cells in vitro and in vivo. Extracellular vesicles can contain proteins, lipids, and nucleic acids and can mediate intercellular communication between different cells, including different cell types, in the body. Two types of extracellular vesicles are exosomes and microvesicles. Exosomes range in size from approximately 30 nm to about 200 nm. Exosomes are released from a cell by fusion of multivesicular endosomes (MVE) with the plasma membrane. Microvesicles, on the other hand, are released from a cell upon direct budding from the plasma membrane (PM). Microvesicles are typically larger than exosomes and range from approximately 100 nm to 1 μm. Also intended within this term are liposomes and apoptotic bodies.

Modes for Carrying Out the Disclosure

This disclosure provides an isolated engineered extracellular vesicle comprising, or alternatively consisting essentially of, or yet further consisting of one or more antigen binding domain(s) fused to an extracellular vesicle addressing domain (also termed as an exosomal membrane protein) expressed on the surface of the vesicle. FIGS. 1A, 1B, 3 and 4A schematically show the general structures of the engineered extracellular vesicles. The extracellular vesicles can be one or more of an exosome, a liposome, a microvesicle, and an apoptotic body. In one aspect, the extracellular vesicle is an exosome and the diameter is from about 30 nm to 300 nm. In one aspect the vesicle further comprises, or alternatively consists essentially of, or yet further consists of a purification and/or a detectable label. Examples of such are described herein, e.g., HA, FLAG and 6×His (SEQ ID NO: 1).

The vesicles can be isolated from a eukaryotic or a prokaryotic cell. Examples of eukaryotic cells are a mammalian cell, a yeast cell or a plant cell. An example of a prokaryotic cell is a bacterial cell. Non-limiting examples include Expi293F cells, HeLa cells, HEK293T, MDA-MB-231, immature dendritic cells, and stem cells.

Figures 1A, 1B:
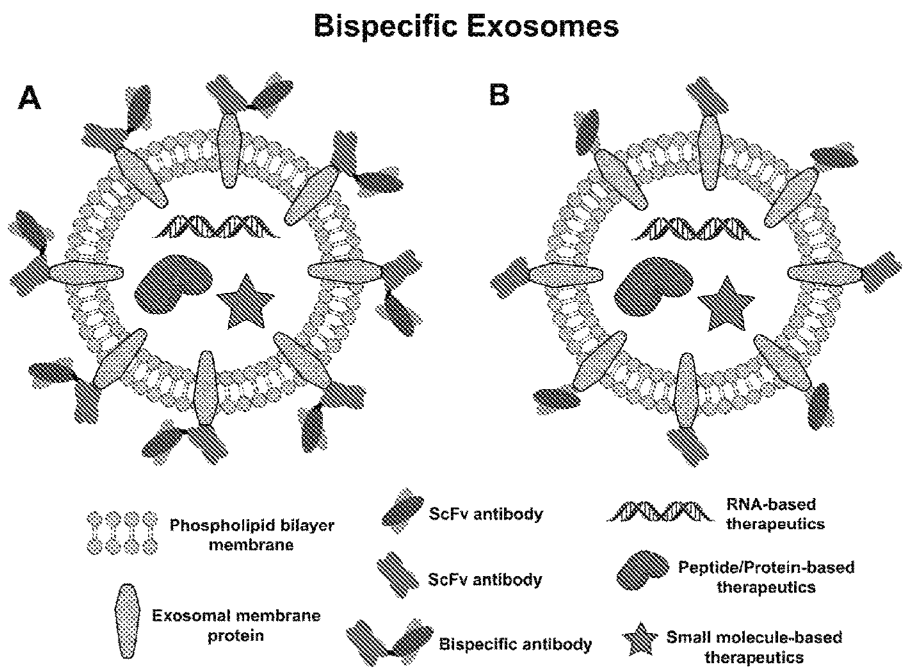
FIGS. 1A-1B are structures of the bispecific exosomes.
Figure 2A:
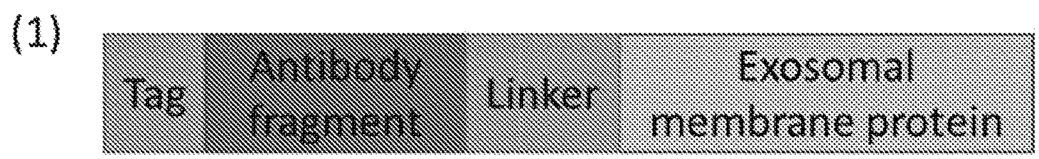
FIGS. 2A-2B show a general description of the fusion polypeptides. As depicted in the schemes, representative tags include: HA, FLAG, and 6×His (SEQ ID NO: 1). Representative linkers include.
Figure 2B:
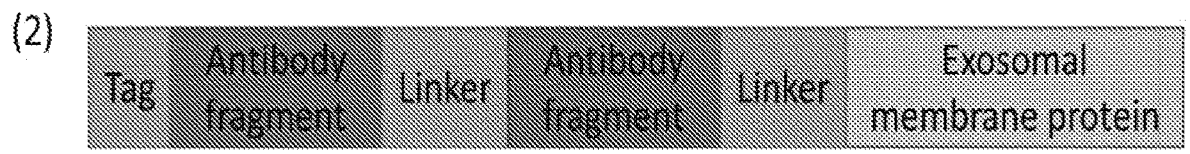

In one aspect, the one or more antigen binding domains are the same or different. FIG. 1A shows an engineered vesicle have all the same antigen binding domains. FIG. 1B shows an engineered vesicle wherein the antigen binding domains that are different (2 non-identical scFv antibodies). The one or more antigen binding domains are selected from the group of: an antibody, a multi-specific antibody, a monoclonal antibody, an antibody derivative, an antibody fragment, a multi-specific antibody fragment, an scFv antibody fragment, a single domain antibody, a bispecific antibody, or a bispecific antibody fragment, a VH domain, a VL domain, and these are non-limited by species. In one aspect the antibody, fragment, or derivative is from a human antibody or a humanized antibody. The antigen binding domains can also be murine, bovine, ovine or human or from any other appropriate species. In one aspect, the antibody is a monoclonal antibody, a derivative, or a fragment thereof. In another aspect, the antibody, derivative or fragment thereof is a human antibody, a humanized antibody or a derivative of each thereof.

Non-limiting examples of antibodies and fragments and derivatives thereof that are used for the antigen binding domains are of the group of antibodies: anti-HER2; anti-HER3; anti-EGFR; anti-CD3; anti-CD16; anti-CD4; anti-CD8; anti-CD11a; anti-CD19; anti-CD20; anti-CD25; anti-CD33; anti-CD40; anti-CD40L; anti-CD70; anti-CD123; anti-EpCAM; anti-CLL-1; anti-CTLA-4; anti-PD-1; anti-PD-L1; anti-OX40; anti-GITR; anti-ICOS; anti-B7-H3; anti-B7-H4; anti-LAG3; anti-TIM3; anti-PSMA; anti-factor IXa; anti-factor X; and anti-folate receptor, fragments and derivatives thereof.

In one aspect, the vesicle contains more than one antigen binding domains fused to the vesicle and the plurality of the domains are identical to each other, see for example FIG. 1A. In another aspect, the vesicle comprises, or alternatively consists essentially of, or yet further consists of more than one antigen binding domains fused to the vesicle, and wherein at least two of the plurality of the domains are different from each other, as shown for example in FIG. 1B.

In a further aspect, the antigen binding domain contains a bispecific antibody that binds to independent and distinct targets (see, e.g., FIGS. 1A and 3).

The antigen binding domains are selected to specifically recognize and bind an antigen of the group of: a tumor antigen; a cancer antigen; an antigen expressed on an immune cell; an antigen expressed on an immune effector cell; an activated coagulation factor IX; factor X; PD1; PDL1; CTLA4; and an antigen involved in immune regulation of a cell from the group of: a T cell, a macrophage, a NK cell, CD4+ T cell, CD8+ T cell, CD19+ cell, CD20+ cell, and a B cell, or a checkpoint inhibitor, e.g., PDL1, CTLA-4, B7-H3, B7-H4, LAG3, PD1, TIM-3, or a checkpoint activator, e.g. CD40, OX40, GITR, ICOS. In a further aspect, the antigen binding domain specifically recognizes and binds a cancer antigen that can be selected from the groups of breast cancer, lung cancer, colorectal cancer, kidney cancer, prostate cancer, brain cancer, pancreatic cancer, a solid malignant cancer or a blood cancer. In a further aspect, the cancer is a breast cancer or a colorectal cancer, and the antigen binding domain specifically recognizes and binds HER2 or EGFR. Additional non-limiting examples of antibodies and fragments and derivatives thereof are of the group of antibodies: anti-HER3; anti-CD3; anti-CD16; anti-CD4; anti-CD8; anti-CD11a; anti-CD19; anti-CD20; anti-CD25; anti-CD33; anti-CD40; anti-CD40L; anti-CD70; anti-CD123; anti-EpCAM; anti-CLL-1; anti-CTLA-4; anti-PD-1; anti-PD-L1; anti-OX40; anti-GITR; anti-ICOS; anti-B7-H3; anti-B7-H4; anti-LAG3; anti-TIM3; anti-PSMA; anti-factor IXa; anti-factor X; anti-folate receptor, and fragments and derivatives thereof. Antibodies and fragments thereof directed to HER2 and EGFR are known in the art and commercially available. Exemplary amino acid sequences of these antigen binding domain are provided below in the sequences of exemplary fusion polypeptides. Biological equivalents of such polypeptides are also within the scope of this disclosure.

In a further aspect, the engineered vesicle comprises, or alternatively consists essentially of, or yet further consists of more than one antigen binding domain that are different, and wherein a first plurality of antigen binding domains selectively recognize and bind a tumor or cancer associated antigen and a second plurality of antigen binding domains recognize an antigen expressed on an immune cell. Non-limiting examples of cancer antigens are selected from the group of breast cancer, lung cancer, colorectal cancer, kidney cancer, prostate cancer, brain cancer, pancreatic cancer, a solid malignant cancer or a blood cancer and the antigen expressed on an immune cell is selected from the group of a T cell, a macrophage, a NK cell, CD4+ T cell, CD8+ T cell, CD19+ cell, CD20+ cell, and a B cell. In a specific embodiment, the cancer is a breast cancer or a colorectal cancer, and the antigen binding domain is specific to the HER2 or EGFR cell surface receptors. Non-limiting examples of antibodies and fragments and derivatives thereof are of the group of antibodies: anti-HER2; anti-HER3; anti-EGFR; anti-CD3; anti-CD16; anti-CD4; anti-CD8; anti-CD11a; anti-CD19; anti-CD20; anti-CD25; anti-CD33; anti-CD40; anti-CD40L; anti-CD70; anti-CD123; anti-EpCAM; anti-CLL-1; anti-CTLA-4; anti-PD-1; anti-PD-L1; anti-OX40; anti-GITR; anti-ICOS; anti-B7-H3; anti-B7-H4; anti-LAG3; anti-TIM3; anti-PSMA; anti-factor IXa; anti-factor X; anti-folate receptor, and fragments and derivatives thereof. In a further aspect, the antigen binding domain is specific to the HER2 or EGFR cell surface receptors and the antigen binding domain specific to an immune cell is a CD3+ T cell or an CD16+(NK cell). FIG. 4 depicts this embodiment.

The vesicle also comprises, or alternatively consists essentially of, or yet further consists of an extracellular vesicle addressing domain (also referred to herein as an exosomal membrane protein). Non-limiting examples of such include platelet-derived growth factor receptor (PDGFR), Lam2b, lactadherin C1C2 domain, CD13 and CD9. Examples of the amino acid sequences of the polypeptides and encoding nucleic acids are provided in the sequence listings of the fusion polypeptides, provided herein. Biological equivalents of these sequences are within the scope of this disclosure.

The vesicles can further comprise, or alternatively consist essentially of, or yet further consist of located N- or C-terminal to the antigen binding domains one or more linker polypeptide. Non-limiting examples of such include (GGGGS)n, n=0-5 (SEQ ID NO: 2); (GGGS)n, n=0-6 (SEQ ID NO: 3); (GGS)n, n=0-7 (SEQ ID NO: 4); (EAAAK)n, n=0-4 (SEQ ID NO: 5); PSGQAGAAASESLFVSNHAY (SEQ ID NO: 6) and GSTSGSGKPGSGEGS (SEQ ID NO: 7); and equivalents of each thereof.

The vesicles can also comprise, or alternatively consist essentially of, or yet further consist of a detectable label and/or purification tag (or label) for imaging or purification. Examples of such are provided infra, e.g., HA, FLAG and 6×His tags (SEQ ID NO: 1).

In yet further aspect, the vesicles comprise, or alternatively consist essentially of, or yet further consist of a myc polypeptide or protein, or an equivalent of each thereof. Exemplary sequences are provided herein.

As depicted in FIGS. 1A, 1B, 3 and 4, in one aspect the vesicles further comprise, or alternatively consist essentially of, or yet further consist of an effective amount of a therapeutic agent or "payload." Non-limiting examples of therapeutic agents are selected from a small molecular immune checkpoint modulators, a small molecular chemotherapy drug, an RNA-based therapeutic (siRNA, or miRNA), a therapeutic protein, a therapeutic peptide, an immune regulatory factor, an immune checkpoint inhibitor, an immune agonist, anti-PD1 siRNA, anti-PDL1 siRNA, anti-CTLA4 siRNA, an inhibitor of indoleamine-pyrrole 2,3-dioxygenase (IDO), GDC-0919, an indoximod, an agonist of Toll-like receptors (TLR) TLRs, Motolimod, and Resiquimod. Additional examples are provided herein.

One or more therapeutic agent can be encapsulated in the vesicle, examples of such are disclosed herein. In one aspect, the more than one therapeutic agent is selected to target both tumor cell and tumor stroma cells in a solid tumor for synergistic anti-tumor effect. In another aspect, the more than one therapeutic agents are selected to block two immune checkpoint inhibitors simultaneously. Examples of immune checkpoint inhibitors are anti-PDL1 siRNA and anti-CTLA4 siRNA.

Antibodies, Antigen Binding Fragments and Methods of Production

In some aspects, antigen binding fragments (antibodies, fragments and derivatives thereof as described herein) are known in the art or commercially available. However, it may be necessary to produce the antigen binding fragment that is selective for the target. The following description describes techniques known in the art for such production.

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum.

Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well-described in the literature. For example, a hybridoma is produced by fusing a suitable immortal cell line (e.g., a myeloma cell line such as, but not limited to, Sp2/0, Sp2/0-AG14, NS0, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, those at the following web addresses, e.g., atcc.org, lifetech.com, last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, in particular embodiments, the spleen or lymph nodes, of humans or other suitable animals that have been immunized with the antigen of interest and then screened for the activity of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; and 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052; Wen et al. (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody disclosed herein to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fe-mediated cellular toxicity, and glycoproteins so generated.

The antibodies disclosed herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide disclosed herein to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally part or all of the non-human or human CDR sequences are maintained while the non-human sequences of the variable and constant regions are replaced with human or other amino acids or variable or constant regions from other isotypes.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762; and 6,180,370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies disclosed herein also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies disclosed herein can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species antibodies. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise, or alternatively consist essentially of, or yet further consist of a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al., which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies & Hudson (2005) Nature Biotech 23(9):1126-36; U.S. Pat. Application Publication No. 2006/0211088; PCT International Application Publication No. WO 2007/059782; U.S. Pat. No. 5,831,012).

The term "antibody derivative" further includes "linear antibodies." The procedure for making linear antibodies is known in the art and described in Zapata et al. (1995) Protein Eng. 8(10):1057-1062. Briefly, these antibodies comprise, or alternatively consist essentially of, or yet further consist of a pair of tandem Ed segments ($V_H$-$C_H$1-VH-$C_H$1) which form a pair of antigen binding regions. Linear antibodies can be bispecific or monospecific.

The antibodies disclosed herein can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58: 671-685.

If an antibody being tested binds with protein or polypeptide, then the antibody being tested and the antibodies provided by this disclosure are equivalent. It also is possible to determine without undue experimentation, whether an antibody has the same specificity as the antibody disclosed herein by determining whether the antibody being tested prevents an antibody disclosed herein from binding the protein or polypeptide with which the antibody is normally reactive. If the antibody being tested competes with the antibody disclosed herein as shown by a decrease in binding by the monoclonal antibody disclosed herein, then it is likely that the two antibodies bind to the same or a closely related epitope. Alternatively, one can pre-incubate the antibody disclosed herein with a protein with which it is normally reactive, and determine if the antibody being tested is inhibited in its ability to bind the antigen. If the antibody being tested is inhibited then, in all likelihood, it has the same, or a closely related, epitopic specificity as the antibody disclosed herein.

The term "antibody" also is intended to include antibodies of all immunoglobulin isotypes and subclasses. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The variable region of the antibodies of the present disclosure can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. In certain embodiments, conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies disclosed herein may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677,425) and amino acid mutations in the Fc hinge region to decrease the biological half-life of the antibody (U.S. Pat. No. 6,165,745).

Antibodies can be produced by inducing in vivo production in the lymphocyte population or by screening recombinant immunoglobulin libraries or panels of highly specific binding reagents (Orlandi et al., PNAS 86: 3833-3837 (1989); Winter, G. et al., Nature, 349: 293-299 (1991)).

Alternatively, techniques for the production of single chain antibodies may be used. Single chain antibodies (scFvs) comprise, or alternatively consist essentially of, or yet further consist of a heavy chain variable region and a light chain variable region connected with a linker peptide (typically around 5 to 25 amino acids in length). In the scFv, the variable regions of the heavy chain and the light chain may be derived from the same antibody or different antibodies. scFys may be synthesized using recombinant techniques, for example by expression of a vector encoding the scF, in a host organism such as *E. coli*. DNA encoding scFv can be obtained by performing amplification using a partial DNA encoding the entire or a desired amino acid sequence of a DNA selected from a DNA encoding the heavy chain or the variable region of the heavy chain of the above-mentioned antibody and a DNA encoding the light chain or the variable region of the light chain thereof as a template, by PCR using a primer pair that defines both ends thereof, and further performing amplification combining a DNA encoding a polypeptide linker portion and a primer pair that defines both ends thereof, so as to ligate both ends of the linker to the heavy chain and the light chain, respectively. An expression vector containing the DNA encoding scFv and a host transformed by the expression vector can be obtained according to conventional methods known in the art.

Antigen binding fragments may also be generated, for example the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse et al., Science, 256: 1275-1281 (1989)).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HLA-G, or any fragment or oligopeptide thereof and its specific antibody. A two-site, monoclonal-based immunoassay utilizing monoclonal antibodies specific to two non-interfering HLA-G epitopes may be used, but a competitive binding assay may also be employed (Maddox et al., J. Exp. Med., 158: 1211-1216 (1983)).

The antibodies disclosed herein can be purified to homogeneity. The separation and purification of the antibodies can be performed by employing conventional protein separation and purification methods.

By way of example only, the antibody can be separated and purified by appropriately selecting and combining use of chromatography columns, filters, ultrafiltration, salt precipitation, dialysis, preparative polyacrylamide gel electrophoresis, isoelectric focusing electrophoresis, and the like. Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988).

Examples of chromatography include affinity chromatography, ion exchange chromatography, hydrophobic chromatography, gel filtration chromatography, reverse phase chromatography, and adsorption chromatography. In one aspect, chromatography can be performed by employing liquid chromatography such as HPLC or FPLC.

In one aspect, a Protein A column or a Protein G column may be used in affinity chromatography. Other exemplary columns include a Protein A column, Hyper D, POROS, Sepharose F. F. (Pharmacia) and the like.

Fusion Polypeptides and Polynucleotides Encoding Them

Also provided herein is a fusion polypeptide comprising, or alternatively consisting essentially of, or yet further consisting of: an antigen binding domain, a linker polypeptide, and an exosome addressing domain. In one aspect, the fusion polypeptide further comprises, consists essentially of, or yet further consists of more than one antigen binding domains and optionally more than one linker polypeptides. In a yet further aspect, the fusion polypeptide further comprising, or alternatively consisting essentially of, or yet further consisting of a purification and/or a detectable label. Non-limiting examples are provided infra, e.g., HA, FLAG and 6×His. In yet a further aspect, the fusion polypeptide further comprises, or alternatively consists essentially of, or yet further consists of a myc protein or polypeptide. FIGS. 2B, 5, 15, and 21 are non-limiting examples of embodiments of the fusion polypeptides. Amino acid sequences of the polypeptides and polynucleotides encoding these embodiments are provided herein. Also provided are the fusion polypeptides depicted in the Exemplary Fusion Polypeptide section, and equivalents of each thereof. Also provided herein are these amino acid and polynucleotide sequences encoding the polypeptides, as well as equivalents of each thereof.

In a further aspect, the one or more antigen binding domains are selected from the group of: an antibody, a multi-specific antibody, a multi-specific antibody fragment, an antibody fragment, a VH, a VL, an scFv antibody fragment, a single domain antibody, a bispecific antibody, or a bispecific antibody fragment, a monoclonal antibody or a derivative thereof. In one aspect the antibody, fragment, or derivative is from a human antibody or a humanized antibody. The antigen binding domains can also be murine, bovine, ovine or human or from any other appropriate species. In one aspect, the antibody is a monoclonal antibody, a derivative, or a fragment thereof. In another aspect, the antibody, derivative or fragment thereof is a human antibody, a humanized antibody or a derivative of each thereof.

Non-limiting examples of antibodies and fragments and derivatives thereof in the fusion polypeptide that are used for the antigen binding domains are of the group of antibodies: anti-HER2; anti-HER3; anti-EGFR; anti-CD3; anti-CD16; anti-CD4; anti-CD8; anti-CD11a; anti-CD19; anti-CD20; anti-CD25; anti-CD33; anti-CD40; anti-CD40L; anti-CD70; anti-CD123; anti-EpCAM; anti-CLL-1; anti-CTLA-4; anti-PD-1; anti-PD-L1; anti-OX40; anti-GITR; anti-ICOS; anti-B7-H3; anti-B7-H4; anti-LAG3; anti-TIM3; anti-PSMA; anti-factor IXa; anti-factor X; or anti-folate receptor.

In one aspect, the fusion polypeptide comprises, or alternatively consists essentially of, or yet further consists of more than one antigen binding domains, that may be the same or different from each other. In a further aspect, polypeptide comprises, or alternatively consists essentially of, or yet further consists of an antigen binding domain that is a bispecific antibody that binds to independent and distinct targets (see, e.g., FIG. 21).

The antigen binding domains of the fusion polypeptides are selected to specifically recognize and bind an antigen of the group of: a tumor antigen; a cancer antigen; an antigen expressed on an immune cell; an antigen expressed on an immune effector cell; an activated coagulation factor IX; factor X; PD1; PDL1; CTLA4; and an antigen involved in immune regulation of a cell from the group of: a T cell, a macrophage, a NK cell, CD4+ T cell, CD8+ T cell, CD19+ cell, CD16+ cell, CD20+ cell, and a B cell. In a further aspect, the antigen binding domain specifically recognizes and binds a cancer antigen that can be selected from the groups of breast cancer, lung cancer, colorectal cancer, kidney cancer, prostate cancer, brain cancer, pancreatic cancer, a solid malignant cancer or a blood cancer. In a further aspect, the cancer is a breast cancer or a colorectal cancer, and the antigen binding domain specifically recognizes and binds HER2 or EGFR. Additional non-limiting examples of antibodies and fragments and derivatives thereof are of the group of antibodies: anti-HER3; anti-CD3; anti-CD16; anti-CD4; anti-CD8; anti-CD11a; anti-CD19; anti-CD20; anti-CD25; anti-CD33; anti-CD40; anti-CD40L; anti-CD70; anti-CD123; anti-EpCAM; anti-CLL-1; anti-CTLA-4; anti-PD-1; anti-PD-L; anti-OX40; anti-GITR; anti-ICOS; anti-B7-H3; anti-B7-H4; anti-LAG3; anti-TIM3; anti-PSMA; anti-factor IXa; anti-factor X; anti-folate receptor, and fragments or derivatives thereof. Antibodies and fragments thereof directed to HER2 and EGFR are known in the art and commercially available. Exemplary amino acid sequences of these antigen binding domain are provided below in the sequences of exemplary fusion polypeptides. Biological equivalents of such polypeptides are also within the scope of this disclosure.

In a further aspect, the fusion polypeptide comprises, or alternatively consists essentially of, or yet further consists of more than one antigen binding domain that are different, and wherein an antigen binding domain selectively recognizes and bind a tumor or cancer associated antigen and the second antigen binding domain recognizes an antigen expressed on an immune cell. Non-limiting examples of cancer antigens are selected from the group of breast cancer, lung cancer, colorectal cancer, kidney cancer, prostate cancer, brain cancer, pancreatic cancer, a solid malignant cancer or a blood cancer and the antigen expressed on an immune cell is selected from the group of a T cell, a macrophage, a NK cell, CD4+ T cell, CD8+ T cell, CD16+ cell, CD19+ cell, CD20+ cell, and a B cell. FIG. 4 depicts one aspect of this embodiment. In a specific embodiment, the cancer is a breast cancer or a colorectal cancer, and the antigen binding domain is specific to the HER2 or EGFR cell surface receptors. Non-limiting examples of antibodies and fragments and derivatives thereof are of the group of antibodies: anti-HER2; anti-HER3; anti-EGFR; anti-CD3; anti-CD16; anti-CD4; anti-CD8; anti-CD11a; anti-CD19; anti-CD20; anti-CD25; anti-CD33; anti-CD40; anti-CD40L; anti-CD70; anti-CD123; anti-EpCAM; anti-CLL-1; anti-CTLA-4; anti-PD-1; anti-PD-L1; anti-OX40; anti-GITR; anti-ICOS; anti-B7-H3; anti-B7-H4; anti-LAG3; anti-TIM3; anti-PSMA; anti-factor IXa; anti-factor X; anti-folate receptor, and fragments and derivatives thereof. In a further aspect, the antigen binding domain is specific to the HER2 or EGFR cell surface receptors and the antigen binding domain specific to an immune cell is a CD3+ T cell or an CD16+(NK cell).

The fusion polypeptide also comprises, or alternatively consists essentially of, or yet further consists of an extracellular vesicle addressing domain (also referred to herein as an exosomal membrane protein). Non-limiting examples of such include platelet-derived growth factor receptor (PDGFR), Lam2b, lactadherin C1C2 domain, CD13 and CD9. Examples of the amino acid sequences of the polypeptides and encoding nucleic acids are provided in the sequence listings of the fusion polypeptides, provided herein. Biological equivalents of these sequences are within the scope of this disclosure.

The fusion polypeptides also can comprise, or alternatively consist essentially of, or yet further consist of (located N- or C-terminal to the antigen binding domains) one or more linker polypeptide. Non-limiting examples of such include (GGGGS)n, n=0-5 (SEQ ID NO: 2); (GGGS)n, n=0-6 (SEQ ID NO: 3); (GGS)n, n=0-7 (SEQ ID NO: 4); (EAAAK)n, n=0-4 (SEQ ID NO: 5); PSGQAGAAASESLFVSNHAY (SEQ ID NO: 6) and GSTSGSGKPGSGEGS (SEQ ID NO: 7); and equivalents of each thereof.

In yet further aspect, the fusion polypeptides comprise, or alternatively consist essentially of, or yet further consist of a myc polypeptide or protein, or an equivalent of each thereof. Exemplary sequences are provided herein.

Also provided are polynucleotides encoding the fusion polypeptides. The polynucleotides can be operatively linked to regulatory elements to drive expression of the polynucleotide and can be further contained within a vector, e.g. a plasmid or a viral vector. Host cells, prokaryotic and eukaryotic cells, containing the polynucleotides and/or polypeptides and methods of expressing the polynucleotides are further provided herein, as well as the polypeptides encoded by the polynucleotides. The polynucleotides and polypeptides can further comprise, or alternatively consist essentially of, or yet further consist of a detectable and/or a purification label. Examples of such are provided infra. The polynucleotides are useful to prepare the vesicles and for recombinant production of the fusion polypeptides by transducing a cell with the polynucleotide contained within an expression vector and culturing the cell under conditions that promote expression of the polynucleotide. The vesicles can be further isolated from the culture media.

Methods for Preparing the Engineered Extracellular Vesicles

Also provided are recombinant methods to prepare an extracellular vesicle of this disclosure, the method comprising, or alternatively consisting essentially of, or yet further consisting of contacting a cell comprising, or alternatively consisting essentially of, or yet further consisting of the extracellular vesicle with an effective amount of the polynucleotide encoding a fusion polypeptide and expressing the polynucleotide on the vesicle. The cells can be eukaryotic or prokaryotic, mammalian, reptilian, avian, human, plant, or bacterial. They can be of any appropriate species, e.g. canine, feline, murine, equine or human, for example. In one aspect, the method further comprises, or alternatively consists essentially of, or yet further consists of isolating the extracellular vesicle from the engineered vesicle from the cell culture media. Methods for such are described herein.

Bispecific exosomes could be expressed in any types of eukaryotic cells through transient or stable transfection of the generated expression constructs for antibody-membrane protein fusions. For example, in addition to Expi293F cells, HeLa cells, HEK293T, MDA-MB-231, immature dendritic cells, and stem cells could be utilized for production of the extracellular vesicles such as bispecific exosomes. Cells expressing bispecific exosomes are grown in chemically defined medium or medium supplemented with exosome-depleted serum. The exosomes released into the culture media are purified using different approaches, including differential centrifugation, density-gradient- or cushion-based tlr-aeentifugaIen ultracentrifugation, precipitation with commercial kits (ExoQuick™ and Total Exosome Isolation™), and affinity and size exclusion chromatography.

In addition to above genetic engineering approach, bispecific exosomes could be prepared through chemical conjugation. Native or endogenous exosomes released by various types of cells could be isolated using above mentioned approaches. Antigen binding fragments, e.g., bispecific antibodies or two distinct monoclonal antibodies could be recombinantly expressed and purified from prokaryotic or eukaryotic cells. Using chemical linkers with groups reactive to antibodies and exosome surface for covalent attachments, the bispecific exosomes could be generated and purified through affinity and size exclusion chromatography.

In one aspect and as an example only, native vesicles, e.g., exosomes, are purified from culture media of cells such as Expi293 cells through differential centrifugation and ultracentrifugation. Antigen binding fragments, e.g. bispecific antibodies (e.g. anti-CD3/anti-EGFR scFv) are expressed from Expi293 cells through transient transfection with constructed expression vector, followed by Ni-NTA affinity chromatography. 100 μL of purified exosomes (0.2 mg/mL) in PBS are mixed with tetrazine-PEG5-NHS ester (10 μL, 200 μM) at room temperature for 60 minutes. The free tetrazine-PEG5-NHS ester is removed by passing the mixture through size exclusion chromatography using a Superdex 200 Increase 10/300 GL column. 100 μL of purified bispecific antibody (1 mg/ml) in PBS would be mixed with trans-cyclooctene-PEG4-NHS ester (10 μL, 400 μM) at room temperature for 60 minutes. The free trans-cyclooctene-PEG4-NHS ester is removed by passing the mixture through size exclusion chromatography using a Superdex 200 Increase 10/300 GL column. The exosomes labeled with tetrazin-PEG5 and the bispecific antibody labeled with trans-cyclooctene-PEG4 are incubated at a molar ratio of (1:2000) for 120 minutes at room temperature. The exosome-antibody conjugates are isolated by size exclusion chromatography using a Superdex 200 Increase 10/300 GL column.

Isolation of Extracellular Vesicles

The purified populations of cell-derived vesicles (e.g., exosomes and/or microvesicles) of the present disclosure can be isolated using any method known by those in the art. Non-limiting examples include differential centrifugation by ultracentrifugation (Thery et al. (2006) Curr. Protoc. Cell Biol. 30:3.22.1-3.22.29; Witmer et al. (2013) J. Extracellular v.2), sucrose gradient purification (Escola et al. (1998) J. Biol. Chem. 273:20121-20127), and combination filtration/concentration (Lamparski et al. (2002) J. Immunol. Methods 270:211-226).

After isolation, the cell-derived vesicles, e.g., exosomes can be concentrated to provide a purified population of cell-derived vesicles. Any appropriate method can be used to concentrate the cell-derived vesicles, e.g. exosomes. Non-limiting examples of such include centrifugation, ultrafiltration, filtration, differential centrifugation and column filtration. Further sub-populations can be isolated using antibodies or other agents that are specific for a specific marker expressed by the desired exosome population.

In some embodiments, the methods disclosed herein further comprise, or alternatively consist essentially of, or yet further consist of formulating the purified population of cell-derived vesicles by mixing the population with a carrier and/or a therapeutic agent. Non-limiting examples are suitable carriers are described below. In addition or alternatively, the exosome composition can be combined with trehalose for enhanced stability, e.g., at a concentration of about 15 nM to about 50 nM of trehalose in carrier (e.g., PBS), or alternatively about 25 nM of trehalose in carrier (e.g., PBS). Methods to formulate exosomes with trehalose are described in Bosch et al. (2016) "Trehalose prevents aggregation of exosomes and cryodamage" Scientific Reports 6, Article number 36162, doe:10.1038/srep36162, incorporated herein by reference.

Encapsulation of Therapeutics Agents

FIG. 4B is a schematic of methods to encapsulate therapeutic drugs into the vesicles.

Electroporation:

For example, 10 μg of exosome (approximately 109) and 10 μg of siRNA were mixed in 200 ul electroporation buffer (1.15 mM potassium phosphate pH=7.2, 25 mM potassium chloride, 21% Optiprep, 1 mM EDTA). The siRNA-Exosome mixture was electroporated in 4 mm cuvette, at 400V, 125 μF, and the cuvette was immediately transferred to ice. Exosomes were recovered from mixture by 30 kDa protein concentrator.

Incubation:

Purified exosomes (0.2 mg/mL) were first mixed with drugs (10 mM Resiquimod) in 200 μL PBS. The mixture was incubated at 37° C. for 1 hour with shaking. Excess free drug was separated from drug-encapsulated exosomes by size exclusion chromatography using a Superdex 200 Increase 10/300 GL column (GE Healthcare, Buckinghamshire, UK).

Sonication:

Purified exosomes (0.2 mg/mL) were first mixed with drugs (10 mM Resiquimod) in 200 μL PBS. The mixture was sonicated (20% power, 6 cycles of 4 s pulse/2 s pause), cooled down on ice for 2 min, and then sonicated again using Misonix Ultrasonic Liquid Processor S-4000 (Misonix, Inc. N.Y. USA). After sonication, Drug-encapsulated exosome solution was incubated at 37° C. for 30 min to allow for recovery of the exosomal membrane. Excess free drug was separated from drug-encapsulated exosomes by size exclusion chromatography using a Superdex 200 Increase 10/300 GL column (GE Healthcare, Buckinghamshire, UK).

Freeze-Thaw:

Purified exosomes (0.2 mg/mL) were first mixed with drugs (10 mM Resiquimod) in 200 μL PBS. The mixture was incubated for 20 min on ice, then rapidly freezed at −80° C., and thawed at RT. The freeze-thaw cycle was repeated five times. After sonication, drug-encapsulated exosome solution was incubated at 37° C. for 30 min to allow for recovery of the exosomal membrane. Excess free drug was separated from drug-encapsulated exosomes by size exclusion chromatography using a Superdex 200 Increase 10/300 GL column (GE Healthcare, Buckinghamshire, UK).

Formulations and Pharmaceutical Compositions

The present disclosure provides purified populations of extracellular vesicles. In some embodiments, the population of vesicles is substantially homogeneous. In other embodiments, the population of vesicles is heterogeneous.

The purified populations of vesicles can be purified on the basis of average size of the vesicles in the composition.

The compositions disclosed herein may further comprise, or alternatively consist essentially of, or yet further consist of a carrier, for example, a pharmaceutically acceptable carrier. In some embodiments, more than one pharmaceutically acceptable carrier can be used. Any pharmaceutically acceptable carrier known to those of skill in the art or described herein.

In some embodiments, the pharmaceutically acceptable carrier is a preservative, for example, a polymeric preservative or a stabilizing agent.

In some embodiments, the pharmaceutically acceptable carrier is selected from the group consisting of a polyethylene glycol (PEG, e.g., PEG 150 Distearate), honey, a large molecular weight protein (e.g., bovine serum albumin or soy protein), polyvinyl alcohol, glyceryl monostearate, hyaluronic acid, glycerin, preferably vegetable-derived, proteins, preferably hydrolyzed proteins, (e.g., soy protein and silk protein), vasoline, citrosept, parabens, xanthan gum, i-carregaan, phytagel, Carbopol© polymers, and polyvinyl pyrrolidone.

In some embodiments, exosomes are preserved in serum albumin. Non-limiting examples of serum albumins appropriate for preservation of exosomes include bovine serum albumin (BSA), human serum albumin (HSA), ovalbumin (OVA), and lactalbumin.

Pharmaceutically acceptable carriers may include biocompatible gelation agents including thermosensitive sol-gel reversible hydrogels such as aqueous solutions of poloxamers. In one aspect, the poloxamer is a nonionic triblock copolymer composed of a central hydrophobic chain of polyoxypropylene (e.g., (poly(propylene oxide)) flanked by two hydrophilic chains of polyoxyethylene (e.g., poly(ethylene oxide)). In one aspect, poloxamer has the formula

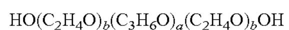

$$HO(C_2H_4O)_b(C_3H_6O)_a(C_2H_4O)_bOH$$

wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the tradename Pluronic© manufactured by BASF. Non-limiting examples of poloxamers useful herein include, but are not limited to, Pluronic©F68, P103, P105, P123, F127, and L121.

In one aspect, the biocompatible gelation agent is an agent that is liquid prior to application to a subject (e.g., at room temperature or colder) and becomes a gel after application to the subject (e.g., at body temperature). In one embodiment, the biocompatible gelation agent is a hydrogel.

In some aspects, the pharmaceutically acceptable carrier is a pharmaceutically acceptable aqueous carrier such as water or an aqueous carrier. Examples of pharmaceutically acceptable aqueous carrier include sterile water, saline, phosphate buffered saline, aqueous hyaluronic acid, Ringer's solution, dextrose solution, Hank's solution, and other aqueous physiologically balanced salt solutions. In some embodiments, the pharmaceutically acceptable aqueous carrier is Normosol™-R.

Nonaqueous pharmaceutically acceptable carriers include, fixed oils, vegetable oils such as olive oil and sesame oil, triglycerides, propylene glycol, polyethylene glycol, and injectable organic esters such as ethyl oleate can also be used.

Pharmaceutically acceptable carriers can also contain minor amounts of additives, such as substances that enhance isotonicity, chemical stability, or cellular stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. In some aspect, the composition has a pH in the physiological pH range, such as pH 7 to 9.

In one aspect, depending on the type of a pharmaceutically acceptable carrier used, the compositions described herein can comprise, or alternatively consist essentially of, or yet further consist of about 0.1-100%, 0.1-50%, or 0.1-30%, such as 0.1%, 0.25%, 0.5%, 0.75%, 1%, 2%, 5%, 7%, 10%, 15%, 20%, 25%, 30%, 40%, 45%, 50%, 55%, 60%, 65%, 70%, 75%, 80%, 85%, 90% or 95% of the pharmaceutically acceptable carrier used in the total weight of the composition, or any range between two of the numbers (end point inclusive).

In some embodiments, any one of the above listed pharmaceutically acceptable carriers is expressly excluded.

In some embodiments, the vesicles described herein are frozen (e.g., snap-frozen) or freeze-dried (e.g., lyophilized) to promote stability, preserve activity and increase shelf-life. One skilled in the art would understand how to reconstitute the lyophilized product before use.

In some embodiments, the populations of vesicles described herein are used immediately after isolation. In other embodiments, the populations of cell-derived vesicles are cryopreserved (e.g. frozen), for example, using any cryopreservation techniques well-known to those skilled in the art. In some embodiments, all or substantially of the cells and/or cellular debris are removed from the culture medium prior to cryopreservation. In some embodiments, all or substantially of the cells and/or cellular debris are removed from the culture medium after cryopreservation.

Applications and Uses

The vesicles of this disclose have various in vitro and in vivo uses. For example, the vesicles can be used to determine if a particular vesicle therapy will be effective by contacting a biological sample suspect of containing the cells or tissue to be treated (e.g., cancer cells) with an vesicle engineered to target that cell and then assaying for effectiveness of the therapy, e.g., by determining if cell growth has been inhibited or an immune response has been elicited in the appropriate tissue. Thus, this disclosure also provides an isolated complex comprising, or alternatively consisting essentially of, or yet further consisting of a vesicle as described herein complexed to the target cell or tissue to be treated.

The vesicles have various therapeutic uses as well. In one aspect, a method is provided for treating a subject in need thereof or inducing an immune response in a subject in need thereof, comprising, or alternatively consisting essentially of, or yet further consisting of, administering to the subject an effective amount of the isolated engineered vesicles or a composition of this disclosure, wherein the vesicle an antigen binding domain specific to a disease to be treated. In a further aspect, the subject has been selected for the therapy by diagnostic criteria as determined by the treating physician or health care professional.

Further provided is a method for cancer immunotherapy for a subject in need thereof, comprising, or alternatively consisting essentially of, or yet further consisting of, administering an effective amount of a vesicle or composition containing the same, wherein the vesicle expresses a cancer targeted antigen binding domain and an antigen binding domain that binds an immune cell, such as an immune effector cell. In a further aspect, the vesicles comprise, or alternatively consist essentially of, or yet further consist of an anti-cancer chemotherapeutic agent. The therapies can be administered as a first line, second line, third line, fourth line or fifth line therapy. Additional chemotherapeutic agents may be subsequently administered as determined by the treating physician. Non-limiting examples of chemotherapeutic agents include Actinomycin, All-trans retinoic acid, azacitidin, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vemurafenib, vinblastine, vincristine, vindesine, and vinorelbine.

The vesicles can further comprise, or alternatively consist essentially of, or yet further consist of immune regulatory factors to augment the vesicle-mediated cancer immunotherapy. The exosomes can be are mono-specific or bispecific exosomes. Bispecificity is achieved by either fusing bispecific antibody with exosomal membrane proteins, or separately fusing distinct scFv antibody with the same or different exosomal membrane proteins. The bispecific exosomes can be used to target both the cancer cell and immune cells. One antibody scFv, is capable to recruit the activity of a human immune effector cell by specifically binding to an effector antigen on the human immune effector cell, and a second bispecific scFv, specifically binds to a target antigen on the target cell, resulting in the redirection of immune effector cell to kill targeted cancer cells.

For the fusion expression of bi-specific scFvs, two kinds of orientation are generated. Depending on the specificity of the antibody scFv selected, the resulting bispecific exosomes can bind to breast, lung, colorectal, kidney, prostate, brain, pancreas, or solid malignant tumor cells or blood cancer cells for immune cell-mediated killing. For breast and colorectal cancer, in one aspect, the targets are HER2 positive cells, EGFR positive cells or others. HER2 and EGFR are chosen as tumor targets and CD3+ T cells are the immune effector cells. HER2 positive cancer cell lines include SK-BR-3 cells, HCC1954 cells. MDA-MB-468 is HER2 negative cells; EGFR positive cells include MDA-MB-468 cells. MDA-MB-453 is EGFR negative cell. The immune effector cell include for example, CD3+ T cell, CD16+NK cell or others.

The vesicles are therapeutic for a variety of diseases selected from the group of: cancer, hyperplasia, neurodegenerative disease, Alzheimer's disease, cardiovascular disease, metabolic disease, vasculitis, viral infection, fungal infection, bacterial infection, diabetic retinopathy, macular degeneration, autoimmune disease, edema, pulmonary hypertension, sepsis, myocardial angiogenesis, plaque neovascularization, restenosis, neointima formation after vascular trauma, telangiectasia, hemophiliac joints, angiofibroma, fibrosis associated with chronic inflammation, lung fibrosis, deep venous thrombosis or wound granulation.

The vesicles and compositions herein can be administered to the subject by any method known by those of skill in the art. In some embodiments, the compositions are administered by intravenous injection, direct injection, intramuscular injection, intracranial injection, or topically.

In one aspect, the bispecific exosomes are loaded with anti-cancer drugs and can be used to target two different antigens on a same tumor cell for more effective target tumor therapy. The bispecific exosomes loaded with anti-cancer drugs can be used to target both tumor cell and tumor stroma cells in a solid tumor for synergistic anti-tumor effect. The tumor stroma is composed of different cell types, such as fibroblasts, pericytes, endothelial cells and immune cells, including T cells, granulocytes and macrophages. The bispecific exosomes also can be used to modulate tumor immune microenvironment by blocking two immune checkpoint simultaneously, such as Anti-PDL1/Anti-CTLA4 bispecific exosomes. The Anti-PDL1 and CTLA4 bispecific exosome encapsulated with immune agonists can be used to activate tumor immune microenvironment. Bispecific exosomes can bind to both the activated coagulation factor IX and to factor X, mediating the activation of factor X, which can be used for the treatment of haemophilia A.

By redirecting T cells or other immune effector cells (e.g. NK cells), bispecific exosomes can be used to treat cancer, hyperplasia, neurodegenerative disease, Alzheimer's disease, cardiovascular disease, metabolic disease, vasculitis, viral infection, fungal infection, bacterial infection, diabetic retinopathy, macular degeneration, autoimmune disease, edema, pulmonary hypertension, sepsis, myocardial angiogenesis, plaque neovascularization, restenosis, neointima formation after vascular trauma, telangiectasia, hemophiliac joints, angiofibroma, fibrosis associated with chronic inflammation, lung fibrosis, deep venous thrombosis or wound granulation.

The engineered exosomes with distinct bispecific antibodies and payloads demonstrate such unique extracellular vesicles as a general and versatile platform for development of novel immuno-nanoparticles with high potency. Applications of exosomes in clinic can be further expanded through leveraging a broad scope of mono- and multifunctional antibodies and therapeutic agents. The exosomes are developed to have transformative impact in the development of next-generation immuno-nanomedicines with desired pharmacological properties. Furthermore, bispecific exosome-based technology can treat many different types of cancer as well. Those antibody-directed bispecific exosomes may allow tissue- and cell-specific engaging of immune effector cells in a safe and highly efficient manner, opening doors to novel cancer immunotherapies.

To achieve therapeutically effective concentrations in cytosol, the developed synthetic exosome nanoparticles linked with tumor-specific peptides and antibodies require fast internalization through endocytosis and subsequent escape from the endosomal-lysosomal pathway, which have been proven challenging. Moreover, they are prone to induce robust immune responses due to their foreign antigen nature and can be rapidly cleared from circulatory system through absorbed complement, coagulation, opsonins factors, and neutralizing antibodies. In contrast, exosome-mediated delivery relies on direct membrane fusion to target cells, circumventing the endosomal-lysosomal pathway and boosting cellular delivery of therapeutics. Moreover, the nanoscale exosomes carrying a substantial amount of therapeutic agents can extravasate into tumor interstitium and diffuse in tumor tissue without inducing phagocytosis by the mononuclear phagocyte system. In particular, exosomes produced from immature DCs tend to show significantly reduced immunogenic activity due to the lack of major histocompatibility complex (MHC) class II and co-stimulatory molecules on their membrane surface. Clinically, exosomes isolated from patients' cells are unlikely to have immunogenicity issues encountered with artificial nanocarriers. Thus, these unique features for exosomes can be exploited for development of new anti-tumor nanomedicines with improved efficacy and safety.

Applicant generated novel exosome nanoparticles that can simultaneously target both cancer and immune effector cells for combinatorial immunotherapy. Relative to conventional, immunotherapeutic bispecific antibodies with geometrically and orientationally defined antigen-binding arms, the multivalent dual-targeted exosomes displayed on spherical exosomes have higher potential to promote formation of immunological synapses as well as enhanced efficacy to activate immune cells. Combined with immune checkpoint inhibitors, such bispecific exosomes are likely to augment efficacy of immunotherapy. Therefore, the engineered multifunctional exosomes represent novel nanomedicines with enhanced efficacy and safety, leading to the development of first-in-class immunotherapeutics for cancer.

The engineered exosomes with distinct bispecific antibodies and payloads demonstrate such unique extracellular vesicles as a general and versatile platform for development of novel immuno-nanoparticles with high potency. Applications of exosomes in clinic can be further expanded through leveraging a broad scope of mono- and multifunctional antibodies and therapeutic agents. These inventions will have transformative impact in the development of next-generation immuno-nanomedicines with desired pharmacological properties. Furthermore, bispecific exosome-based technology can be extended to treat many different types of cancer as well. Those antibody-directed bispecific exosomes may allow tissue- and cell-specific engaging of immune effector cells in a safe and highly efficient manner, opening doors to novel cancer immunotherapies.

The methods are useful to treat any appropriate subject and the vesicles and antigen binding domains are specific to the species of the subject to be treated. Examples of subjects include mammals such as canines, felines, equines or human patients.

The following examples are provided to illustrate, and not limit the inventions as described herein.

EXAMPLES

Given developing resistance of tumor cells to current chemotherapeutic and targeted therapeutic agents, novel cancer therapies with enhanced potency and specificity are substantially required. This disclosure addresses the overarching challenge of revolutionizing treatment regimens by replacing them with ones that are more effective, less toxic, and impact survival. Exosomes are endogenous nanoparticles secreted by many types of cells and play important roles in intercellular communication. Exosome-mediated delivery relies on direct membrane fusion to target cells, circumventing endosomal-lysosomal pathway required for synthetic vehicles and promoting cellular delivery of therapeutic agents. Moreover, compared with synthetic virus, lipid and polymeric nanomedicines which are immunogenic due to their foreign antigen nature, exosomes exhibit significantly reduced immunogenicity. In particular, exosomes derived from patients' own immature dendritic cells are expected to induce no immune responses. As disclosed herein, Applicant generated innovative bispecific exosome nanoparticles as a highly potent form of immunotherapeutics with excellent safety profiles. By creatively combining exosome nanotechnology with protein engineering, bispecific exosome nanoparticles were generated that redirect immune effector cells towards cancer cells for killing. Relative to conventional immunotherapeutic antibodies with defined orientation and geometry for their distinct antigen-binding arms, the multivalent dual-targeted antibodies displayed on spherical exosomes can promote formation of immunological synapses as well as enhanced efficacy to activate immune cells. Moreover, by effectively delivering immune checkpoint inhibitors, such bispecific exosomes are likely to augment efficacy of immunotherapy. The resulting exosomes display superb efficacy towards target cells and minimal toxicity, leading to the development of first-in-class immunotherapeutics for cancer and a broadly applicable and highly versatile technology for next-generation immuno-nanomedicines.

Molecular Cloning

To construct scFv-PDGFR fusion proteins (FIGS. 5 and 15), the DNA fragments encoding the anti-HER2 single-chain antibody (scFv), anti-EGFR scFv and anti-CD3 were amplified by polymerase chain reaction (PCR). The DNA fragments encoding anti-HER2/anti-CD3, anti-CD3/anti-HER2, anti-EGFR/anti-CD3 and anti-CD3/anti-EGFR bispecific scFvs were generated by overlap extension PCR with the amplified anti-HER2, anti-EGFR and anti-CD3. Three repeats of glycine linker $(GGGGS)_3$ (SEQ ID NO: 8) were added between anti-HER2, anti-EGFR scFv and anti-CD3 scFv. One glycine linker (GGGGS) (SEQ ID NO: 9) was added to the C-termini of the antibodies. The resulting genes were inserted into the pDisplay vector between BglII and SalI by in-frame ligation.

To construct scFv-Lamp2b fusion proteins (FIG. 21), the DNA fragment encoding mouse Lamp2b was amplified by PCR. The DNA sequence of Lamp2b was added to the C-termini of anti-EGFR scFv, anti-CD3 scFv, anti-EGFR/anti-CD3 and anti-CD3/anti-EGFR bi-specific scFvs by overlap extension PCR. The resulting DNA fragments encoding scFv-Lamp2b fusion proteins were inserted into pcDNA3.1 vector with a FLAG tag added into the N-termini by in-frame ligation.

The resulting plasmids were confirmed by DNA sequencing.

Transfection

ScFv-PDGFR and scFv-Lamp2b fusion proteins were expressed through transient transfection of Expi293F cells. Expi293F cells were cultured at 37° C. with 8% $CO_2$ in Expi293 expression medium in shaker flask (125 rpm). For every 75 millions of Expi293F cells, 30 ug of plasmids encoding fusion proteins and 80 ul of ExpiFectamine 293 reagent were used for transfection, and transfection enhancers were added after 16-18 hours. Culture media containing secreted exosomes were harvested every 3 days for twice after transfection.

Exosome Purification

Exosomes were purified from culture media by differential centrifugation processes. Media were centrifuged at 4000 μg for 30 min, and then at 12,000 μg for 40 min to remove cell debris. The resulting supernatant was then spun at 120,000 μg for 2 h, and a pellet was recovered after the ultracentrifugation. The supernatant was aspirated and the pellet was washed and then resuspended with PBS. The purified exosomes were then analyzed and used for experimental procedures.

Western Blotting

Western blotting (FIGS. 6, 7, 16, 22, and 25: Protein concentrations of purified exosomes were measured using Bradford assay kit. 5 ug of exosomes were loaded onto SDS-PAGE gel. Following electrophoresis, the proteins were transferred to a polyvinylidene difluoride (PVDF) membrane. The membrane was then blocked for 1 h at room temperature with 5% BSA in PBS with 0.05% Tween-20, and incubated overnight at 4° C. with the following primary antibodies: anti-HA (Thermo Fisher Scientific, 1:1000), anti-FLAG (Thermo Fisher Scientific, 1:1000), anti-CD63 (H5C6), Biolegend; anti-CD81(1.3.3.22) Thermo Fisher; anti-CD9(D801A), Cell Signaling Technology. Secondary antibodies were incubated for 1 h at room temperature. Washes after antibody incubations were done with an orbital shaker, three times at 5-min intervals, with PBS containing 0.05% Tween-20. Membranes were developed with chemiluminescent reagents. For the blotting of HA tag, FLAG tag and CD9, exosome samples were boiled in LDS sample buffer with dithiothreitol (DTT). For the blotting of CD81 and CD63, exosome samples were boiled in LDS sample buffer without DTT.

Nanoparticle Tracking Analysis (NTA)

NTA was carried out using the NanoSight NS200-HS system (NanoSight) on exosomes resuspended in PBS at a concentration of ~20 μg/ml, and were further diluted from 10- to 100-fold for analysis. The system focused a laser beam through a suspension of the particles of interest. These were visualized by light scattering, using a conventional optical microscope aligned normally to the beam axis, which collected light scattered from every particle in the field of view. A video recorded all events for further analysis by NTA software. The Brownian motion of each particle was tracked between frames, ultimately allowing calculation of the size through application of the Stokes-Einstein equation.

FIGS. 10, 18 and 26 were acquired via Nanoparticle Tracking Analysis (NTA): Size distribution of exosomes was analyzed through dynamic light scattering (DLS) using Nanosight LM10 (Malvern Instruments, UK) according to the manufacturer's instructions. Exosomes suspended in PBS were diluted from 10- to 1000-fold for analysis. Samples were injected to NTA instrument. Ten replicates of analysis by 60 seconds each were performed. PBS was used as a control. The system focused a laser beam through a suspension of the particles of interest. These were visualized by light scattering, using a conventional optical microscope aligned normally to the beam axis, which collected light scattered from every particle in the field of view. A video recorded all events for further analysis by NTA software. The Brownian motion of each particle was tracked between frames, ultimately allowing calculation of the size through application of the Stokes-Einstein equation.

Transmission Electron Microscopy (TEM)

Transmission electron microscopy (TEM): TEM grids (FIGS. 19 and 27) were pretreated by placing 20 μL of the 0.1% poly-lysine solution on the grid and incubating for 10 minutes. Residual solvent was removed with filter paper. Exosome samples were prepared for TEM analysis by placing 20 μL of the sample solution on 200 μm mesh grids and incubating for 15 minutes. Residual solvent was removed from the grids with filter paper. After that, 20 L of 2% Uranyl Acetate solution was placed on the grids for 5 minutes. After incubation, solution was removed with filter paper and exosome samples were loaded to Jeol 2010F TEM (JEOL, Peabody, MA) for analysis.

Flow Cytometry

Cells were incubated with exosomes at the concentration of 0.1 μg/μl for 1 h at 4° C. Excess exosomes were washed away with 2% FBS in PBS. Exosome-bound cells were identified with anti-HA/Flag antibodies (Thermo Fisher Scientific) at 0.1 μg/μl, and revealed by Alexa Fluor 488-conjugated anti-Mouse secondary antibody at 0.1 μg/μl (Thermo Fisher Scientific). To measure the cell-surface expression level of HER2, cells were stained with Herceptin and FITC conjugated anti-Human IgG (H+L) (Thermo Fisher Scientific) at 0.1 μg/μl for 1 h at 4° C. To measure the cell-surface expression level of EGFR, cells were stained with anti-EGFR Mouse antibody (BioLegend) and Alexa Fluor 488-conjugated anti-Mouse secondary antibody at 0.1 μg/μl for 1 h at 4° C. To measure the cell-surface expression level of CD3, cells were stained with FITC conjugated anti-Human CD3 antibody (BioLegend) at indicated concentration for 1 h at 4° C. Cell samples were analyzed using FACSCalibur. FACS data was analyzed with FlowJo.

The binding affinity of bispecific exosomes on breast cancer cells (MDA-MB-453, MDA-MB231, MDA-MB-468, HCC 1954, SK-BR-3 and BT20) and human T cells (Jurkat) were determined by flow cytometry (FIGS. 8, 9, 17A and 36A). Cells were incubated with 0.1 mg/mL exosomes in PBS with 0.2% FBS for 1 h at 4° C. After washing twice with PBS containing 0.2% FBS, cells were incubated with anti-HA antibody (2-2.2.14) (Thermo Fisher) for 1 h at 4° C. After washing twice with PBS containing 0.2% FBS, the cells were incubated with Alexa Fluor 488 labeled Anti-Mouse IgG H&L (ab150113, Abcam) for 30 min at 4° C. Fluorescence signals were analyzed using LSR II Flow Cytometer (BD biosciences) and FlowJo_V10 software (Treestar).

Fluorescence Imaging

SK-BR-3 (HER2+), HCC-1954 (HER2+), MDA-MB-468 (EGFR+, HER2−) and MDA-MB-453 (EGFR−) cells were stained with CFSE, and Jurkat (CD3+) cells ($1\times10^6$) were stained with Mito Tracker Red following manufacturer's protocol. Jurkat cells were incubated with bi-specific exosomes (0.1 μg/μl) in 100 μl of PBS for 30 min at 4° C. As negative controls, Jurkat cells were incubated with a 1:1 mixture of anti-HER2/anti-EGFR and anti-CD3 mono-specific exosomes (0.05 μg/μl each). After washing with 1 mL of cold PBS, the Jurkat cells were resuspended with 300 of RPMI1640 media with 10% FBS, then mixed with SK-BR-3, HCC-1954, MDA-MB-468 or MDA-MB-453 cells ($1\times10^5$) in the same media (300 μl). The cell mixtures were added into 24-well plates on top of cover slips, and incubated at 37° C. and 5% $CO_2$. After 6 h, cover slips were gently washed with PBS three times to remove free Jurkat cells, and fixed with 4% PFA. The cover slips were mounted onto glass slides and imaged using Leica SP8 confocal microscope.

SK-BR-3 (HER2+) AND MDA-MB-468 (EGFR+, HER2−) cells were stained with Mito Tracker Red, and Jurkat (CD3+) cells ($1\times10^6$) were stained with CFSE following manufacturer's protocol (FIGS. 11, 12 and 28). Jurkat cells were incubated with bi-specific exosomes (0.1 μg/μl) in 100 of PBS for 30 min at 4° C. As negative controls, Jurkat cells were incubated with a 1:1 mixture of anti-HER2 and anti-CD3 mono-specific exosomes (0.05 μg/μl each). After washing with 1 mL of cold PBS, the Jurkat cells were resuspended with 300 μl of RPMI1640 media with 10% FBS, then mixed with SK-BR-3, or MDA-MB-468 cells ($1\times10^5$) in the same media (300 μl). The cell mixtures were added into 24-well plates on top of cover slips, and incubated at 37° C. and 5% $CO_2$. After 6 h, cover slips were gently washed with PBS three times to remove free Jurkat cells, and fixed with 4% PFA. The cover slips were mounted onto glass slides and imaged using a fluorescent microscope (Eclipse Ti, Nikon).

MDA-MB-468 (EGFR+) and MDA-MB-453 (EGFR−) cells were stained with MitoTracker Red (Biolegend), and Jurkat (CD3+) cells ($1\times10^6$) were stained with carboxyfluorescein succinimidyl ester (CFSE, Biolegend) (FIGS. 20 and 39) following manufacturer's protocol. Jurkat cells were incubated with bi-specific exosomes (0.1 μg/μl) in 100 of PBS for 30 min at 4° C. As negative controls, Jurkat cells were incubated with a 1:1 mixture of anti-EGFR and anti-CD3 mono-specific exosomes (0.05 μg/μl each). After washing with 1 mL of cold PBS, the Jurkat cells were resuspended with 300 of RPMI1640 media with 10% FBS, then mixed with MDA-MB-468 or MDA-MB-453 ($1\times10^5$) in the same media (300 μl). The cell mixtures were added into 24-well plates on top of cover slips, and incubated at 37° C. and 5% $CO_2$. After 6 h, cover slips were gently washed with PBS three times to remove free Jurkat cells, and fixed with 4% PFA. The cover slips were mounted onto glass slides and imaged using Leica SP8 confocal microscope.

In Vitro Cytotoxicity Assay

Purified human peripheral blood mononuclear cells (PBMCs) were purchased from HemaCare Corporation (Los Angeles, CA). Non-activated PBMCs (effector cells) were washed and incubated in flasks in RPMI1640 media with 10% FBS for 2 hours to remove adherent cells. SK-BR-3 (HER2+), HCC-1954 (HER2+), BT-474 (HER2+), and MDA-MB-468 (HER2−) cells (target cells) were dissociated with 0.05% tryspin/EDTA solution and washed with RPMI1640 with 10% FBS. Non-activated human PBMCs were mixed with target cells at an E:T ratio of 10 in 100 μl, and incubated with different concentrations of bi-specific exosomes, as well as mixtures of mono-specific exosomes, for 40 hours at 37° C. Cytotoxicity of each well was measured by MTT assay. Briefly, 96-well plates were washed three times with PBS to remove PBMC suspension, and 100 μl/well of RPMI1640 media (10% FBS) with 0.5 mg/ml MTT (3-(4,5-Dimethylthiazol-2-yl)-2,5-diphenyltetrazolium bromide) was added. The plates were incubated for 4 h at 37° C. 100 μl of lysis buffer (20% sodium dodecyl sulfate (SDS) in 50% N,N-dimethylformamide, containing 0.5% [v:v] 80% acetic acid and 0.4% [v:v] 1N HCL) was added to each well and incubated at 37° C. After 4 h incubation, absorbance at 570 nm was measured by the plate reader.

Percent cell viability was calculated by: % Cell viability=(Absorbance$_{expt}$−Absorbance$_{untreated\ control\ cells}$−Absorbance background)/(Absorbance$_{untreated\ control\ cells}$−Absorbance$_{background}$).

In vitro cytotoxicity assay: Purified human peripheral blood mononuclear cells (PBMCs) were purchased from HemaCare Corporation (Los Angeles, CA). Non-activated PBMCs (effector cells) were washed and incubated in flasks in RPMI1640 media with 10% FBS for 2 hours to remove adherent cells. MDA-MB-468 (EGFR+), BT20 (EGFR+), MDA-MB-231 (EGFR+), and MDA-MB-453 (EGFR−) cells (target cells) (FIGS. 17B and 36B) were dissociated with 0.05% tryspin/EDTA solution and washed with RPMI1640 with 10% FBS. Non-activated human PBMCs were mixed with target cells at an E:T ratio of 8 in 100 μl, and incubated with different concentrations of bi-specific exosomes, as well as mixtures of mono-specific exosomes, for 40 hours at 37° C. Cytotoxicity of each well was measured by MTT assay. Briefly, 96-well plates were washed three times with PBS to remove PBMC suspension, and 100 μl/well of RPMI1640 media (10% FBS) with 0.5 mg/ml MTT (3-(4,5-Dimethylthiazol-2-yl)-2,5-diphenyltetrazolium bromide) was added. The plates were incubated for 4 h at 37° C. 100 μl of lysis buffer (20% sodium dodecyl sulfate (SDS) in 50% N,N-dimethylformamide, containing 0.5% [v:v] 80% acetic acid and 0.4% [v:v] 1N HCL) was added to each well and incubated at 37° C. After 4 h incubation, absorbance at 570 nm was measured by the plate reader.

T Cell Activation Assay

Freshly-thawed human PBMCs were incubated with target cells in the presence of bispecific exosomes or control monospecific exosomes. After 20 h, cells were labeled with FITC-conjugated anti-CD3, APC-Cy7-conjugated anti-human CD25, APC-conjugated anti-human CD69 (Biolegend) and analyzed by flow cytometry. The release of IFN-$\gamma$ in the cultured supernatant was measured by enzyme-linked immunosorbent assay (ELISA) kit (R&D System). Results are shown as mean of duplicated samples (FIG. 37).

Zeta Potential Analysis

A Zetasizer Nano ZS (Malvern Instruments, U.K.) was used to determine the zeta potential of the exosomes (FIG. 34). Sample solution was loaded to a new Zeta-potential DTS1070 cell and inserted into Zetasizer Nano ZS.

In Vivo Efficacy Study

All efficacy studies (FIG. 38) were conducted with 6 to 8-week-old female NSG (NOD.Cg-Prkdcscid Il2rgtm1Wj1/SzJ) mice (Jackson Laboratory). Human breast cancer cell lines (MDA-MB-468, BT20, MDA-MB-231) were used to evaluate the in vivo efficacy of the $\alpha$-CD3/$\alpha$-EGFR bispecific exosomes. For MDA-MB-468, BT20 and MDA-MB-231 xenograft tumor models, $5\times10^6$ MDA-MB-468 cells or BT20 cells or $1.5\times10^6$ MDA-MB-231 cells in 50% Matrigel (BD Bioscience) were subcutaneously implanted into the right buttock of the mice, respectively. When the tumor size reach around 80-120 $mm^3$ after 15-30 days, $20\times10^6$ non-activated human PBMCs were injected into mice via intraperitoneal injection. One day later, mice were administered intravenously with six doses of $\alpha$-CD3/$\alpha$-EGFR bispecific exosomes (10 mg/kg) or PBS every other day. Tumors were measured three times weekly by calipers. Tumor volume was calculated based on length×width×width/2. All procedures were approved by USC Animal Care and Use Committee.

EQUIVALENTS

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All publications, patent applications, patents, and other references mentioned herein are expressly incorporated by reference in their entirety, including all formulas and figures, to the same extent as if each were incorporated by reference individually. In case of conflict, the present specification, including definitions, will control.

Other embodiments are set forth within the following claims.

The below section contains color text highlighted to indicate the termini of amino acid and polynucleotide segments of embodiments of this disclosure.

Exemplary Fusion Proteins

1. HA-*anti-CD3 scFv*-GGGGS-*myc*-PDGFR transmembrane domain
DNA sequence:
TATCCATATGATGTTCCAGATTATGCTGGGGCCCAGCCGGCCAGATCT*GATATC*
*CAGATGACACAGACAACCTCAAGTCTTAGTGCATCACTGGGAGATCGTGTGACTATAA*
*GCTGCCGCGCATCACAGGACATTCGCAATTATCTGAATTGGTATCAACAGAAGCCTGAT*
*GGCACCGTGAAACTTCTGATCTATTACACCAGTCGTCTGCATAGCGGTGTTCCGAGCA*
*AATTTTCAGGCTCAGGGTCAGGAACCGATTATTCACTGACGATTAGTAATTTAGAACAA*
*GAAGATATTGCAACCTATTTCTGTCAACAGGGTAATACCCTGCCGTGGACCTTTGCAGG*
*TGGTACCAAACTGGAAATTAAAGGAGGTGGCAGTGGAGGGGGAAGCGGCGGCGGTTC*
*AGGAGGCGGTTCTGAGGTCCAGTTACAGCAGAGCGGTCCGGAACTGGTTAAACCGGG*
*TGCAAGCATGAAAATTAGCTGTAAAGCAAGCGGTTATAGCTTTACCGGTTATACCATGA*
*ATTGGGTTAAACAGAGCCATGGTAAAAATCTGGAATGGATGGGTCTGATTAATCCGTAT*
*AAAGGTGTTAGCACCTATAATCAGAAATTTAAAGATAAAGCAACCCTGACCGTTGATAAA*
*AGCAGCAGCACCGCATATATGGAACTGCTGAGCCTGACCAGCGAAGATAGCGCCGTTT*
*ACTATTGCGCACGCAGCGGTTATTATGGTGATAGCGATTGGTATTTTGATGTTTGGGGT*
*GCAGGTACCACCGTTACCGTTAGCAGC*GGGGGTGGCGGAAGCGTCGAC*GAACAAA*
*AACTCATCTCAGAAGAGGATCTG*AATGCTGTGGGCCAGGACACGCAGGAGGTC
ATCGTGGTGCCACACTCCTTGCCCTTTAAGGTGGTGGTGATCTCAGCCATCC
TGGCCCTGGTGGTGCTCACCATCATCTCCCTTATCATCCTCATCATGCTTTG
GCAGAAGAAGCCACGTTAG (SEQ ID NO: 10)

HA-*anti-CD3 scFv*-GGGGS-*myc*-PDGFR transmembrane domain
Protein sequence:
YPYDVPDYAGAQPARS
*DIQMTQTTSSLSASLGDRVTISCRASQDIRNYLNWYQQKPDGTV*
*KLLIYYTSRLHSGVPSKFSGSGSGTDYSLTISNLEQEDIATYFCQQGNTLPWTFAGGTKL*
*EIKGGGSGGGSGGGSGGGSEVQLQQSGPELVKPGASMKISCKASGYSFTGYTMNWVKQS*
*HGKNLEWMGLINPYKGVSTYNQKFKDKATLTVDKSSSTAYMELLSLTSEDS*
*AVYYCARSGY*
YGDSDWYFDVWGAGTTVTVSSGGGGSVD*EQKLISEEDL*NAVGQDTQEVIVVPHS
LPFKVVVISAILALVVLTIISLIILIMLWQKKPR (SEQ ID NO: 11)

2. HA-*anti-HER2 scFv*-GGGGS-*myc*-PDGFR transmembrane domain
DNA sequence:
TATCCATATGATGTTCCAGATTATGCTGGGGCCCAGCCGGCCAGATCT*gacatcca*
*gatgacccagtctccatcctccctgtctgcatctgtaggagacagagtcaccatcacttgccgggcaagtcaggatgtgaataccg*
*cggtcgcatggtatcagcagaaaccagggaaagcccctaagctcctgatctattctgcatccttcttgtatagtggggtcccatcaa*
*ggttcagtggcagtaggtctgggacagatttcactctcaccatcagcagtctgcaacctgaagatttttgcaacttactactgtcaaca*
*gcattacactacccctccgacgttcggccaaggtaccaaggtggagatcaaacgaact*GGCTCTACCAGCGGAAG
CGGAAAGCCTGGCAGCGGCGAGGGCTCC*gaagtgcagctggtggagtctggcggaggactggtgcagcc*
*aggggggcagcctgagactgtcttgcgccgcctccggcttcaacatcaaggacacctacatccactgggtccgccaggcaccagg*
*caagggactggaatgggtggcccggatctaccctaccaacggctacaccagatacgccgactccgtgaagggccggttcaccat*
*ctccgccgacacctccaagaacaccgcctacctgcaaatgaactccctgagggccgaggacaccgccgtgtactactgctccag*
*atggggaggcgacggcttctacgcaatggactactggggccagggcaccctggtcacagtgtcctct*GGGGGTGGCGG
AAGCGTCGAC*GAACAAAAACTCATCTCAGAAGAGGATCTG*AATGCTGTGGGCCA
GGACACGCAGGAGGTCATCGTGGTGCCACACTCCTTGCCCTTTAAGGTGGT
GGTGATCTCAGCCATCCTGGCCCTGGTGGTGCTCACCATCATCTCCCTTATC
ATCCTCATCATGCTTTGGCAGAAGAAGCCACGTTAG (SEQ ID NO: 12)

Protein sequence:
YPYDVPDYAGAQPARS
*DIQMTQSPSSLSASVGDRVTITCRASQDVNTAVAWYQQKPGKAPKLHYSASFLYSGVPS*
*RFSGSRSGTDFTLTISSLQPEDFATYYCQQHYTTPPTFGQGTKVEIKRTGSTSGSGKPGS*
*GEGSEVQLVESGGGLVQPGGSLRLSCAASGFNIKDTYIHWVRQAPGKGLEWVARIYPTNG*
*YTRYADSVKGRFTISADTSKNTAYLQMNSLRAEDTAVYYCSRWGGDGFYAMDYWGQGTLV*
*TVSS*GGGGSVD*EQKLISEEDL*NAVGQDTQEVIVVPHSLPFKVV
VISAILALVVLTIISLIILIMLWQKKPR (SEQ ID NO: 13)

3. HA-*anti-HER2 scFv*-(GGGGS)$_3$-*anti-CD3 scFv*-GGGGS-*myc*-PDGFR transmembrane domain
DNA sequence:
TATCCATATGATGTTCCAGATTATGCTGGGGCCCAGCCGGCCAGATCT*gacatcca*
*gatgacccagtctccatcctccctgtctgcatctgtaggagacagagtcaccatcacttgccgggcaagtcaggatgtgaataccg*
*cggtcgcatggtatcagcagaaaccagggaaagcccctaagctcctgatctattctgcatccttcttgtatagtggggtcccatcaa*
*ggttcagtggcagtaggtctgggacagatttcactctcaccatcagcagtctgcaacctgaagatttttgcaacttactactgtcaaca*
*gcattacactacccctccgacgttcggccaaggtaccaaggtggagatcaaacgaact*GGCTCTACCAGCGGAAG
CGGAAAGCCTGGCAGCGGCGAGGGCTCC*gaagtgcagctggtggagtctggcggaggactggtgcagcc*
*aggggggcagcctgagactgtcttgcgccgcctccggcttcaacatcaaggacacctacatccactgggtccgccaggcaccagg*
*caagggactggaatgggtggcccggatctaccctaccaacggctacaccagatacgccgactccgtgaagggccggttcaccat*
*ctccgccgacacctccaagaacaccgcctacctgcaaatgaactccctgagggccgaggacaccgccgtgtactactgctccag*
*atggggaggcgacggcttctacgcaatggactactggggccagggcaccctggtcacagtgtcctct*GGCGGTGGCGG
ATCAGGCGGGGGAGGCTCAGGCGGAGGTGGCAGC*GATATCCAGATGACACAGACA*
*ACCTCAAGTCTTAGTGCATCACTGGGAGATCGTGTGACTATAAGCTGCCGCGCATCAC*
*AGGACATTCGCAATTATCTGAATTGGTATCAACAGAAGCCTGATGGCACCGTGAAACTT*
*CTGATCTATTACACCAGTCGTCTGCATAGCGGTGTTCCGAGCAAATTTTCAGGCTCAGG*
*GTCAGGAACCGATTATTCACTGACGATTAGTAATTTAGAACAAGAAGATATTGCAACCTA*
*TTTCTGTCAACAGGGTAATACCCTGCCGTGGACCTTTGCAGGTGGTACCAAACTGGAA*
*ATTAAAGGAGGTGGCAGTGGAGGGGGAAGCGGCGGCGGTTCAGGAGGCGGTTCTGA*
*GGTCCAGTTACAGCAGAGCGGTCCGGAACTGGTTAAACCGGGTGCAAGCATGAAAATT*
*AGCTGTAAAGCAAGCGGTTATAGCTTTACCGGTTATACCATGAATTGGGTTAAACAGAG*
*CCATGGTAAAAATCTGGAATGGATGGGTCTGATTAATCCGTATAAAGGTGTTAGCACCT*
*ATAATCAGAAATTTAAAGATAAAGCAACCCTGACCGTTGATAAAAGCAGCAGCACCGCA*
*TATATGGAACTGCTGAGCCTGACCAGCGAAGATAGCGCCGTTTACTATTGCGCACGCA*
*GCGGTTATTATGGTGATAGCGATTGGTATTTTGATGTTTGGGGTGCAGGTACCACCGTT*
*ACCGTTAGCAGC*GGGGGTGGCGGAAGCGTCGAC*GAACAAAAACTCATCTCAGAAG*
*AGGATCTG*AATGCTGTGGGCCAGGACACGCAGGAGGTCATCGTGGTGCCAC
ACTCCTTGCCCTTTAAGGTGGTGGTGATCTCAGCCATCCTGGCCCTGGTGGT
GCTCACCATCATCTCCCTTATCATCCTCATCATGCTTTGGCAGAAGAAGCCA
CGTTAG (SEQ ID NO: 14)

Protein sequence:
YPYDVPDYAGAQPARS*DIQMTQSPSSLSASVGDRVTITCRASQDVNTAVAWYQQKPGKA*
*PKLHYSASFLYSGVPSRFSGSRSGTDFTLTISSLQPEDFATYYCQQHYTTPPTFGQGTKVEI*
*KRTGSTSGSGKPGSGEGSEVQLVESGGGLVQPGGSLRLSCAASGFNIKDTYIHWVRQAPG*
*KGLEWVARIYPTNGYTRYADSVKGRFTISADTSKNTAYLQMNSLRAEDTAVYYCSRWGGD*
*GFYAMDYWGQGTLVTVSS*GGGGSGGGGSGGGGS
*DIQMTQTTSSLSASLGDRVTISCRASQDIRNYLNWYQQKPDGTV*
*KLLIYYTSRLHSGVPSKFSGSGSGTDYSLTISNLEQEDIATYFCQQGNTLPWTFAGGTKL*
*EIKGGGSGGGSGGGSGGGSEVQLQQSGPELVKPGASMKISCKASGYSF*
*TGYTMNWVKQSHGKNLEWMGLINPYKGVSTYNQKFKDKATLTVDKSSSTAYM*
*ELLSLTSEDSAVYYCARSGYYGDSDWYFDVWGAGTTVTVSS*GGGGSVD*EQKLISEEDL*
NAVGQDTQEVIVVPHSLPFKVVVISAILALVVLTIISLIILIMLWQKKPR (SEQ ID NO: 15)

4. HA-*anti-CD3 scFv*-(GGGGS)$_3$-*anti-HER2 scFv*-GGGGS-*myc*-PDGFR transmembrane domain
DNA sequence:
*TATCCATATGATGTTCCAGATTATGCTGGGGCCCAGCCGGCCAGATCTGATATCCAGAT*
*GACACAGACAACCTCAAGTCTTAGTGCATCACTGGGAGATCGTGTGACTATAAGCTGC*
*CGCGCATCACAGGACATTCGCAATTATCTGAATTGGTATCAACAGAAGCCTGATGGCA*

-continued

CCGTGAAACTTCTGATCTATTACACCAGTCGTCTGCATAGCGGTGTTCCGAGCAAATTT
TCAGGCTCAGGGTCAGGAACCGATTATTCACTGACGATTAGTAATTTAGAACAAGAAGA
TATTGCAACCTATTTCTGTCAACAGGGTAATACCCTGCCGTGGACCTTTGCAGGTGGTA
CCAAACTGGAAATTAAAGGAGGTGGCAGTGGAGGGGGAAGCGGCGGCGGTTCAGGA
GGCGGTTCTGAGGTCCAGTTACAGCAGAGCGGTCCGGAACTGGTTAAACCGGGTGCA
AGCATGAAAATTAGCTGTAAAGCAAGCGGTTATAGCTTTACCGGTTATACCATGAATTG
GGTTAAACAGAGCCATGGTAAAAATCTGGAATGGATGGGTCTGATTAATCCGTATAAAG
GTGTTAGCACCTATAATCAGAAATTTAAAGATAAAGCAACCCTGACCGTTGATAAAAGC
AGCAGCACCGCATATATGGAACTGCTGAGCCTGACCAGCGAAGATAGCGCCGTTTACT
ATTGCGCACGCAGCGGTTATTATGGTGATAGCGATTGGTATTTTGATGTTTGGGGTGCA
GGTACCACCGTTACCGTTAGCAGCGGCGGTGGCGGATCAGGCGGGGGAGGCTCAG
GCGGAGGTGGCAGCgacatccagatgacccagtctccatcctccctgtctgcatctgtaggagacagagtcaccatca
cttgccgggcaagtcaggatgtgaataccgcggtcgcatggtatcagcagaaaccagggaaagcccctaagctcctgatctattc
tgcatccttcttgtatagtggggtcccatcaaggttcagtggcagtaggtctgggacagatttcactctcaccatcagcagtctgcaa
cctgaagattttgcaacttactactgtcaacagcattacactacccctccgacgttcggccaaggtaccaaggtggagatcaaacg
aactGGCTCTACCAGCGGAAGCGGAAAGCCTGGCAGCGGCGAGGGCTCCgaagtgcagctg
gtggagtctggcggaggactggtgcagccagggggcagcctgagactgtcttgcgccgcctccggcttcaacatcaaggacacc
tacatccactgggtccgccaggcaccaggcaagggactggaatgggtggcccggatctaccctaccaacggctacaccagata
cgccgactccgtgaagggccggttcaccatctccgccgacacctccaagaacaccgcctacctgcaaatgaactccctgagggc
cgaggacaccgccgtgtactactgctccagatggggaggcgacggcttctacgcaatggactactggggccagggcaccctggt
cacagtgtcctctGGGGGTGGCGGAAGCGTCGACGAACAAAAACTCATCTCAGAAGAGGA
TCTGAATGCTGTGGGCCAGGACACGCAGGAGGTCATCGTGGTGCCACACTC
CTTGCCCTTTAAGGTGGTGGTGATCTCAGCCATCCTGGCCCTGGTGGTGCTC
ACCATCATCTCCCTTATCATCCTCATCATGCTTTGGCAGAAGAAGCCACGTT
AG (SEQ ID NO: 16)

Protein sequence:
YPYDVPDYAGAQPARSDIQMTQTTSSLSASLGDRVTISCRASQDIRNYLNWYQQKPDGT
VKLLIYYTSRLHSGVPSKFSGSGSGTDYSLTISNLEQEDIATYFCQQGNTLPWTFAGGTKL
EIKGGGSGGGSGGGSGGGSEVQLQQSGPELVKPGASMKISCKASGYSFTGYTMNWVKQS
HGKNLEWMGLINPYKGVSTYNQKFKDKATLTVDKSSSTAYMELLSLTSED
SAVYYCARSGYYGDSDWYFDVWGAGTTVTVSSGGGGSGGGGSGGGGS
DIQMTQSPSSLSASVGDRVTITCRASQDVNTAVAWYQQKPGKAPKLHYSASFLYSGVPSRF
SGSRSGTDFTLTISSLQPEDFATYYCQQHYTTPPTFGQGTKVEIKRTGSTSGSGKPGSGEGS
EVQLVESGGGLVQPGGSLRLSCAASGFNIKDTYIHWVRQAPGKGLEWVARIYPTNGYTRYA
DSVKGRFTISADTSKNTAYLQMNSLRAEDTAVYYCSRWGGDGFYAMDYWGQGTLVTVSSG
GGGSVDEQKLISEEDLNAVGQDTQEVIVVPHSLPFKVVVISAILALVVLTIISLIILI
MLWQKKPR (SEQ ID NO: 17)

5. *Flag*-Linker-anti-EGFR scFv-linker-*Lamp2b*:
DNA:
*gactacaaagacgatgacgacaag*ggtaccggaggaagccaggtgcagctgaagcagtctggccctggactggtgcagcct
agccagagcctgagcatcacctgtaccgtgtccggcttcagcctgaccaactacggcgtgcactgggtgcgacagagccctgg
caaaggcctggaatggctgggagtgatttggagcggcggcaacaccgactacaacaccccctcaccagcagactgtccatc
aacaaggacaacagcaagagccaggtgttcttcaagatgaacagcctgcagagcaacgacaccgccatctactactgcgct
agagccctgacctactatgactacgagttcgcctactggggccagggcacactcgtgacagtgtctgccggcggaggtggatc
tggaggcggtggcagcggtggaggcggatctgacatcctgctgacccagagccccgtgatcctgtccgtgtctcctggcgaga
gagtgtccttcagctgcagagccagccagagcatcggcaccaacatccactggtatcagcagaggaccaacggcagcccca
gactgctgattaagtacgccagcgagtccatcagcggcatccccagcagattcagcggcagcggctctggcaccgacttcacc
ctgagcatcaacagcgtggaaagcgaggatatcgccgactactactgccagcagaacaacaactggcccaccaccttcggc
**gctggcaccaagctggaactgaagggcgggagc*ttgatagttaatttgacagattcaaagggtacttgcctttatgcagaatggg***
*agatgaacttcacaataacctacgaaactacaaaccaaaccaataaaactataaccatagcagtaccggacaaggcgacaca*
*cgatggaagcagttgtggggacgaccggaatagtgatacaatttggattcgctgtctcttgggctgtgaactttactgccaaaataa*
*caaagaagcatctcattattcaattcatgacatcgtgctttcctacaacacttctgatagcacagtatttcctggtgctgtagctaaagg*
*agttcatactgttaaaaatcctgagaacttcaaagttccattggacgtgatctttaagtgcaatagtgttttaacttacaacctgactcct*
*gtcgttcagaagtattggggtattcacctccaggcttttgtccaaaatggtacagtgagtaaaaatgaacaagtgtgtgaagaggat*
*caaactccgaccactgtagcacccatcattcacaccactgccccatcgactacaactacactcactccaacttcaacacccactcc*
*aacgccaactccaacaccaaccgttggaaactacagcattagaaatggcaatactacctgtctgctggctactatggggttacaa*
*ctgaacatcactgaggagaaagtgcctttcattttaacatcaaccctgccacaaccaacttcaccggaagctgtcaacctcaaagt*
*gctcaacttaggctgaacaacagccaaattaagtatcttgactttatctttgctgtgaaaaatgaaaaacggttctatctgaaggaag*
*tgaatgtctatatgtatttggctaatggatcagctttcaacatttccaacaagaaccttagcttctgggacgcccctctgggaagttctt*
*atatgtgcaacaaagagcaggtgctttctgtgtcgagggcgtttcagatcaacacctttaacctaaaggtgcaacctttaatgtgac*
*aaaaggacagtattctacagcagaggaatgcgccgctgactccgacctgaacttcctgatccccgtcgccgtgggcgtcgccctc*
*ggcttcctcatcatcgctgtgttcatcagctacatgatcggcaggagaaagagcagaaccggctaccaaagcgtgtaataa*
(SEQ ID NO: 18)

Protein:

| | |
|---|---|
| 1 | *DYKDDDDKGT GGS*QVQLKQS |
| 21 | **GPGLVQPSQS LSITCTVSGF** |
| 41 | **SLTNYGVHWV RQSPGKGLEW** |
| 61 | **LGVIWSGGNT DYNTPFTSRL** |
| 81 | **SINKDNSKSQ VFFKMNSLQS** |
| 101 | **NDTAIYYCAR ALTYYDYEFA** |

121 YWGQGTLVTV SAGGGGSGGG

141 GSGGGGSDIL LTQSPVILSV

161 SPGERVSFSC RASQSIGTNI

181 HWYQQRTNGS PRLLIKYASE

201 SISGIPSRFS GSGSGTDFTL

221 SINSVESEDI ADYYCQQNNN

241 WPTTFGAGTK LELK*GGSLIV*

261 *NLTDSKGTCL YAEWEMNFTI*

281 *TYETTNQTNK TITIAVPDKA*

301 *THDGSSCGDD RNSAKIMIQF*

321 *GFAVSWAVNF TKEASHYSIH*

341 *DIVLSYNTSD STVFPGAVAK*

361 *GVHTVKNPEN FKVPLDVIFK*

381 *CNSVLTYNLT PVVQKYWGIH*

401 *LQAFVQNGTV SKNEQVCEED*

421 *QTPTTVAPII HTTAPSTTTT*

441 *LTPTSTPTPT PTPTPTVGNY*

461 *SIRNGNTTCLLATMGLQLNI*

481 *TEEKVPFIFN INPATTNFTG*

501 *SCQPQSAQLR LNNSQIKYLD*

521 *FIFAVKNEKR FYLKEVNVYM*

541 *YLANGSAFNI SNKNLSFWDA*

561 *PLGSSYMCNK EQVLSVSRAF*

581 *QINTFNLKVQ PFNVTKGQYS*

601 *TAEECAADSDLNFLIPVAVG*

621 *VALGFLIIAV FISYMIGRRK*

641 *SRTGYQSV*** (SEQ ID NO: 19)

6. *Flag*-Linker-anti-CD3 scFv-linker-*Lamp2b*:

DNA:

*gactacaaagacgatgacgacaag*GGTACCggtggcagcGATATCCAGATGACACAGACAACCTC
AAGTCTTAGTGCATCACTGGGAGATCGTGTGACTATAAGCTGCCGCGCATCACAG
GACATTCGCAATTATCTGAATTGGTATCAACAGAAGCCTGATGGCACCGTGAAAC
TTCTGATCTATTACACCAGTCGTCTGCATAGCGGTGTTCCGAGCAAATTTTCAGG
CTCAGGGTCAGGAACCGATTATTCACTGACGATTAGTAATTTAGAACAAGAAGA
TATTGCAACCTATTTCTGTCAACAGGGTAATACCCTGCCGTGGACCTTTGCAGGT
GGTACCAAACTGGAAATTAAAGGAGGTGGCAGTGGAGGGGGAAGCGGCGGCGG
TTCAGGAGGCGGTTCTGAGGTCCAGTTACAGCAGAGCGGTCCGGAACTGGTTAA
ACCGGGTGCAAGCATGAAAATTAGCTGTAAAGCAAGCGGTTATAGCTTTACCGG
TTATACCATGAATTGGGTTAAACAGAGCCATGGTAAAAATCTGGAATGGATGGG
TCTGATTAATCCGTATAAAGGTGTTAGCACCTATAATCAGAAATTTAAAGATAAA
GCAACCCTGACCGTTGATAAAAGCAGCAGCACCGCATATATGGAACTGCTGAGC
CTGACCAGCGAAGATAGCGCCGTTTACTATTGCGCACGCAGCGGTTATTATGGTG
ATAGCGATTGGTATTTTGATGTTTGGGGTGCAGGTACCACCGTTACCGTTAGCAG
Cggcgggagc*ttgatagttaatttgacagattcaaagggtacttgcctttatgcagaatgggagatgaacttcacaataacctacg*
*aaactacaaccaaaccaataaactataaccatagcagtaccggacaaggcgacacacgatggaagcagttgtggggacg*
*accggaatagtgccaaaataatgatacaatttggattcgctgtctcttgggctgtgaactttaccaaagaagcatctcattattcaatt*
*catgacatcgtgctttcctacaacacttctgatagcacagtatttcctggtgctgtagctaaaggagttcatactgttaaaaatcctga*
*gaacttcaaagttccattggacgtgatctttaagtgcaatagtgttttaacttacaacctgactcctgtcgttcagaagtattggggtatt*
*cacctccaggcttttgtccaaaatggtacagtgagtaaaaatgaacaagtgtgtgaagaggatcaaactccgaccactgtagcac*
*ccatcattcacaccactgccccatcgactacaactacactcactccaacttcaacacccactccaacgccaactccaacaccaac*
*cgttggaaactacagcattagaaatggcaatactacctgtctgctggctactatggggttacaactgaacatcactgaggagaaag*

-continued

*tgcctttcattttaacatcaaccctgccacaaccaacttcaccggaagctgtcaacctcaaagtgctcaacttaggctgaacaaca gccaaattaagtatcttgactttatctttgctgtgaaaaatgaaaaacggttctatctgaaggaagtgaatgtctatatgtatttggcta atggatcagctttcaacatttccaacaagaaccttagcttctgggacgcccctctgggaagttcttatatgtgcaacaaagagcagg tgctttctgtgtcgagggcgtttcagatcaacacctttaacctaaaggtgcaaccttttaatgtgacaaaaggacagtattctacagc agaggaatgcgccgctgactccgacctgaacttcctgatcccgtcgccgtgggcgtcgccctcggcttcctcatcatcgctgtgttc atcagctacatgatcggcaggagaaagagcagaaccggctaccaaagcgtgtaataa* (SEQ ID NO: 20)

Protein:

1 *DYKDDDDKGT* GGSDIQMTQT

21 TSSLSASLGD RVTISCRASQ

41 DIRNYLNWYQ QKPDGTVKLL

61 IYYTSRLHSG VPSKFSGSGS

81 GTDYSLTISN LEQEDIATYF

101 CQQGNTLPWT FAGGTKLEIK

121 GGGSGGGSGG GSGGGSEVQL

141 QQSGPELVKP GASMKISCKA

161 SGYSFTGYTM NWVKQSHGKN

181 LEWMGLINPY KGVSTYNQKF

201 KDKATLTVDK SSSTAYMELL

221 SLTSEDSAVY YCARSGYYGD

241 SDWYFDVWGA GTTVTVSSGG

261 *SLIVNLTDSK GTCLYAEWEM*

281 *NFTITYETTN QTNKTITIAV*

301 *PDKATHDGSS CGDDRNSAKI*

321 *MIQFGFAVSW AVNFTKEASH*

341 *YSIHDIVLSY NTSDSTVFPG*

361 *AVAKGVHTVK NPENFKVPLD*

381 *VIFKCNSVLT YNLTPVVQKY*

401 *WGIHLQAFVQ NGTVSKNEQV*

421 *CEEDQTPTTV APIIHTTAPS*

441 *TTTTLTPTST PTPTPTPTPT*

461 *VGNYSIRNGN TTCLLATMGL*

481 *QLNITEEKVP FIFNINPATT*

501 *NFTGSCQPQS AQLRLNNSQI*

521 *KYLDFIFAVK NEKRFYLKEV*

541 *NVYMYLANGS AFNISNKNLS*

561 *FWDAPLGSSY MCNKEQVLSV*

581 *SRAFQINTFN LKVQPFNVTK*

601 *GQYSTAEECA ADSDLNFLIP*

621 *VAVGVALGFL IIAVFISYMI*

641 *GRRKSRTGYQ SV*** (SEQ ID NO: 21)

7. *Flag*-***Linker*-anti-EGFR scFv-*Linker*-anti-CD3 scFv-*linker*-Lamp2b**:

DNA:

*gactacaaagacgatgacgacaag*GGTACC***ggaggaagc*caggtgcagctgaagcagtctggccctggactggtgcag cctagccagagcctgagcatcacctgtaccgtgtccggcttcagcctgaccaactacggcgtgcactgggtgcgacagagccc tggcaaaggcctggaatggctgggagtgatttggagcggcggcaacaccgactacaacaccccttcaccagcagactgtcc**

-continued atcaacaaggacaacagcaagagccaggtgttcttcaagatgaacagcctgcagagcaacgacaccgccatctactactgc
gctagagccctgacctactatgactacgagttcgcctactggggccagggcacactcgtgacagtgtctgccggcggaggtgg
atctggaggcggtggcagcggtggaggcggatctgacatcctgctgacccagagccccgtgatcctgtccgtgtctcctggcg
agagagtgtccttcagctgcagagccagccagagcatcggcaccaacatccactggtatcagcagaggaccaacggcagcc
ccagactgctgattaagtacgccagcgagtccatcagcggcatccccagcagattcagcggcagcggctctggcaccgacttc
accctgagcatcaacagcgtggaaagcgaggatatcgccgactactactgccagcagaacaacaactggcccaccaccttcg
gcgctggcaccaagctggaactgaagGGCGGTGGCGGATCAGGCGGGGGAGGCTCAGGCGGA
GGTGGCAGCGATATCCAGATGACACAGACAACCTCAAGTCTTAGTGCATCACTG
GGAGATCGTGTGACTATAAGCTGCCGCGCATCACAGGACATTCGCAATTATCTGA
ATTGGTATCAACAGAAGCCTGATGGCACCGTGAAACTTCTGATCTATTACACCAG
TCGTCTGCATAGCGGTGTTCCGAGCAAATTTTCAGGCTCAGGGTCAGGAACCGAT
TATTCACTGACGATTAGTAATTTAGAACAAGAAGATATTGCAACCTATTTCTGTC
AACAGGGTAATACCCTGCCGTGGACCTTTGCAGGTGGTACCAAACTGGAAATTA
AAGGAGGTGGCAGTGGAGGGGGAAGCGGCGGCGGTTCAGGAGGCGGTTCTGAG
GTCCAGTTACAGCAGAGCGGTCCGGAACTGGTTAAACCGGGTGCAAGCATGAAA
ATTAGCTGTAAAGCAAGCGGTTATAGCTTTACCGGTTATACCATGAATTGGGTTA
AACAGAGCCATGGTAAAAATCTGGAATGGATGGGTCTGATTAATCCGTATAAAG
GTGTTAGCACCTATAATCAGAAATTTAAAGATAAAGCAACCCTGACCGTTGATAA
AAGCAGCAGCACCGCATATATGGAACTGCTGAGCCTGACCAGCGAAGATAGCGC
CGTTTACTATTGCGCACGCAGCGGTTATTATGGTGATAGCGATTGGTATTTTGAT
GTTTGGGGTGCAGGTACCACCGTTACCGTTAGCAGCggcgggagcttgatagttaatttgacaga
ttcaaagggtacttgcctttatgcagaatgggagatgaacttcacaataacctacgaaactacaaaccaaaccaataaaacta
taaccatagcagtaccggacaaggcgacacacgatggaagcagttgtggggacgaccggaatagtgccaaaataatgatac
aatttggattcgctcctcttgttctcgaactttaccaaagattcatctcattattcaattcatgacatcgtgattcctacaaca
cttctgatagcacagtatttcctggtgctgtagctaaaggagttcatactgttaaaaatcctgagaacttcaaagttccattggac
gtgatctttaagtgcaatagtctttaacttacaacctgactcctccgttcagaagtatttttttattcacctccattcttttccc
aaaattttacagtgagtaaaaatgaacaagtcgtgaagaggatcaaactccgaccactgtagcacccatcattcacaccac
tttcccatcgactacaactacactcactccaacttcaacacccactccaacgccaactccaacaccaaccgttttaaactaca
gcattagaaatggcaatactacctgtctgctggctactatggggttacaactgaacatcactgaggagaaagtgcctttcatttt
taacatcaaccctgccacaaccaacttcaccggattctccaacctcaaagtgctcaacttaggctgaacaacagccaaatta
agtatcttgactttatattgctcgaaaaatgaaaaacttttctatctgaaggaagtgaatcctatatgtatttggctaattta
tcagattcaacatttccaacaagaaccttagcttctttgacgcccctctttgaagttcttatatcgcaacaaagagcatttgc
tttctgtgtcgagggcgtttcagatcaacacctttaacctaaaggtgcaaccttttaatgtgacaaaaggacagtattctacagc
agaggaattttccgctgactccgacctgaacttcctgatccccgtcgcccttgcgtcgccctcttcttcctcatcatcgctcg
ttcatcagctacatgatcggcaggagaaagagcagaaccggctaccaaagcgtgtaataa (SEQ ID NO: 22)

Protein:

1 DYKDDDDKGT GGSQVQLKQS

21 GPGLVQPSQS LSITCTVSGF

41 SLTNYGVHWV RQSPGKGLEW

61 LGVIWSGGNT DYNTPFTSRL

81 SINKDNSKSQ VFFKMNSLQS

101 NDTAIYYCAR ALTYYDYEFA

121 YWGQGTLVTV SAGGGGSGGG

141 GSGGGGSDIL LTQSPVILSV

161 SPGERVSFSC RASQSIGTNI

181 HWYQQRTNGS PRLLIKYASE

201 SISGIPSRFS GSGSGTDFTL

221 SINSVESEDI ADYYCQQNNN

241 WPTTFGAGTK LELKGGGGSG

261 GGGSGGGGSD IQMTQTTSSL

281 SASLGDRVTI SCRASQDIRN

301 YLNWYQQKPD GTVKLLIYYT

321 SRLHSGVPSK FSGSGSGTDY

341 SLTISNLEQE DIATYFCQQG

361 NTLPWTFAGG TKLEIKGGGS

381 GGGSGGGSGG GSEVQLQQSG

401 PELVKPGASM KISCKASGYS

-continued

421 FTGYTMNWVK QSHGKNLEWM

441 GLINPYKGVS TYNQKFKDKA

461 TLTVDKSSST AYMELLSLTS

481 EDSAVYYCAR SGYYGDSDWY

501 FDVWGAGTTV TVSSGGSLIV

521 NLTDSKGTCL YAEWEMNFTI

541 TYETTNQTNK TITIAVPDKA

561 THDGSSCGDD RNSAKIMIQF

581 GFAVSWAVNF TKEASHYSIH

601 DIVLSYNTSD STVFPGAVAK

621 GVHTVKNPEN FKVPLDVIFK

641 CNSVLTYNLT PVVQKYWGIH

661 LQAFVQNGTV SKNEQVCEED

681 QTPTTVAPII HTTAPSTTTT

701 LTPTSTPTPT PTPTPTVGNY

721 SIRNGNTTCL LATMGLQLNI

741 TEEKVPFIFN INPATTNFTG

761 SCQPQSAQLR LNNSQIKYLD

781 FIFAVKNEKR FYLKEVNVYM

801 YLANGSAFNI SNKNLSFWDA

821 PLGSSYMCNK EQVLSVSRAF

841 QINTFNLKVQ PFNVTKGQYS

861 TAEECAADSD LNFLIPVAVG

881 VALGFLIIAV FISYMIGRRK

901 SRTGYQSV** (SEQ ID NO: 23)

8. Flag-Linker-anti-CD3 scFv-Linker-Linker-linker-Lamp2b:
DNA:
gactacaaagacgatgacgacaagGGTACCggtggcagcGATATCCAGATGACACAGACAACCTC
AAGTCTTAGTGCATCACTGGGAGATCGTGTGACTATAAGCTGCCGCGCATCACAG
GACATTCGCAATTATCTGAATTGGTATCAACAGAAGCCTGATGGCACCGTGAAAC
TTCTGATCTATTACACCAGTCGTCTGCATAGCGGTGTTCCGAGCAAATTTTCAGG
CTCAGGGTCAGGAACCGATTATTCACTGACGATTAGTAATTTAGAACAAGAAGA
TATTGCAACCTATTTCTGTCAACAGGGTAATACCCTGCCGTGGACCTTTGCAGGT
GGTACCAAACTGGAAATTAAAGGAGGTGGCAGTGGAGGGGGAAGCGGCGGCGG
TTCAGGAGGCGGTTCTGAGGTCCAGTTACAGCAGAGCGGTCCGGAACTGGTTAA
ACCGGGTGCAAGCATGAAAATTAGCTGTAAAGCAAGCGGTTATAGCTTTACCGG
TTATACCATGAATTGGGTTAAACAGAGCCATGGTAAAAATCTGGAATGGATGGG
TCTGATTAATCCGTATAAAGGTGTTAGCACCTATAATCAGAAATTTAAAGATAAA
GCAACCCTGACCGTTGATAAAAGCAGCAGCACCGCATATATGGAACTGCTGAGC
CTGACCAGCGAAGATAGCGCCGTTTACTATTGCGCACGCAGCGGTTATTATGGTG
ATAGCGATTGGTATTTTGATGTTTGGGGTGCAGGTACCACCGTTACCGTTAGCAG
Cggaggtggcggaagtggaggaggtggctctggcggtggaggaagccaggtgcagctgaagcagtctggccctggactggt
gcagcctagccagagcctgagcatcacctgtaccgtgtccggcttcagcctgaccaactacggcgtgcactgggtgcgacaga
gccctggcaaaggcctggaatggctgggagtgatttggagcggcggcaacaccgactacaacaccccttcaccagcagact
gtccatcaacaaggacaacagcaagagccaggtgttcttcaagatgaacagcctgcagagcaacgacaccgccatctactac
tgcgctagagccctgacctactatgactacgagttcgcctactggggccagggcacactcgtgacagtgtctgccggcggagg
tggatctggaggcggtggcagcggtggaggcggatctgacatcctgctgacccagagccccgtgatcctgtccgtgtctcctg
gcgagagagtgtccttcagctgcagagccagccagagcatcggcaccaacatccactggtatcagcagaggaccaacggca
gccccagactgctgattaagtacgccagcgagtccatcagcggcatccccagcagattcagcggcagcggctctggcaccga
cttcaccctgagcatcaacagcgtggaaagcgaggatatcgccgactactactgccagcagaacaacaactggcccaccacc
ttcggcgctggcaccaagctggaactgaagggcgggagcttgatagttaatttgacagattcaaagggtacttgcctttatgca
gaatgggagatgaacttcacaataacctacgaaactacaaaccaaaccaataaaactataaccatagcagtaccggacaag
gcgacacacgatggaagcagttcggggacgaccggaatagtgccaaaataatgatacaatttggattcgctcctcttgggc
tcgaactttaccaaagaagcatctcattattcaattcatgacatcgtgattcctacaacacttctgatagcacagtatttcctgg -continued tgctgtagctaaaggagttcatactgttaaaaatcctgagaacttcaaagttccattggacgtgatctttaagtgcaatagtgttt
taacttacaacctgactcctccgttcagaagtattttggtattcacctccaggcttttgtccaaaattttacagtgagtaaaaa
tgaacaagtcgtgaagaggatcaaactccgaccactgtagcacccatcattcacaccactttcccatcgactacaactacac
tcactccaacttcaacacccactccaacgccaactccaacaccaaccgttggaaactacagcattagaaatggcaatactacc
tgtctgctggctactatggggttacaactgaacatcactgaggagaaagtgcctttcattttttaacatcaaccctgccacaacca
acttcaccggattctccaacctcaaagttttcaacttaggctgaacaacacccaaattaagtatcttgactttatctttgctc
gaaaaatgaaaaacggttctatctgaaggaagtgaatgtctatatgtatttggctaatggatcagctttcaacatttccaacaa
gaaccttattttctttgacttccctctttgatttcttatatcgcaacaaagagcatttttttttctcgtcgagggcgtttcag
atcaacacctttaacctaaattttttaaccttttaatcgacaaaaggacagtattctacagcagaggaattttcctttgactc
cgacctgaacttcctgatccccgtcgcccgggcgtcgccctcgttttcctcatcatcgctcgttcatcatttacatgatcgtta
ggagaaagagcagaaccttctaccaattccgtaataa (SEQ ID NO: 24)

Protein:

1 *DYKDDDDKGT* *GGSDIQMTQT*

21 TSSLSASLGD RVTISCRASQ

41 DIRNYLNWYQ QKPDGTVKLL

61 IYYTSRLHSG VPSKFSGSGS

81 GTDYSLTISN LEQEDIATYF

101 CQQGNTLPWT FAGGTKLEIK

121 GGGSGGGSGG GSGGGSEVQL

141 QQSGPELVKP GASMKISCKA

161 SGYSFTGYTM NWVKQSHGKN

181 LEWMGLINPY KGVSTYNQKF

201 KDKATLTVDK SSSTAYMELL

221 SLTSEDSAVY YCARSGYYGD

241 SDWYFDVWGAGTTVTVSS*GG*

261 *GGSGGGGSGG GGS*QVQLKQS

281 GPGLVQPSQS LSITCTVSGF

301 SLTNYGVHWV RQSPGKGLEW

321 LGVIWSGGNT DYNTPFTSRL

341 SINKDNSKSQ VFFKMNSLQS

361 NDTAIYYCAR ALTYYDYEFA

381 YWGQGTLVTV SAGGGGSGGG

401 GSGGGGSDIL LTQSPVILSV

421 SPGERVSFSC RASQSIGTNI

441 HWYQQRTNGS PRLLIKYASE

461 SISGIPSRFS GSGSGTDFTL

481 SINSVESEDI ADYYCQQNNN

501 **WPTTFGAGTK LELK*GGS*LIV**

521 NLTDSKGTCL YAEWEMNFTI

541 TYETTNQTNK TITIAVPDKA

561 THDGSSCGDD RNSAKIMIQF

581 GFAVSWAVNF TKEASHYSIH

601 DIVLSYNTSD STVFPGAVAK

621 GVHTVKNPEN FKVPLDVIFK

641 CNSVLTYNLT PVVQKYWGIH

-continued

661 LQAFVQNGTV SKNEQVCEED

681 QTPTTVAPII HTTAPSTTTT

701 LTPTSTPTPT PTPTPTVGNY

721 SIRNGNTTCL LATMGLQLNI

741 TEEKVPFIFN INPATTNFTG

761 SCQPQSAQLR LNNSQIKYLD

781 FIFAVKNEKR FYLKEVNVYM

801 YLANGSAFNI SNKNLSFWDA

821 PLGSSYMCNK EQVLSVSRAF

841 QINTFNLKVQ PFNVTKGQYS

861 TAEECAADSD LNFLIPVAVG

881 VALGFLHAV FISYMIGRRK

901 SRTGYQSV** (SEQ ID NO: 25)

9. HA-anti-EGFR scFv-Linker-myc-PDGFR:

DNA:

*TATCCATATGATGTTCCAGATTATGCT*GGGGCCCAGCCGGCCAGATCT**caggtgcagctga
agcagtctggccctggactggtgcagcctagccagagcctgagcatcacctgtaccgtgtccggcttcagcctgaccaactac
ggcgtgcactgggtgcgacagagccctggcaaaggcctggaatggctgggagtgatttggagcggcggcaacaccgactac
aacacccccttcaccagcagactgtccatcaacaaggacaacagcaagagccaggtgttcttcaagatgaacagcctgcaga
gcaacgacaccgccatctactactgcgctagagccctgacctactatgactacgagttcgcctactggggccagggcacactc
gtgacagtgtctgccggcggaggtggatctggaggcggtggcagcggtggaggcggatctgacatcctgctgacccagagcc
ccgtgatcctgtccgtgtctcctggcgagagagtgtccttcagctgcagagccagccagagcatcggcaccaacatccactggt
atcagcagaggaccaacggcagccccagactgctgattaagtacgccagcgagtccatcagcggcatccccagcagattca
gcggcagcggctctggcaccgacttcaccctgagcatcaacagcgtggaaagcgaggatatcgccgactactactgccagca
gaacaacaactggcccaccaccttcggcgctggcaccaagctggaactgaag**ggcgggGGCGGAAGCGTCGAC
*GAACAAAAACTCATCTCAGAAGAGGATCTG*AAT**GCTGTGGGCCAGGACACGCAGG
AGGTCATCGTGGTGCCACACTCCTTGCCCTTTAAGGTGGTGGTGATCTCAGC
CATCCTGGCCCTGGTGGTGCTCACCATCATCTCCCTTATCATCCTCATCATG
CTTTGGCAGAAGAAGCCACGTTAG** (SEQ ID NO: 26)

Protein:

1 *YPYDVPDYA*G AQPARSQVQL

21 KQSGPGLVQP SQSLSITCTV

41 SGFSLTNYGV HWVRQSPGKG

61 LEWLGVIWSG GNTDYNTPFT

81 SRLSINKDNS KSQVFFKMNS

101 LQSNDTAIYY CARALTYYDY

121 EFAYWGQGTL VTVSAGGGGS

141 GGGGSGGGGS DILLTQSPVI

161 LSVSPGERVS FSCRASQSIG

181 TNIHWYQQRT NGSPRLLIKY

201 ASESISGIPS RFSGSGSGTD

221 FTLSINSVES EDIADYYCQQ

241 NNNWPTTFGA GTKLELKGGG

261 GSVDEQKLIS EEDLNAVGQD

281 TQEVIVVPHS LPFKVVVISA

301 ILALVVLTII SLIILIMLWQ

321 KKPR* (SEQ ID NO: 27)

10. HA-anti-CD3 scFv-*linker*-*myc*-PDGFR:

DNA:

*TATCCATATGATGTTCCAGATTATGCT*GGGGCCCAGCCGGCCAGATCTGATATCCAG
ATGACACAGACAACCTCAAGTCTTAGTGCATCACTGGGAGATCGTGTGACTATAA
GCTGCCGCGCATCACAGGACATTCGCAATTATCTGAATTGGTATCAACAGAAGCC
TGATGGCACCGTGAAACTTCTGATCTATTACACCAGTCGTCTGCATAGCGGTGTT
CCGAGCAAATTTTCAGGCTCAGGGTCAGGAACCGATTATTCACTGACGATTAGTA
ATTTAGAACAAGAAGATATTGCAACCTATTTCTGTCAACAGGGTAATACCCTGCC
GTGGACCTTTGCAGGTGGTACCAAACTGGAAATTAAAGGAGGTGGCAGTGGAGG
GGGAAGCGGCGGCGGTTCAGGAGGCGGTTCTGAGGTCCAGTTACAGCAGAGCGG
TCCGGAACTGGTTAAACCGGGTGCAAGCATGAAAATTAGCTGTAAAGCAAGCGG
TTATAGCTTTACCGGTTATACCATGAATTGGGTTAAACAGAGCCATGGTAAAAAT
CTGGAATGGATGGGTCTGATTAATCCGTATAAAGGTGTTAGCACCTATAATCAGA
AATTTAAAGATAAAGCAACCCTGACCGTTGATAAAAGCAGCAGCACCGCATATA
TGGAACTGCTGAGCCTGACCAGCGAAGATAGCGCCGTTTACTATTGCGCACGCA
GCGGTTATTATGGTGATAGCGATTGGTATTTTGATGTTTGGGGTGCAGGTACCAC
CGTTACCGTTAGCAGC*ggcgggGGCGGAAGC*GTCGAC*GAACAAAAACTCATCTCAGAA*
*GAGGATCTG*AATGCTGTGGGCCAGGACACGCAGGAGGTCATCGTGGTGCCAC
ACTCCTTGCCCTTTAAGGTGGTGGTGATCTCAGCCATCCTGGCCCTGGTGGT
GCTCACCATCATCTCCCTTATCATCCTCATCATGCTTTGGCAGAAGAAGCCA
CGTTAG (SEQ ID NO: 28)

Protein:

1 *YPYDVPDYA*G AQPARSDIQM

21 TQTTSSLSAS LGDRVTISCR

41 ASQDIRNYLN WYQQKPDGTV

61 KLLIYYTSRL HSGVPSKFSG

81 SGSGTDYSLT ISNLEQEDIA

101 TYFCQQGNTL PWTFAGGTKL

121 EIKGGGSGGG SGGGSGGGSE

141 VQLQQSGPEL VKPGASMKIS

161 CKASGYSFTG YTMNWVKQSH

181 GKNLEWMGLI NPYKGVSTYN

201 QKFKDKATLT VDKSSSTAYM

221 ELLSLTSEDS AVYYCARSGY

241 YGDSDWYFDV WGAGTTVTVS

261 *SGGGGSVDEQ KLISEEDLN*A**

281 VGQDTQEVIV VPHSLPFKVV

301 VISAILALVV LTIISLIILI

321 MLWQKKPR* (SEQ ID NO: 11)

11. HA-anti-EGFR scFv-*Linker*-anti-CD3 scFv-*linker*-*myc*-PDGFR:

DNA:

*TATCCATATGATGTTCCAGATTATGCT*GGGGCCCAGCCGGCCAGATCTcaggtgcagctga
agcagtctggccctggactggtgcagcctagccagagcctgagcatcacctgtaccgtgtccggcttcagcctgaccaactac
ggcgtgcactgggtgcgacagagccctggcaaaggcctggaatggctgggagtgatttggagcggcggcaacaccgactac
aacacccccttcaccagcagactgtccatcaacaaggacaacagcaagagccaggtgttcttcaagatgaacagcctgcaga
gcaacgacaccgccatctactactgcgctagagccctgacctactatgactacgagttcgcctactggggccagggcacactc
gtgacagtgtctgccggcggaggtggatctggaggcggtggcagcggtggaggcggatctgacatcctgctgacccagagcc
ccgtgatcctgtccgtgtctcctggcgagagagtgtccttcagctgcagagccagccagagcatcggcaccaacatccactggt
atcagcagaggaccaacggcagccccagactgctgattaagtacgccagcgagtccatcagcggcatccccagcagattca
gcggcagcggctctggcaccgacttcaccctgagcatcaacagcgtggaaagcgaggatatcgccgactactactgccagca
**gaacaacaactggcccaccaccttcggcgctggcaccaagctggaactgaag*GGCGGTGGCGGATCAGGCG***
*GGGGAGGCTCAGGCGGAGGTGGCAGC*GATATCCAGATGACACAGACAACCTCAA
GTCTTAGTGCATCACTGGGAGATCGTGTGACTATAAGCTGCCGCGCATCACAGGA
CATTCGCAATTATCTGAATTGGTATCAACAGAAGCCTGATGGCACCGTGAAACTT
CTGATCTATTACACCAGTCGTCTGCATAGCGGTGTTCCGAGCAAATTTTCAGGCT
CAGGGTCAGGAACCGATTATTCACTGACGATTAGTAATTTAGAACAAGAAGATA
TTGCAACCTATTTCTGTCAACAGGGTAATACCCTGCCGTGGACCTTTGCAGGTGG
TACCAAACTGGAAATTAAAGGAGGTGGCAGTGGAGGGGGAAGCGGCGGCGGTT
CAGGAGGCGGTTCTGAGGTCCAGTTACAGCAGAGCGGTCCGGAACTGGTTAAAC
CGGGTGCAAGCATGAAAATTAGCTGTAAAGCAAGCGGTTATAGCTTTACCGGTT -continued ATACCATGAATTGGGTTAAACAGAGCCATGGTAAAAATCTGGAATGGATGGGTC
TGATTAATCCGTATAAAGGTGTTAGCACCTATAATCAGAAATTTAAAGATAAAGC
AACCCTGACCGTTGATAAAAGCAGCAGCACCGCATATATGGAACTGCTGAGCCT
GACCAGCGAAGATAGCGCCGTTTACTATTGCGCACGCAGCGGTTATTATGGTGAT
AGCGATTGGTATTTTGATGTTTGGGGTGCAGGTACCACCGTTACCGTTAGCAGC*gg*
*cggqGGCGGAAGC*GTCGAC*GAACAAAAACTCATCTCAGAAGAGGATCTGAAT*GCTGTG
GGCCAGGACACGCAGGAGGTCATCGTGGTGCCACACTCCTTGCCCTTTAAG
GTGGTGGTGATCTCAGCCATCCTGGCCCTGGTGGTGCTCACCATCATCTCCC
TTATCATCCTCATCATGCTTTGGCAGAAGAAGCCACGTTAG (SEQ ID NO: 29)

Protein:

1 *YPYDVPDYA*G AQPARSQVQL

21 KQSGPGLVQP SQSLSITCTV

41 SGFSLTNYGV HWVRQSPGKG

61 LEWLGVIWSG GNTDYNTPFT

81 SRLSINKDNS KSQVFFKMNS

101 LQSNDTAIYY CARALTYYDY

121 EFAYWGQGTL VTVSAGGGGS

141 GGGGSGGGGS DILLTQSPVI

161 LSVSPGERVS FSCRASQSIG

181 TNIHWYQQRT NGSPRLLIKY

201 ASESISGIPS RFSGSGSGTD

221 FTLSINSVES EDIADYYCQQ

241 **NNNWPTTFGA GTKLELK*GGG***

261 *GSGGGGSGGG GS*DIQMTQTT

281 SSLSASLGDR VTISCRASQD

301 IRNYLNWYQQ KPDGTVKLLI

321 YYTSRLHSGV PSKFSGSGSG

341 TDYSLTISNL EQEDIATYFC

361 QQGNTLPWTF AGGTKLEIKG

381 GGSGGGSGGG SGGGSEVQLQ

401 QSGPELVKPG ASMKISCKAS

421 GYSFTGYTMN WVKQSHGKNL

441 EWMGLINPYK GVSTYNQKFK

461 DKATLTVDKS SSTAYMELLS

481 LTSEDSAVYY CARSGYYGDS

501 DWYFDVWGAG TTVTVSS*GGG*

521 *GS*VD*EQKLIS EEDL*NAVGQD

541 TQEVIVVPHS LPFKVVVISA

561 ILALVVLTII SLIILIMLWQ

581 KKPR* (SEQ ID NO: 30)

12. HA- anti-CD3 scFv-linker- anti-EGFR scFv-Linker-myc-PDGFR:
DNA:
*TATCCATATGATGTTCCAGATTATGCT*GGGGCCCAGCCGGCCAGATCTGATATCCAG
ATGACACAGACAACCTCAAGTCTTAGTGCATCACTGGGAGATCGTGTGACTATAA
GCTGCCGCGCATCACAGGACATTCGCAATTATCTGAATTGGTATCAACAGAAGCC
TGATGGCACCGTGAAACTTCTGATCTATTACACCAGTCGTCTGCATAGCGGTGTT
CCGAGCAAATTTTCAGGCTCAGGGTCAGGAACCGATTATTCACTGACGATTAGTA
ATTTAGAACAAGAAGATATTGCAACCTATTTCTGTCAACAGGGTAATACCCTGCC -continued GTGGACCTTTGCAGGTGGTACCAAACTGGAAATTAAAGGAGGTGGCAGTGGAGG
GGGAAGCGGCGGCGGTTCAGGAGGCGGTTCTGAGGTCCAGTTACAGCAGAGCGG
TCCGGAACTGGTTAAACCGGGTGCAAGCATGAAAATTAGCTGTAAAGCAAGCGG
TTATAGCTTTACCGGTTATACCATGAATTGGGTTAAACAGAGCCATGGTAAAAAT
CTGGAATGGATGGGTCTGATTAATCCGTATAAAGGTGTTAGCACCTATAATCAGA
AATTTAAAGATAAAGCAACCCTGACCGTTGATAAAAGCAGCAGCACCGCATATA
TGGAACTGCTGAGCCTGACCAGCGAAGATAGCGCCGTTTACTATTGCGCACGCA
GCGGTTATTATGGTGATAGCGATTGGTATTTTGATGTTTGGGGTGCAGGTACCAC
CGTTACCGTTAGCAG*ggaggtggcggaagtggaggaggtggctctggcggtggaggaagc*caggtgcagctg
aagcagtctggccctggactggtgcagcctagccagagcctgagcatcacctgtaccgtgtccggcttcagcctgaccaacta
cggcgtgcactgggtgcgacagagccctggcaaaggcctggaatggctgggagtgatttggagcggcggcaacaccgacta
caacaccccccttcaccagcagactgtccatcaacaaggacaacagcaagagccaggtgttcttcaagatgaacagcctgcag
agcaacgacaccgccatctactactgcgctagagccctgacctactatgactacgagttcgcctactggggccagggcacact
cgtgacagtgtctgccggcggaggtggatctggaggcggtggcagcggtggaggcggatctgacatcctgctgacccagagc
cccgtgatcctgtccgtgtctcctggcgagagagtgtccttcagctgcagagccagccagagcatcggcaccaacatccactg
gtatcagcagaggaccaacggcagccccagactgctgattaagtacgccagcgagtccatcagcggcatccccagcagattc
agcggcagcggctctggcaccgacttcaccctgagcatcaacagcgtggaaagcgaggatatcgccgactactactgccagc
agaacaacaactggcccaccaccttcggcgctggcaccaagctggaactgaag*ggcggg*GGCGGAAGC*GTCGA
C*GAACAAAAACTCATCTCAGAAGAGGATCTGAAT*GCTGTGGGCCAGGACACGCAG
GAGGTCATCGTGGTGCCACACTCCTTGCCCTTTAAGGTGGTGGTGATCTCA
GCCATCCTGGCCCTGGTGGTGCTCACCATCATCTCCCTTATCATCCTCATCA
TGCTTTGGCAGAAGAAGCCACGTTAG (SEQ ID NO: 31)

Protein:

1 *YPYDVPDYA*G AQPARSDIQM

21 TQTTSSLSAS LGDRVTISCR

41 ASQDIRNYLN WYQQKPDGTV

61 KLLIYYTSRL HSGVPSKFSG

81 SGSGTDYSLT ISNLEQEDIA

101 TYFCQQGNTL PWTFAGGTKL

121 EIKGGGSGGG SGGGSGGGSE

141 VQLQQSGPEL VKPGASMKIS

161 CKASGYSFTG YTMNWVKQSH

181 GKNLEWMGLI NPYKGVSTYN

201 QKFKDKATLT VDKSSSTAYM

221 ELLSLTSEDS AVYYCARSGY

241 YGDSDWYFDV WGAGTTVTVS

261 *SGGGGSGGGG SGGGGS*QVQL

281 KQSGPGLVQP SQSLSITCTV

301 SGFSLTNYGV HWVRQSPGKG

321 LEWLGVIWSG GNTDYNTPFT

341 SRLSINKDNS KSQVFFKMNS

361 LQSNDTAIYY CARALTYYDY

381 EFAYWGQGTL VTVSAGGGGS

401 GGGGSGGGGS DILLTQSPVI

421 LSVSPGERVS FSCRASQSIG

441 TNIHWYQQRT NGSPRLLIKY

461 ASESISGIPS RFSGSGSGTD

481 FTLSINSVES EDIADYYCQQ

501 NNNWPTTFGA GTKLELK*GGG*

521 *GSVDEQKLIS EEDLN*AVGQD**

541 TQEVIVVPHS LPFKVVVISA

-continued

| | |
|---|---|
| 561 | ILALVVLTII SLIILIMLWQ |
| 581 | KKPR* (SEQ ID NO: 32) |

Exemplary Protein and Polypeptide Sequences

Platelet derived growth factor receptor beta (PDGFRB) (Entrez gene: 5159; RefSeq: NM_002609, NP_002600), Lysosome-associated membrane protein 2 Variant B (LAMP2b) (Entrez gene: 3920; RefSeq: NM_013995, NP_054701), Milk fat globule-EGF factor 8 protein (Mfge8) also known as lactadherin (Entrez gene: 4240; RefSeq: NM_001114614, NM_001310319, NM_001310320, NM_001310321, NM_005928, NP_054701, NP_001108086, NP_001297248, NP_001297249, NP_001297250, NP_005919), CD13 also known as Alanyl aminopeptidase, membrane (ANPEP) (Entrez gene: 290; RefSeq: NM_001150, NP_001141), CD9 (Entrez gene: 928; RefSeq: NM_001769, NM_001330312, NP_001317241, NP_001760), anti-CD3 scFV, anti-HER2 scFV, anti-EGFR scFV, Human epidermal growth factor receptor 2 (HER2) (Entrez gene: 2064; RefSeq: NP_001005862, NP_001276865, NP_001276866, NP_001276867, NP_004439), Human epidermal growth factor receptor 3 (HER3) (Entrez gene: 2065; RefSeq: NP_001005915, NP_001973), Epidermal growth factor receptor (EGFR) (Entrez gene: 1956; RefSeq: NP_001333826, NP_001333827, NP_001333828, NP_001333829, NP_001333870), Cluster of differentiation 3d (CD3d) (Entrez gene: 915; RefSeq: NP_000723, NP_001035741), Cluster of differentiation 3e (CD3e) (Entrez gene: 916; RefSeq: NP_000724), Cluster of differentiation 3 μg (CD3g) (Entrez gene: 917; RefSeq: NP_000064), Cluster of differentiation 16a (CD16a) (Entrez gene 2214; RefSeq: NP_000560, NP_001121064, NP_001121065, NP_001121067, NP_001121068), Cluster of differentiation 16b (CD16b) (Entrez gene: 2215; RefSeq: NP_000561, NP_001231682, NP_001257964, NP_001257965, NP_001257966), Cluster of differentiation 4 (CD4) (Entrez gene: 920; RefSeq: NP_000607, NP_001181943, NP_001181944, NP_001181945, NP_001181946), Cluster of differentiation 8a (CD8a) (Entrez gene: 925; RefSeq: NP_001139345, NP_001759, NP_741969), Cluster of differentiation 8b (CD8b) (Entrez gene: 926; RefSeq: NP_001171571, NP_004922, NP_742099, NP_742100, NP_757362), Cluster of differentiation 11a (CD11a) (Entrez gene: 3683; RefSeq: NP_001107852, NP_002200), Cluster of differentiation 19 (CD19) (Entrez gene:930; RefSeq: NP_001171569, NP_001761), Cluster of differentiation 20 (CD20) (Entrez gene: 931; RefSeq: NP_068769, NP_690605), Interleukin-2 receptor alpha chain (CD25) (Entrez gene: 3559; RefSeq: NP_000408, NP_001295171, NP_001295172), Cluster of differentiation 33 (CD33) (Entrez gene: 945; RefSeq: NP_001076087, NP_001171079, NP_001763), Cluster of differentiation 40 (CD40) (Entrez gene: 958; RefSeq: NP_001241, NP_001289682, NP_001309350, NP_001309351, NP_690593), CD40 ligand (CD40L) (Entrez gene: 959; RefSeq: NP_000065), Cluster of differentiation 70 (CD70) (Entrez gene: 970; RefSeq: NP_001243, NP_001317261), Interleukin-3 receptor alpha (CD123) (Entrez gene: 3563; RefSeq: NP_001254642, NP_002174), Epithelial cell adhesion molecule (EpCAM) (Entrez gene: 4072; RefSeq: NP_002345), C-type lectin domain family 12 member A (CLL-1) (Entrez gene: 160364; RefSeq: NP_001193939, NP_001287659, NP_612210NP_963917), Cytotoxic T-lymphocyte-associated protein 4 (CTLA-4) (Entrez gene: 1493; RefSeq: NP_001032720, NP_005205), Programmed cell death protein 1 (PD-1) (Entrez gene: 5133; RefSeq: NP_005009), Programmed death-ligand 1 (PD-L1) (Entrez gene: 29126; RefSeq: NP_001254635, NP_001300958, NP_054862), Tumor necrosis factor receptor superfamily, member 4 (OX40) (Entrez gene: 7293; RefSeq: NP_003318), Glucocorticoid-induced TNFR-related protein (GITR) (Entrez gene: 8784; RefSeq: NP_004186, NP_683699, NP_683700), Inducible T-cell COStimulator (ICOS) (Entrez gene: 29851; RefSeq: NP_036224), Cluster of Differentiation 276 (B7-H3) (Entrez gene: 80381; RefSeq: NP_001019907, NP_001316557, NP_001316558, NP_079516), V-set domain-containing T-cell activation inhibitor 1 (B7-H4) (Entrez gene: 79679; RefSeq: NP_001240778, NP_001240779, NP_078902), Lymphocyte-activation gene 3 (LAG3) (Entrez gene: 3902; RefSeq: NP_002277), T-cell immunoglobulin and mucin-domain containing-3 (TIM-3) (Entrez gene: 84868; RefSeq: NP_116171), Prostate-specific membrane antigen (PSMA) (Entrez gene: 2346; RefSeq: NP_001014986, NP_001180400, NP_001180401, NP_001180402, NP_004467), Factor IX (Entrez gene: 2158; RefSeq: NP_000124, NP_001300842), Factor X (Entrez gene: 2159; RefSeq: NP_000495, NP_001299603, NP_001299604), Folate receptor alpha (FOLR1) (Entrez gene: 2348; RefSeq: NP_000793, NP_057936, NP_057937, NP_057941), Folate receptor beta (FOLR2) (Entrez gene: 2350; RefSeq: NP_000794, NP_001107006, NP_001107007, NP_001107008), Folate receptor gamma (FOLR3) (Entrez gene: 2352; RefSeq: NP_000795, NP_001304974). *************

HA-tag DNA sequence: 5'-TATCCATATGATGTTCCAGATTATGCT-3' (SEQ ID NO: 33) or 5'-TAC CCA TAC GAT GTT CCA GAT TAC GCT-3' (SEQ ID NO: 34), amino acid sequence is YPYDVPDYA (SEQ ID NO: 35)

FLAG-tag DNA sequence: GACTACAAAGACGATGACGACAAG (SEQ ID NO: 36), amino acid sequence is DYKDDDDK (SEQ ID NO: 89) (1012 Da). Additionally, it may be used in tandem, commonly the RFLAG peptide. DYKDHDG-DYKDHDI-DYKDDDDK (SEQ ID NO: 37).

6XHis-tag Protein sequence: HHHHHH (SEQ ID NO: 1)

PDGFRB (Entrez gene: 5159; RefSeq: NM_002609, NP_002600)
CTCCTGAGGCTGCCAGCAGCCAGCAGTGACTGCCCGCCCTATCTGGGACCCAGG
ATCGCTCTGTGAGCAACTTGGAGCCAGAGAGGAGATCAACAAGGAGGAGGAGA
GAGCCGGCCCCTCAGCCCTGCTGCCCAGCAGCAGCCTGTGCTCGCCCTGCCCAAC
GCAGACAGCCAGACCCAGGGCGGCCCCTCTGGCGGCTCTGCTCCTCCCGAAGGA TGCTTGGGGAGTGAGGCGAAGCTGGGCCGCTCCTCTCCCCTACAGCAGCCCCCTT
CCTCCATCCCTCTGTTCTCCTGAGCCTTCAGGAGCCTGCACCAGTCCTGCCTGTCC
TTCTACTCAGCTGTTACCCACTCTGGGACCAGCAGTCTTTCTGATAACTGGGAGA
GGGCAGTAAGGAGGACTTCCTGGAGGGGGTGACTGTCCAGAGCCTGGAACTGTG
CCCACACCAGAAGCCATCAGCAGCAAGGACACCATGCGGCTTCCGGGTGCGATG
CCAGCTCTGGCCCTCAAAGGCGAGCTGCTGTTGCTGTCTCTCCTGTTACTTCTGGA
ACCACAGATCTCTCAGGGCCTGGTCGTCACACCCCCGGGGCCAGAGCTTGTCCTC
AATGTCTCCAGCACCTTCGTTCTGACCTGCTCGGGTTCAGCTCCGGTGGTGTGGG
AACGGATGTCCCAGGAGCCCCCACAGGAAATGGCCAAGGCCCAGGATGGCACCT
TCTCCAGCGTGCTCACACTGACCAACCTCACTGGGCTAGACACGGGAGAATACTT
TTGCACCCACAATGACTCCCGTGGACTGGAGACCGATGAGCGGAAACGGCTCTA
CATCTTTGTGCCAGATCCCACCGTGGGCTTCCTCCCTAATGATGCCGAGGAACTA
TTCATCTTTCTCACGGAAATAACTGAGATCACCATTCCATGCCGAGTAACAGACC
CACAGCTGGTGGTGACACTGCACGAGAAGAAAGGGGACGTTGCACTGCCTGTCC
CCTATGATCACCAACGTGGCTTTTCTGGTATCTTTGAGGACAGAAGCTACATCTG
CAAAACCACCATTGGGGACAGGGAGGTGGATTCTGATGCCTACTATGTCTACAG
ACTCCAGGTGTCATCCATCAACGTCTCTGTGAACGCAGTGCAGACTGTGGTCCGC
CAGGGTGAGAACATCACCCTCATGTGCATTGTGATCGGGAATGAGGTGGTCAAC
TTCGAGTGGACATACCCCCGCAAAGAAAGTGGGCGGCTGGTGGAGCCGGTGACT
GACTTCCTCTTGGATATGCCTTACCACATCCGCTCCATCCTGCACATCCCCAGTGC
CGAGTTAGAAGACTCGGGGACCTACACCTGCAATGTGACGGAGAGTGTGAATGA
CCATCAGGATGAAAAGGCCATCAACATCACCGTGGTTGAGAGCGGCTACGTGCG
GCTCCTGGGAGAGGTGGGCACACTACAATTTGCTGAGCTGCATCGGAGCCGGAC
ACTGCAGGTAGTGTTCGAGGCCTACCCACCGCCCACTGTCCTGTGGTTCAAAGAC
AACCGCACCCTGGGCGACTCCAGCGCTGGCGAAATCGCCCTGTCCACGCGCAAC
GTGTCGGAGACCCGGTATGTGTCAGAGCTGACACTGGTTCGCGTGAAGGTGGCA
GAGGCTGGCCACTACACCATGCGGGCCTTCCATGAGGATGCTGAGGTCCAGCTCT
CCTTCCAGCTACAGATCAATGTCCCTGTCCGAGTGCTGGAGCTAAGTGAGAGCCA
CCCTGACAGTGGGGAACAGACAGTCCGCTGTCGTGGCCGGGGCATGCCCCAGCC
GAACATCATCTGGTCTGCCTGCAGAGACCTCAAAAGGTGTCCACGTGAGCTGCCG
CCCACGCTGCTGGGGAACAGTTCCGAAGAGGAGAGCCAGCTGGAGACTAACGTG
ACGTACTGGGAGGAGGAGCAGGAGTTTGAGGTGGTGAGCACACTGCGTCTGCAG
CACGTGGATCGGCCACTGTCGGTGCGCTGCACGCTGCGCAACGCTGTGGGCCAG
GACACGCAGGAGGTCATCGTGGTGCCACACTCCTTGCCCTTTAAGGTGGTGGTGA
TCTCAGCCATCCTGGCCCTGGTGGTGCTCACCATCATCTCCCTTATCATCCTCATC
ATGCTTTGGCAGAAGAAGCCACGTTACGAGATCCGATGGAAGGTGATTGAGTCT
GTGAGCTCTGACGGCCATGAGTACATCTACGTGGACCCCATGCAGCTGCCCTATG
ACTCCACGTGGGAGCTGCCGCGGGACCAGCTTGTGCTGGGACGCACCCTCGGCT
CTGGGGCCTTTGGGCAGGTGGTGGAGGCCACGGCTCATGGCCTGAGCCATTCTCA
GGCCACGATGAAAGTGGCCGTCAAGATGCTTAAATCCACAGCCCGCAGCAGTGA
GAAGCAAGCCCTTATGTCGGAGCTGAAGATCATGAGTCACCTTGGGCCCCACCTG
AACGTGGTCAACCTGTTGGGGGCCTGCACCAAAGGAGGACCCATCTATATCATC
ACTGAGTACTGCCGCTACGGAGACCTGGTGGACTACCTGCACCGCAACAAACAC
ACCTTCCTGCAGCACCACTCCGACAAGCGCCGCCCGCCCAGCGCGGAGCTCTAC
AGCAATGCTCTGCCCGTTGGGCTCCCCCTGCCCAGCCATGTGTCCTTGACCGGGG
AGAGCGACGGTGGCTACATGGACATGAGCAAGGACGAGTCGGTGGACTATGTGC
CCATGCTGGACATGAAAGGAGACGTCAAATATGCAGACATCGAGTCCTCCAACT
ACATGGCCCCTTACGATAACTACGTTCCCTCTGCCCCTGAGAGGACCTGCCGAGC
AACTTTGATCAACGAGTCTCCAGTGCTAAGCTACATGGACCTCGTGGGCTTCAGC
TACCAGGTGGCCAATGGCATGGAGTTTCTGGCCTCCAAGAACTGCGTCCACAGA
GACCTGGCGGCTAGGAACGTGCTCATCTGTGAAGGCAAGCTGGTCAAGATCTGT
GACTTTGGCCTGGCTCGAGACATCATGCGGGACTCGAATTACATCTCCAAAGGCA
GCACCTTTTTGCCTTTAAAGTGGATGGCTCCGGAGAGCATCTTCAACAGCCTCTA
CACCACCCTGAGCGACGTGTGGTCCTTCGGGATCCTGCTCTGGGAGATCTTCACC
TTGGGTGGCACCCCTTACCCAGAGCTGCCCATGAACGAGCAGTTCTACAATGCCA
TCAAACGGGGTTACCGCATGGCCCAGCCTGCCCATGCCTCCGACGAGATCTATGA
GATCATGCAGAAGTGCTGGGAAGAGAAGTTTGAGATTCGGCCCCCCTTCTCCCAG
CTGGTGCTGCTTCTCGAGAGACTGTTGGGCGAAGGTTACAAAAAGAAGTACCAG
CAGGTGGATGAGGAGTTTCTGAGGAGTGACCACCCAGCCATCCTTCGGTCCCAG
GCCCGCTTGCCTGGGTTCCATGGCCTCCGATCTCCCCTGGACACCAGCTCCGTCC
TCTATACTGCCGTGCAGCCCAATGAGGGTGACAACGACTATATCATCCCCCTGCC
TGACCCCAAACCCGAGGTTGCTGACGAGGGCCCACTGGAGGGTTCCCCCAGCCT
AGCCAGCTCCACCCTGAATGAAGTCAACACCTCCTCAACCATCTCCTGTGACAGC
CCCCTGGAGCCCCAGGACGAACCAGAGCCAGAGCCCCAGCTTGAGCTCCAGGTG
GAGCCGGAGCCAGAGCTGGAACAGTTGCCGGATTCGGGGTGCCCTGCGCCTCGG
GCGGAAGCAGAGGATAGCTTCCTGTAGGGGGCTGGCCCCTACCCTGCCCTGCCT
GAAGCTCCCCCCCTGCCAGCACCCAGCATCTCCTGGCCTGGCCTGACCGGGCTTC
CTGTCAGCCAGGCTGCCCTTATCAGCTGTCCCCTTCTGGAAGCTTTCTGCTCCTGA
CGTGTTGTGCCCCAAACCCTGGGGCTGGCTTAGGAGGCAAGAAAACTGCAGGGG
CCGTGACCAGCCCTCTGCCTCCAGGGAGGCCAACTGACTCTGAGCCAGGGTTCCC
CCAGGGAACTCAGTTTTCCCATATGTAAGATGGGAAAGTTAGGCTTGATGACCCA
GAATCTAGGATTCTCTCCCTGGCTGACAGGTGGGGAGACCGAATCCCTCCCTGGG
AAGATTCTTGGAGTTACTGAGGTGGTAAATTAACTTTTTTCTGTTCAGCCAGCTAC
CCCTCAAGGAATCATAGCTCTCTCCTCGCACTTTTATCCACCCAGGAGCTAGGGA
AGAGACCCTAGCCTCCCTGGCTGCTGGCTGAGCTAGGGCCTAGCCTTGAGCAGTG
TTGCCTCATCCAGAAGAAAGCCAGTCTCCTCCCTATGATGCCAGTCCCTGCGTTC
CCTGGCCCGAGCTGGTCTGGGGCCATTAGGCAGCCTAATTAATGCTGGAGGCTGA
GCCAAGTACAGGACACCCCCAGCCTGCAGCCCTTGCCCAGGGCACTTGGAGCAC
ACGCAGCCATAGCAAGTGCCTGTGTCCCTGTCCTTCAGGCCCATCAGTCCTGGGG CTTTTTCTTTATCACCCTCAGTCTTAATCCATCCACCAGAGTCTAGAAGGCCAGAC
GGGCCCCGCATCTGTGATGAGAATGTAAATGTGCCAGTGTGGAGTGGCCACGTG
TGTGTGCCAGTATATGGCCCTGGCTCTGCATTGGACCTGCTATGAGGCTTTGGAG
GAATCCCTCACCCTCTCTGGGCCTCAGTTTCCCCTTCAAAAAATGAATAAGTCGG
ACTTATTAACTCTGAGTGCCTTGCCAGCACTAACATTCTAGAGTATTCCAGGTGG
TTGCACATTTGTCCAGATGAAGCAAGGCCATATACCCTAAACTTCCATCCTGGGG
GTCAGCTGGGCTCCTGGGAGATTCCAGATCACACATCACACTCTGGGGACTCAGG
AACCATGCCCCTTCCCCAGGCCCCCAGCAAGTCTCAAGAACACAGCTGCACAGG
CCTTGACTTAGAGTGACAGCCGGTGTCCTGGAAAGCCCCCAGCAGCTGCCCCAG
GGACATGGGAAGACCACGGGACCTCTTTCACTACCCACGATGACCTCCGGGGGT
ATCCTGGGCAAAAGGGACAAAGAGGGCAAATGAGATCACCTCCTGCAGCCCACC
ACTCCAGCACCTGTGCCGAGGTCTGCGTCGAAGACAGAATGGACAGTGAGGACA
GTTATGTCTTGTAAAAGACAAGAAGCTTCAGATGGGTACCCCAAGAAGGATGTG
AGAGGTGGGCGCTTTGGAGGTTTGCCCCTCACCCACCAGCTGCCCCATCCCTGAG
GCAGCGCTCCATGGGGGTATGGTTTTGTCACTGCCCAGACCTAGCAGTGACATCT
CATTGTCCCCAGCCCAGTGGGCATTGGAGGTGCCAGGGGAGTCAGGGTTGTAGC
CAAGACGCCCCCGCACGGGGAGGGTTGGGAAGGGGGTGCAGGAAGCTCAACCC
CTCTGGGCACCAACCCTGCATTGCAGGTTGGCACCTTACTTCCCTGGGATCCCCA
GAGTTGGTCCAAGGAGGGAGAGTGGGTTCTCAATACGGTACCAAAGATATAATC
ACCTAGGTTTACAAATATTTTTAGGACTCACGTTAACTCACATTTATACAGCAGA
AATGCTATTTTGTATGCTGTTAAGTTTTTCTATCTGTGTACTTTTTTTTAAGGGAA
AGATTTTAATATTAAACCTGGTGCTTCTCACTCACAAAAA (SEQ ID NO: 38)

Protein Sequence:
MRLPGAMPALALKGELLLLSLLLLLEPQISQGLVVTPPGPELVLNVSSTFVLTCSGSA
PVVWERMSQEPPQEMAKAQDGTFSSVLTLTNLTGLDTGEYFCTHNDSRGLETDERK
RLYIEVPDPTVGFLPNDAEELFIFLTEITEITIPCRVTDPQLVVTLHEKKGDVALPVPYD
HQRGFSGIFEDRSYICKTTIGDREVDSDAYYVYRLQVSSINVSVNAVQTVVRQGENIT
LMCIVIGNEVVNFEWTYPRKESGRLVEPVTDFLLDMPYHIRSILHIPSAELEDSGTYTC
NVTESVNDHQDEKAINITVVESGYVRLLGEVGTLQFAELHRSRTLQVVFEAYPPPTV
LWFKDNRTLGDSSAGEIALSTRNVSETRYVSELTLVRVKVAEAGHYTMRAFHEDAE
VQLSFQLQINVPVRVLELSESHPDSGEQTVRCRGRGMPQPNIIWSACRDLKRCPRELP
PTLLGNSSEEESQLETNVTYWEEEQEFEVVSTLRLQHVDRPLSVRCTLRNAVGQDTQ
EVIVVPHSLPFKVVVISAILALVVLTIISLIILIMLWQKKPRYEIRWKVIESVSSDGHEYI
YVDPMQLPYDSTWELPRDQLVLGRTLGSGAFGQVVEATAHGLSHSQATMKVAVK
MLKSTARSSEKQALMSELKIMSHLGPHLNVVNLLGACTKGGPIYIITEYCRYGDLVD
YLHRNKHTFLQHHSDKRRPPSAELYSNALPVGLPLPSHVSLTGESDGGYMDMSKDE
SVDYVPMLDMKGDVKYADIESSNYMAPYDNYVPSAPERTCRATLINESPVLSYMDL
VGFSYQVANGMEFLASKNCVHRDLAARNVLICEGKLVKICDFGLARDIMRDSNYIS
KGSTFLPLKWMAPESIFNSLYTTLSDVWSFGILLWEIFTLGGTPYPELPMNEQFYNAI
KRGYRMAQPAHASDEIYEIMQKCWEEKFEIRPPFSQLVLLLERLLGEGYKKKYQQV
DEEFLRSDHPAILRSQARLPGFHGLRSPLDTSSVLYTAVQPNEGDNDYIIPLPDPKPEV
ADEGPLEGSPSLASSTLNEVNTSSTISCDSPLEPQDEPEPEPQLELQVEPEPELEQLPDS
GCPAPRAEAEDSFL (SEQ ID NO: 39)

LAMP2b (Entrez gene: 3920; RefSeq: NM_013995, NP_054701)
AAGAAAGAGCCCCGCCCCTAGTCTTATGACTCGCACTGAAGCGCCGATTCCTGGC
TTTTGCAAGGCTGTGGTCGGTGGTCATCAGTGCTCTTGACCCAGGTCCAGCGAGC
CTTTTCCCTGGTGTTGCAGCTGTTGTTGTACCGCCGCCGTCGCCGCCGTCGCCGCC
TGCTCTGCGGGGTCATGGTGTGCTTCCGCCTCTTCCCGGTTCCGGGCTCAGGGCTC
GTTCTGGTCTGCCTAGTCCTGGGAGCTGTGCGGTCTTATGCATTGGAACTTAATTT
GACAGATTCAGAAAATGCCACTTGCCTTTATGCAAAATGGCAGATGAATTTCACA
GTACGCTATGAAACTACAAATAAAACTTATAAAACTGTAACCATTTCAGACCATG
GCACTGTGACATATAATGGAAGCATTTGTGGGGATGATCAGAATGGTCCCAAAA
TAGCAGTGCAGTTCGGACCTGGCTTTTCCTGGATTGCGAATTTTACCAAGGCAGC
ATCTACTTATTCAATTGACAGCGTCTCATTTTCCTACAACACTGGTGATAACACA
ACATTTCCTGATGCTGAAGATAAAGGAATTCTTACTGTTGATGAACTTTTGGCCA
TCAGAATTCCATTGAATGACCTTTTTAGATGCAATAGTTTATCAACTTTGGAAAA
GAATGATGTTGTCCAACACTACTGGGATGTTCTTGTACAAGCTTTTGTCCAAAAT
GGCACAGTGAGCACAAATGAGTTCCTGTGTGATAAAGACAAAACTTCAACAGTG
GCACCCACCATACACACCACTGTGCCATCTCCTACTACAACACCTACTCCAAAGG
AAAAACCAGAAGCTGGAACCTATTCAGTTAATAATGGCAATGATACTTGTCTGCT
GGCTACCATGGGGCTGCAGCTGAACATCACTCAGGATAAGGTTGCTTCAGTTATT
AACATCAACCCCAATACAACTCACTCCACAGGCAGCTGCCGTTCTCACACTGCTC
TACTTAGACTCAATAGCAGCACCATTAAGTATCTAGACTTTGTCTTTGCTGTGAA
AAATGAAAACCGATTTTATCTGAAGGAAGTGAACATCAGCATGTATTTGGTTAAT
GGCTCCGTTTTCAGCATTGCAAATAACAATCTCAGCTACTGGGATGCCCCCCTGG
GAAGTTCTTATATGTGCAACAAAGAGCAGACTGTTTCAGTGTCTGGAGCATTTCA
GATAAATACCTTTGATCTAAGGGTTCAGCCTTTCAATGTGACACAAGGAAAGTAT
TCTACAGCCCAAGAGTGTTCGCTGGATGATGACACCATTCTAATCCCAATTATAG
TTGGTGCTGGTCTTTCAGGCTTGATTATCGTTATAGTGATTGCTTACGTAATTGGC
AGAAGAAAAAGTTATGCTGGATATCAGACTCTGTAACACTAATCAATACGTGAT
CTCTGTTACAAAAGAAAAAAGCAAGTACAAGTTCCAACATGCAATACTGGTCAA
CTTAAGGTATATTTAGTTGCAGTCCAGCTCTTTAGAATGGGTGGTATGGGGGATT
TCAAACTTAAACAAAAAACTATCAACTACAAATTAGTTGCCTGACTTTGGTTTTT
CCAACCAAGGAATTTAAAACTGTTATTTTTACAGCAAAAGATGTGCAAAATCACT
GGATTATAAGTTCTATTTTACTGTCTTGAATTAGTATTTCAGTGTTTTCATTTTAG
ACATTCAGACTAAAAATACACCGTTTAGAAAAAACAATTTTTGAAAAAGAGATT
TTTTTTCCCTGCAGGTAGTTGAGTTGGAACAACATGTTCTACCGTGGATTTGTACT TGCTCCTTTTGCTCTTTTTGTGTGTGTGTGTGTGTGTGTGTGTGTGTGTGTGTGT
GATTTTTGTTTGCAGGTTAACTTAGCTACTTTGGCATTGCTGCATATTTGACCTTT
GAGAGATATAATAGTAGATTTGAACAGGGGCTGGTATTATTATGTTCTTAGCAAT
AAATGCTTTTCTAATGCCTTTTGAATACATTTGTATTTATGTGGCTGTAATGACAA
AAGATACAAAAGCTTTTTAAAATTTAGAGTAGGTATTAATCTTATTGTTTAATCTT
TTTTTTAAAAAAACTGGATATTTCAATCTTTTAAATTGCAATATATAAGACTATTC
CAACTGGGCATTTCAATCCATTTTTTAGGTGCTTTAGAGATAATTGCTTGCCAGTG
CCAATTGAGGGCATTAGTACTTTGTGCTCATAAATTGGCCTCTGTATGCAGTACT
AAAATTAATGCAGATTTCTCTTTAGCCTTCCAACATTTCTTGTTGATAGTGATGTA
TTTTATTATTTTCTTTTTCTTAAGAAATGCCAGTGTGTCCTAGAACCTAGATAACG
AAGTGCACTTACACTTATAAAATAACTTGCATCTAGGCTGGGCGTGGCGGCTCAC
GCCTGTAATCCCAGCACTTTGGGAGGCCGAAGTGGGTGGATCACTTGAGGCCAG
GAGTTTGAGACCAGCCTGGCCAACATGGTGAAACCCCATCTCTATCAGAAATAC
AAAAAATTAGCTGGGCGTGGTGGTGGGCGCCTGTAATCCCAGTTACTCGGGAGG
CTGAGGCAGGAGAATCACTTGAACCCGGGAGGCAGAGGTTGCGGTGAGCCAAGA
GCGCACCATTGCACTCCAGCCTGGGCGACAAAAACGAAACTCCATCTCAAAACA
AAACAAAACAAAACAAACAAACAAACAAAACTTGCATCTAACCAAAAAGTCTTG
GTTTTATCTTAATCCATTAAAAAGTTGTTCTTTGTTTCCAGCTTGCATTGATTGCT
ACAACATCACTAATTTGGCTTTCACATTTAAATGGTTCTGTGCTAATCAAAACTTT
CGTTGTTATTATTCATTATGGTAGAATCATTTTTAATTCACGTGCTTTGTGTTCAG
TTTTGTGGTCTGAGAGATGTACCAATTGTCAAATTACCGTGTACCACCTAATGTTT
ATAGGAGAAAGCAAAATACATCAGCTTGGTAGTTAACACATCAAATATTTCTTGC
TGCTTCTAGGAGAACTTTTTTGGTGTGTGTTGGAATGGCTGAGCAAATATTAAAA
TTGTTAATATGCAGCCATATATGGAAGGTTCCTGTGGGGTTGTTTTTTCGTGTTTT
TTTTTTTTTTGTGGTGGGATTATGTGCCTCCCATTCACTAGAAAATGAGAAAATTG
TCTGGGTTCCAAAATATTGACATTGAATGGATCAATACACACACACACAGACATATA
TATATATATGCACACATATATAGGCAGTTGCATGCTAGCATGGGTATTTTTTATAA
CAATATAACTGAGTTATATTGGAATTATAAATATTTTCCGTCACTTAAATTTGTTC
TTTGTTTAGCCTGAAAACCTTTATGGCTCAAGATCAGATTCCTGACTAACCCCTCT
CTTAGAGCTACAGCGAGCTGCATTACCAGCTTAAAACACTTCTTAGGGATTAAAT
ATAGATGTAATTTTTCAAAATCGTTTTTAATTTAAACTGTGTTTTAGTGTAAAATT
GTTAACCTTGTAAGATGGATAATGTGTATAAGAATGTAGGCCTTAACTATTTCAC
ATGAGTCAAAACAAAGCAGCTTTAAAAAAATAATTGGAAGCACAAGTGCATGGC
ACTGACTGAATGCTGTTAATATTTCTAAAAGTTTCTACATTCAGATTATATGCCTG
ATTCATAGTAAAATACCTCTAATAAACACTGTTTTATAGAAAACCTGACTTCAGT
GAATATTTTTGTATTTTACATGGGCCAGTTTATATACTGCTATTTACACTATTATT
TCCTATAGCTACATGTTCTTTGTACCTTTTGTAGTTTTATTTGTATTACTAGATTCA
TACCTTGATGGTAACGCTCTATCTGGTTTTGGGTGTTTTTCATGTTTTAGCATTTGT
ATAAAGAAACTGGTCCATGTAAATACTTTCCATGTTTTTTCTTCAAATGTTTAAAC
CACTAGTTGATGTATGGTATCTTTAGATATTTGCCTGTCTGTTTGCTCAAAATTGC
TTCTAAAACAATAAAGATTCTTTTATTTCTTAAGGCAAAAA (SEQ ID NO: 40)

Protein sequence:
MVCFRLFPVPGSGLVLVCLVLGAVRSYALELNLTDSENATCLYAKWQMNFTVRYET
TNKTYKTVTISDHGTVTYNGSICGDDQNGPKIAVQFGPGFSWIANFTKAASTYSIDSV
SFSYNTGDNTTFPDAEDKGILTVDELLAIRIPLNDLFRCNSLSTLEKNDVVQHYWDVL
VQAFVQNGTVSTNEFLCDKDKTSTVAPTIHTTVPSPTTTPTPKEKPEAGTYSVNNGN
DTCLLATMGLQLNITQDKVASVININPNTTHSTGSCRSHTALLRLNSSTIKYLDFVFA
VKNENRFYLKEVNISMYLVNGSVFSIANNNLSYWDAPLGSSYMCNKEQTVSVSGAF
QINTFDLRVQPFNVTQGKYSTAQECSLDDDTILIPIIVGAGLSGLIIVIVIAYVIGRRKSY
AGYQTL (SEQ ID NO: 41)

1. Mfge8 (Entrez gene: 4240; RefSeq: NM_001114614, NP_001108086)
AGTCCGCCTCTGGCCAGCTTGGGCGGAGCGCACGGCCAGTGGGAGGTGCTGAGC
CGCCTGATTTATTCCGGTCCCAGAGGAGAAGGCGCCAGAACCCCGCGGGGTCTG
AGCAGCCCAGCGTGCCCATTCCAGCGCCCGCGTCCCCGCAGCATGCCGCGCCCCC
GCCTGCTGGCCGCGCTGTGCGGCGCGCTGCTCTGCGCCCCCAGCCTCCTCGTCGC
CCTGGATATCTGTTCCAAAAACCCCTGCCACAACGGTGGTTTATGCGAGGAGATT
TCCCAAGAAGTGCGAGGAGATGTCTTCCCCTCGTACACCTGCACGTGCCTTAAGG
GCTACGCGGGCAACCACTGTGAGACGAAATGTGTCGAGCCACTGGGCCTGGAGA
ATGGGAACATTGCCAACTCACAGATCGCCGCCTCGTCTGTGCGTGTGACCTTCTT
GGGTTTGCAGCATTGGGTCCCGGAGCTGGCCCGCCTGAACCGCGCAGGCATGGT
CAATGCCTGGACACCCAGCAGCAATGACGATAACCCCTGGATCCAGGTGAACCT
GCTGCGGAGGATGTGGGTAACAGGTGTGGTGACGCAGGGTGCCAGCCGCTTGGC
CAGTCATGAGTACCTGAAGGCCTTCAAGGTGGCCTACAGCCTTAATGGACACGA
ATTCGATTTCATCCATGATGTTAATAAAAAACACAAGGAGTTTGTGGGTAACTGG
AACAAAAACGCGGTGCATGTCAACCTGTTTGAGACCCCTGTGGAGGCTCAGTAC
GTGAGATTGTACCCCACGAGCTGCCACACGGCCTGCACTCTGCGCTTTGAGCTAC
TGGGCTGTGAGCTGAACGGATGCGCCAATCCCCTGGGCCTGAAGAATAACAGCA
TCCCTGACAAGCAGATCACGGCCTCCAGCAGCTACAAGACCTGGGGCTTGCATCT
CTTCAGCTGGAACCCCTCCTATGCACGGCTGGACAAGCAGGGCAACTTCAACGC
CTGGGTTGCGGGGAGCTACGGTAACGATCAGTGGCTGCAGATCTTCCCTGGCAAC
TGGGACAACCACTCCCACAAGAAGAACTTGTTTGAGACGCCCATCCTGGCTCGCT
ATGTGCGCATCCTGCCTGTAGCCTGGCACAACCGCATCGCCCTGCGCCTGGAGCT
GCTGGGCTGTTAGTGGCCACCTGCCACCCCCAGGTCTTCCTGCTTTCCATGGGCC
CGCTGCCTCTTGGCTTCTCAGCCCCTTTAAATCACCATAGGGCTGGGGACTGGGG
AAGGGGAGGGTGTTCAGAGGCAGCACCACCACACAGTCACCCCTCCCTCCCTCTT
TCCCACCCTCCACCTCTCACGGGCCCTGCCCCAGCCCCTAAGCCCCGTCCCCTAA
CCCCCAGTCCTCACTGTCCTGTTTTCTTAGGCACTGAGGGATCTGAGTAGGTCTG -continued GGATGGACAGGAAAGGGCAAAGTAGGGCGTGTGGTTTCCCTGCCCCTGTCCGGA
CCGCCGATCCCAGGTGCGTGTGTCTCTGTCTCTCCTAGCCCCTCTCTCACACATCA
CATTCCCATGGTGGCCTCAAGAAAGGCCCGGAAGCGCCAGGCTGGAGATAACAG
CCTCTTGCCCGTCGGCCCTGCGTCGGCCCTGGGGTACCATGTGGCCACAACTGCT
GTGGCCCCCTGTCCCCAAGACACTTCCCCTTGTCTCCCTGGTTGCCTCTCTTGCCC
CTTGTCCTGAAGCCCAGCGACACAGAAGGGGGTGGGGCGGGTCTATGGGGAGAA
AGGGAGCGAGGTCAGAGGAGGGCATGGGTTGGCAGGGTGGGCGTTTGGGGCCCT
CTATGCTGGCTTTTCACCCCAGAGGACACAGGCAGCTTCCAAAATATATTTATCT
TCTTCACGGGAAAAAAAAAAAAAAAAAA (SEQ ID NO: 42)

Protein sequence:
MPRPRLLAALCGALLCAPSLLVALDICSKNPCHNGGLCEEISQEVRGDVFPSYTCTCL
KGYAGNHCETKCVEPLGLENGNIANSQIAASSVRVTFLGLQHWVPELARLNRAGMV
NAWTPSSNDDNPWIQVNLLRRMWVTGVVTQGASRLASHEYLKAFKVAYSLNGHEF
DFIHDVNKKHKEFVGNWNKNAVHVNLFETPVEAQYVRLYPTSCHTACTLRFELLGC
ELNGCANPLGLKNNSIPDKQITASSSYKTWGLHLFSWNPSYARLDKQGNFNAWVAG
SYGNDQWLQIFPGNWDNHSHKKNLFETPILARYVRILPVAWHNRIALRLELLGC
(SEQ ID NO: 43)

2. CD13 (Entrez gene: 290; RefSeq: NM_001150, NP_001141)
GGGACGGCGGCGGCGCAGCTCGGAACCCGCCAGGGTCCAGGGTCCAGGTTCCAG
CGCCCGGCGGCCCAGGCACCCCCCGAGCCCAGCTCCACACACCGTTCCTGGATCT
CCTCTCCCCAGGCGGAGCGTGCCCCTGCCCAGTCCAGTGACCTTCGCCTGTTGGA
GCCCTGGTTAATTTTTGCCCAGTCTGCCTGTTGTGGGGCTCCTCCCCTTTGGGGAT
ATAAGCCCGGCCTGGGGCTGCTCCGTTCTCTGCCTGGCCTGAGGCTCCCTGAGCC
GCCTCCCCACCATCACCATGGCCAAGGGCTTCTATATTTCCAAGTCCCTGGGCAT
CCTGGGGATCCTCCTGGGCGTGGCAGCCGTGTGCACAATCATCGCACTGTCAGTG
GTGTACTCCCAGGAGAAGAACAAGAACGCCAACAGCTCCCCCGTGGCCTCCACC
ACCCCGTCCGCCTCAGCCACCACCAACCCCGCCTCGGCCACCACCTTGGACCAAA
GTAAAGCGTGGAATCGTTACCGCCTCCCCAACACGCTGAAACCCGATTCCTACCG
GGTGACGCTGAGACCGTACCTCACCCCCAATGACAGGGGCCTGTACGTTTTTAAG
GGCTCCAGCACCGTCCGTTTCACCTGCAAGGAGGCCACTGACGTCATCATCATCC
ACAGCAAGAAGCTCAACTACACCCTCAGCCAGGGGCACAGGGTGGTCCTGCGTG
GTGTGGGAGGCTCCCAGCCCCCCGACATTGACAAGACTGAGCTGGTGGAGCCCA
CCGAGTACCTGGTGGTGCACCTCAAGGGCTCCCTGGTGAAGGACAGCCAGTATG
AGATGGACAGCGAGTTCGAGGGGGAGTTGGCAGATGACCTGGCGGGCTTCTACC
GCAGCGAGTACATGGAGGGCAATGTCAGAAAGGTGGTGGCCACTACACAGATGC
AGGCTGCAGATGCCCGGAAGTCCTTCCCATGCTTCGATGAGCCGGCCATGAAGG
CCGAGTTCAACATCACGCTTATCCACCCCAAGGACCTGACAGCCCTGTCCAACAT
GCTTCCCAAAGGTCCCAGCACCCCACTTCCAGAAGACCCCAACTGGAATGTCACT
GAGTTCCACACCACGCCCAAGATGTCCACGTACTTGCTGGCCTTCATTGTCAGTG
AGTTCGACTACGTGGAGAAGCAGGCATCCAATGGTGTCTTGATCCGGATCTGGGC
CCGGCCCAGTGCCATTGCGGCGGGCCACGGCGATTATGCCCTGAACGTGACGGG
CCCCATCCTTAACTTCTTTGCTGGTCATTATGACACACCCTACCCACTCCCAAAAT
CAGACCAGATTGGCCTGCCAGACTTCAACGCCGGCGCCATGGAGAACTGGGGAC
TGGTGACCTACCGGGAGAACTCCCTGCTGTTCGACCCCCTGTCCTCCTCCAGCAG
CAACAAGGAGCGGGTGGTCACTGTGATTGCTCATGAGCTGGCCCACCAGTGGTTC
GGGAACCTGGTGACCATAGAGTGGTGGAATGACCTGTGGCTGAACGAGGGCTTC
GCCTCCTACGTGGAGTACCTGGGTGCTGACTATGCGGAGCCCACCTGGAACTTGA
AAGACCTCATGGTGCTGAATGATGTGTACCGCGTGATGGCAGTGGATGCACTGG
CCTCCTCCCACCCGCTGTCCACACCCGCCTCGGAGATCAACACGCCGGCCCAGAT
CAGTGAGCTGTTTGACGCCATCTCCTACAGCAAGGGCGCCTCAGTCCTCAGGATG
CTCTCCAGCTTCCTGTCCGAGGACGTATTCAAGCAGGGCCTGGCGTCCTACCTCC
ACACCTTTGCCTACCAGAACACCATCTACCTGAACCTGTGGGACCACCTGCAGGA
GGCTGTGAACAACCGGTCCATCCAACTCCCCACCACCGTGCGGGACATCATGAA
CCGCTGGACCCTGCAGATGGGCTTCCCGGTCATCACGGTGGATACCAGCACGGG
GACCCTTTCCCAGGAGCACTTCCTCCTTGACCCCGATTCCAATGTTACCCGCCCCT
CAGAATTCAACTACGTGTGGATTGTGCCCATCACATCCATCAGAGATGGCAGACA
GCAGCAGGACTACTGGCTGATAGATGTAAGAGCCCAGAACGATCTCTTCAGCAC
ATCAGGCAATGAGTGGGTCCTGCTGAACCTCAATGTGACGGGCTATTACCGGGTG
AACTACGACGAAGAGAACTGGAGGAAGATTCAGACTCAGCTGCAGAGAGACCA
CTCGGCCATCCCTGTCATCAATCGGGCACAGATCATTAATGACGCCTTCAACCTG
GCCAGTGCCCATAAGGTCCCTGTCACTCTGGCGCTGAACAACACCCTCTTCCTGA
TTGAAGAGAGACAGTACATGCCCTGGGAGGCCGCCCTGAGCAGCCTGAGCTACT
TCAAGCTCATGTTTGACCGCTCCGAGGTCTATGGCCCCATGAAGAACTACCTGAA
GAAGCAGGTCACACCCCTCTTCATTCACTTCAGAAATAATACCAACAACTGGAGG
GAGATCCCAGAAAACCTGATGGACCAGTACAGCGAGGTTAATGCCATCAGCACC
GCCTGCTCCAACGGAGTTCCAGAGTGTGAGGAGATGGTCTCTGGCCTTTTCAAGC
AGTGGATGGAGAACCCCAATAATAACCCGATCCACCCCAACCTGCGGTCCACCG
TCTACTGCAACGCTATCGCCCAGGGCGGGGAGGAGGAGTGGGACTTCGCCTGGG
AGCAGTTCCGAAATGCCACACTGGTCAATGAGGCTGACAAGCTCCGGGCAGCCC
TGGCCTGCAGCAAAGAGTTGTGGATCCTGAACAGGTACCTGAGCTACACCCTGA
ACCCGGACTTAATCCGGAAGCAGGACGCCACCTCTACCATCATCAGCATTACCA
ACAACGTCATTGGGCAAGGTCTGGTCTGGGACTTTGTCCAGAGCAACTGGAAGA
AGCTTTTTAACGATTATGGTGGTGGCTCGTTCTCCTTCTCCAACCTCATCCAGGCA
GTGACACGACGATTCTCCACCGAGTATGAGCTGCAGCAGCTGGAGCAGTTCAAG
AAGGACAACGAGGAAACAGGCTTCGGCTCAGGCACCCGGGCCCTGGAGCAAGC
CCTGGAGAAGACGAAAGCCAACATCAAGTGGGTGAAGGAGAACAAGGAGGTGG
TGCTCCAGTGGTTCACAGAAAACAGCAAATAGTCCCCAGCCCTTGAAGTCACCC GGCCCCCATGCAAGGTGCCCACATGTGTCCATCCCAGCGGCTGGTGCAGGGCCTC
CATTCCTGGAGCCCGAGGCACCAGTGTCCTCCCCTCAAGGACAAAGTCTCCAGCC
CACGTTCTCTCTGCCTGTGAGCCAGTCTAGTTCCTGATGACCCAGGCTGCCTGAG
CACCTCCCAGCCCCTGCCCCTCATGCCAACCCCGCCCTAGGCCTGGCATGGCACC
TGTCGCCCAGTGCCCTGGGGCTGATCTCAGGGAAGCCCAGCTCCAGGGCCAGAT
GAGCAGAAGCTCTCGATGGACAATGAACGGCCTTGCTGGGGGCCGCCCTGTACC
CTCTTTCACCTTTCCCTAAAGACCCTAAATCTGAGGAATCAACAGGGCAGCAGAT
CTGTATATTTTTTTCTAAGAGAAAATGTAAATAAAGGATTTCTAGATGAAAAAAA
AAAAAAAAAAAAAAAAAAAAAAAAAAAAAAAAAAAAAAAAAAAAAAAAAAAAAA
AAAAAAAAAAAAAAAAAAAAAAAAAAAAAAAAA (SEQ ID NO: 44)

Protein sequence:
MAKGFYISKSLGILGILLGVAAVCTHALSVVYSQEKNKNANSSPVASTTPSASATTNP
ASATTLDQSKAWNRYRLPNTLKPDSYRVTLRPYLTPNDRGLYVFKGSSTVRFTCKE
ATDVIIIHSKKLNYTLSQGHRVVLRGVGGSQPPDIDKTELVEPTEYLVVHLKGSLVKD
SQYEMDSEFEGELADDLAGFYRSEYMEGNVRKVVATTQMQAADARKSFPCFDEPA
MKAEFNITLIHPKDLTALSNMLPKGPSTPLPEDPNWNVTEFHTTPKMSTYLLAFIVSE
FDYVEKQASNGVLIRIWARPSAIAAGHGDYALNVTGPILNFFAGHYDTPYPLPKSDQI
GLPDFNAGAMENWGLVTYRENSLLFDPLSSSSSNKERVVTVIAHELAHQWFGNLVTI
EWWNDLWLNEGFASYVEYLGADYAEPTWNLKDLMVLNDVYRVMAVDALASSHP
LSTPASEINTPAQISELFDAISYSKGASVLRMLSSFLSEDVFKQGLASYLHTFAYQNTI
YLNLWDHLQEAVNNRSIQLPTTVRDIMNRWTLQMGFPVITVDTSTGTLSQEHFLLDP
DSNVTRPSEFNYVWIVPITSIRDGRQQQDYWLIDVRAQNDLFSTSGNEWVLLNLNVT
GYYRVNYDEENWRKIQTQLQRDHSAIPVINRAQIINDAFNLASAHKVPVTLALNNTL
FLIEERQYMPWEAALSSLSYFKLMFDRSEVYGPMKNYLKKQVTPLFIHFRNNTNNW
REIPENLMDQYSEVNAISTACSNGVPECEEMVSGLFKQWMENPNNNPIHPNLRSTVY
CNAIAQGGEEEWDFAWEQFRNATLVNEADKLRAALACSKELWILNRYLSYTLNPDL
IRKQDATSTIISITNNVIGQGLVWDFVQSNWKKLFNDYGGGSFSFSNLIQAVTRRFSTE
YELQQLEQFKKDNEETGFGSGTRALEQALEKTKANIKWVKENKEVVLQWFTENSK
(SEQ ID NO: 45)

3. CD9 (Entrez gene: 928; RefSeq: NM_001769, NP_001760)
CTTTTCCCGGCACATGCGCACCGCAGCGGGTCGCGCGCCCTAAGGAGTGGCACTT
TTTAAAAGTGCAGCCGGAGACCAGCCTACAGCCGCCTGCATCTGTATCCAGCGCC
AGGTCCCGCCAGTCCCAGCTGCGCGCGCCCCCCAGTCCCGCACCCGTTCGGCCCA
GGCTAAGTTAGCCCTCACCATGCCGGTCAAAGGAGGCACCAAGTGCATCAAATA
CCTGCTGTTCGGATTTAACTTCATCTTCTGGCTTGCCGGGATTGCTGTCCTTGCCA
TTGGACTATGGCTCCGATTCGACTCTCAGACCAAGAGCATCTTCGAGCAAGAAAC
TAATAATAATAATTCCAGCTTCTACACAGGAGTCTATATTCTGATCGGAGCCGGC
GCCCTCATGATGCTGGTGGGCTTCCTGGGCTGCTGCGGGGCTGTGCAGGAGTCCC
AGTGCATGCTGGGACTGTTCTTCGGCTTCCTCTTGGTGATATTCGCCATTGAAATA
GCTGCGGCCATCTGGGGATATTCCCACAAGGATGAGGTGATTAAGGAAGTCCAG
GAGTTTTACAAGGACACCTACAACAAGCTGAAAACCAAGGATGAGCCCCAGCGG
GAAACGCTGAAAGCCATCCACTATGCGTTGAACTGCTGTGGTTTGGCTGGGGGCG
TGGAACAGTTTATCTCAGACATCTGCCCCAAGAAGGACGTACTCGAAACCTTCAC
CGTGAAGTCCTGTCCTGATGCCATCAAAGAGGTCTTCGACAATAAATTCCACATC
ATCGGCGCAGTGGGCATCGGCATTGCCGTGGTCATGATATTTGGCATGATCTTCA
GTATGATCTTGTGCTGTGCTATCCGCAGGAACCGCGAGATGGTCTAGAGTCAGCT
TACATCCCTGAGCAGGAAAGTTTACCCATGAAGATTGGTGGGATTTTTTGTTTGT
TTGTTTTGTTTTGTTTGTTGTTTGTTGTTTGTTTTTTTGCCACTAATTTTAGTATTCA
TTCTGCATTGCTAGATAAAAGCTGAAGTTACTTTATGTTTGTCTTTTAATGCTTCA
TTCAATATTGACATTTGTAGTTGAGCGGGGGGTTTGGTTTGCTTTGGTTTATATTT
TTTCAGTTGTTTGTTTTTGCTTGTTATATTAAGCAGAAATCCTGCAATGAAAGGTA
CTATATTTGCTAGACTCTAGACAAGATATTGTACATAAAAGAATTTTTTTGTCTTT
AAATAGATACAAATGTCTATCAACTTTAATCAAGTTGTAACTTATATTGAAGACA
ATTTGATACATAATAAAAAATTATGACAATGTCCTGGACTGGTAAAAAAA (SEQ
ID NO: 46)

Protein sequence:
MPVKGGTKCIKYLLFGFNFIFWLAGIAVLAIGLWLRFDSQTKSIFEQETNNNNSSFYT
GVYILIGAGALMMLVGFLGCCGAVQESQCMLGLFFGFLLVIFAIEIAAAIWGYSHKD
EVIKEVQEFYKDTYNKLKTKDEPQRETLKAIHYALNCCGLAGGVEQFISDICPKKDV
LETFTVKSCPDAIKEVFDNKFHIIGAVGIGIAVVMIFGMIFSMILCCAIRRNREMV
(SEQ ID NO: 47)

4. anti-CD3 scFv
GATATCCAGATGACACAGACAACCTCAAGTCTTAGTGCATCACTGGGAGATCGT
GTGACTATAAGCTGCCGCGCATCACAGGACATTCGCAATTATCTGAATTGGTATC
AACAGAAGCCTGATGGCACCGTGAAACTTCTGATCTATTACACCAGTCGTCTGCA
TAGCGGTGTTCCGAGCAAATTTTCAGGCTCAGGGTCAGGAACCGATTATTCACTG
ACGATTAGTAATTTAGAACAAGAAGATATTGCAACCTATTTCTGTCAACAGGGTA
ATACCCTGCCGTGGACCTTTGCAGGTGGTACCAAACTGGAAATTAAAGGAGGTG
GCAGTGGAGGGGGAAGCGGCGGCGGTTCAGGAGGCGGTTCTGAGGTCCAGTTAC
AGCAGAGCGGTCCGGAACTGGTTAAACCGGGTGCAAGCATGAAAATTAGCTGTA
AAGCAAGCGGTTATAGCTTTACCGGTTATACCATGAATTGGGTTAAACAGAGCCA
TGGTAAAAATCTGGAATGGATGGGTCTGATTAATCCGTATAAAGGTGTTAGCACC
TATAATCAGAAATTTAAAGATAAAGCAACCCTGACCGTTGATAAAAGCAGCAGC ACCGCATATATGGAACTGCTGAGCCTGACCAGCGAAGATAGCGCCGTTTACTATT
GCGCACGCAGCGGTTATTATGGTGATAGCGATTGGTATTTTGATGTTTGGGGTGC
AGGTACCACCGTTACCGTTAGCAGC (SEQ ID NO: 48)

5. anti-HER2 scFv
GACATCCAGATGACCCAGTCTCCATCCTCCCTGTCTGCATCTGTAGGAGACAGAG
TCACCATCACTTGCCGGGCAAGTCAGGATGTGAATACCGCGGTCGCATGGTATCA
GCAGAAACCAGGGAAAGCCCCTAAGCTCCTGATCTATTCTGCATCCTTCTTGTAT
AGTGGGGTCCCATCAAGGTTCAGTGGCAGTAGGTCTGGGACAGATTTCACTCTCA
CCATCAGCAGTCTGCAACCTGAAGATTTTGCAACTTACTACTGTCAACAGCATTA
CACTACCCCTCCGACGTTCGGCCAAGGTACCAAGGTGGAGATCAAACGAACTGG
CTCTACCAGCGGAAGCGGAAAGCCTGGCAGCGGCGAGGGCTCCGAAGTGCAGCT
GGTGGAGTCTGGCGGAGGACTGGTGCAGCCAGGGGGCAGCCTGAGACTGTCTTG
CGCCGCCTCCGGCTTCAACATCAAGGACACCTACATCCACTGGGTCCGCCAGGCA
CCAGGCAAGGGACTGGAATGGGTGGCCCGGATCTACCCTACCAACGGCTACACC
AGATACGCCGACTCCGTGAAGGGCCGGTTCACCATCTCCGCCGACACCTCCAAG
AACACCGCCTACCTGCAAATGAACTCCCTGAGGGCCGAGGACACCGCCGTGTAC
TACTGCTCCAGATGGGGAGGCGACGGCTTCTACGCAATGGACTACTGGGGCCAG
GGCACCCTGGTCACAGTGTCCTCT (SEQ ID NO: 49)

6. anti-EGFR scFv
CAGGTGCAGCTGAAGCAGTCTGGCCCTGGACTGGTGCAGCCTAGCCAGAGCCTG
AGCATCACCTGTACCGTGTCCGGCTTCAGCCTGACCAACTACGGCGTGCACTGGG
TGCGACAGAGCCCTGGCAAAGGCCTGGAATGGCTGGGAGTGATTTGGAGCGGCG
GCAACACCGACTACAACACCCCCTTCACCAGCAGACTGTCCATCAACAAGGACA
ACAGCAAGAGCCAGGTGTTCTTCAAGATGAACAGCCTGCAGAGCAACGACACCG
CCATCTACTACTGCGCTAGAGCCCTGACCTACTATGACTACGAGTTCGCCTACTG
GGGCCAGGGCACACTCGTGACAGTGTCTGCCGGCGGAGGTGGATCTGGAGGCGG
TGGCAGCGGTGGAGGCGGATCTGACATCCTGCTGACCCAGAGCCCCGTGATCCT
GTCCGTGTCTCCTGGCGAGAGAGTGTCCTTCAGCTGCAGAGCCAGCCAGAGCATC
GGCACCAACATCCACTGGTATCAGCAGAGGACCAACGGCAGCCCCAGACTGCTG
ATTAAGTACGCCAGCGAGTCCATCAGCGGCATCCCCAGCAGATTCAGCGGCAGC
GGCTCTGGCACCGACTTCACCCTGAGCATCAACAGCGTGGAAAGCGAGGATATC
GCCGACTACTACTGCCAGCAGAACAACAACTGGCCCACCACCTTCGGCGCTGGC
ACCAAGCTGGAACTGAAG (SEQ ID NO: 50)

7. HER2 (Entrez gene: 2064; RefSeq: NP_001005862)
MKLRLPASPETHLDMLRHLYQGCQVVQGNLELTYLPTNASLSFLQDIQEVQGYVLIA
HNQVRQVPLQRLRIVRGTQLFEDNYALAVLDNGDPLNNTTPVTGASPGGLRELQLRS
LTEILKGGVLIQRNPQLCYQDTILWKDIFHKNNQLALTLIDTNRSRACHPCSPMCKGS
RCWGESSEDCQSLTRTVCAGGCARCKGPLPTDCCHEQCAAGCTGPKHSDCLACLHF
NHSGICELHCPALVTYNTDTFESMPNPEGRYTFGASCVTACPYNYLSTDVGSCTLVC
PLHNQEVTAEDGTQRCEKCSKPCARVCYGLGMEHLREVRAVTSANIQEFAGCKKIF
GSLAFLPESFDGDPASNTAPLQPEQLQVFETLEEITGYLYISAWPDSLPDLSVFQNLQV
IRGRILHNGAYSLTLQGLGISWLGLRSLRELGSGLALIHENTHLCFVHTVPWDQLFRN
PHQALLHTANRPEDECVGEGLACHQLCARGHCWGPGPTQCVNCSQFLRGQECVEE
CRVLQGLPREYVNARHCLPCHPECQPQNGSVTCFGPEADQCVACAHYKDPPFCVAR
CPSGVKPDLSYMPIWKFPDEEGACQPCPINCTHSCVDLDDKGCPAEQRASPLTSIISA
VVGILLVVVLGVVFGILIKRRQQKIRKYTMRRLLQETELVEPLTPSGAMPNQAQMRIL
KETELRKVKVLGSGAFGTVYKGIWIPDGENVKIPVAIKVLRENTSPKANKEILDEAYV
MAGVGSPYVSRLLGICLTSTVQLVTQLMPYGCLLDHVRENRGRLGSQDLLNWCMQI
AKGMSYLEDVRLVHRDLAARNVLVKSPNHVKITDFGLARLLDIDETEYHADGGKVP
IKWMALESILRRRFTHQSDVWSYGVTVWELMTFGAKPYDGIPAREIPDLLEKGERLP
QPPICTIDVYMIMVKCWMIDSECRPRFRELVSEFSRMARDPQRFVVIQNEDLGPASPL
DSTFYRSLLEDDDMGDLVDAEEYLVPQQGFFCPDPAPGAGGMVHHRHRSSSTRSGG
GDLTLGLEPSEEEAPRSPLAPSEGAGSDVFDGDLGMGAAKGLQSLPTHDPSPLQRYS
EDPTVPLPSETDGYVAPLTCSPQPEYVNQPDVRPQPPSPREGPLPAARPAGATLERPK
TLSPGKNGVVKDVFAFGGAVENPEYLTPQGGAAPQPHPPPAFSPAFDNLYYWDQDP
PERGAPPSTFKGTPTAENPEYLGLDVPV (SEQ ID NO: 51)

8. HER3 (Entrez gene: 2065; RefSeq: NP_001005915)
MRANDALQVLGLLFSLARGSEVGNSQAVCPGTLNGLSVTGDAENQYQTLYKLYER
CEVVMGNLEIVLTGHNADLSFLQWIREVTGYVLVAMNEFSTLPLPNLRVVRGTQVY
DGKFAIFVMLNYNTNSSHALRQLRLTQLTGQFPMVPSGLTPQPAQDWYLLDDDPRL
LTLSASSKVPVTLAAV (SEQ ID NO: 52)

9. EGFR (Entrez gene: 1956; RefSeq: NP_001333826)
MRPSGTAGAALLALLAALCPASRALEEKKVCQGTSNKLTQLGTFEDHFLSLQRMFN
NCEVVLGNLEITYVQRNYDLSFLKTIQEVAGYVLIALNTVERIPLENLQIIRGNMYYE
NSYALAVLSNYDANKTGLKELPMRNLQGQKCDPSCPNGSCWGAGEENCQKLTKIIC
AQQCSGRCRGKSPSDCCHNQCAAGCTGPRESDCLVCRKFRDEATCKDTCPPLMLYN
PTTYQMDVNPEGKYSFGATCVKKCPRNYVVTDHGSCVRACGADSYEMEEDGVRKC
KKCEGPCRKVCNGIGIGEFKDSLSINATNIKHFKNCTSISGDLHILPVAFRGDSFTHTPP
LDPQELDILKTVKEITGFLLIQAWPENRTDLHAFENLEIIRGRTKQHGQFSLAVVSLNI
TSLGLRSLKEISDGDVIISGNKNLCYANTINWKKLFGTSGQKTKIISNRGENSCKATGQ
VCHALCSPEGCWGPEPRDCVSCRNVSRGRECVDKCNLLEGEPREFVENSECIQCHPE
CLPQAMNITCTGRGPDNCIQCAHYIDGPHCVKTCPAGVMGENNTLVWKYADAGHV
CHLCHPNCTYGCTGPGLEGCPTNGPKIPSIATGMVGALLLLLVVALGIGLFMRRRHIV
RKRTLRRLLQERELVEPLTPSGEAPNQALLRILKETEFKKIKVLGSGAFGTVYKGLWI PEGEKVKIPVAIKELREATSPKANKEILDEAYVMASVDNPHVCRLLGICLTSTVQLIT
QLMPFGCLLDYVREHKDNIGSQYLLNWCVQIAKGMNYLEDRRLVHRDLAARNVLV
KTPQHVKITDFGLAKLLGAEEKEYHAEGGKVPIKWMALESILHRIYTHQSDVWSYG
VTVWELMTFGSKPYDGIPASEISSILEKGERLPQPPICTIDVYMIMVKCWMIDADSRP
KFRELIIEFSKMARDPQRYLVIQGDERMHLPSPTDSNFYRALMDEEDMDDVVDADE
YLIPQQGFFSSPSTSRTPLLSSLSATSNNSTVACIDRNGLQSCPIKEDSFLQRYSSDPTG
ALTEDSIDDTFLPVPGEWLVWKQSCSSTSSTHSAAASLQCPSQVLPPASPEGETVADL
QTQ (SEQ ID NO: 53)

10. CD3d (Entrez gene: 915; RefSeq: NP_000723)
MEHSTFLSGLVLATLLSQVSPFKIPIEELEDRVFVNCNTSITWVEGTVGTLLSDITRLD
LGKRILDPRGIYRCNGTDIYKDKESTVQVHYRMCQSCVELDPATVAGIIVTDVIATLL
LALGVFCFAGHETGRLSGAADTQALLRNDQVYQPLRDRDDAQYSHLGGNWARNK
(SEQ ID NO: 54)

11. CD3e (Entrez gene: 916; RefSeq: NP_000724)
MQSGTHWRVLGLCLLSVGVWGQDGNEEMGGITQTPYKVSISGTTVILTCPQYPGSEI
LWQHNDKNIGGDEDDKNIGSDEDHLSLKEFSELEQSGYYVCYPRGSKPEDANFYLY
LRARVCENCMEMDVMSVATIVIVDICITGGLLLLVYYWSKNRKAKAKPVTRGAGAG
GRQRGQNKERPPPVPNPDYEPIRKGQRDLYSGLNQRRI (SEQ ID NO: 55)

12. CD3g (Entrez gene: 917; RefSeq: NP_000064)
MEQGKGLAVLILAIILLQGTLAQSIKGNHLVKVYDYQEDGSVLLTCDAEAKNITWFK
DGKMIGFLTEDKKKWNLGSNAKDPRGMYQCKGSQNKSKPLQVYYRIVICQNCIELNA
ATISGFLFAEIVSIFVLAVGVYFIAGQDGVRQSRASDKQTLLPNDQLYQPLKDREDDQ
YSHLQGNQLRRN (SEQ ID NO: 56)

13. CD16a (Entrez gene 2214; RefSeq: NP_000560)
MAEGTLWQILCVSSDAQPQTFEGVKGADPPTLPPGSFLPGPVLWWGSLARLQTEKS
DEVSRKGNWWVTEMGGGAGERLFTSSCLVGLVPLGLRISLVTCPLQCGIMWQLLLP
TALLLLVSAGMRTEDLPKAVVFLEPQWYRVLEKDSVTLKCQGAYSPEDNSTQWFHN
ESLISSQASSYFIDAATVDDSGEYRCQTNLSTLSDPVQLEVHIGWLLLQAPRWVFKEE
DPIHLRCHSWKNTALHKVTYLQNGKGRKYFHHNSDFYIPKATLKDSGSYFCRGLFG
SKNVSSETVNITITQGLAVSTISSFFPPGYQVSFCLVMVLLFAVDTGLYFSVKTNIRSST
RDWKDHKFKWRKDPQDK (SEQ ID NO: 57)

14. CD16b (Entrez gene: 2215; RefSeq: NP_000561)
MWQLLLPTALLLLVSAGMRTEDLPKAVVFLEPQWYSVLEKDSVTLKCQGAYSPEDN
STQWFHNENLISSQASSYFIDAATVNDSGEYRCQTNLSTLSDPVQLEVHIGWLLLQAP
RWVFKEEDPIHLRCHSWKNTALHKVTYLQNGKDRKYFHHNSDFHIPKATLKDSGSY
FCRGLVGSKNVSSETVNITITQGLAVSTISSFSPPGYQVSFCLVMVLLFAVDTGLYFSV
KTNI (SEQ ID NO: 58)

15. CD4 (Entrez gene: 920; RefSeq: NP_000607)
MNRGVPFREILLLVLQLALLPAATQGKKVVLGKKGDTVELTCTASQKKSIQFHWKNS
NQIKILGNQGSFLTKGPSKLNDRADSRRSLWDQGNFPLIIKNLKIEDSDTYICEVEDQK
EEVQLLVFGLTANSDTHLLQGQSLTLTLESPPGSSPSVQCRSPRGKNIQGGKTLSVSQ
LELQDSGTWTCTVLQNQKKVEFKIDIVVLAFQKASSIVYKKEGEQVEFSFPLAFTVEK
LTGSGELWWQAERASSSKSWITFDLKNKEVSVKRVTQDPKLQMGKKLPLHLTLPQA
LPQYAGSGNLTLALEAKTGKLHQEVNLVVMRATQLQKNLTCEVWGPTSPKLMLSL
KLENKEAKVSKREKAVWVLNPEAGMWQCLLSDSGQVLLESNIKVLPTWSTPVQPM
ALIVLGGVAGLLLFIGLGIFFCVRCRHRRRQAERMSQIKRLLSEKKTCQCPHRFQKTC
SPI (SEQ ID NO: 59)

16. CD8a (Entrez gene: 925; RefSeq: NP_001139345)
MALPVTALLLPLALLLHAARPSQFRVSPLDRTWNLGETVELKCQVLLSNPTSGCSWL
FQPRGAAASPTFLLYLSQNKPKAAEGLDTQRFSGKRLGDTFVLTLSDFRRENEGYYF
CSALSNSIMYFSHFVPVFLPAKPTTTPAPRPPTPAPTIASQPLSLRPEACRPAAGGAVH
TRGLDFACDIYIWAPLAGTCGVLLLSLVITLYCNHRNRRRVCKCPRPVVKSGDKPSL
SARYV (SEQ ID NO: 60)

17. CD8b (Entrez gene: 926; RefSeq: NP_001171571)
MRPRLWLLLAAQLTVLHGNSVLQQTPAYIKVQTNKMVMLSCEAKISLSNMRIYWLR
QRQAPSSDSHHEFLALWDSAKGTIHGEEVEQEKIAVFRDASRFILNLTSVKPEDSGIY
FCMIVGSPELTFGKGTQLSVVDFLPTTAQPTKKSTLKKRVCRLPRPETQKGLKGKVY
QEPLSPNACMDTTAILQPHRSCLTHGS (SEQ ID NO: 61)

18. CD11a (Entrez gene: 3683; RefSeq: NP_001107852)
MKDSCITVMAMALLSGFFFFAPASSYNLDVRGARSFSPPRAGRHFGYRVLQVGNGVI
VGAPGEGNSTGSLYQCQSGTGHCLPVTLRGSNYTSKYLGMTLATDPTDGSILFAAVQ
FSTSYKTEFDFSDYVKRKDPDALLKHVKHMLLLTNTFGAINYVATEVFREELGARPD
ATKVLIIITDGEATDSGNIDAAKDIIRYIIGIGKHFQTKESQETLHKFASKPASEFVKILD
TFEKLKDLFTELQKKIYVIEGTSKQDLTSFNMELSSSGISADLSRGHAVVGAVGAKD
WAGGFLDLKADLQDDTFIGNEPLTPEVRAGYLGYTVTWLPSRQKTSLLASGAPRYQ
HMGRVLLFQEPQGGGHWSQVQTIHGTQIGSYFGGELCGVDVDQDGETELLLIGAPLF
YGEQRGGRVFIYQRRQLGFEEVSELQGDPGYPLGRFGEAITALTDINGDGLVDVAVG
APLEEQGAVYIFNGRHGGLSPQPSQRIEGTQVLSGIQWFGRSIHGVKDLEGDGLADV
AVGAESQMIVLSSRPVVDMVTLMSFSPAEIPVHEVECSYSTSNKMKEGVNITICFQIK
SLIPQFQGRLVANLTYTLQLDGHRTRRRGLFPGGRHELRRNIAVTTSMSCTDFSFHFP VCVQDLISPINVSLNFSLWEEEGTPRDQRAGKDIPPILRPSLHSETWEIPFEKNCGEDK
KCEANLRVSFSPARSRALRLTAFASLSVELSLSNLEEDAYWVQLDLHFPPGLSFRKVE
MLKPHSQIPVSCEELPEESRLLSRALSCNVSSPIFKAGHSVALQMMFNTLVNSSWGDS
VELHANVTCNNEDSDLLEDNSATTIIPILYPINILIQDQEDSTLYVSFTPKGPKIHQVKH
MYQVRIQPSIHDHNIPTLEAVVGVPQPPSEGPITHQWSVQMEPPVPCHYEDLERLPDA
AEPCLPGALFRCPVVFRQEILVQVIGTLELVGEIEASSMFSLCSSLSISFNSSKHFHLYG
SNASLAQVVMKVDVVYEKQMLYLYVLSGIGGLLLLLLIFIVLYKVGFFKRNLKEKM
EAGRGVPNGIPAEDSEQLASGQEAGDPGCLKPLHEKDSESGGGKD (SEQ ID NO: 62)

19. CD19 (Entrez gene:930; RefSeq: NP_001171569)
MPPPRLLFFLLFLTPMEVRPEEPLVVKVEEGDNAVLQCLKGTSDGPTQQLTWSRESP
LKPFLKLSLGLPGLGIHMRPLAIWLFIFNVSQQMGGFYLCQPGPPSEKAWQPGWTVN
VEGSGELFRWNVSDLGGLGCGLKNRSSEGPSSPSGKLMSPKLYVWAKDRPEIWEGE
PPCLPPRDSLNQSLSQDLTMAPGSTLWLSCGVPPDSVSRGPLSWTHVHPKGPKSLLSL
ELKDDRPARDMWVMETGLLLPRATAQDAGKYYCHRGNLTMSFHLEITARPVLWH
WLLRTGGWKVSAVTLAYLIFCLCSLVGILHLQRALVLRRKRKRMTDPTRRFFKVTPP
PGSGPQNQYGNVLSLPTPTSGLGRAQRWAAGLGGTAPSYGNPSSDVQADGALGSRS
PPGVGPEEEEGEGYEEPDSEEDSEFYENDSNLGQDQLSQDGSGYENPEDEPLGPEDED
SFSNAESYENEDEELTQPVARTMDFLSPHGSAWDPSREATSLAGSQSYEDMRGILYA
APQLRSIRGQPGPNHEEDADSYENIVIDNPDGPDPAWGGGGRIVIGTWSTR (SEQ ID
NO: 63)

20. CD20 (Entrez gene: 931; RefSeq: NP_068769)
MTTPRNSVNGTFPAEPMKGPIAMQSGPKPLFRRMSSLVGPTQSFFMRESKTLGAVQI
MNGLFHIALGGLLMIPAGIYAPICVTVWYPLWGGIMYIISGSLLAATEKNSRKCLVKG
KMIMNSLSLFAAISGMILSIMDILNIKISHFLKMESLNFIRAHTPYINIYNCEPANPSEK
NSPSTQYCYSIQSLFLGILSVMLIFAFFQELVIAGIVENEWKRTCSRPKSNIVLLSAEEK
KEQTIEIKEEVVGLTETSSQPKNEEDIEIIPIQEEEEEETETNFPEPPQDQESSPIENDSSP
(SEQ ID NO: 65)

21. CD25 (Entrez gene: 3559; RefSeq: NP_000408)
MDSYLLMWGLLTFIMVPGCQAELCDDDPPEIPHATFKAMAYKEGTMLNCECKRGF
RRIKSGSLYMLCTGNSSHSSWDNQCQCTSSATRNTTKQVTPQPEEQKERKTTEMQSP
MQPVDQASLPGHCREPPPWENEATERIYHFVVGQMVYYQCVQGYRALHRGPAESV
CKMTHGKTRWTQPQLICTGEMETSQFPGEEKPQASPEGRPESETSCLVTTTDFQIQTE
MAATMETSIFTTEYQVAVAGCVFLLISVLLLSGLTWQRRQRKSRRTI (SEQ ID NO:
65)

22. CD33 (Entrez gene: 945; RefSeq: NP_001076087)
MPLLLLLPLLWADLTHRPKILIPGTLEPGHSKNLTCSVSWACEQGTPPIFSWLSAAPTS
LGPRTTHSSVLIITPRPQDHGTNLTCQVKFAGAGVTTERTIQLNVTYVPQNPTTGIFPG
DGSGKQETRAGVVHGAIGGAGVTALLALCLCLIFFIVKTHRRKAARTAVGRNDTHPT
TGSASPKHQKKSKLHGPTETSSCSGAAPTVEMDEELHYASLNFHGMNPSKDTSTEYS
EVRTQ (SEQ ID NO: 66)

23. CD40 (Entrez gene: 958 ; RefSeq: NP_001241)
MVRLPLQCVLWGCLLTAVHPEPPTACREKQYLINSQCCSLCQPGQKLVSDCTEFTET
ECLPCGESEFLDTWNRETHCHQHKYCDPNLGLRVQQKGTSETDTICTCEEGWHCTSE
ACESCVLHRSCSPGFGVKQIATGVSDTICEPCPVGFFSNVSSAFEKCHPWTSCETKDL
VVQQAGTNKTDVVCGPQDRLRALVVIPIIFGILFAILLVLVFIKKVAKKPTNKAPHPK
QEPQEINFPDDLPGSNTAAPVQETLHGCQPVTQEDGKESRISVQERQ (SEQ ID NO: 67)

24. CD40L (Entrez gene: 959; RefSeq: NP_000065)
MIETYNQTSPRSAATGLPISMKIFMYLLTVFLITQMIGSALFAVYLHRRLDKIEDERNL
HEDFVFMKTIQRCNTGERSLSLLNCEEIKSQFEGFVKDIMLNKEETKKENSFEMQKG
DQNPQIAAHVISEASSKTTSVLQWAEKGYYTMSNNLVTLENGKQLTVKRQGLYYIY
AQVTFCSNREASSQAPFIASLCLKSPGRFERILLRAANTHSSAKPCGQQSIHLGGVFEL
QPGASVFVNVTDPSQVSHGTGFTSFGLLKL (SEQ ID NO: 68)

25. CD70 (Entrez gene: 970; RefSeq: NP_001243)
MPEEGSGCSVRRRPYGCVLRAALVPLVAGLVICLVVCIQRFAQAQQQLPLESLGWD
VAELQLNHTGPQQDPRLYWQGGPALGRSFLHGPELDKGQLRIHRDGIYMVHIQVTL
AICSSTTASRHHPTTLAVGICSPASRSISLLRLSFHQGCTIASQRLTPLARGDTLCTNLT
GTLLPSRNTDETFFGVQWVRP (SEQ ID NO: 69)

26. CD123 (Entrez gene: 3563; RefSeq: NP_001254642)
MVLLWLTLLLIALPCLLQTKEGGKPWAGAENLTCWIHDVDFLSCSWAVGPGAPADV
QYDLYLNVANRRQQYECLHYKTDAQGTRIGCRFDDISRLSSGSQSSHILVRGRSAAF
GIPCTDKFVVFSQIEILTPPNMTAKCNKTHSFMHWKMRSHFNRKFRYELQIQKRMQP
VITEQVRDRTSFQLLNPGTYTVQIRARERVYEFLSAWSTPQRFECDQEEGANTRAWR
TSLLIALGTLLALVCVFVICRRYLVMQRLFPRIPHMKDPIGDSFQNDKLVVWEAGKA
GLEECLVTEVQVVQKT (SEQ ID NO: 70)

27. EpCAM (Entrez gene: 4072; RefSeq: NP_002345)
MAPPQVLAFGLLLAAATATFAAAQEECVCENYKLAVNCFVNNNRQCQCTSVGAQN
TVICSKLAAKCLVMKAEMNGSKLGRRAKPEGALQNNDGLYDPDCDESGLFKAKQC
NGTSMCWCVNTAGVRRTDKDTEITCSERVRTYWIIIELKHKAREKPYDSKSLRTALQ KEITTRYQLDPKFITSILYENNVITIDLVQNSSQKTQNDVDIADVAYYFEKDVKGESLF HSKKMDLTVNGEQLDLDPGQTLIYYVDEKAPEFSMQGLKAGVIAVIVVVVIAVVAGI VVLVISRKKRMAKYEKAEIKEMGEMHRELNA (SEQ ID NO: 71)

28. CLL-1 (Entrez gene: 160364; RefSeq: NP_001193939) MWIDFFTYSSMSEEVTYADLQFQNSSEMEKIPEIGKFGEKAPPAPSHVWRPAALFLTL LCLLLLIGLGVLASMEHVTLKIEMKKMNKLQNISEELQRNISLQLMSNMNISNKIRNL STTLQTIATKLCRELYSKEQEHKCKPCPRRWIWHKDSCYFLSDDVQTWQESKMACA AQNASLLKINNKNALEFIKSQSRSYDYWLGLSPEEDSTRGMRVDNIINSSAWVIRNAP DLNNMYCGYINRLYVQYYHCTYKKRMICEKMANPVQLGSTYFREA (SEQ ID NO: 72)

29. CTLA-4 (Entrez gene: 1493; RefSeq: NP_001032720) MACLGFQRHKAQLNLATRTWPCTLLFFLLFIPVFCKAMHVAQPAVVLASSRGIASFV CEYASPGKATEVRVTVLRQADSQVTEVCAATYMMGNELTFLDDSICTGTSSGNQVN LTIQGLRAMDTGLYICKVELMYPPPYYLGIGNGTQIYVIAKEKKPSYNRGLCENAPN RARM (SEQ ID NO: 73)

30. PD-1 (Entrez gene: 5133; RefSeq: NP_005009) MQIPQAPWPVVWAVLQLGWRPGWFLDSPDRPWNPPTFSPALLVVTEGDNATFTCSF SNTSESFVLNWYRMSPSNQTDKLAAFPEDRSQPGQDCRERVTQLPNGRDEHMSVVR ARRNDSGTYLCGAISLAPKAQIKESLRAELRVTERRAEVPTAHPSPSPRPAGQFQTLV VGVVGGLLGSLVLLVWVLAVICSRAARGTIGARRTGQPLKEDPSAVPVFSVDYGEL DFQWREKTPEPPVPCVPEQTEYATIVFPSGMGTSSPARRGSADGPRSAQPLRPEDGHC SWPL (SEQ ID NO: 74)

31. PD-L1 (Entrez gene: 29126; RefSeq: NP_001254635) MRIFAVFIFMTYWHLLNAPYNKINQRILVVDPVTSEHELTCQAEGYPKAEVIWTSSD HQVLSGKTTTTNSKREEKLFNVTSTLRINTTTNEIFYCTFRRLDPEENHTAELVIPELPL AHPPNERTHLVILGAILLCLGVALTFIFRLRKGRMMDVKKCGIQDTNSKKQSDTHLE ET (SEQ ID NO: 75)

32. OX40 (Entrez gene: 7293; RefSeq: NP_003318) MCVGARRLGRGPCAALLLLGLGLSTVTGLHCVGDTYPSNDRCCHECRPGNGMVSR CSRSQNTVCRPCGPGFYNDVVSSKPCKPCTWCNLRSGSERKQLCTATQDTVCRCRA GTQPLDSYKPGVDCAPCPPGHFSPGDNQACKPWTNCTLAGKHTLQPASNSSDAICED RDPPATQPQETQGPPARPITVQPTEAWPRTSQGPSTRPVEVPGGRAVAAILGLGLVLG LLGPLAILLALYLLRRDQRLPPDAHKPPGGGSFRTPIQEEQADAHSTLAKI (SEQ ID NO: 76)

33. GITR (Entrez gene: 8784; RefSeq: NP_004186) MAQHGAMGAFRALCGLALLCALSLGQRPTGGPGCGPGRLLLGTGTDARCCRVHTT RCCRDYPGEECCSEWDCMCVQPEFHCGDPCCTTCRHHPCPPGQGVQSQGKFSFGFQ CIDCASGTFSGGHEGHCKPWTDCTQFGFLTVFPGNKTHNAVCVPGSPPAEPLGWLTV VLLAVAACVLLLTSAQLGLHIWQLRSQCMWPRETQLLLEVPPSTEDARSCQFPEEER GERSAEEKGRLGDLWV (SEQ ID NO: 77)

34. ICOS (Entrez gene: 29851; RefSeq: NP_036224) MKSGLWYFFLFCLRIKVLTGEINGSANYEMFIFEINGGVQILCKYPDIVQQFKMQLLK GGQILCDLTKTKGSGNTVSIKSLKFCHSQLSNNSVSFFLYNLDHSHANYYFCNLSIFD PPPFKVTLTGGYLHIYESQLCCQLKFWLPIGCAAFVVVCILGCILICWLTKKKYSSSVH DPNGEYMFMRAVNTAKKSRLTDVTL (SEQ ID NO: 78)

35. B7-H3 (Entrez gene: 80381; RefSeq: NP_001019907) MLRRRGSPGMGVHVGAALGALWFCLTGALEVQVPEDPVVALVGTDATLCCSFSPEP GFSLAQLNLIWQLTDTKQLVHSFAEGQDQGSAYANRTALFPDLLAQGNASLRLQRV RVADEGSFTCFVSIRDFGSAAVSLQVAAPYSKPSMTLEPNKDLRPGDTVTITCSSYQG YPEAEVFWQDGQGVPLTGNVTTSQMANEQGLFDVHSILRVVLGANGTYSCLVRNPV LQQDAHSSVTITPQRSPTGAVEVQVPEDPVVALVGTDATLRCSFSPEPGFSLAQLNLI WQLTDTKQLVHSFTEGRDQGSAYANRTALFPDLLAQGNASLRLQRVRVADEGSFTC FVSIRDFGSAAVSLQVAAPYSKPSMTLEPNKDLRPGDTVTITCSSYRGYPEAEVFWQ DGQGVPLTGNVTTSQMANEQGLFDVHSVLRVVLGANGTYSCLVRNPVLQQDAHGS VTITGQPMTFPPEALWVTVGLSVCLIALLVALAFVCWRKIKQSCEEENAGAEDQDGE GEGSKTALQPLKHSDSKEDDGQEIA (SEQ ID NO: 79)

36. B7-H4 (Entrez gene: 79679; RefSeq: NP_001240778) MFRGRTAVFADQVIVGNASLRLKNVQLTDAGTYKCYIITSKGKGNANLEYKTGAFS MPEVNVDYNASSETLRCEAPRWFPQPTVVWASQVDQGANFSEVSNTSFELNSENVT MKVVSVLYNVTINNTYSCMIENDIAKATGDIKVTESEIKRRSHLQLLNSKASLCVSSF FAISWALLPLSPYLMLK (SEQ ID NO: 80)

37. LAG3 (Entrez gene: 3902; RefSeq: NP_002277) MWEAQFLGLLFLQPLWVAPVKPLQPGAEVPVVWAQEGAPAQLPCSPTIPLQDLSLL RRAGVTWQHQPDSGPPAAAPGHPLAPGPHPAAPSSWGPRPRRYTVLSVGPGGLRSG RLPLQPRVQLDERGRQRGDFSLWLRPARRADAGEYRAAVHLRDRALSCRLRLRLGQ ASMTASPPGSLRASDWVILNCSFSRPDRPASVHWFRNRGQGRVPVRESPHEIHLAESF LFLPQVSPMDSGPWGCILTYRDGFNVSIMYNLTVLGLEPPTPLTVYAGAGSRVGLPC RLPAGVGTRSFLTAKWTPPGGGPDLLVTGDNGDFTLRLEDVSQAQAGTYTCHIHLQ EQQLNATVTLAIITVTPKSFGSPGSLGKLLCEVTPVSGQERFVWSSLDTPSQRSFSGP WLEAQEAQLLSQPWQCQLYQGERLLGAAVYFTELSSPGAQRSGRAPGALPAGHLLL
FLILGVLSLLLLLVTGAFGFHLWRRQWRPRRFSALEQGIHPPQAQSKIEELEQEPEPEPE
PEPEPEPEPEPEQL (SEQ ID NO: 81)

38. TIM-3 (Entrez gene: 84868; RefSeq: NP_116171)
MFSHLPFDCVLLLLLLLLTRSSEVEYRAEVGQNAYLPCFYTPAAPGNLVPVCWGKG
ACPVFECGNVVLRTDERDVNYWTSRYWLNGDFRKGDVSLTIENVTLADSGIYCCRI
QIPGIMNDEKFNLKLVIKPAKVTPAPTRQRDFTAAFPRMLTTRGHGPAETQTLGSLPD
INLTQISTLANELRDSRLANDLRDSGATIRIGIYIGAGICAGLALALIFGALIFKWYSHS
KEKIQNLSLISLANLPPSGLANAVAEGIRSEENIYTIEENVYEVEEPNEYYCYVSSRQQ
PSQPLGCRFAMP (SEQ ID NO: 82)

39. PSMA (Entrez gene: 2346; RefSeq: NP_001014986)
MWNLLHETDSAVATARRPRWLCAGALVLAGGFFLLGFLFGWFIKSSNEATNITPKH
NMKAFLDELKAENIKKFLYNFTQIPHLAGTEQNFQLAKQIQSQWKEFGLDSVELAHY
DVLLSYPNKTHPNYISIINEDGNEIFNTSLFEPPPPGYENVSDIVPPFSAFSPQGMPEGD
LVYVNYARTEDFFKLERDMKINCSGKIVIARYGKVFRGNKVKNAQLAGAKGVILYS
DPADYFAPGVKSYPDGWNLPGGGVQRGNILNLNGAGDPLTPGYPANEYAYRRGIAE
AVGLPSIPVHPIGYYDAQKLLEKMGGSAPPDSSWRGSLKVPYNVGPGFTGNFSTQKV
KMHIHSTNEVTRIYNVIGTLRGAVEPDRYVILGGHRDSWVFGGIDPQSGAAVVHEIV
RSFGTLKKEGWRPRRTILFASWDAEEFGLLGSTEWAEENSRLLQERGVAYINADSSIE
GNYTLRVDCTPLMYSLVHNLTKELKSPDEGFEGKSLYESWTKKSPSPEFSGMPRISK
LGSGNDFEVFFQRLGIASGRARYTKNWETNKFSGYPLYHSVYETYELVEKFYDPMF
KYHLTVAQVRGGMVFELANSIVLPFDCRDYAVVLRKYADKIYSISMKHPQEMKTYS
VSFDSLFSAVKNFTEIASKFSERLQDFDKSKHVIYAPSSHNKYAGESFPGIYDALFDIE
SKVDPSKAWGEVKRQIYVAAFTVQAAAETLSEVA (SEQ ID NO: 83)

40. Factor IX (Entrez gene: 2158; RefSeq: NP_000124)
MQRVNMIMAESPGLITICLLGYLLSAECTVFLDHENANKILNRPKRYNSGKLEEFVQ
GNLERECMEEKCSFEEAREVFENTERTTEFWKQYVDGDQCESNPCLNGGSCKDDINS
YECWCPFGFEGKNCELDVTCNIKNGRCEQFCKNSADNKVVCSCTEGYRLAENQKSC
EPAVPFPCGRVSVSQTSKLTRAETVFPDVDYVNSTEAETILDNITQSTQSFNDFTRVV
GGEDAKPGQFPWQVVLNGKVDAFCGGSIVNEKWIVTAAHCVETGVKITVVAGEHNI
EETEHTEQKRNVIRIIPHENYNAAINKYNHDIALLELDEPLVLNSYVTPICIADKEYTNI
FLKFGSGYVSGWGRVFHKGRSALVLQYLRVPLVDRATCLRSTKFTIYNNMFCAGFH
EGGRDSCQGDSGGPHVTEVEGTSFLTGIISWGEECAMKGKYGIYTKVSRYVNWIKEK
TKLT (SEQ ID NO: 84)

41. Factor X (Entrez gene: 2159; RefSeq: NP_000495)
MGRPLHLVLLSASLAGLLLLGESLFIRREQANNILARVTRANSFLEEMKKGHLEREC
MEETCSYEEAREVFEDSDKTNEFWNKYKDGDQCETSPCQNQGKCKDGLGEYTCTC
LEGFEGKNCELFTRKLCSLDNGDCDQFCHEEQNSVVCSCARGYTLADNGKACIPTGP
YPCGKQTLERRKRSVAQATSSSGEAPDSITWKPYDAADLDPTENPFDLLDFNQTQPE
RGDNNLTRIVGGQECKDGECPWQALLINEENEGFCGGTILSEFYILTAAHCLYQAKR
FKVRVGDRNTEQEEGGEAVHEVEVVIKHNRFTKETYDFDIAVLRLKTPITFRIVINVAP
ACLPERDWAESTLMTQKTGIVSGFGRTHEKGRQSTRLKMLEVPYVDRNSCKLSSSFII
TQNMFCAGYDTKQEDACQGDSGGPHVTRFKDTYFVTGIVSWGEGCARKGKYGIYT
KVTAFLKWIDRSMKTRGLPKAKSHAPEVITSSPLK (SEQ ID NO: 85)

42. Folate receptor alpha (FOLR1) (Entrez gene: 2348; RefSeq: NP_000793)
MAQRMTTQLLLLLVWVAVVGEAQTRIAWARTELLNVCMNAKHHKEKPGPEDKLH
EQCRPWRKNACCSTNTSQEAHKDVSYLYRFNAVNHCGEMAPACKRHFIQDTCLYEC
SPNLGPWIQQVDQSWRKERVLNVPLCKEDCEQWWEDCRTSYTCKSNWHKGWNWT
SGFNKCAVGAACQPFHFYFPTPTVLCNEIWTHSYKVSNYSRGSGRCIQMWFDPAQG
NPNEEVARFYAAAMSGAGPWAAWPFLLSLALMLLWLLS (SEQ ID NO: 86)

43. Folate receptor beta (FOLR2) (Entrez gene: 2350; RefSeq: NP_000794)
MVWKWMPLLLLLVCVATMCSAQDRTDLLNVCMDAKHHKTKPGPEDKLHDQCSP
WKKNACCTASTSQELHKDTSRLYNFNWDHCGKMEPACKRHFIQDTCLYECSPNLGP
WIQQVNQSWRKERFLDVPLCKEDCQRWWEDCHTSHTCKSNWHRGWDWTSGVNK
CPAGALCRTFESYFPTPAALCEGLWSHSYKVSNYSRGSGRCIQMWFDSAQGNPNEE
VARFYAAAMHVNAGEMLHGTGGLLLSLALMLQLWLLG (SEQ ID NO: 87)

44. Folate receptor gamma (FOLR3) (Entrez gene: 2352; RefSeq: NP_000795)
MDMAWQMMQLLLLALVTAAGSAQPRSARARTDLLNVCMNAKHHKTQPSPEDELY
GQCSPWKKNACCTASTSQELHKDTSRLYNFNWDHCGKMEPTCKRHFIQDSCLYECS
PNLGPWIRQVNQSWRKERILNVPLCKEDCERWWEDCRTSYTCKSNWHKGWNWTS
GINECPAGALCSTFESYFPTPAALCEGLWSHSFKVSNYSRGSGRCIQMWFDSAQGNP
NEEVAKFYAAAMNAGAPSRGIIDS (SEQ ID NO: 88)

What is claimed is:

1. An isolated engineered extracellular vesicle comprising a first antigen binding domain that comprises an anti-EGFR scFv antibody fragment and a second antigen binding domain that comprises an anti-CD3 scFv antibody fragment and, the first and second antigen binding domains being fused to one or more extracellular vesicle addressing domains expressed on the surface of the vesicle, wherein the one or more extracellular vesicle addressing domain comprises platelet-derived growth factor receptor (PDGFR) transmembrane domain.

2. The isolated engineered extracellular vesicle of claim 1, wherein the extracellular vesicle is selected from the group of: an exosome, a liposome, a microvesicle, and an apoptotic body.

3. The isolated engineered extracellular vesicle of claim 1, further comprising a purification and/or a detectable label.

4. The isolated engineered extracellular vesicle of claim 1, further comprising an effective amount of a therapeutic agent encapsulated in the vesicle.

5. A composition comprising an isolated engineered extracellular vesicle of claim 1 and a carrier.

6. A method for treating a subject in need thereof or inducing an immune response in a subject in need thereof, comprising administering to the subject an effective amount of the isolated engineered extracellular vesicle of claim 1, wherein the isolated engineered extracellular vesicle comprises an exosome that expresses an antigen binding domain specific to a disease to be treated.

7. A method for cancer immunotherapy for a subject in need thereof, comprising administering an effective amount of the isolated engineered extracellular vesicle of claim 1, wherein the exosome expresses an antigen binding domain specific to the cancer to be treated.

8. A fusion polypeptide comprising: a first antigen binding domain that comprises an anti-EGFR scFv antibody fragment and a second antigen binding domain that comprises an anti-CD3 scFv antibody fragment, a linker polypeptide, and an exosome addressing domain and an exosome addressing domain that comprises platelet-derived growth factor receptor (PDGFR) transmembrane domain.

9. An isolated polynucleotide encoding the fusion polypeptide of claim 8.

10. A method to prepare an extracellular vesicle comprising contacting a cell comprising the extracellular vesicle with an effective amount of the polynucleotide of claim 9 and expressing the polynucleotide on the surface of the vesicle.

11. The isolated engineered extracellular vesicle of claim 1, further comprising one or more linker polypeptides.

12. A method for treating a subject in need thereof or inducing an immune response in a subject in need thereof, comprising administering to the subject an effective amount of the isolated engineered extracellular vesicle the fusion polypeptide of claim 8.

13. A method for cancer immunotherapy for a subject in need thereof, comprising administering an effective amount of the fusion polypeptide of claim 8, wherein the exosome expresses an antigen binding domain specific to the cancer to be treated.

14. A method for treating a subject in need thereof or inducing an immune response in a subject in need thereof, comprising administering to the subject an effective amount of an isolated engineered extracellular vesicle comprising the fusion polypeptide of claim 8, wherein the isolated engineered extracellular vesicle comprises an exosome that expresses an antigen binding domain specific to a disease to be treated.

15. A method for cancer immunotherapy for a subject in need thereof, comprising administering an effective amount of an isolated engineered extracellular vesicle comprising the fusion polypeptide of claim 8, wherein the exosome expresses an antigen binding domain specific to the cancer to be treated.

* * * * *